(12) United States Patent
Beers et al.

(10) Patent No.: US 8,142,909 B2
(45) Date of Patent: Mar. 27, 2012

(54) BLUE PHOSPHORESCENT IMIDAZOPHENANTHRIDINE MATERIALS

(75) Inventors: Scott Beers, Flemington, NJ (US); Peter B. Mackenzie, Kingsport, TN (US); Jui-Yi Tsai, Lawrenceville, NJ (US); Chun Lin, Langhorne, PA (US); Walter Yeager, Yardley, PA (US); Edward Barron, Hamilton, NJ (US); David B. Knowles, Apollo, PA (US); Robert W. Walters, Export, PA (US); Cory S. Brown, Pittsburgh, PA (US)

(73) Assignee: Universal Display Corporation, Ewing, NJ (US)

( * ) Notice: Subject to any disclaimer, the term of this patent is extended or adjusted under 35 U.S.C. 154(b) by 995 days.

(21) Appl. No.: 12/044,605

(22) Filed: Mar. 7, 2008

(65) Prior Publication Data

US 2008/0297033 A1     Dec. 4, 2008

Related U.S. Application Data

(63) Continuation-in-part of application No. 11/704,585, filed on Feb. 9, 2007, now Pat. No. 7,915,415.

(60) Provisional application No. 60/936,643, filed on Jun. 20, 2007, provisional application No. 60/874,190, filed on Dec. 11, 2006, provisional application No. 60/856,824, filed on Nov. 3, 2006, provisional application No. 60/772,154, filed on Dec. 10, 2006.

(51) Int. Cl.
*H01L 51/54* (2006.01)
*C09K 11/06* (2006.01)

(52) U.S. Cl. ........ 428/690; 428/917; 313/504; 313/506; 252/301.16; 257/40; 257/E51.044; 548/103; 546/10

(58) Field of Classification Search .................. None
See application file for complete search history.

(56) References Cited

U.S. PATENT DOCUMENTS

| | | | |
|---|---|---|---|
| 4,769,292 A | 9/1988 | Tang et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |

(Continued)

FOREIGN PATENT DOCUMENTS

EP    1 647 554    4/2006

(Continued)

OTHER PUBLICATIONS

Baldo et al., "Very high-efficiency green organic light-emitting devices based on electrophosphorescence," Appl. Phys. Lett., vol. 75, No. 1, 4-6 (1999).

(Continued)

*Primary Examiner* — Jennifer A Chriss
*Assistant Examiner* — Michael H Wilson
(74) *Attorney, Agent, or Firm* — Kilpatrick Townsend & Stockton LLP

(57) ABSTRACT

Compounds comprising phosphorescent metal complexes comprising cyclometallated imidazo[1,2-f]phenanthridine and diimidazo[1,2-a:1',2'-c]quinazoline ligands, or isoelectronic or benzannulated analogs thereof, are described. Organic light emitting devices comprising these compounds are also described.

44 Claims, 22 Drawing Sheets

U.S. PATENT DOCUMENTS

| | | | |
|---|---|---|---|
| 6,097,147 | A | 8/2000 | Baldo et al. |
| 6,294,398 | B1 | 9/2001 | Kim et al. |
| 6,303,238 | B1 | 10/2001 | Thompson et al. |
| 6,310,360 | B1 | 10/2001 | Forrest et al. |
| 6,337,102 | B1 | 1/2002 | Forrest et al. |
| 6,468,819 | B1 | 10/2002 | Kim et al. |
| 6,548,956 | B2 | 4/2003 | Forrest et al. |
| 6,576,134 | B1 | 6/2003 | Agner |
| 6,602,540 | B2 | 8/2003 | Gu et al. |
| 6,830,828 | B2 | 12/2004 | Thompson et al. |
| 6,835,469 | B2 | 12/2004 | Kwong et al. |
| 7,071,615 | B2 | 7/2006 | Lu et al. |
| 7,431,968 | B1 | 10/2008 | Shtein et al. |
| 7,915,415 | B2 * | 3/2011 | Knowles et al. ............. 546/10 |
| 2002/0182441 | A1 | 12/2002 | Lamansky et al. |
| 2003/0230980 | A1 | 12/2003 | Forrest et al. |
| 2004/0239237 | A1 | 12/2004 | Matsusue |
| 2005/1025843 | | 11/2005 | Djumvich et al. |
| 2006/0251923 | A1 | 11/2006 | Lin et al. |
| 2007/0075631 | A1 | 4/2007 | Tung et al. |
| 2007/0190359 | A1 | 8/2007 | Knowles et al. |

FOREIGN PATENT DOCUMENTS

| | | |
|---|---|---|
| JP | 2005 042106 | 2/2005 |
| JP | 2005 298483 | 10/2005 |
| WO | WO 02/074015 | 9/2002 |
| WO | WO 2004/085450 | 10/2004 |
| WO | WO 2005/007767 | 1/2005 |
| WO | WO 2005/049762 | 6/2005 |
| WO | WO 2007/095118 | 8/2007 |

OTHER PUBLICATIONS

Baldo et al., "Highly Efficient Phosphorescent Emission from Organic Electroluminescent Devices," Nature, vol. 395, p. 151-154, 1998.

Adachi et al., "Nearly 100% Internal Phosphorescent Efficiency in an Organic Light Emitting Device," J. Appl. Phys., 90, 5048 (2001).

Yang et.al. "Synthesis of Dithienopyridines through Pd(0)-Catalysed Coupling of ortho-Formylthiopheneboronic Acids with t-Butyl-N-(ortho-halothienyl)carbamates," Chemica Scripta 1988, 28, p. 275-279.

Yang et.al. "The First Synthesis of Thieno[c]isoquinolines and an Improved Synthesis of Phenanthridine and Thieno[c]quinolines through Pd(0) Catalyzed Coupling of ortho-Formylarylboronic Acids with Functionalized Aryl Halides," J. Heterocyclic Chem., 26, pp. 865-868 (1989).

Garg et. al. "Regioselective Bromomethylation of 1,2-Dialkylbenzenes," SYNLETT p. 310-312 (1997).

Parenty et.al. "A General and Efficient Five-Step One-Pot Procedure Leading to Nitrogen-Bridgehead Heterocycles Containing an Imidazole Ring", Organic Letters, vol. 9 (12) pp. 2253-2256 (2007).

Gary L. Miessler and Donald A. Tarr, "Inorganic Chemistry" (2nd Edition) Prentice Hall (1998), pp. 1-3; 422-424.

Tang et al., "Rapid intersystem crossing in highly phosphorescent iridium complexes," Chemical Physics Letters 386 (2004) p. 437-441.

Rao et al., "A new high-yielding method for the preparation of 2-alkyl- and 1,2-dialkyl-4-nitro-5-bromoimidazoles" J. Org. Chem. 1992, 57, p. 3240-3242.

David Ryan "Quanta v. LGE: The "Exhaustion" Doctrine & Multi-level Royalties", The Computer and Internet Lawyer, vol. 25, No. 5, pp. 14-20, May 2008.

Roger Cook "Why the Supreme Court appears poised to get Quanta v. LG wrong" Townsend and Townsend and Crew LLP.

Nakayama et al., "Preparation of congested thiophenes carrying bulky substituents on the 3- and 4-positions and their conversion to the benzene derivatives" The Journal of Organic Chemistry, 1998, 63 (15) pp. 4912-4924.

International Search Report for PCT/US2008/056297 dated Sep. 5, 2008.

U.S. Appl. No. 60/936,643, filed Jun. 20, 2007.
U.S. Appl. No. 60/874,190, filed Dec. 11, 2006.
U.S. Appl. No. 60/856,824, filed Nov. 3, 2006.
U.S. Appl. No. 60/772,154, filed Feb. 10, 2006.
European Search Report for EP 10 007603 mailed Sep. 10, 2010.
International Search Report for PCT/US2007/003569 mailed Oct. 2, 2007.

* cited by examiner

CuPc [10nm] / NPD [30nm] / mCBP:dopant 9% [30nm] / BAlq [40nm] / LiF [0.5nm] / Al [100nm]

CuPc [10nm] / NPD [30nm] / mCBP:dopant 9% [30nm] / BAlq [40nm] / LiF [0.5nm] / Al [100nm]

CuPc [10nm] / NPD [30nm] / mCBP:dopant 9% [30nm] / BAlq [40nm] / LiF [0.5nm] / Al [100nm]

BLUE PHOSPHORESCENT IMIDAZOPHENANTHRIDINE MATERIALS

CROSS-REFERENCE TO RELATED APPLICATIONS

This is a continuation-in-part application and claims priority to and benefit under 35 U.S.C. §120 to U.S. application Ser. No. 11/704,585 filed Feb. 9, 2007, now U.S. Pat. No. 7,915,415, which claims priority to U.S. provisional application Ser. No. 60/874,190, filed Dec. 11, 2006, U.S. provisional application Ser. No. 60/856,824, filed Nov. 3, 2006, and U.S. provisional application Ser. No. 60/772,154, filed Feb. 10, 2006. This application also claims priority and benefit under 35 U.S.C. §119(e) to U.S. provisional application 60/936,643 filed Jun. 20, 2007. The contents of all of these applications are expressly incorporated fully herein by reference in their entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

TECHNICAL FIELD

The present invention generally relates to organic light emitting devices (OLEDs), and organic compounds used in these devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight, whereas a polymer has a chemical formula and a molecular weight that may vary from molecule to molecule. As used herein, "organic" includes metal complexes of hydrocarbyl and heteroatom-substituted hydrocarbyl ligands.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic optoelectronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

The development of long-lived blue emissive phosphorescent dopants is recognized as a key unfulfilled objective of current OLED research and development. While phosphorescent OLED devices with emission peaks in the deep blue or near-UV have been demonstrated, the lifetimes of blue-emissive devices exhibiting 100 nits initial luminance have been on the order of several hundred hours (where "lifetime" refers to the time for the luminance to decline to 50% of the initial level, at constant current). For example, iridium(III) complexes of bidentate ligands derived from N-methyl-2-phenylimidazoles can be used to prepare blue OLED devices, but very short lifetimes are observed with these dopants (about 250 hours at 100 nits initial luminescence).

Since most commercial applications are expected to require lifetimes in excess of 10,000 hours at 200 nits initial luminescence, major improvements in blue phosphorescent OLED device lifetimes are sought.

SUMMARY

Pursuant to the aforementioned objective, we describe herein several new classes of phosphorescent metal complexes and OLED devices comprising cyclometallated imidazo[1,2-f]phenanthridine or diimidazo[1,2-a:1',2'-c]quinazoline ligands, or isoelectronic or benzannulated analogs thereof, useful in the preparation of long-lived and efficient blue, green and red emissive OLED devices. Many of these complexes have surprisingly narrow phosphorescent emission lineshapes, or triplet energies which are surprisingly high for such highly conjugated molecules, or both. Density Functional Theory (DFT) calculations using the G98/B31yp/cep-31 g basis set suggest that many of the blue-emissive complexes of the current invention have relatively small singlet-triplet gaps, less than about 0.25 eV. Without wishing to be bound by theory, the inventors believe that the 18 pi electron count and specific arrangement of fused rings is associated with the small singlet-triplet band gap and may have beneficial effects on the spectral lineshape and device lifetime. A small singlet-triplet gap may also facilitate the design of low voltage OLED devices and beneficially reduce the power consumption of OLED devices comprising such compounds.

In one aspect, iridium complexes are provided, having Formula I:

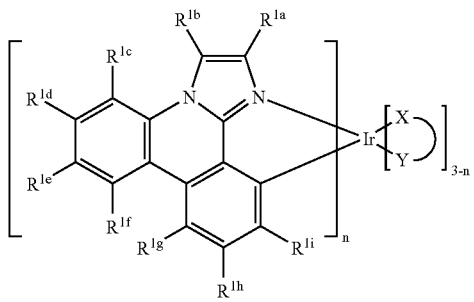

where n=1, 2 or 3; $R^{1a}$, $R^{1b}$, $R^{1c}$, $R^{1d}$, $R^{1e}$, $R^{1f}$, $R^{1g}$, $R^{1h}$, and $R^{1i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a-c}$ are each, independently, hydrocarbyl or heteroatom substituted hydrocarbyl, and where any two of $R^{1a-i}$ and $R^{2a-c}$, may be linked to form a saturated or unsaturated, aromatic or non-aromatic ring; and X—Y is an ancillary ligand.

In one aspect, iridium complexes having Formula I are provided, where $R^{1e}$ is a branched alkyl containing at least 4 carbon atoms and where the branching occurs at a position further than the benzylic position.

In one aspect, iridium complexes having Formula I are provided, where $R^{1b}$ is an aryl group having the structure:

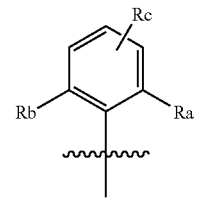

where Ra, Rb and Rc are independently H, alkyl or aryl, and at least one of Ra and Rb is an alkyl or aryl. Ra, Rb and Rc can join to form fused rings.

In one aspect, iridium complexes having Formula I are provided, where $R^{1a}$ is an electron donating group.

Various emissive complexes provided herein, and particularly iridium complexes having Formula I, may be incorporated into organic light emitting devices. The emissive layer of such devices may include a host in addition to the emissive complex. Preferred hosts include organic material that contains a carbazole group. mCBP is a particularly preferred host.

DETAILED DESCRIPTION

Figure 1:
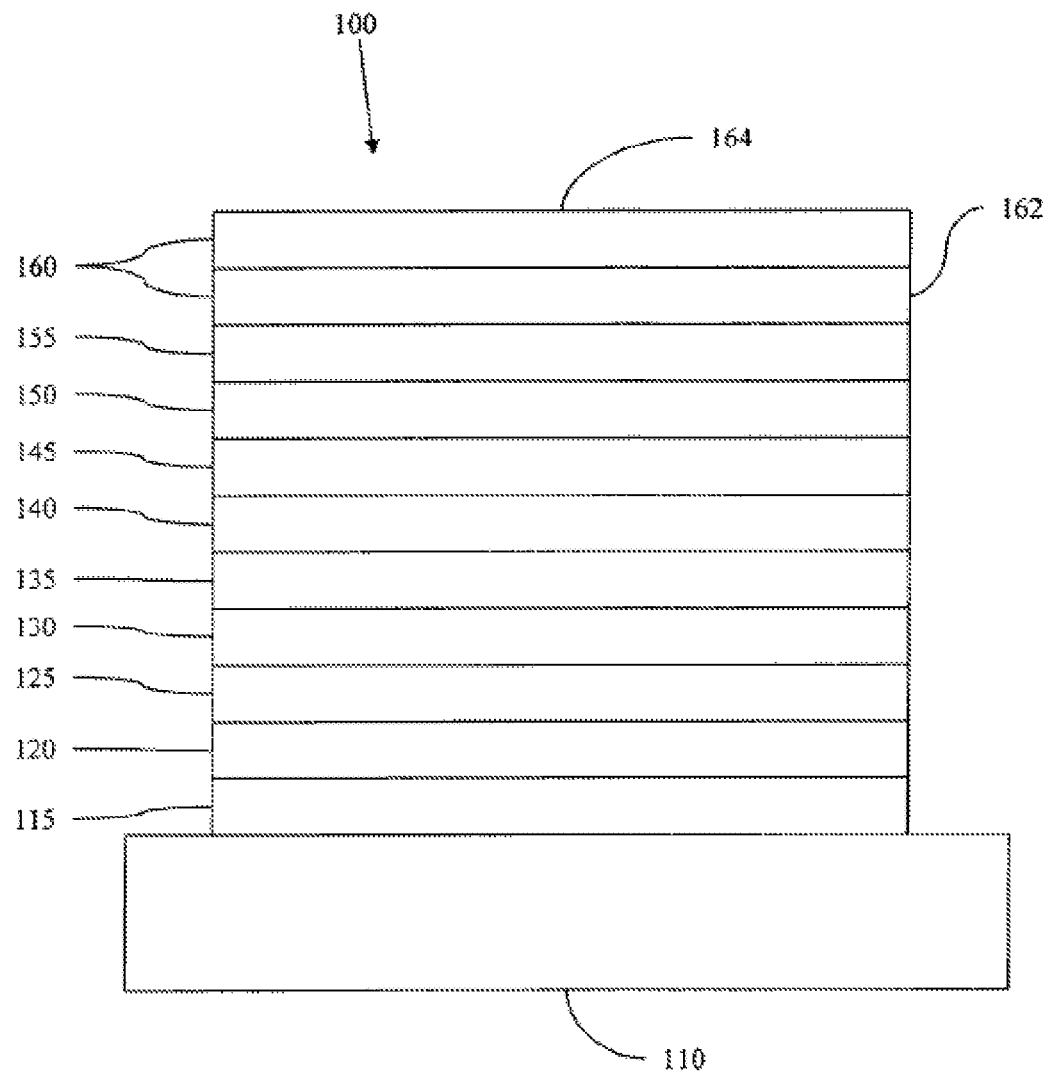
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or un-doped phosphorescent organometallic materials such as disclosed in U.S. Pat. Nos. 6,303,238; 6,310,360; 6,830,828; and 6,835,469; U.S. Patent Application Publication No. 2002-0182441; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III). While not wishing to be bound by theory, it is believed that the organic metal to carbon bond in an organometallic complex is an especially preferred method of achieving the desired proximity of the organic molecule to an atom of high atomic number. Specifically, in the context of this application, the presence of the organic carbon-metal bond in the organometallic complex may promote greater MLCT character, which can be useful for the production of highly efficient devices.

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

The term "organometallic" as used herein is as generally understood by one of ordinary skill in the art and as given, for example, in "Inorganic Chemistry" (2nd Edition) by Gary L. Miessler and Donald A. Tarr, Prentice Hall (1998). Thus, the term organometallic refers to compounds which have an organic group bonded to a metal through a carbon-metal bond. This class does not include per se coordination compounds, which are substances having only donor bonds from heteroatoms, such as metal complexes of amines, halides, pseudohalides (CN, etc.), and the like. In practice organometallic compounds may comprise, in addition to one or more carbon-metal bonds to an organic species, one or more donor bonds from a heteroatom. The carbon-metal bond to an organic species refers to a direct bond between a metal and a carbon atom of an organic group, such as phenyl, alkyl, alkenyl, etc., but does not refer to a metal bond to an "inorganic carbon," such as the carbon of CN or CO.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540 B2, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003-0230980 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include $Ir(Ppy)_3$. Examples of fluorescent emissive materials include DCM and DMQA. Examples of host materials include $Alq_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecule emissive material may be present as the core of a dendrimer.

Many useful emissive materials include one or more ligands bound to a metal center. A ligand may be referred to as "photoactive" if it contributes directly to the photoactive properties of an organometallic emissive material. A "photoactive" ligand may provide, in conjunction with a metal, the energy levels from which and to which an electron moves when a photon is emitted. Other ligands may be referred to as "ancillary." Ancillary ligands may modify the photoactive properties of the molecule, for example by shifting the energy levels of a photoactive ligand, but ancillary ligands do not directly provide the energy levels involved in light emission. A ligand that is photoactive in one molecule may be ancillary in another. These definitions of photoactive and ancillary are intended as non-limiting theories.

Electron transport layer 145 may include a material capable of transporting electrons. Electron transport layer 145 may be intrinsic (undoped), or doped. Doping may be used to enhance conductivity. $Alq_3$ is an example of an intrinsic electron transport layer. An example of an n-doped electron transport layer is BPhen doped with Li at a molar ratio of 1:1, as disclosed in United States Patent Application Publication No. 2003-0230980 to Forrest et al., which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) energy level of the electron transport layer. The "charge carrying component" is the material responsible for the LUMO energy level that actually transports electrons. This component may be the base material, or it may be a dopant. The LUMO energy level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2 and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 145. Blocking layers may also be used to block excitons from diffusing out of the emissive layer. The theory and use of blocking layers is described in more detail in U.S. Pat. No. 6,097,147 and United States Patent Application Publication No. 2003-0230980 to Forrest et al., which are incorporated by reference in their entireties.

As used herein, and as would be understood by one skilled in the art, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948, now U.S. Pat. No. 7,071,615, to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO energy level that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
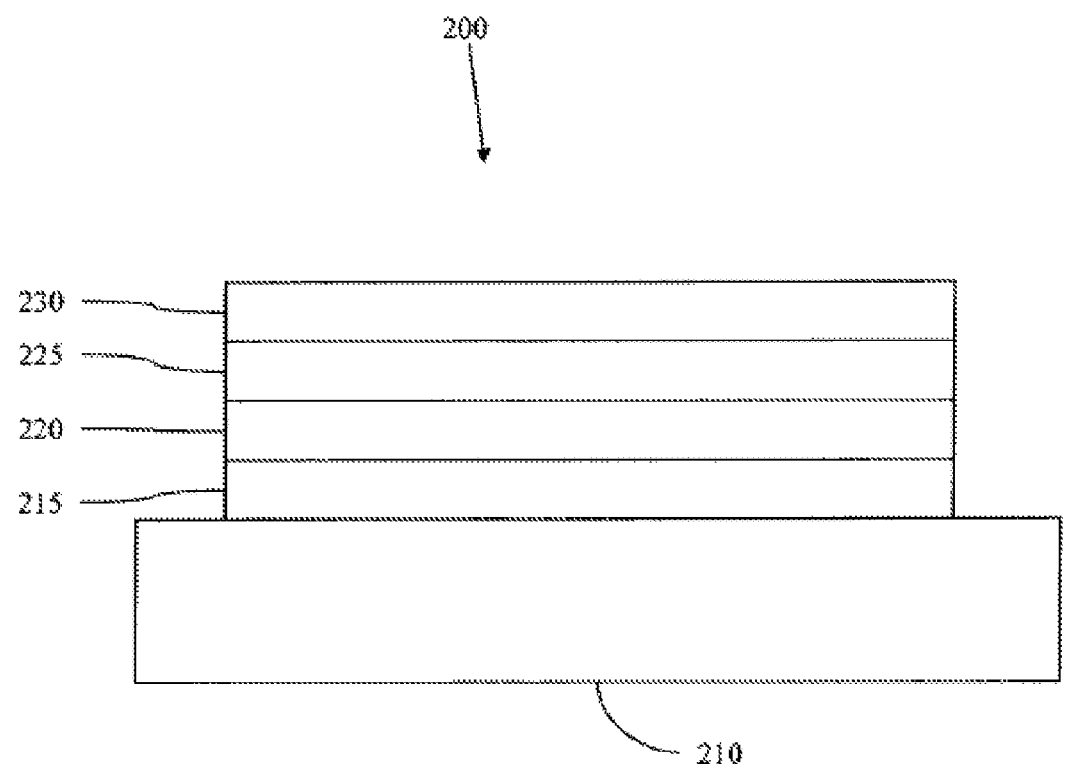
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

The molecules disclosed herein may be substituted in a number of different ways without departing from the scope of the invention. For example, substituents may be added to a compound having three bidentate ligands, such that after the substituents are added, one or more of the bidentate ligands are linked together to form, for example, a tetradentate or hexadentate ligand. Other such linkages may be formed. It is believed that this type of linking may increase stability relative to a similar compound without linking, due to what is generally understood in the art as a "chelating effect."

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "aryl" refers to an aromatic carbocyclic monoradical. Unless otherwise specified, the aromatic carbocyclic monoradical may be substituted or unsubstituted. The substituents can be F, hydrocarbyl, heteroatom-substituted hydrocarbyl, cyano, and the like.

A "hydrocarbyl" group means a monovalent or divalent, linear, branched or cyclic group which contains only carbon and hydrogen atoms. Examples of monovalent hydrocarbyls include the following: $C_1$-$C_{20}$ alkyl; $C_1$-$C_{20}$ alkyl substituted with one or more groups selected from $C_1$-$C_{20}$ alkyl, $C_3$-$C_8$ cycloalkyl, and aryl; $C_3$-$C_8$ cycloalkyl; $C_3$-$C_8$ cycloalkyl substituted with one or more groups selected from $C_1$-$C_{20}$ alkyl, $C_3$-$C_8$ cycloalkyl, and aryl; $C_6$-$C_{18}$ aryl; and $C_6$-$C_{18}$ aryl substituted with one or more groups selected from $C_1$-$C_{20}$ alkyl, $C_3$-$C_8$ cycloalkyl, and aryl. Examples of divalent (bridging) hydrocarbyls include: —$CH_2$—; —$CH_2CH_2$—; —$CH_2CH_2CH_2$—; and 1,2-phenylene.

A "heteroatom" refers to an atom other than carbon or hydrogen. Examples of heteroatoms include oxygen, nitrogen, phosphorus, sulfur, selenium, arsenic, chlorine, bromine, silicon, and fluorine.

A "heteroaryl" refers to a heterocyclic monoradical that is aromatic. Unless otherwise specified, the aromatic heterocyclic monoradical may be substituted or unsubstituted. The substituents can be F, hydrocarbyl, heteroatom-substituted hydrocarbyl, cyano, and the like. Examples of heteroaryls include 1-pyrrolyl, 2-pyrrolyl, 3-pyrrolyl, furyl, thienyl, indenyl, imidazolyl, oxazolyl, isoxazolyl, carbazolyl, thiazolyl, pyrimidinyl, pyridyl, pyridazinyl, pyrazinyl, benzothienyl, and the like, and substituted derivatives thereof.

By "ortho positions," we mean the positions on the aryl or heteroaryl group which are adjacent to the point of attachment of the second ring to the first ring. In the case of a six-membered ring aryl group attached via the 1-position, such as 2,6-dimethylphenyl, the 2- and 6-positions are the ortho positions. In the case of a 5-membered ring heteroaryl group attached via the 1-position, such as 2,5-diphenylpyrrol-1-yl, the 2- and 5-positions are the ortho positions. In the context of this invention, ring fusion at a carbon adjacent to the point of attachment, as in 2,3,4,5,7,8,9,10-ocathydroanthracen-1-yl, is considered to be a type of ortho substitution.

Thus, in a first aspect, this invention relates to a compound comprising a phosphorescent metal complex comprising a monoanionic, bidentate ligand selected from Set 1, wherein the metal is selected from the group consisting of the non-radioactive metals with atomic numbers greater than 40, and wherein the bidentate ligand may be linked with other ligands to comprise a tridentate, tetradentate, pentadentate or hexadentate ligand;

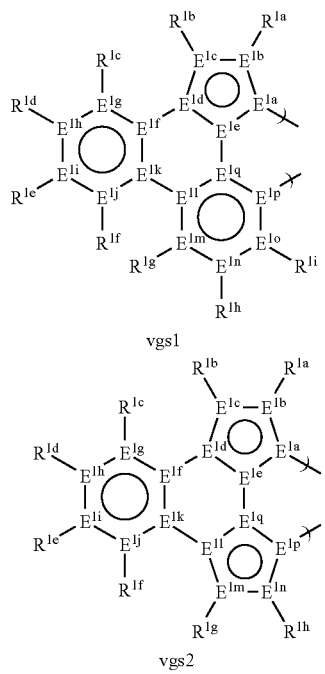

wherein:
$E^{1a-q}$ are selected from the group consisting of C and N and collectively comprise an 18 pi-electron system; provided that $E^{1a}$ and $E^{1p}$ are different; and $R^{1a-i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a-c}$ are each, independently, hydrocarbyl or heteroatom substituted hydrocarbyl, and where any two of $R^{1a-i}$ and $R^{2a-c}$ may be linked to form a saturated or unsaturated, aromatic or non-aromatic ring; provided that $R^{1a-i}$ is other than H when attached to N.

In a first preferred embodiment of this first aspect, the metal is selected from the group consisting of Re, Ru, Os, Rh, Ir, Pd, Pt, Cu, and Au, and the bidentate ligand is selected from Set 2; even more preferably, the bidentate ligand is of formula gs1-1 in Set 2;

Set 2;

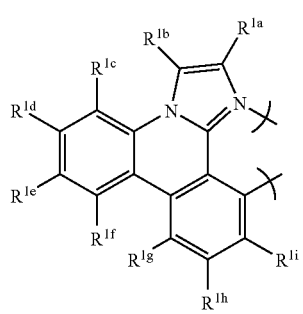

gs1-1

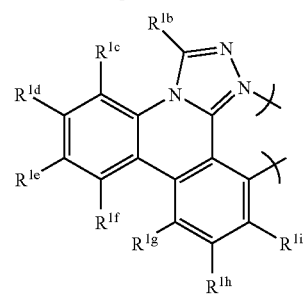

gs1-2

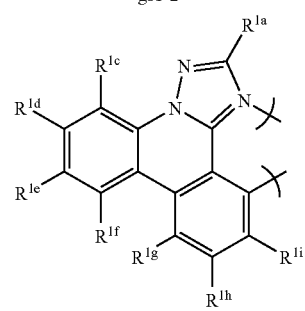

gs1-3

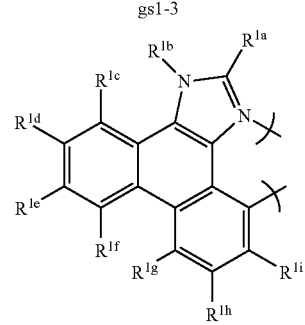

gs1-4

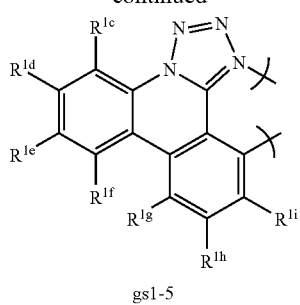
gs1-5
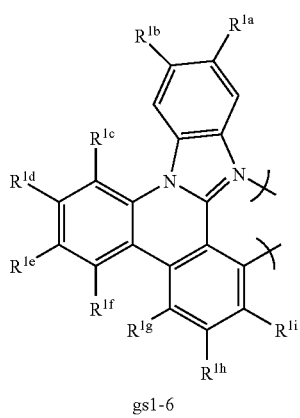
gs1-6
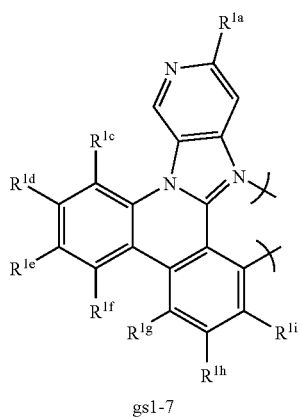
gs1-7
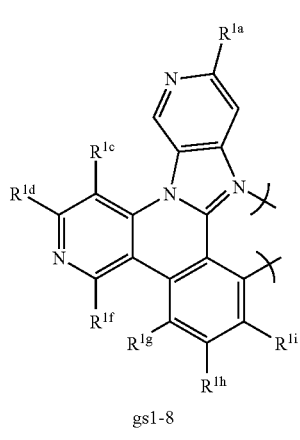
gs1-8
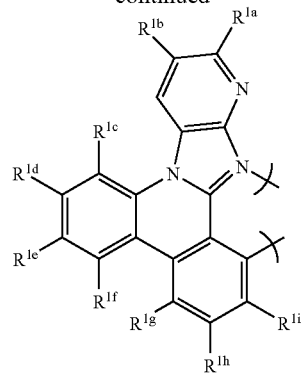
gs1-9
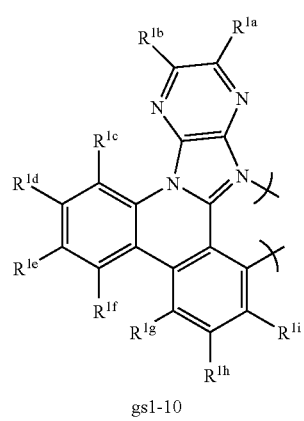
gs1-10
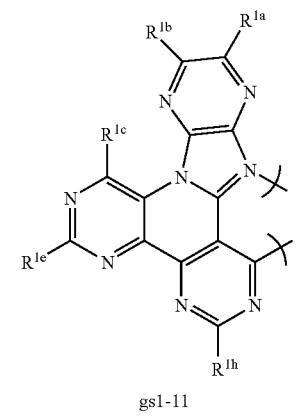
gs1-11
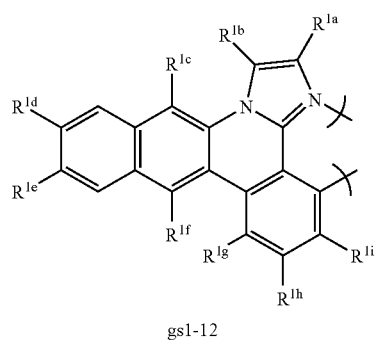
gs1-12

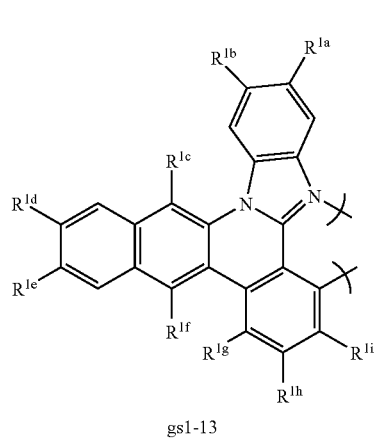
gs1-13
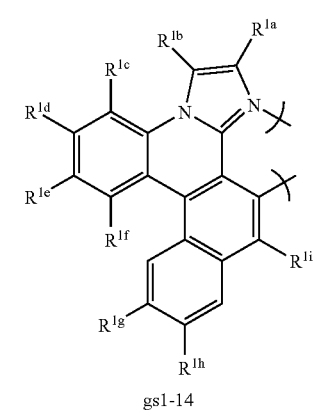
gs1-14
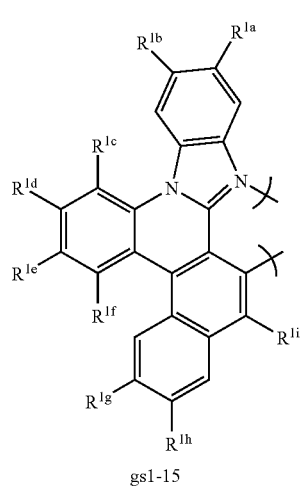
gs1-15
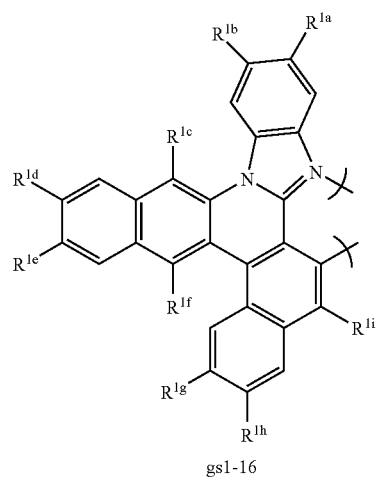
gs1-16
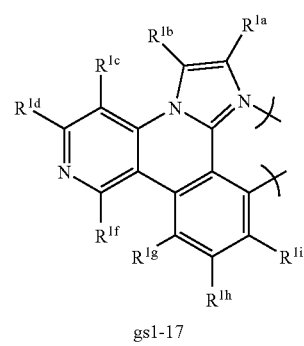
gs1-17
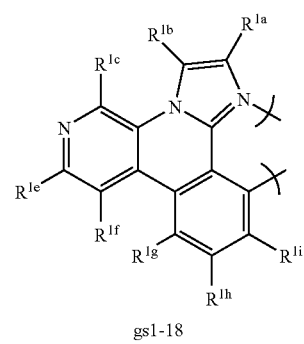
gs1-18
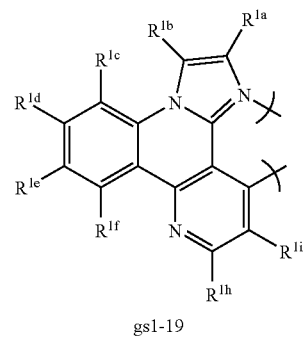
gs1-19

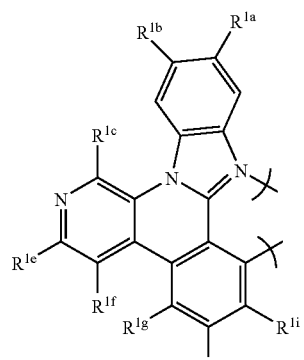
gs1-20
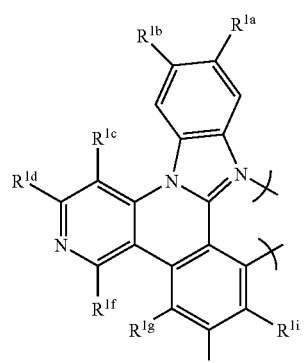
gs1-21
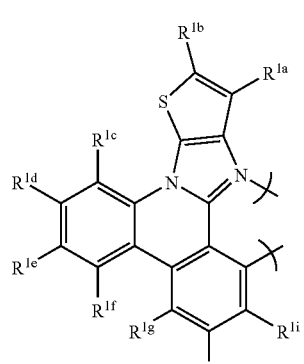
gs1-22
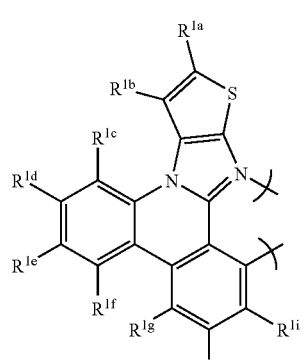
gs1-23
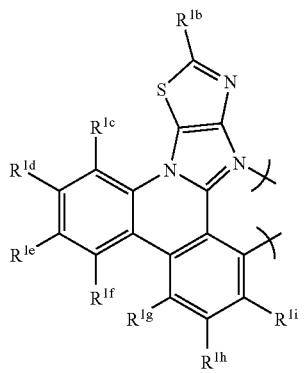
gs1-24
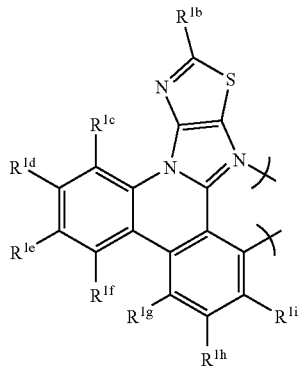
gs1-25
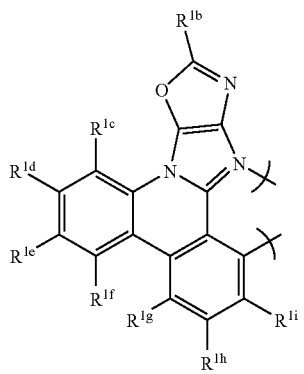
gs1-26
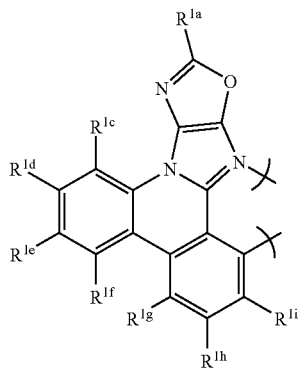
gs1-27

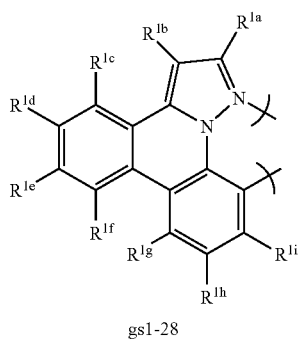
gs1-28
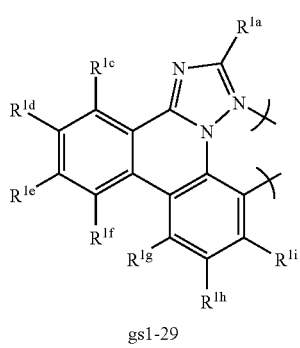
gs1-29
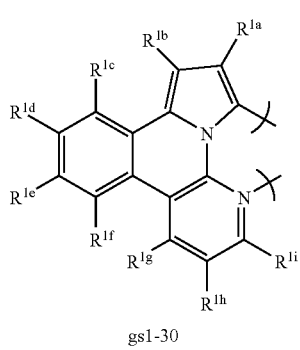
gs1-30
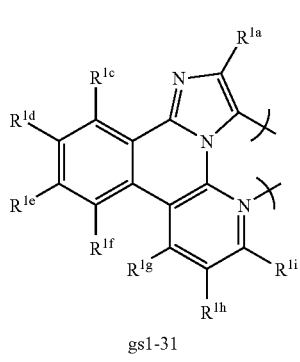
gs1-31
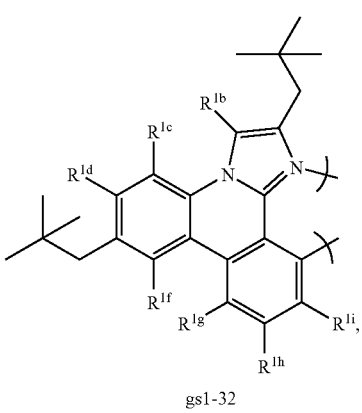
gs1-32
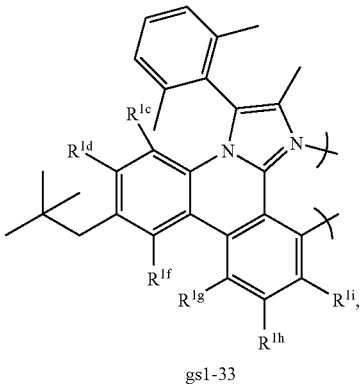
gs1-33
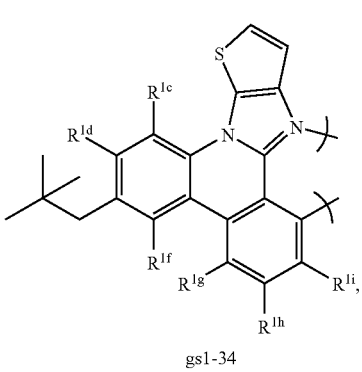
gs1-34
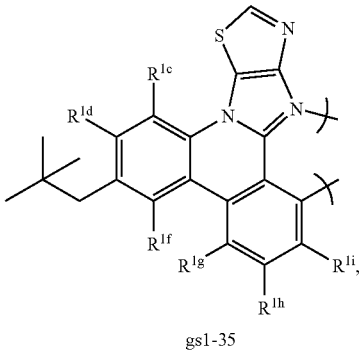
gs1-35

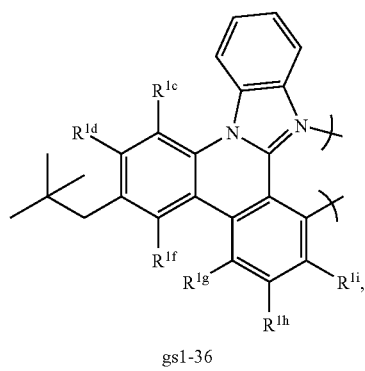
gs1-36
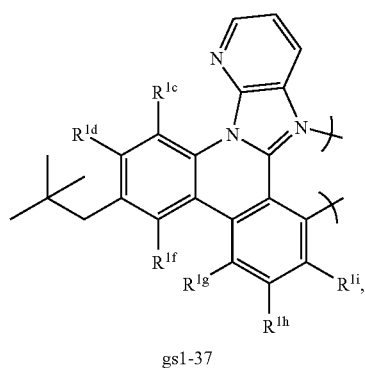
gs1-37
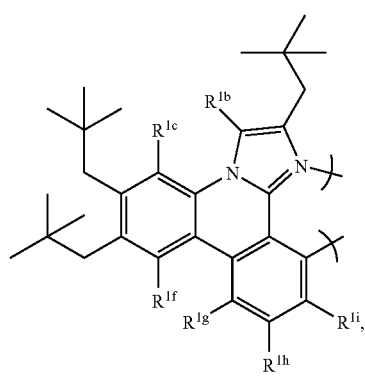
gs1-38
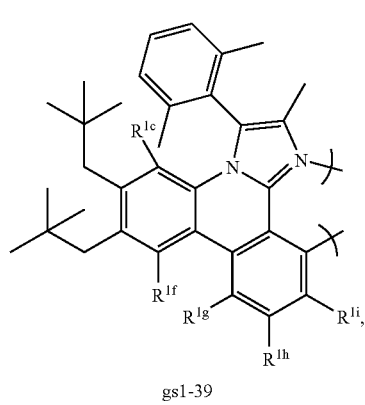
gs1-39
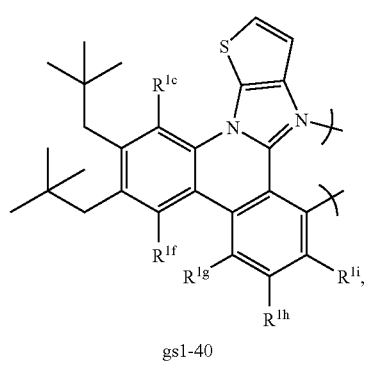
gs1-40
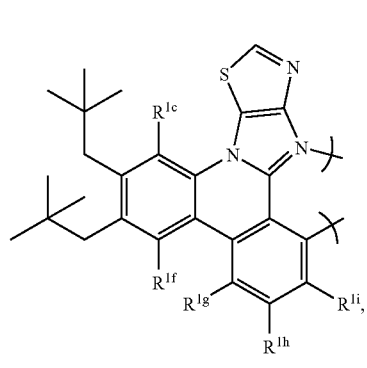
gs1-41
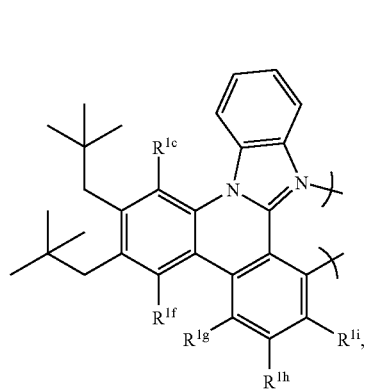
gs1-42
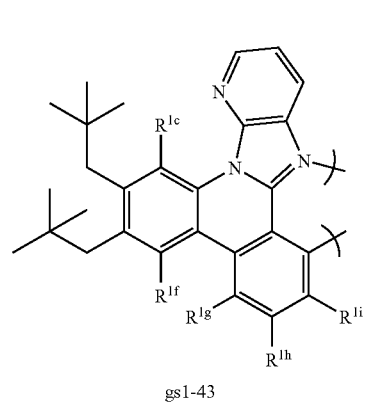
gs1-43

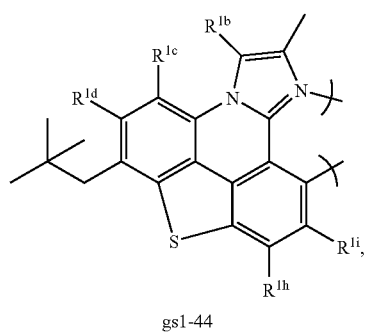
gs1-44
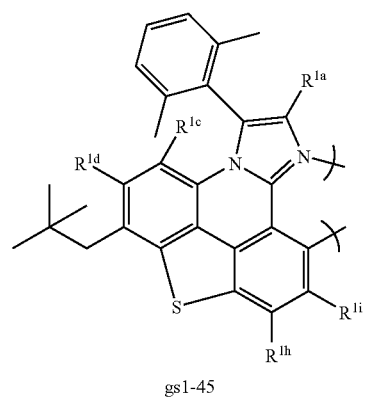
gs1-45
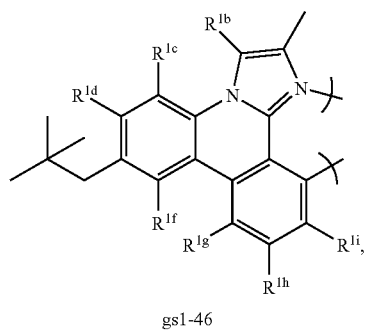
gs1-46
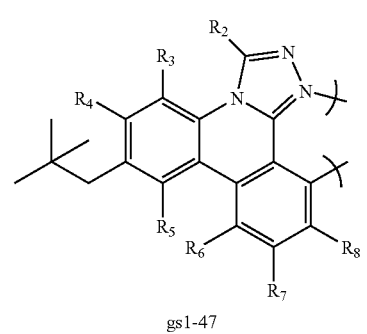
gs1-47
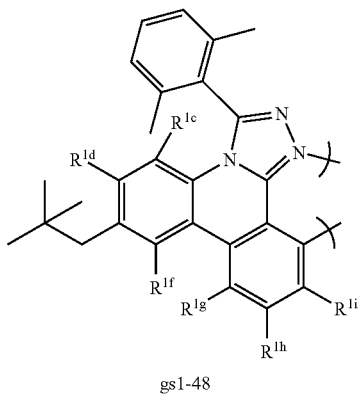
gs1-48
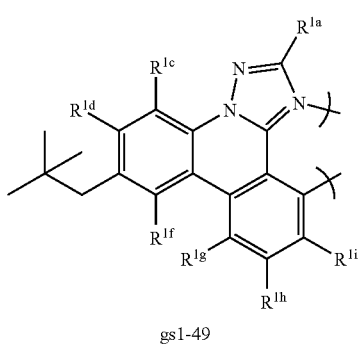
gs1-49
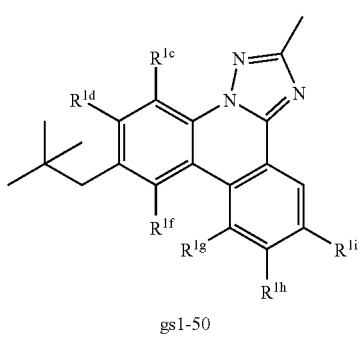
gs1-50
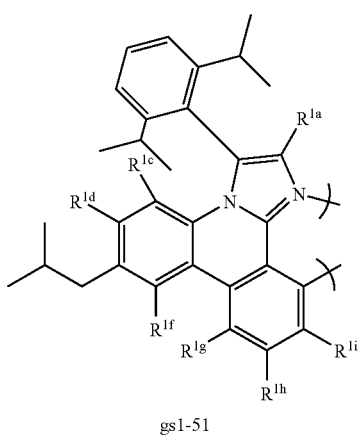
gs1-51

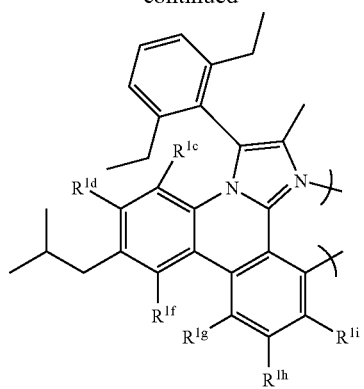
gs1-52
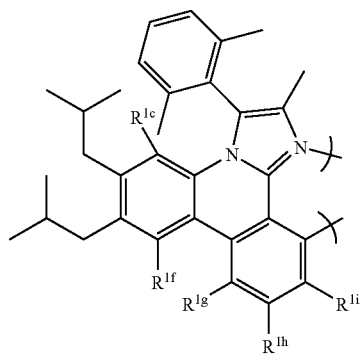
gs1-53
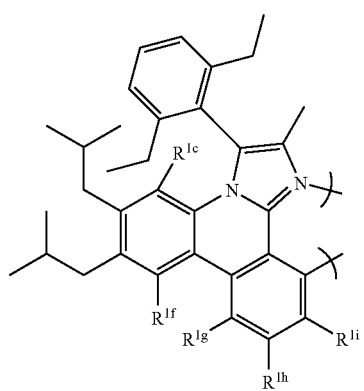
gs1-54
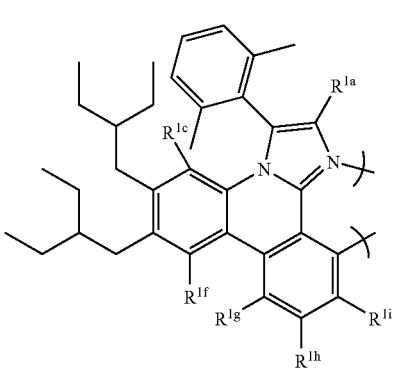
gs1-55
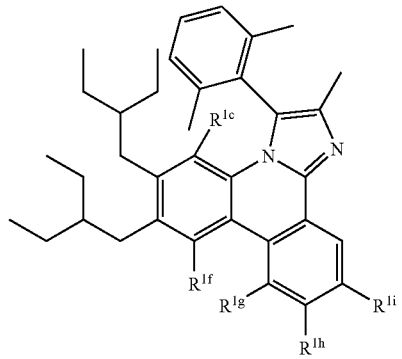
gs1-56
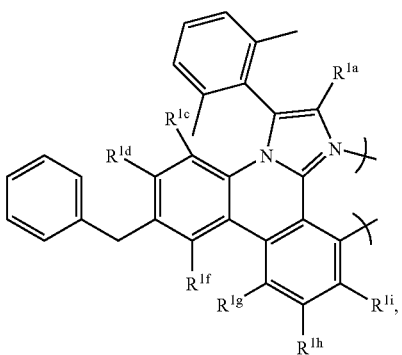
gs1-57
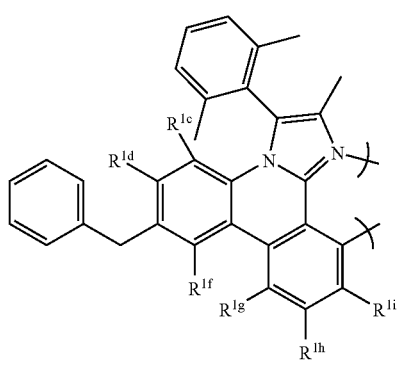
gs1-58
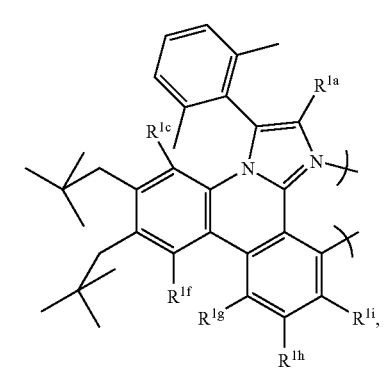
gs1-59

Ru, Os, Rh, Ir, Pd, Pt, Cu, and Au, and at least one of $R^{1a-i}$ is a 2,6-di-substituted aryl group. In a sixth preferred embodiment, the metal is selected from the group consisting of Ir and Pt, the ligand is of formula gs1-1, and $R^{1b}$ is a 2,6-di-substituted aryl group, preferably selected from the group consisting of 2,6-dimethylphenyl; 2,4,6-trimethylphenyl; 2,6-di-isopropylphenyl; 2,4,6-triisopropylphenyl; 2,6-di-isopropyl-4-phenylphenyl; 2,6-dimethyl-4-phenylphenyl; 2,6-dimethyl-4-(2,6-dimethylpyridin-4-yl)phenyl; 2,6-diphenylphenyl; 2,6-diphenyl-4-isopropylphenyl; 2,4,6-triphenylphenyl; 2,6-di-isopropyl-4-(4-isopropylphenyl); 2,6-di-isopropyl-4-(3,5-dimethylphenyl)phenyl; 2,6-dimethyl-4-(2,6-dimethylpyridin-4-yl)phenyl; 2,6-di-isopropyl-4-(pyridine-4-yl)phenyl; and 2,6-di-(3,5-dimethylphenyl)phenyl.

In a second aspect, this invention relates to a compound selected from Set 3, wherein acac is acetylacetonate;

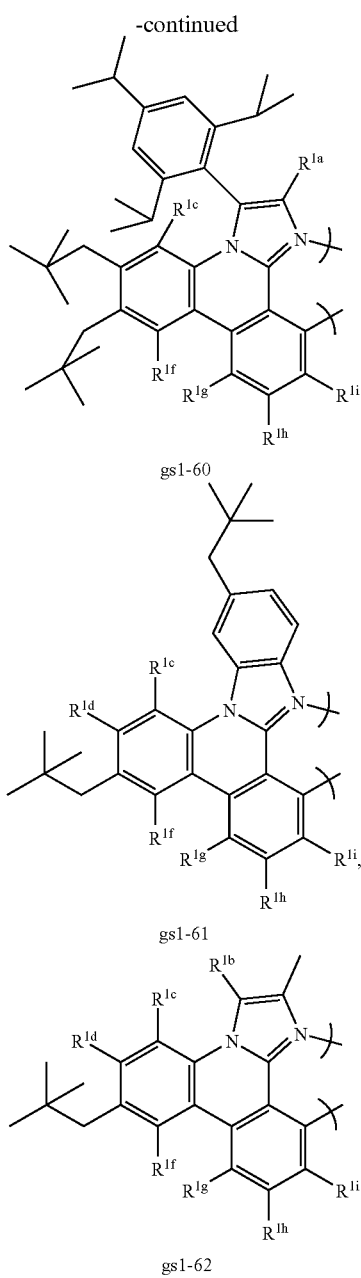

gs1-60 gs1-61 gs1-62 wherein:

$R^{1a-i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a-c}$ are each, independently, hydrocarbyl or heteroatom substituted hydrocarbyl, and where any two of $R^{1a-i}$ and $R^{2a-c}$ may be linked to form a saturated or unsaturated, aromatic or non-aromatic ring.

In a second preferred embodiment, the metal is Ir or Pt and the bidentate ligand is selected from Set 2. In a third preferred embodiment, the metal complex is a homoleptic Ir complex of a ligand selected from Set 2. In a fourth preferred embodiment, the metal complex is a heteroleptic Ir complex comprising two bidentate ligands selected from Set 2 and a third mono anionic bidentate ligand, preferably acetylacetonate or a substituted acetylacetonate. In a fifth preferred embodiment, the metal is selected from the group consisting of Re,

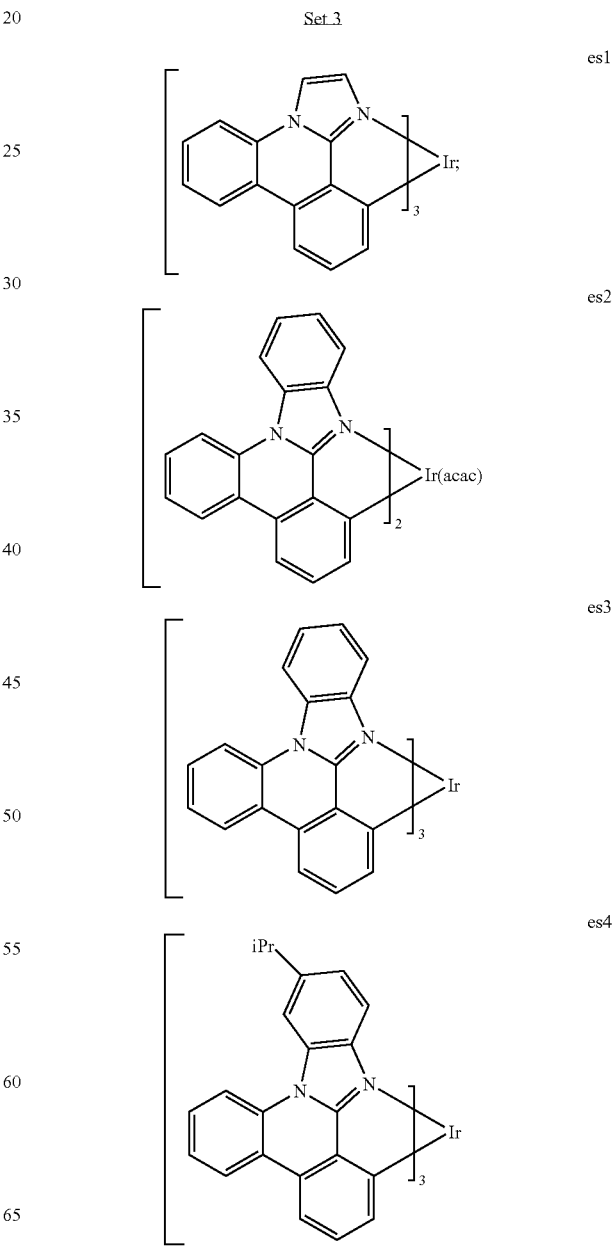

Set 3

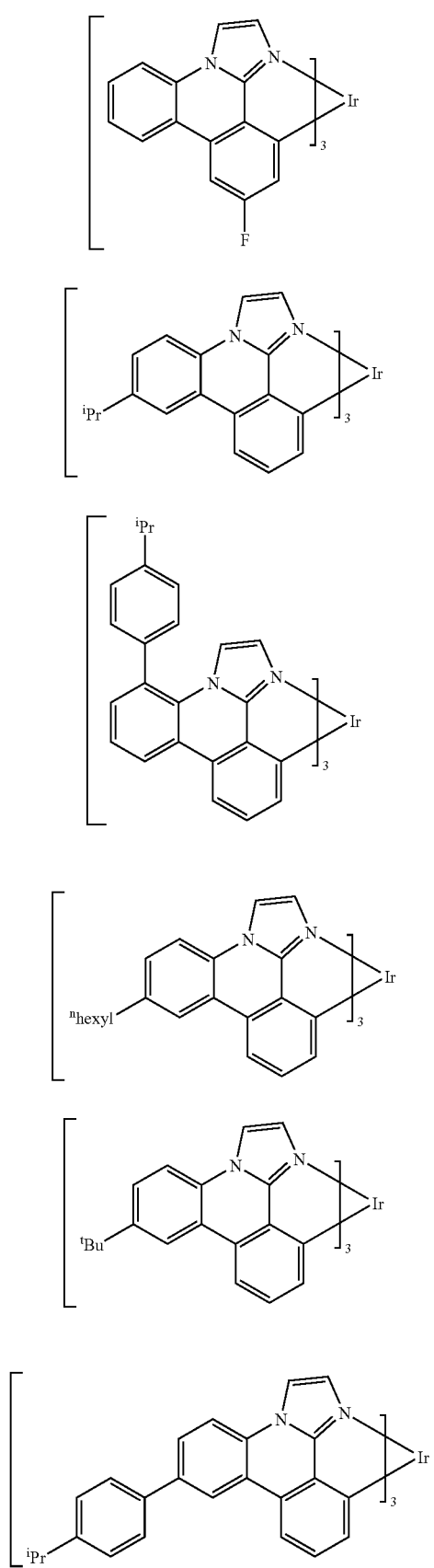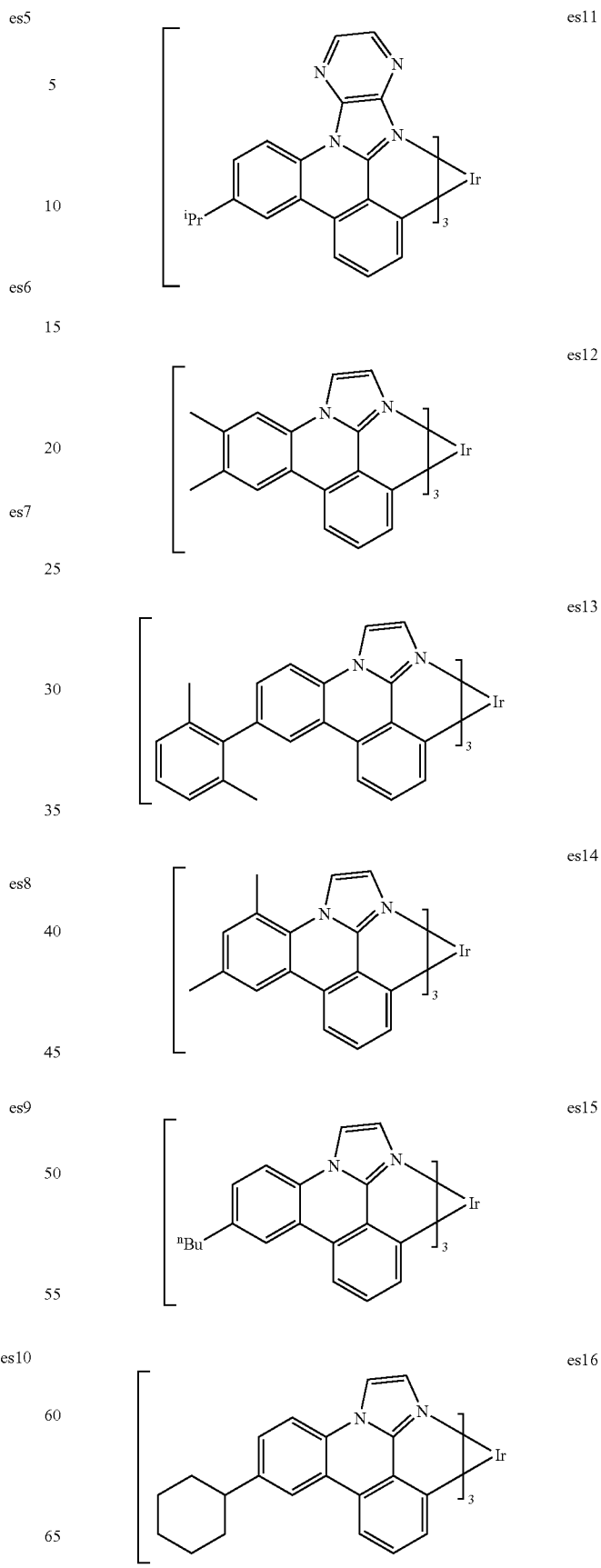

es17
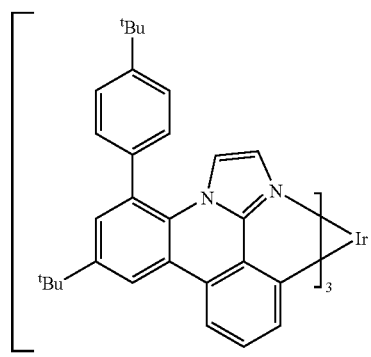
es18
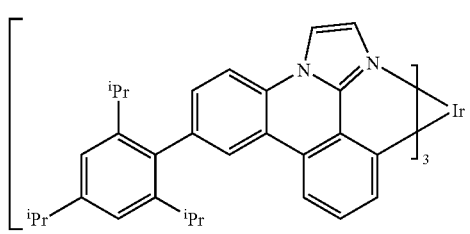
es19
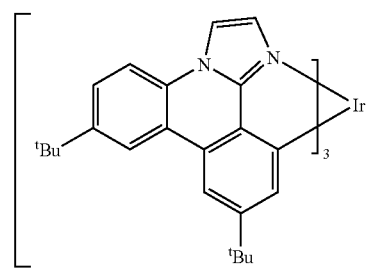
es20
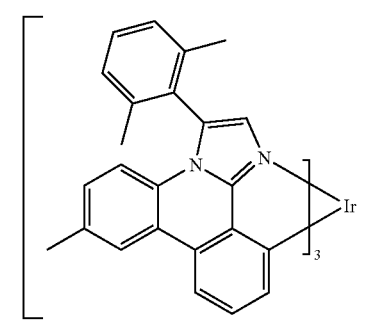
es21
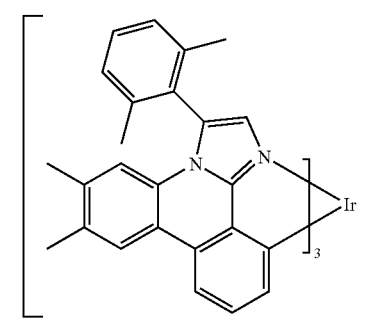
es22
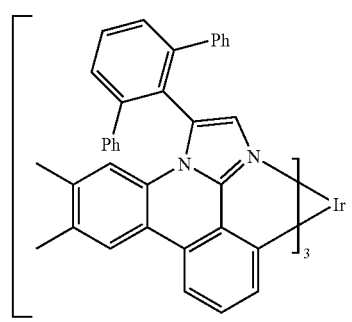
es23
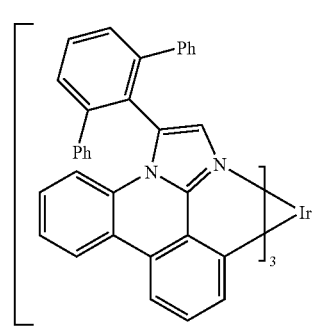
es24
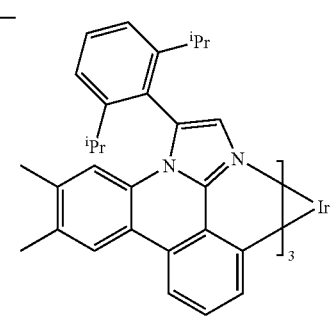
es25
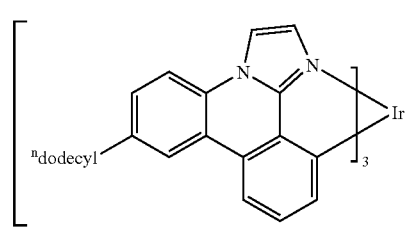
es26
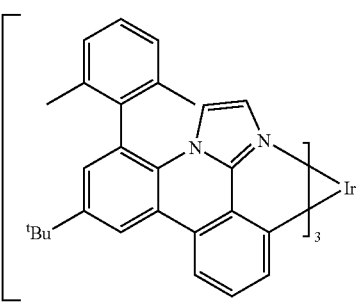

-continued
es27
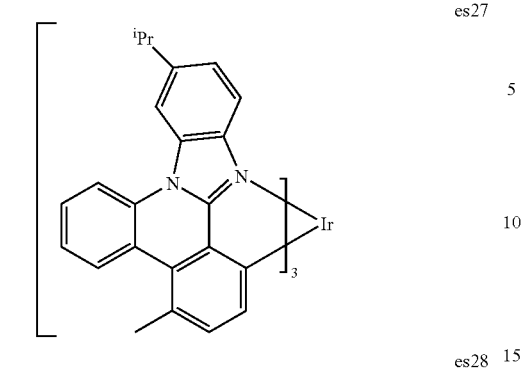
es28
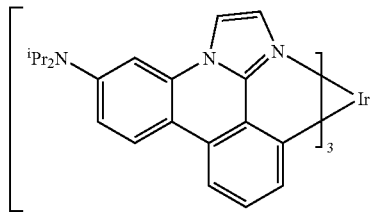
es29
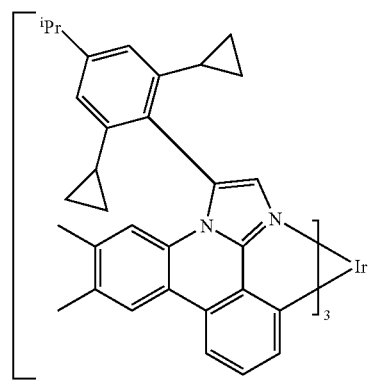
es30
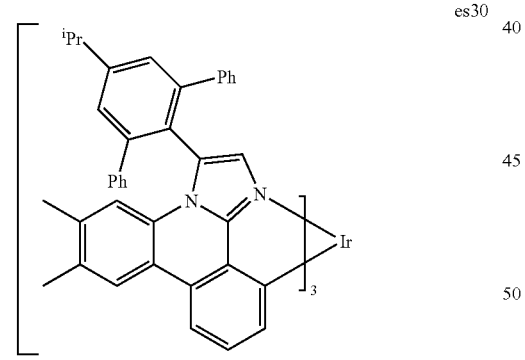
es31
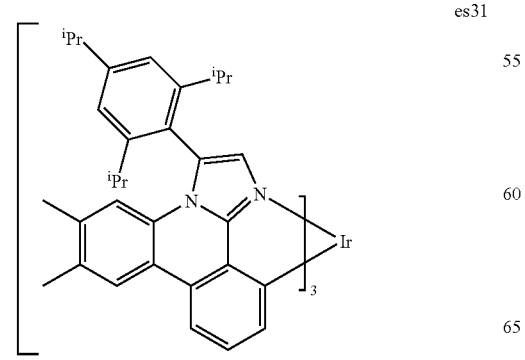
-continued
es32
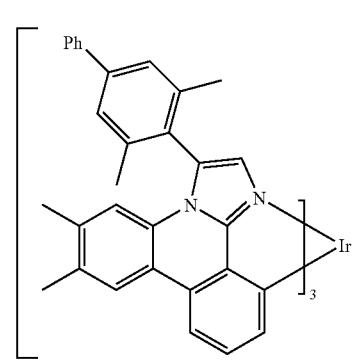
es33
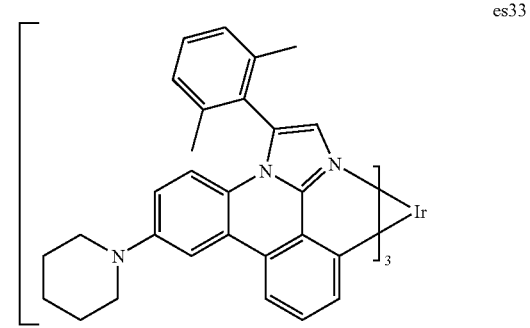
es34
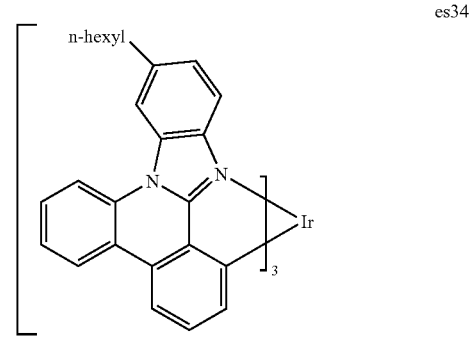
es35
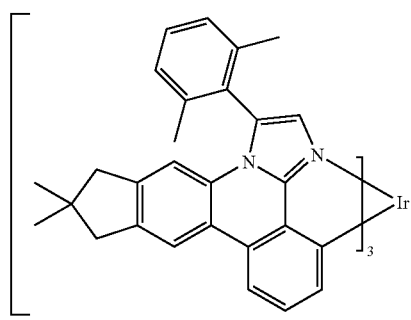

-continued
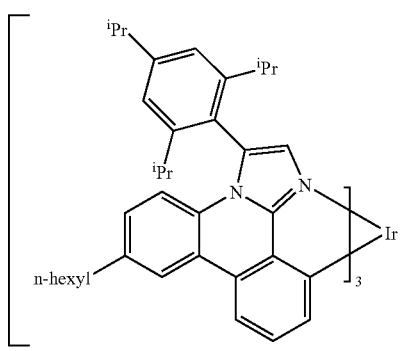
es36
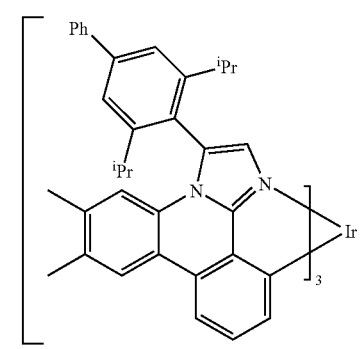
es37
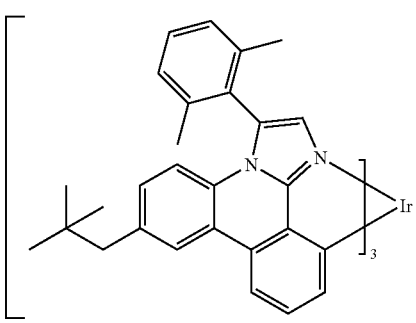
es38
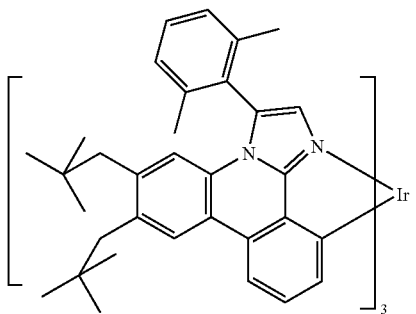
es39
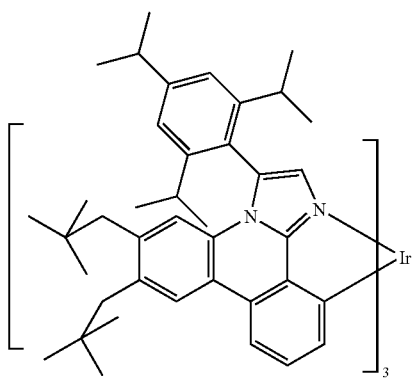
es40
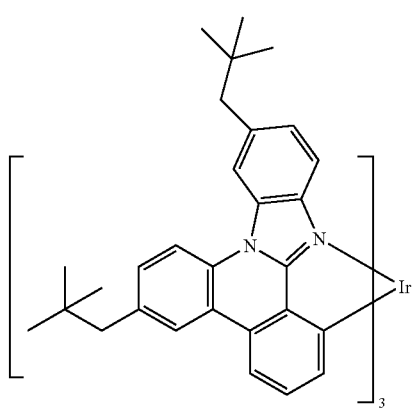
es41
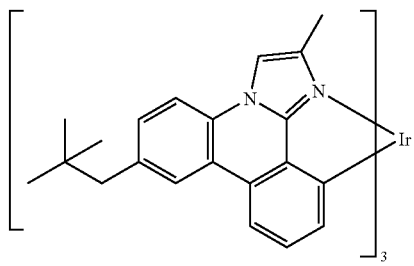
es42
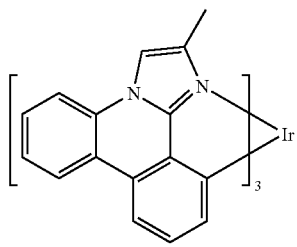
es43
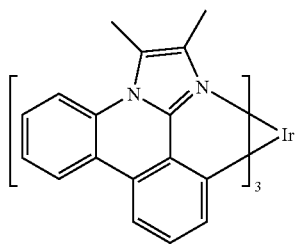
es44

-continued
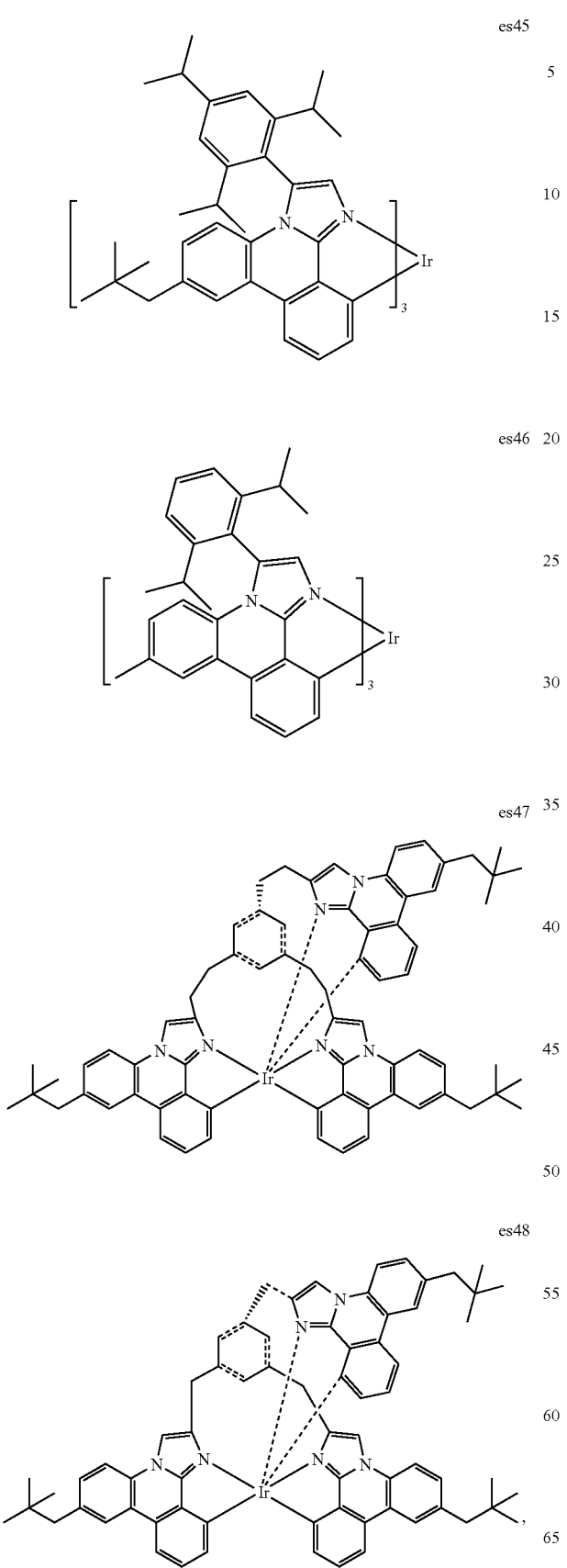
es45
es46
es47
es48
-continued
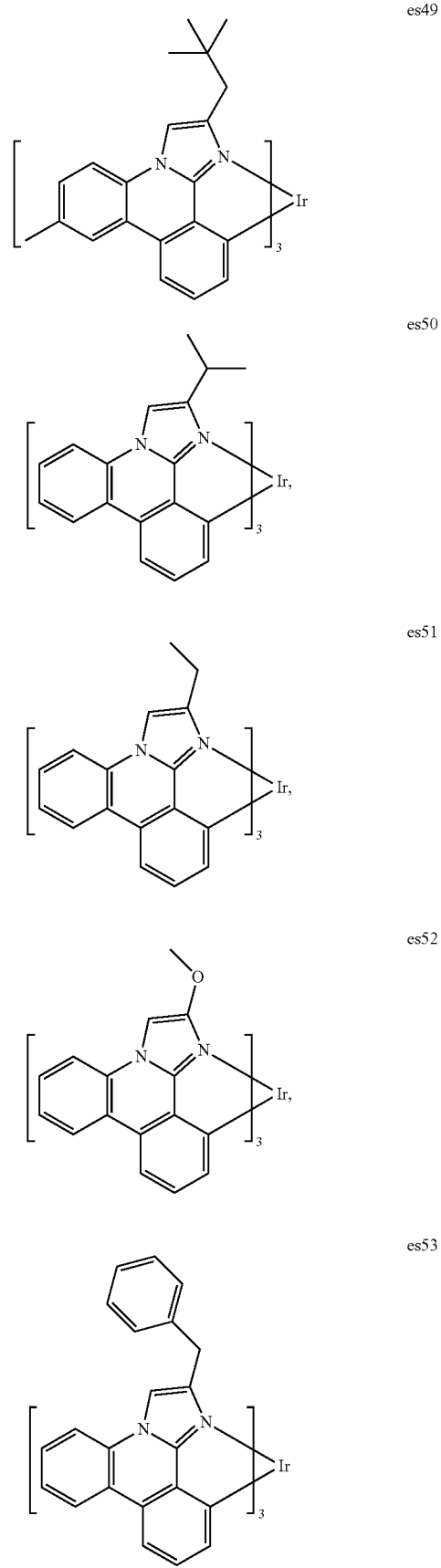
es49
es50
es51
es52
es53

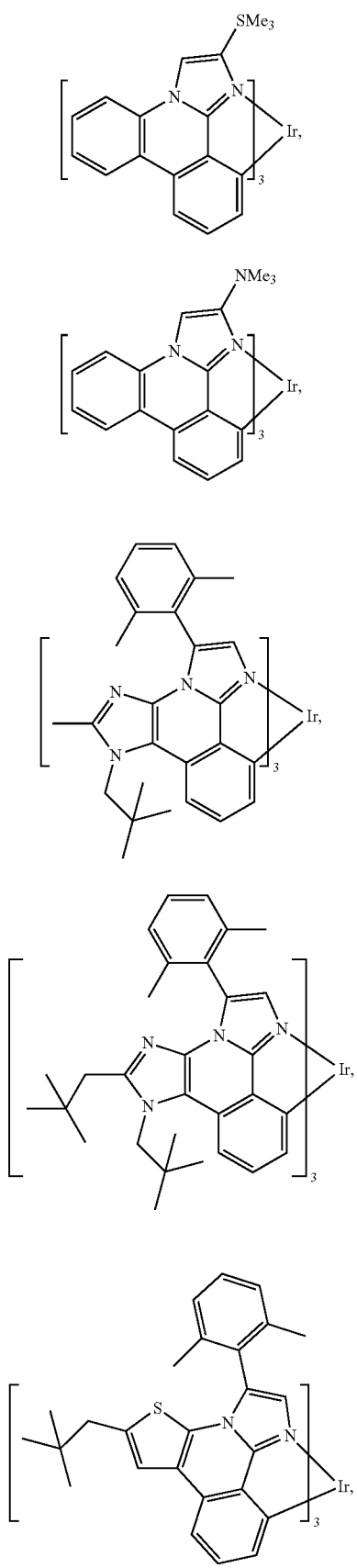
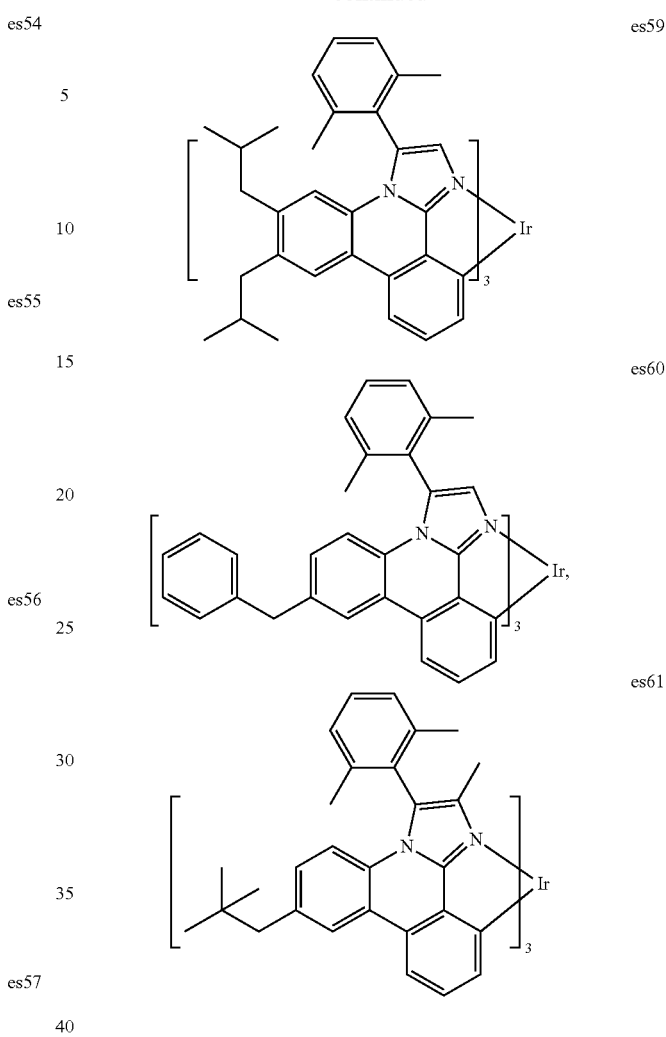

In a third aspect, this invention relates to an OLED device comprising any of the compounds of the first or second aspects.

In a fourth aspect, this invention relates to a compound comprising a phosphorescent metal complex comprising a monoanionic, bidentate ligand selected from Set 4, wherein the metal is selected from the group consisting of the non-radioactive metals with atomic numbers greater than 40, and wherein the bidentate ligand may be linked with other ligands to comprise a tridentate, tetradentate, pentadentate or hexadentate ligand;

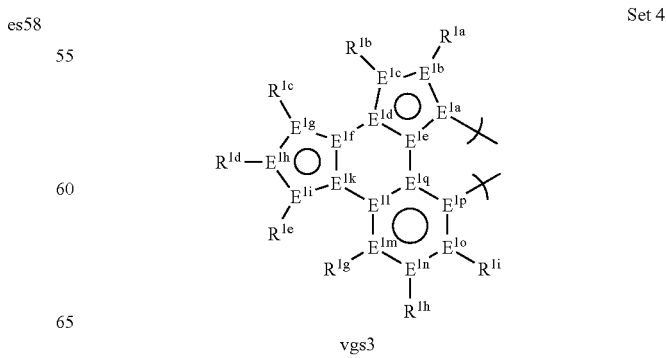

-continued

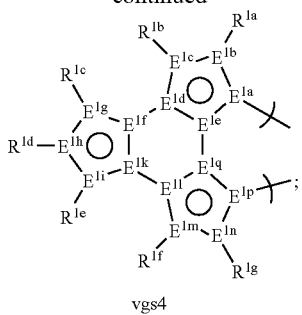
vgs4 wherein:

$E^{1a-q}$ are each, independently, selected from the group consisting of C and N, and collectively comprise an 18 pi-electron system; provided that $E^{1a}$ and $E^{1p}$ are different; and $R^{1a-i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a-c}$ are each, independently, hydrocarbyl or heteroatom substituted hydrocarbyl, and where any two of $R^{1a-i}$ and $R^{2a-c}$ may be linked to form a saturated or unsaturated, aromatic or non-aromatic ring; provided that $R^{1a-i}$ is other than H when attached to N.

In a first preferred embodiment of this fourth aspect, the bidentate ligand is selected from Set 5;

Set 5 gs3-1
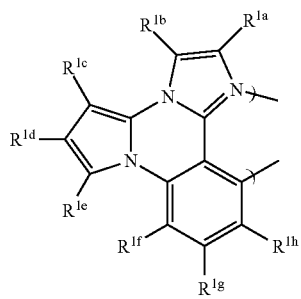

gs3-2
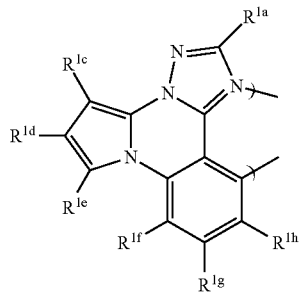

gs3-3
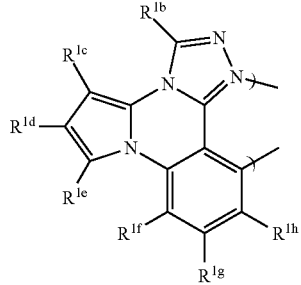

gs3-4
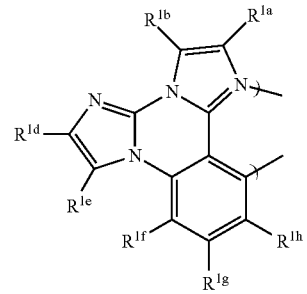

gs3-5
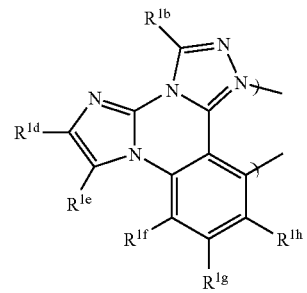

gs3-6
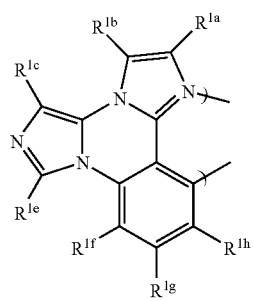

gs3-7
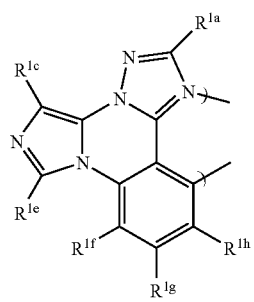

gs3-8

-continued
gs3-9
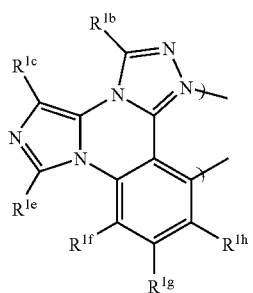
gs3-10
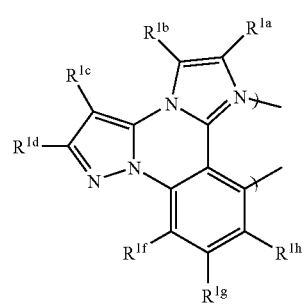
gs3-11
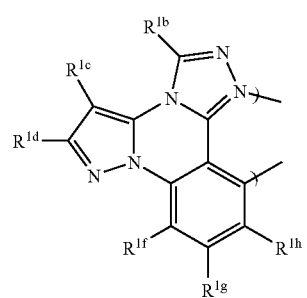
gs3-12
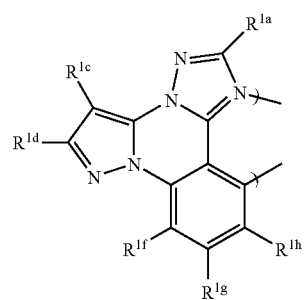
gs3-13
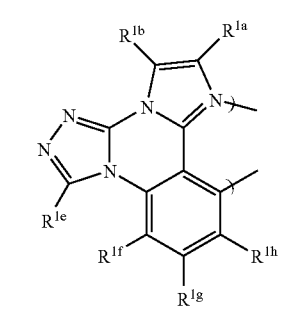
-continued
gs3-14
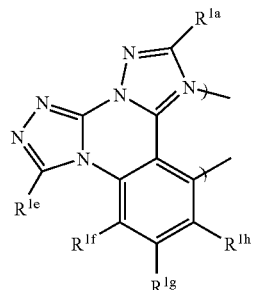
gs3-15
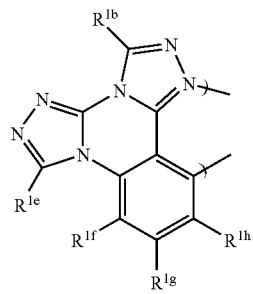
gs3-16
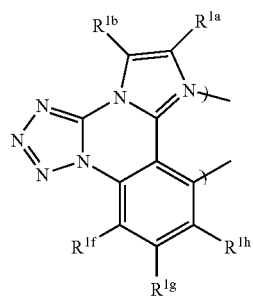
gs3-17
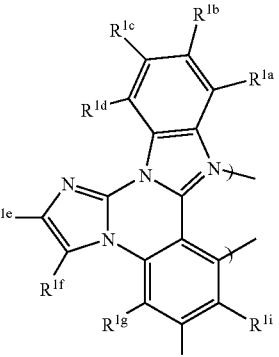
gs3-18
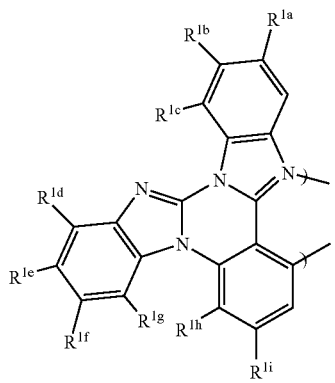

gs3-19
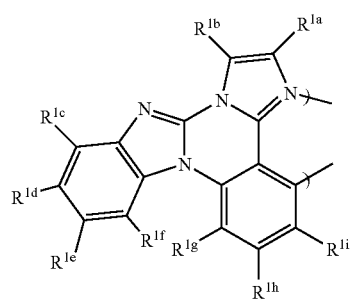
gs3-20
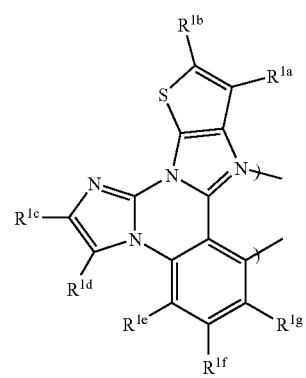
gs3-21
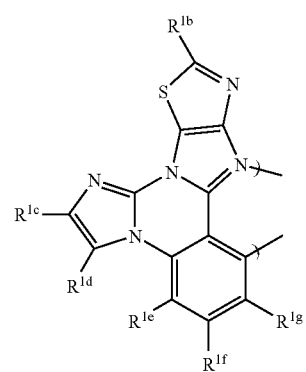
gs3-22
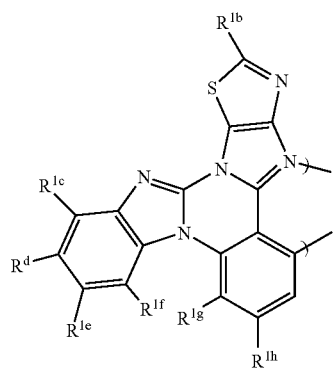
gs3-23
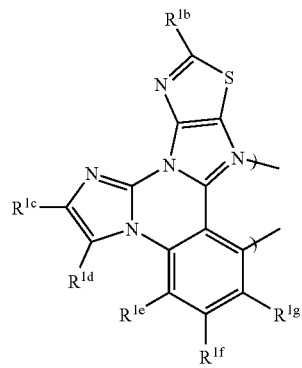
gs3-24
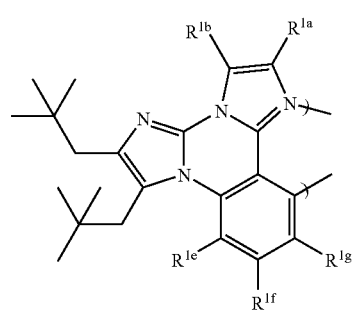
gs3-25
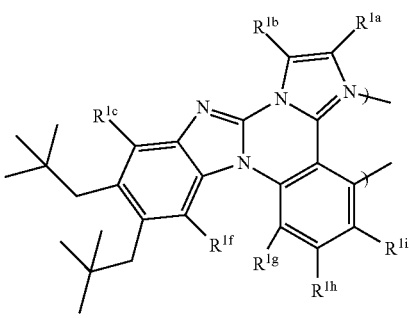
gs3-26
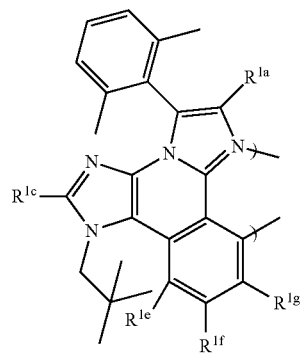

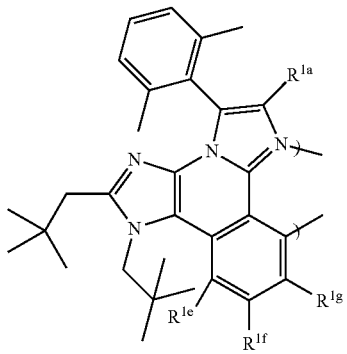

gs3-27

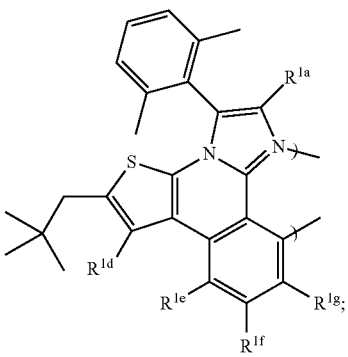

gs3-28 wherein:

$R^{1a\text{-}i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a\text{-}c}$ are each, independently, hydrocarbyl or heteroatom substituted hydrocarbyl, and where any two of $R^{1a\text{-}i}$ and $R^{2a\text{-}c}$ may be linked to form a ring.

In a second preferred embodiment of the fourth aspect, the bidentate ligand is selected from Set 6;

Set 6

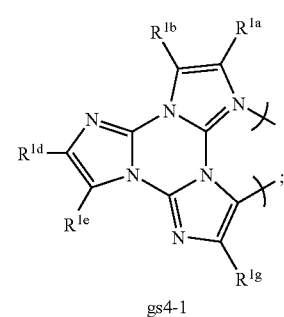

gs4-1

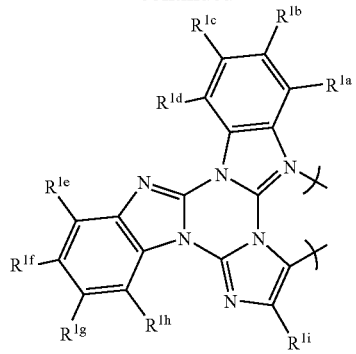

gs4-2

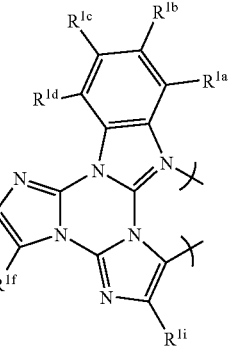

gs4-3

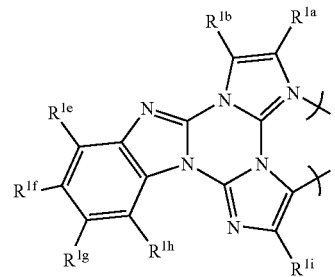

gs4-4 wherein:

$R^{1a\text{-}i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a\text{-}c}$ are each, independently, hydrocarbyl or heteroatom substituted hydrocarbyl, and where any two of $R^{1a\text{-}i}$ and $R^{2a\text{-}c}$ may be linked to form a ring.

In a third preferred embodiment of the fourth aspect, the bidentate ligand is substituted by one or more 2,6-disubstituted aryl or heteroaryl groups, preferably selected from the group consisting of 2,6-dimethylphenyl; 2,4,6-trimethylphenyl; 2,6-di-isopropylphenyl; 2,4,6-triisopropylphenyl; 2,6-di-isopropyl-4-phenylphenyl; 2,6-dimethyl-4-phenylphenyl; 2,6-dimethyl-4-(2,6-dimethylpyridin-4-yl)phenyl; 2,6-diphenylphenyl; 2,6-diphenyl-4-isopropylphenyl; 2,4,6-triphenylphenyl; 2,6-di-isopropyl-4-(4-isopropylphenyl); 2,6-di-isopropyl-4-(3,5-dimethylphenyl)phenyl; 2,6-dimethyl-4-(2,6-dimethylpyridin-4-yl)phenyl; 2,6-di-isopropyl-4-(pyridine-4-yl)phenyl; and 2,6-di-(3,5-dimethylphenyl)phenyl.

In a fourth preferred embodiment of the fourth aspect, the metal is selected from the group consisting of Re, Ru, Os, Rh, Ir, Pd, Pt, Cu and Au, and is more preferably selected from the group consisting of Os, Ir and Pt, and is most preferably Ir.

In a fifth aspect, this invention relates to an OLED device comprising a compound of the fourth aspect.

In a sixth aspect, this invention relates to a compound corresponding to a ligand of the fourth aspect, wherein the metal has been replaced by H.

In a seventh aspect, this invention relates to a compound comprising a phosphorescent metal complex comprising a monoanionic, bidentate ligand selected from Set 7, wherein the metal is selected from the group consisting of the non-radioactive metals with atomic numbers greater than 40, and wherein the bidentate ligand comprises a carbene donor and may be linked with other ligands to comprise a tridentate, tetradentate, pentadentate or hexadentate ligand;

Set 7

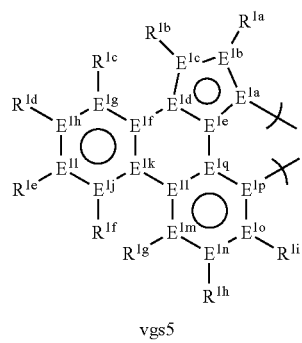

vgs5

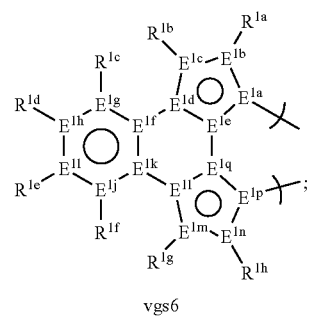

vgs6 wherein:

$E^{1a-q}$ are selected from the group consisting of C and N and collectively comprise an 18 pi-electron system; provided that $E^{1a}$ and $E^{1p}$ are both carbon; and $R^{1a-i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a-c}$ are each, independently, hydrocarbyl or heteroatom substituted hydrocarbyl, and where any two of $R^{1a-i}$ and $R^{2a-c}$ may be linked to form a saturated or unsaturated, aromatic or non-aromatic ring; provided that $R^{1a-i}$ is other than H when attached to N.

In a first preferred embodiment of this seventh aspect, the compound is selected from Set 8;

Set 8

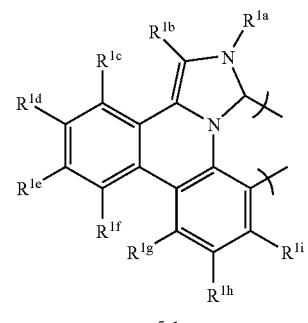

gs5-1

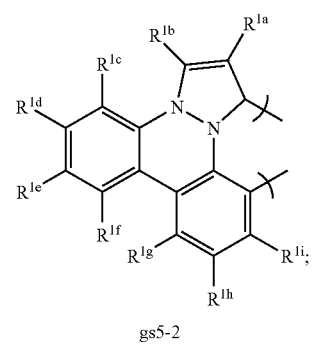

gs5-2 wherein:

$R^{1a-i}$ are each, independently, H, hydrocarbyl, heteroatom substituted hydrocarbyl, cyano, fluoro, $OR^{21}$, $SR^{2a}$, $NR^{2a}R^{2b}$, $BR^{2a}R^{2b}$, or $SiR^{2a}R^{2b}R^{2c}$, where $R^{2a-c}$ c are each, independently, hydrocarbyl or heteroatom substituted hydrocarbyl, and where any two of $R^{1a-i}$ and $R^{2a-c}$ may be linked to form a saturated or unsaturated, aromatic or non-aromatic ring; provided that $R^{1a-i}$ is other than H when attached to N.

In an eighth aspect, this invention relates to an OLED device comprising a compound of the seventh aspect.

In a ninth aspect, this invention relates to a compound comprising a phosphorescent metal complex comprising a monoanionic, bidentate ligand selected from Set 9, wherein the metal is selected from the group consisting of the non-radioactive metals with atomic numbers greater than 40, and wherein the bidentate ligand comprises a carbene donor and may be linked with other ligands to comprise a tridentate, tetradentate, pentadentate or hexadentate ligand;

Set 9

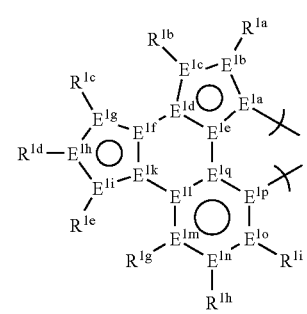

vgs7

-continued

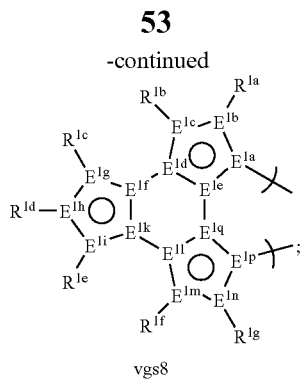

vgs8 wherein:

$E^{1a-q}$ are selected from the group consisting of C and N and collectively comprise an 18 pi-electron system; provided that $E^{1a}$ and $E^{1p}$ are both carbon; and $R^{1a-i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a-c}$ are each, independently, hydrocarbyl or heteroatom substituted hydrocarbyl, and where any two of $R^{1a-i}$ and $R^{2a-c}$ may be linked to form a saturated or unsaturated, aromatic or non-aromatic ring; provided that $R^{1a-i}$ is other than H when attached to N.

In a first preferred embodiment of this ninth aspect, the compound is selected from Set 10;

Set 10

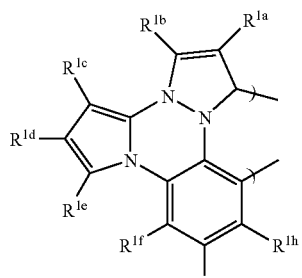
gs7-1

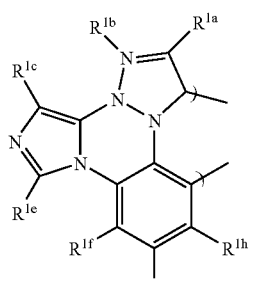
gs7-2

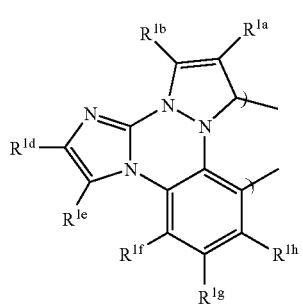
gs7-3

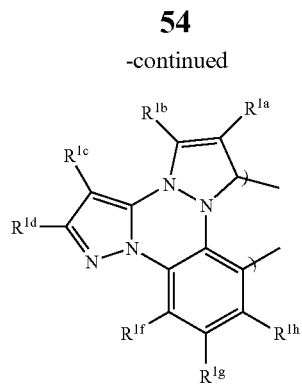
gs7-4

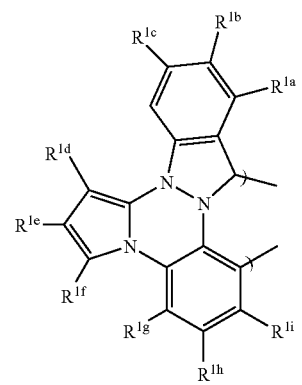
gs7-5

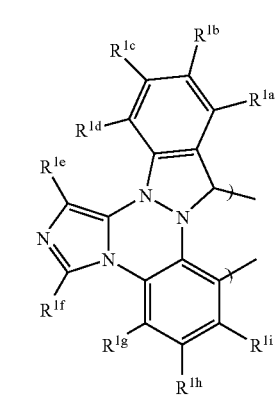
gs7-6

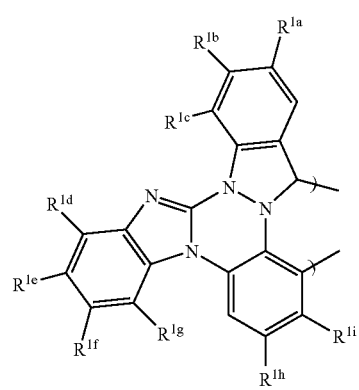
gs7-7

-continued

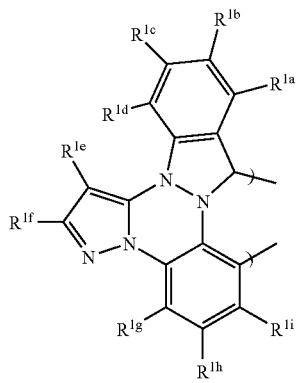

gs7-8 wherein:

$R^{1a-i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a-c}$ c are each, independently, hydrocarbyl or heteroatom substituted hydrocarbyl, and where any two of $R^{1a-i}$ and $R^{2a-c}$ may be linked to form a saturated or unsaturated, aromatic or non-aromatic ring; provided that $R^{1a-i}$ is other than H when attached to N.

In a tenth aspect, this invention relates to an OLED device comprising a compound of the ninth aspect.

In an eleventh aspect, this invention relates to a compound comprising a phosphorescent metal complex comprising a monoanionic, bidentate ligand selected from Set 11, wherein the metal is selected from the group consisting of the non-radioactive metals with atomic numbers greater than 40, and wherein the bidentate ligand may be linked with other ligands to comprise a tridentate, tetradentate, pentadentate or hexadentate ligand;

Set 11

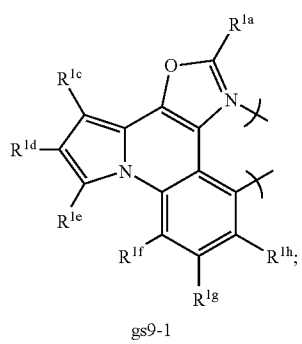

gs9-1

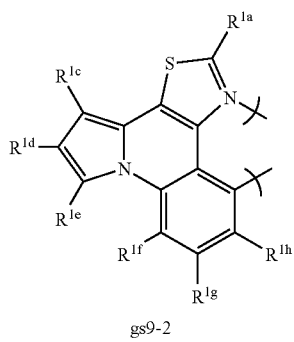

gs9-2

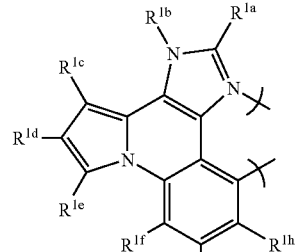

gs9-3

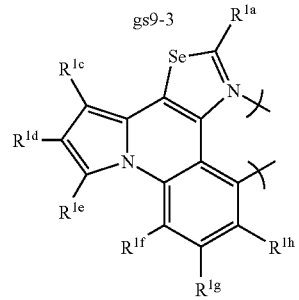

gs9-4

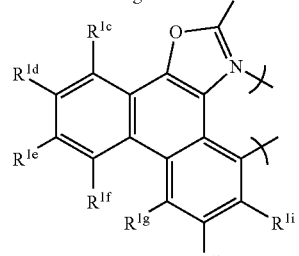

gs9-5

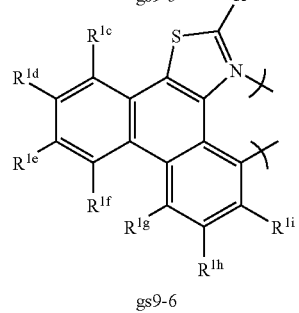

gs9-6 wherein:

$R^{1a-i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a-c}$ are each, independently, hydrocarbyl or heteroatom substituted hydrocarbyl, and where any two of $R^{1a-i}$ and $R^{2a-c}$ may be linked to form a saturated or unsaturated, aromatic or non-aromatic ring; provided that $R^{1a-i}$ is other than H when attached to N.

In a twelfth aspect, this invention relates to an OLED device comprising a compound of the eleventh aspect.

In a thirteenth aspect, this invention relates to a compound corresponding to a ligand of the eleventh aspect, wherein the metal has been replaced by H.

In a fourteenth aspect, this invention relates to a compound comprising a metal complex selected from Table 1.

In a fifteenth aspect, this invention relates to an OLED device comprising a compound of the fourteenth aspect.

Table 1 below provides Density Function Theory (DFT) calculations using the G98/B31yp/cep-31g basis set to obtain estimates of the HOMO, LUMO, gap, dipole, S1, and T1 for various compounds of the present invention.

TABLE 1

| Entry | Compounds | Cal. HOMO (ev) | Cal. LUMO (ev) | Cal. Gap (ev) | Cal. Dipole (Debye) | Cal. S1 (nm) | Cal. T1 (nm) |
| --- | --- | --- | --- | --- | --- | --- | --- |
| 1 |  | −4.73 | −1.17 | 3.57 | 4.72 | 446 | 475 |
| 2 |  | −4.99 | −1.33 | 3.65 | 0.21 | 434 | 470 |
| 3 |  | −5.11 | −1.21 | 3.90 | 3.44 | 394 | 477 |
| 4 |  | −4.88 | −1.42 | 3.46 | 3.06 | 465 | 493 |
| 5 |  | −5.17 | −1.47 | 3.69 | 11.40 | 427 | 467 |
| 6 |  | −4.83 | −0.93 | 3.90 | 8.28 | 425 | 490 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 7 | | −4.52 | −0.77 | 3.75 | 11.91 | 396 | 493 |
| 8 | | −4.96 | −1.04 | 3.92 | 18.02 | 401 | 485 |
| 9 | | −4.92 | −1.43 | 3.49 | 18.06 | 414 | 488 |
| 10 | | −5.15 | −1.65 | 3.49 | 11.79 | 444 | 479 |
| 11 | | −4.38 | −0.81 | 3.57 | 2.90 | 447 | 471 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 12 | | −4.93 | −1.62 | 3.31 | 14.71 | 455 | 492 |
| 13 | | −4.51 | −0.99 | 3.52 | 5.76 | 459 | 495 |
| 14 | | −5.45 | −1.98 | 3.47 | 4.41 | 454 | 478 |
| 15 | | −4.55 | −0.94 | 3.61 | 8.96 | 442 | 478 |
| 16 | | −4.58 | −0.96 | 3.62 | 4.96 | 443 | 476 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 17 | | −4.61 | −1.09 | 3.52 | 6.18 | 450 | 480 |
| 18 | | −4.90 | −1.54 | 3.36 | 4.74 | 476 | 552 |
| 19 | | −4.94 | −1.74 | 3.19 | 2.12 | 485 | 613 |
| 20 | | −5.13 | −2.01 | 3.12 | 1.52 | 511 | 540 |
| 21 | | −4.88 | −1.30 | 3.58 | 3.14 | 450 | 479 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 22 | | −4.53 | −1.01 | 3.52 | 8.65 | 454 | 478 |
| 23 | Imid 125 | −4.67 | −1.06 | 3.60 | 8.96 | 447 | 481 |
| 24 | | −4.82 | −1.36 | 3.46 | 3.33 | 454 | 517 |
| 25 | | −5.28 | −1.60 | 3.68 | 10.11 | 435 | 473 |
| 26 | | −5.21 | −1.64 | 3.57 | 10.21 | 439 | 510 |

TABLE 1-continued
| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 27 | 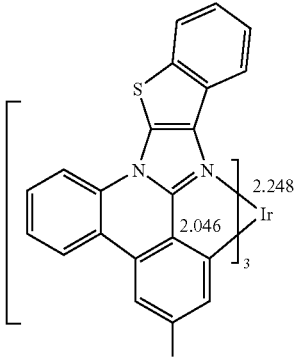
Benzimid20 | −5.25 | −1.61 | 3.64 | 9.35 | 440 | 476 |
| 28 | 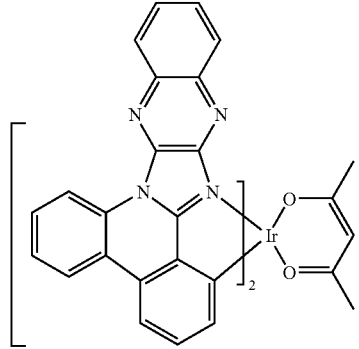 | −5.13 | −2.45 | 2.68 | 2.31 | 590 | 674 |
| 29 | 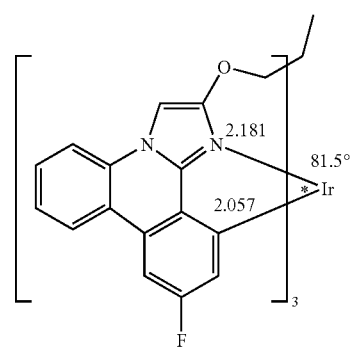 | −5.10 | −1.37 | 3.74 | 16.13 | 430 | 474 |
| 30 | 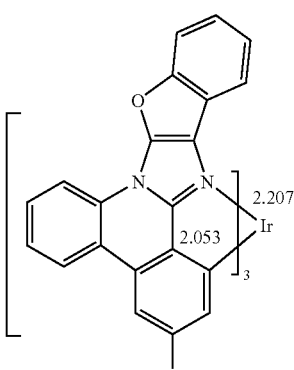 | −5.25 | −1.61 | 3.63 | 10.28 | 438 | 481 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 31 | | −4.66 | −1.17 | 3.49 | 4.35 | 448 | 479 |
| 32 | | −4.50 | −0.91 | 3.59 | 7.98 | 444 | 480 |
| 33 | | −4.33 | −0.67 | 3.66 | 8.45 | 433 | 474 |
| 34 | | −4.38 | −0.80 | 3.57 | 2.77 | 447 | 471 |
| 35 | | −4.64 | −1.31 | 3.33 | 7.04 | 479 | 486 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 36 | (structure with pyridine substituent) | −4.88 | −1.47 | 3.41 | 1.43 | 456 | 483 |
| 37 | (structure with pyrimidine substituent) | −5.02 | −1.90 | 3.12 | 2.82 | 471 | 486 |
| 38 | (structure with SMe substituent) | −4.79 | −1.32 | 3.47 | 0.10 | 456 | 484 |
| 39 | (structure with two SMe substituents) | −4.85 | −1.40 | 3.45 | 3.14 | 458 | 487 |
| 40 | (structure with SiMe₃ substituent) | −4.66 | −1.11 | 3.55 | 5.48 | 445 | 478 |

TABLE 1-continued
| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 41 | 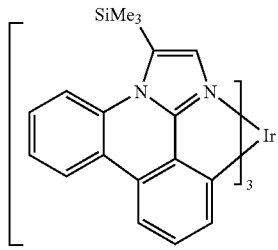 | −4.67 | −1.12 | 3.55 | 5.76 | 448 | 477 |
| 42 | 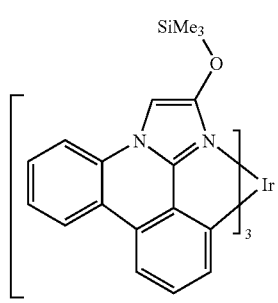 | −4.54 | −1.08 | 3.46 | 7.01 | 460 | 484 |
| 43 | 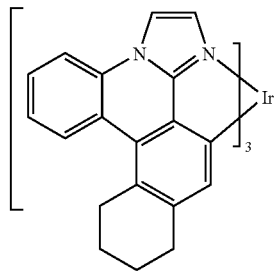 | −4.52 | −1.05 | 3.47 | 2.72 | 462 | 483 |
| 44 | 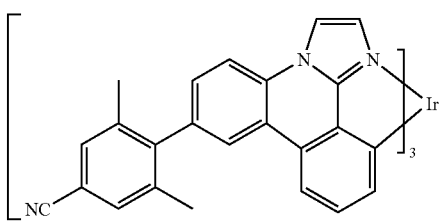 | −5.11 | −1.62 | 3.49 | 10.59 | 453 | 478 |
| 45 | 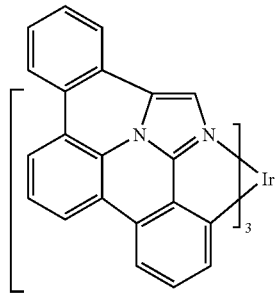 | −4.75 | −1.45 | 3.30 | 5.02 | 487 | 518 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 46 | | −5.08 | −2.18 | 2.90 | 13.63 | 531 | 623 |
| 47 | | −5.22 | −1.76 | 3.46 | 5.70 | 467 | 485 |
| 48 | | −4.87 | −1.37 | 3.50 | 3.13 | 468 | 481 |
| 49 | | −4.56 | −0.97 | 3.85 | 5.02 | 442 | 474 |
| 50 | | −4.57 | −0.97 | 3.60 | 5.03 | 441 | 477 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 51 | | −4.57 | −1.10 | 3.47 | 4.94 | 447 | 480 |
| 52 | | −4.51 | −1.06 | 3.45 | 4.36 | 447 | 479 |
| 53 | | −4.45 | −1.01 | 3.44 | 4.77 | 441 | 478 |
| 54 | | −4.58 | −0.98 | 3.60 | 4.92 | 442 | 476 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 55 | | −4.65 | −1.04 | 3.60 | 5.43 | 442 | 476 |
| 56 | | −4.52 | −0.92 | 3.60 | 6.23 | 442 | 476 |
| 57 | | −4.45 | −0.85 | 3.60 | 7.72 | 442 | 476 |
| 58 | | −4.49 | −0.87 | 3.62 | 5.45 | 438 | 474 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 59 | | −5.27 | −1.91 | 3.36 | 2.99 | 478 | 501 |
| 60 | | −5.75 | −2.39 | 3.37 | 4.27 | 476 | 507 |
| 61 | | −5.22 | −1.46 | 3.77 | 0.08 | 427 | 463 |
| 62 | | −5.68 | −2.05 | 3.64 | 4.12 | 441 | 467 |
| 63 | | −5.88 | −2.40 | 3.48 | 3.83 | 460 | 472 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 64 | | −4.74 | −1.65 | 3.08 | 9.02 | 469 | 484 |
| 65 | | −5.37 | −1.69 | 3.68 | 8.08 | 434 | 472 |
| 66 | | −5.32 | −1.33 | 4.00 | 0.25 | 389 | 476 |
| 67 | | −4.24 | −0.65 | 3.60 | 3.14 | 449 | 480 |
| 68 | | −4.28 | −0.71 | 3.57 | 3.23 | 454 | 479 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 69 | | −4.82 | −1.20 | 3.62 | 1.03 | 440 | 475 |
| 70 | | −4.95 | −1.36 | 3.59 | 0.28 | 441 | 476 |
| 71 | | −4.65 | −1.18 | 3.47 | 5.66 | 442 | 476 |
| 72 | | −4.44 | −0.82 | 3.62 | 5.50 | 439 | 479 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 73 | | −5.19 | −1.79 | 3.40 | 0.50 | 468 | 483 |
| 74 | | −5.16 | −1.64 | 3.51 | 7.01 | 452 | 479 |
| 75 | | −4.49 | −0.80 | 3.69 | 6.62 | 434 | 475 |
| 76 | | −5.01 | −0.97 | 4.04 | 3.07 | 375 | 446 |
| 77 | | −5.46 | −1.44 | 4.01 | 2.34 | 377 | 448 |
| 78 | | −5.22 | −1.24 | 3.97 | 8.24 | 382 | 451 |

TABLE 1-continued
| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 79 | 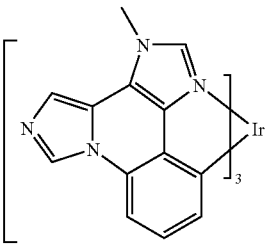 | −5.10 | −0.99 | 4.11 | 10.38 | 400 | 465 |
| 80 | 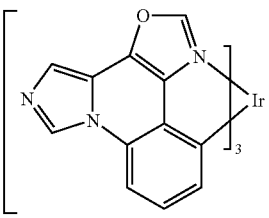 | −5.84 | −1.96 | 3.88 | 0.91 | 409 | 529 |
| 81 | 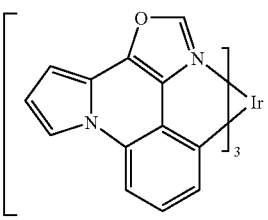 | −5.30 | −1.48 | 3.82 | 1.26 | 412 | 542 |
| 82 | 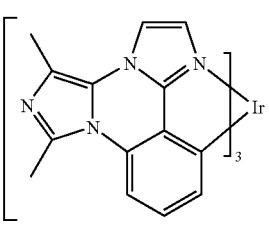 | −5.19 | −1.18 | 4.01 | 2.09 | 377 | 449 |
| 83 | 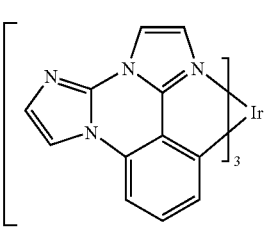 | −5.33 | −1.31 | 4.02 | 2.45 | 376 | 448 |
| 84 | 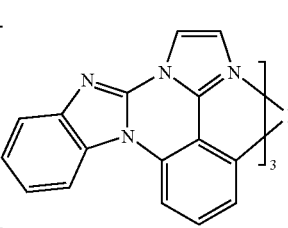 | −5.34 | −1.53 | 3.82 | 1.53 | 403 | 463 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
| --- | --- | --- | --- | --- | --- | --- | --- |
| 85 | | −5.40 | −1.70 | 3.70 | 1.70 | 419 | 480 |
| 86 | | −5.39 | −1.52 | 3.87 | 3.36 | 428 | 461 |
| 87 | | −5.31 | −1.61 | 3.70 | 7.43 | 423 | 473 |
| 88 | | −4.85 | −1.17 | 3.68 | 2.60 | 427 | 485 |
| 89 | | −4.88 | −1.33 | 3.55 | 2.32 | 442 | 496 |
| 90 | | −5.46 | −1.66 | 3.80 | 0.78 | 412 | 494 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 91 | | −5.28 | −1.57 | 3.71 | 2.81 | 419 | 479 |
| 92 | | −5.24 | −1.53 | 3.71 | 1.74 | 421 | 479 |
| 93 | | −5.19 | −1.51 | 3.68 | 2.80 | 432 | 483 |
| 94 | | −6.19 | −2.54 | 3.66 | 9.25 | 429 | 472 |
| 95 | | −5.86 | −2.11 | 3.74 | 10.90 | 426 | 460 |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 96 | | −5.06 | −1.11 | 3.95 | 2.69 | 381 | 456 |
| 97 | | −5.22 | −1.45 | 3.76 | 0.68 | 397 | 473 |
| 98 | | −4.91 | −0.96 | 3.95 | 2.51 | 383 | 460 |
| 99 | | — | — | — | — | — | — |

TABLE 1-continued

| Entry | Compounds | Cal. HOMO (ev) | Cal. LUMO (ev) | Cal. Gap (ev) | Cal. Dipole (Debye) | Cal. S1 (nm) | Cal. T1 (nm) |
|---|---|---|---|---|---|---|---|
| 100 | 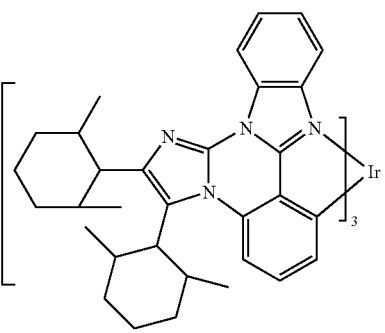 | −5.13 | −1.39 | 3.74 | 2.52 | 422 | 472 |
| 101 | 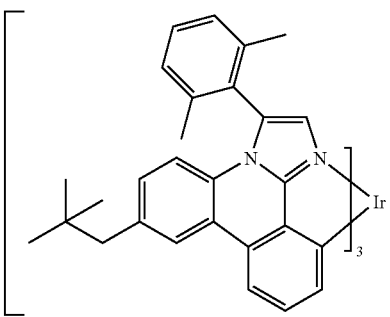 | | | | | | |

Figure 22:
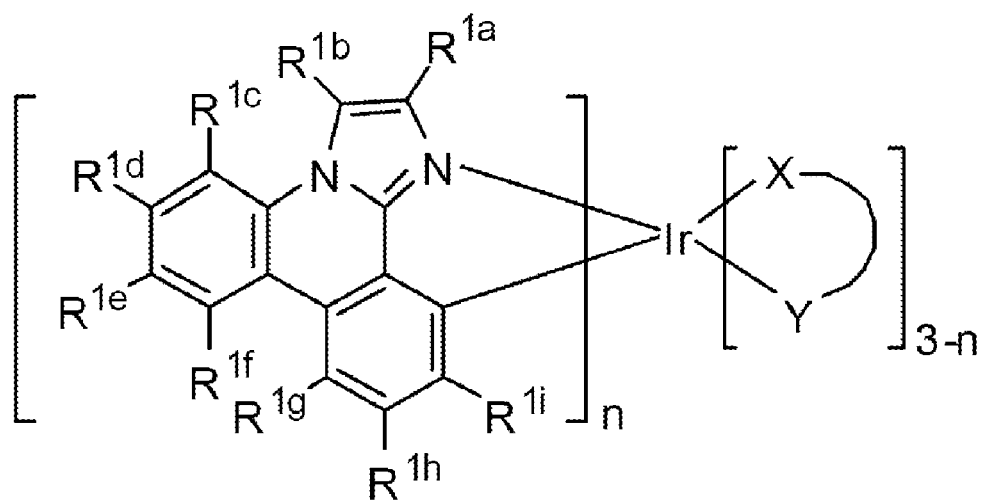
FIG. 22 shows an emissive iridium complex.

In one embodiment, iridium complexes are provided having Formula I:

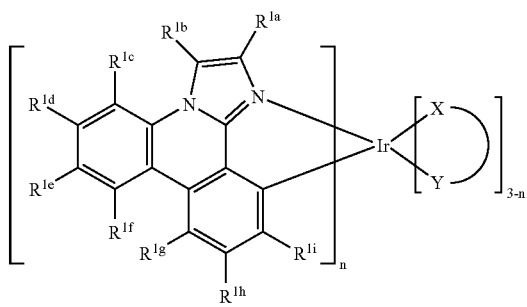

where n=1, 2 or 3; $R^{1a}$, $R^{1b}$, $R^{1c}$, $R^{1d}$, $R^{1e}$, $R^{1g}$, $R^{1h}$, and $R^{1i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a-c}$ are each, independently, hydrocarbyl or heteroatom substituted hydrocarbyl, and where any two of $R^{1a}$ and $R^{2a-c}$ may be linked to form a saturated or unsaturated, aromatic or non-aromatic ring. X—Y is an ancillary ligand. The complex of Formula I is illustrated in FIG. 22.

Compounds are provided having a branched alky group such as neopentyl or benzyl in the $R^{1e}$ position are provided. Both neopentyl and benzyl posses a benzyl methylene group, allowing for free rotation of the alkyl or phenyl group with respect to the ring to which the $R^{1e}$ substituent is attached. Without limiting aspects of the invention to any theory, it is believed that such substituents result in devices with significantly longer lifetimes through the inhibition of pi-pi stacking which in turn allows for cleaner sublimation and deposition as well as limiting exciton migration in the device. In a preferred embodiment, a complex is provided having Formula I, where at least one of $R^{1A}$, $R^{1b}$, $R^{1c}$, $R^{1d}$, $R^{1e}$, $R^{1f}$, $R^{1g}$, $R^{1h}$, and $R^{1i}$ is a branched alkyl containing at least 4 carbon atoms and where the branching occurs at a position further than the benzylic position. Neopentyl is a preferred branched alkyl. In a particularly preferred embodiment, a branched alkyl is provided in the $R^{1e}$ position. Preferred complexes include those having the ligands gs1-32-gs1-62. Preferred complexes also include those having the ligands gs1-32-gs1-62, where all R groups $R^{1a}$-$R^{1i}$ that are not already specified in the formula gs1-32-gs1-62 are H.

Compounds having a "twisted aryl" in the $R^{1b}$ position are provided. Without limiting aspects of the invention to any theory, it is believed that a twisted aryl in the $R^{1b}$ position confers greater stability towards photo oxidation resulting in longer device lifetimes. In a preferred embodiment, a complex is provided having Formula I, where $R^{1b}$ is an aryl group having the structure:

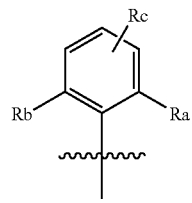

where Ra, Rb and Rc are independently H, alkyl or aryl, where at least one of Ra and Rb is an alkyl or aryl; and where Ra, Rb and Rc can join to form fused rings. Preferably, at least one of Ra and Rb is an alkyl. The steric bulk provided by an alkyl or aryl in the Ra and/or Rb position causes the aryl in the $R^{1b}$ position to twist. Preferably, the twisting results in a complex where $R^{1b}$ is an aryl group with a dihedral angle of more than 70 degrees from the imidazole ring. Ra and Rb may both be alkyl or aryl, which may result in more twisting. Methyl is a preferred alkyl for the Ra and/or Rb positions due to ease of fabrication. Isopropyl is a preferred alkyl for the Ra and/or Rb positions due to a combination of added steric bulk relative to methyl. Preferred compounds having a "twisted aryl" in the $R^{1b}$ position include es45 and es46:

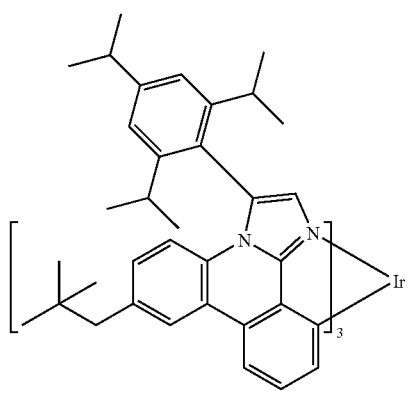

es45

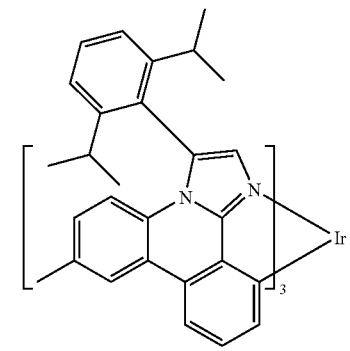

es46

Other preferred compounds including a twisted aryl include gs1-57 and gs1-58.

Compounds are provided having a methyl or small alkyl group in the $R^{1a}$ position. Without limiting aspects of the invention to any theory, it is believed that a methyl or small alkyl group in the $R^{1a}$ position confers greater stability towards photo oxidation resulting in significantly improved external quantum efficiency (EQE).

Compounds are also provided having any combination of the substituents described in the preceding paragraphs, i.e., any combination of a "twisted aryl" in the $R^{1a}$ position, an alky group such as neopentyl or benzyl in the $R^{1a}$ position, and/or a methyl or small alkyl group in the $R^{1a}$ position. In one preferred combination, $R^{1b}$ is an aryl group with a dihedral angle of more than 70 degrees from the imidazole ring and $R^{1a}$ is alkyl. In another preferred combination, the complex is es38:

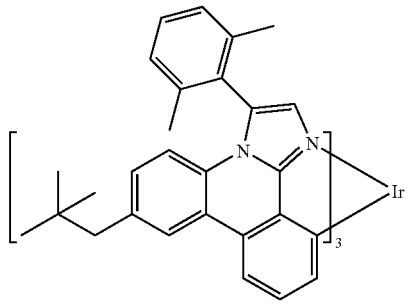

In one embodiment, long lived phosphorescent OLEDs with neopentyl substituted iridium imidazo[1,2-f]phenanthridine and diimidazo[1,2-a: 1',2'-c]quinazoline complexes as emitters are provided. Phosphorescent organic light emitting devices with neopentyl substituted imidazo[1,2-f] phenanthridine and neopentyl substituted diimidazo[1,2-a: 1',2'-c]quinazoline complexes as the emitting materials showed, in many cases, much longer lifetimes than devices with emitting materials lacking the neopentyl group.

The complexes provided herein may advantageously be used as emissive materials in an organic light emitting device. In many situations, such complexes are preferably iridium complexes. Such a device generally includes an anode, a cathode, and an organic emissive layer disposed between the anode and the cathode, where the organic layer includes the emissive complex. In a preferred device configuration, the organic emissive layer also includes a host, and the emissive complex is provided as a dopant in the organic emissive layer. Such devices may include other layers as illustrated and described with respect to FIGS. 1 and 2. Preferred hosts for the emissive materials disclosed herein include organic material that contains a carbazole group, due to the electronic properties of such materials and the superior results observed with such materials. A preferred host is mCBP due to the superior results observed with mCBP.

Device Examples

Device Fabrication and Measurement

All devices are fabricated by high vacuum ($<10^{-7}$ Torr) thermal evaporation. The anode electrode is approximately 80-120 nm of indium tin oxide (ITO). The cathode consists of approximately 0.5-1 nm of LiF followed by 100 nm of Al. All devices are encapsulated with a glass lid sealed with an epoxy resin in a nitrogen glove box (<1 ppm of $H_2O$ and $O_2$) immediately after fabrication, and a moisture getter was incorporated inside the package.

All device examples have organic stacks consisted of sequentially, from the ITO surface, 10 nm of copper phthalocyanine (CuPc), Ir(3-Meppy)$_3$ or es20 as the hole injection layer (HIL), 0 or 30 nm of 4,4'-bis[N-(1-naphthyl)-N-phenylamino]biphenyl (□-NPD), as the hole transport layer (HTL), 30, 60 or 80 nm of 3,3'-bis(N-carbazolyl)biphenyl (mCBP) or 4,4'-bis(N-carbazolyl)biphenyl (CBP) doped with 6-15 wt % of the dopant emitter (invention compounds and comparative compounds) as the emissive layer (EML). The electron transport layers consisted of 5 nm of HPT or mCBP, or 40 nm of BAlq as the ETL2, and 20-45 nm of tris(8-hydroxyquinolinato)aluminum (Alq$_3$) as the ETL1 when HPT or mCBP was used as the ETL, or no ETL1 when BAlq was used as the ETL2. The device structures of all device examples are shown in Table 1.

TABLE 1

Device example structures

| Device Example | HIL | HTL | EML Host | Compound | Doping % | thickness (nm) | ETL2 (nm) | ETL1 (nm) |
|---|---|---|---|---|---|---|---|---|
| Comparative 1 | CuPc | NPD | CBP | A | 9 | 30 | BAlq (40) | none |
| 1 | CuPc | NPD | mCBP | es1 | 9 | 30 | BAlq (40) | none |
| 2 | CuPc | NPD | mCBP | es6 | 9 | 30 | BAlq (40) | none |
| 3 | CuPc | NPD | mCBP | es8 | 9 | 30 | BAlq (40) | none |
| 4 | CuPc | NPD | mCBP | es9 | 9 | 30 | BAlq (40) | none |
| 5 | CuPc | NPD | mCBP | es13 | 9 | 30 | BAlq (40) | none |
| 6 | CuPc | NPD | mCBP | es14 | 9 | 30 | BAlq (40) | none |
| 7 | CuPc | NPD | mCBP | es16 | 9 | 30 | BAlq (40) | none |
| 8 | CuPc | NPD | mCBP | es17 | 9 | 30 | BAlq (40) | none |
| 9 | CuPc | NPD | mCBP | es19 | 9 | 30 | BAlq (40) | none |
| 10 | Ir(3-Meppy)$_3$ | NPD | mCBP | es20 | 9 | 30 | BAlq (40) | none |
| 11 | CuPc | NPD | CBP | es4 | 6 | 30 | HPT (5) | Alq$_3$ (45) |
| 12 | Ir(3-Meppy)$_3$ | none | mCBP | es20 | 15 | 60 | mCBP (5) | Alq$_3$ (20) |
| 13 | es20 | none | mCBP | es20 | 15 | 60 | mCBP (5) | Alq$_3$ (20) |
| 14 | CuPc | none | mCBP | es38 | 15 | 80 | mCBP (5) | Alq$_3$ (20) |
| 15 | CuPc | none | mCBP | es38 | 15 | 60 | mCBP (5) | Alq$_3$ (20) |
| 16 | Ir(3-Meppy)$_3$ | none | mCBP | es38 | 15 | 80 | mCBP (5) | Alq$_3$ (20) |
| 17 | Ir(3-Meppy)$_3$ | none | mCBP | es38 | 15 | 60 | mCBP (5) | Alq$_3$ (20) |
| 18 | LG101 | NPD | mCBP | es38 | 9 | 20 | mCBP (5) | Alq$_3$ (20) |
| 19 | Ir(3-Meppy)$_3$ | NPD | mCBP | es43 | 9 | 30 | mCBP (5) | Alq$_3$ (40) |
| 20 | Ir(3-Meppy)$_3$ | NPD | mCBP | es46 | 9 | 30 | mCBP (5) | Alq$_3$ (40) |
| 21 | Ir(3-Meppy)$_3$ | NPD | mCBP | es49 | 9 | 30 | mCBP (5) | Alq$_3$ (40) |
| 22 | Ir(3-Meppy)$_3$ | NPD | mCBP | es45 | 9 | 30 | none | Alq$_3$ (40) |

The current-voltage-luminance (IVL) characteristics, electroluminescence properties [emission maximum ($Em_{max}$) and CIE coordinates] and operational lifetimes are measured and summarized in the Table 2. The device efficiencies are compared at L=1000 cd/m$^2$.

than one having a CIE of 0.17, 0.38. Although the external quantum efficiency (EQE) of device example 1 is 2.7% compared to 4.7% of comparative example 1, more importantly the $T_{1/2}$ of device example 1 is 270 hours at $L_0$=450 cd/m$^2$ compared to 170 hours at $L_0$=100 cd/m$^2$ of comparative

TABLE 2

Device properties of device examples

| Device Example | J = 10 mA/cm$^2$ | | | At L = 1000 cd/m$^2$ | | | | Stability | | Figure |
|---|---|---|---|---|---|---|---|---|---|---|
| | $Em_{max}$(nm) | CIE x | CIE y | V (V) | LE (cd/A) | EQE (%) | PE (lm/W) | $L_0$ (cd/m$^2$) | $T_{1/2\,(hr)}$ | |
| Comparative 1 | 472 | 0.170 | 0.380 | 10.0 | 10.5 | 4.7 | 3.30 | 100 | 170 | no figure |
| 1 | 460 | 0.150 | 0.210 | 14.0 | 4.116 | 2.672 | 0.92 | 450 | 273 | 3 |
| 2 | 460 | 0.150 | 0.190 | >15 | <2.5 | <1.7 | <0.5 | 270 | 700 | 4 |
| 3 | 460 | 0.140 | 0.190 | 14.6 | 4.433 | 3.079 | 0.95 | 470 | 400 | 5 |
| 4 | 459 | 0.140 | 0.180 | 14.4 | 4.13 | 3.01 | 0.90 | 420 | 210 | 6 |
| 5 | 462 | 0.14 | 0.18 | 13.4 | 6.836 | 4.573 | 1.60 | 680 | 310 | 7 |
| 6 | 460 | 0.15 | 0.21 | 14.4 | 6.352 | 4.169 | 1.39 | 1240 | 115 | 8 |
| 7 | 460 | 0.150 | 0.210 | 13.8 | 5.07 | 3.56 | 1.14 | 525 | 320 | 9 |
| 8 | 464 | 0.16 | 0.28 | 12.8 | 9.387 | 4.957 | 2.30 | 938 | 104 | 10 |
| 9 | 464 | 0.16 | 0.28 | >15 | <2 | <1.2 | <.4 | not tested | not tested | 11 |
| 10 | 462 | 0.150 | 0.240 | 12.0 | 13.378 | 8.042 | 3.50 | 2300 | 106 | 12 |
| 11 | 498 | 0.250 | 0.590 | 9.0 | 13.4 | 4.5 | 4.70 | 4300 | 340 | 13 |
| 12 | 462 | 0.160 | 0.250 | 10.4 | 12.26 | 7.07 | 3.70 | 500 | 2200 | 15 |
| 13 | 462 | 0.160 | 0.240 | 13.0 | 9.534 | 5.603 | 2.30 | 500 | 2500 | 16 |
| 14 | 462 | 0.150 | 0.260 | 16.4 | 7.9 | 4.5 | 1.51 | 500 | >10,000 | 17 |
| 15 | 462 | 0.15 | 0.22 | 13.3 | 6.5 | 4 | 1.54 | 1000 | 1000 | 18 |
| 16 | 462 | 0.160 | 0.270 | 14.9 | 12.7 | 6.9 | 2.67 | 500 | >10,000 | 19 |
| 17 | 462 | 0.160 | 0.240 | 11.9 | 11.7 | 6.7 | 3.07 | 1000 | 1400 | 20 |
| 18 | 462 | 0.15 | 0.200 | 7.2 | 10.1 | 6.8 | 4.40 | 1000 | 200 | 21 |
| 19 | 464 | 0.15 | 0.24 | 8.2 | 19.9 | 12.2 | 7.60 | 1,000 | 270 | no figure |
| 20 | 462 | 0.15 | 0.25 | 9.5 | 14 | 8.1 | 4.60 | 2,000 | 220 | no figure |
| 21 | 462 | 0.15 | 0.23 | 6.9 | 11.5 | 7.1 | 5.20 | 2,000 | 40 | no figure |
| 22 | 460 | 0.15 | 0.24 | 9.3 | 10.8 | 6.5 | 3.70 | 2,000 | 81 | no figure |

Device example 1 with es1 as the phosphorescent emitter has CIE of 0.15, 0.21 compared to 0.17, 0.38 of comparative example 1 using Compound A, a commonly used blue phosphorescent dopant, as the emitter. A blue phosphorescent OLED having a CIE as blue as 0.15, 0.21 is more desirable example 1. This represents that device example 1 is at least 7 times more stable than comparative example 1. Since the major difference is only the phosphorescent emitter, the result suggests that the invention compound family provided is very useful in obtaining relatively long-lived, deep blue phosphorescent OLEDs. For instance, device example 5 has CIE of 0.14, 0.18, EQE of 4.6% and $T_{1/2}$ of 310 hours at $L_0$=680 cd/m². Device example 12 has CIE of 0.16, 0.25, EQE of 7.1% and $T_{1/2}$ of 2,200 hours at $L_0$=500 cd/m². Device example 14 has CIE of 0.15, 0.26, EQE of 4.5% and $T_{1/2}$ of >10,000 hours at $L_0$=500 cd/m².

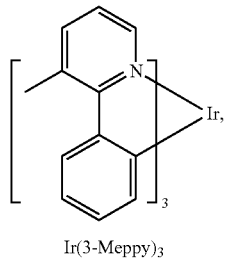

Ir(3-Meppy)₃

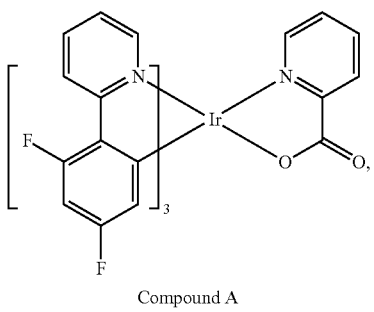

Compound A

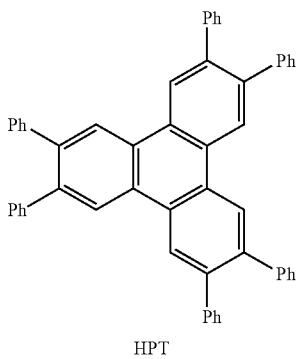

HPT

In the blue phosphorescent metal complexes, due to the higher energy level of the ³MLCT state, the energy gap between ³MLCT and ³MC become smaller and the low-lying MC state may be thermally populated, making it more susceptible to degradation and leading to loss in quantum yield. For example, devices having Ir(imidazophenanthridine) based blue dopants generally have 6-8% EQE (Table 2). Increasing the energy gap between ³MLCT and ³MC for Ir(imidazophenanthridine) based dopants may boost the device efficiency. The MC state of the metal complex is related to the ligand field strength. Generally speaking, a stronger donor leads to an increase in the 10 Dq value and higher MC state. In this case, the ligand field strength of dimethylimidazole>methyl imidazole>imidazole:

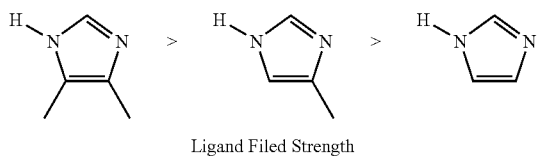

Ligand Filed Strength

For the imidazophenanthridine family, in order to increase the donor ability of the imidazole ring, the addition of a methyl group to the $R^{1a}$ and $R^{1b}$ positions was considered. It was found that methyl substitution on $R^{1a}$ position did not change the color significantly while methyl substitution on both $R^{1a}$ and $R^{1b}$ position substantially red shifts the color. Thus, either substitution may be used, but methyl substitution on the $R^{1a}$ is preferred where is is desired to add a strong donor without red-shifting.

TABLE 3

Effect on color by methyl substitution on the imidazole ring

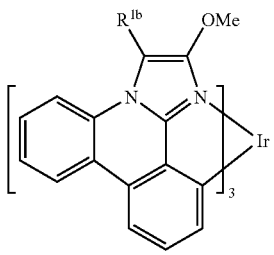

| Cpd # | $R^{1b}$ | $R^{1a}$ | Emission Max. (nm) | CIE (Soln. PL) |
|---|---|---|---|---|
| es1 | H | H | 462 | 0.17, 0.26 |
| es43 | H | Methyl | 460 | 0.17, 0.28 |
| es44 | Methyl | Methyl | 470 | 0.19, 0.35 |

Figure 3:
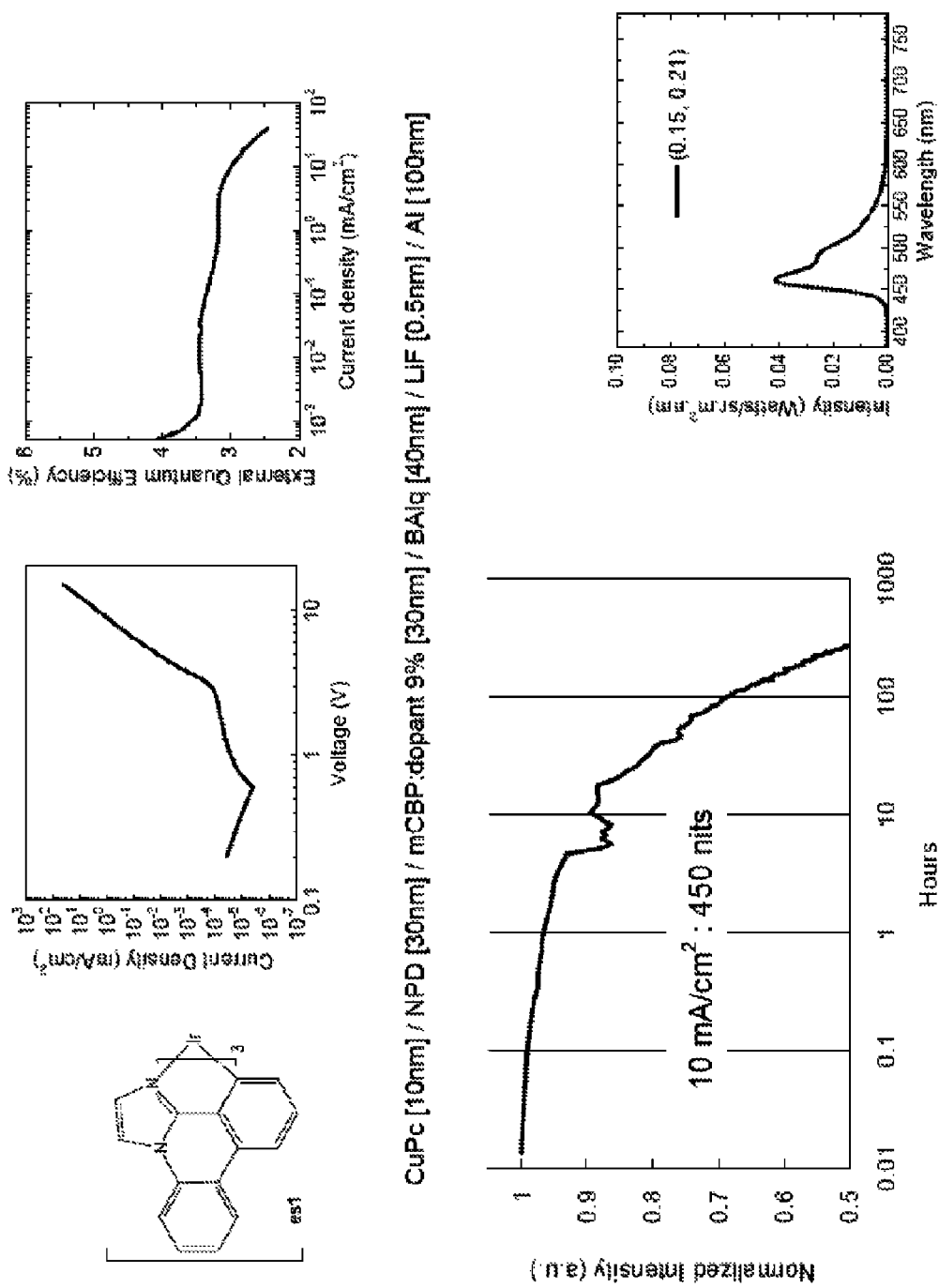
FIG. 3 shows IVL, spectral and lifetime data for a device comprising compound es1.
Figure 4:
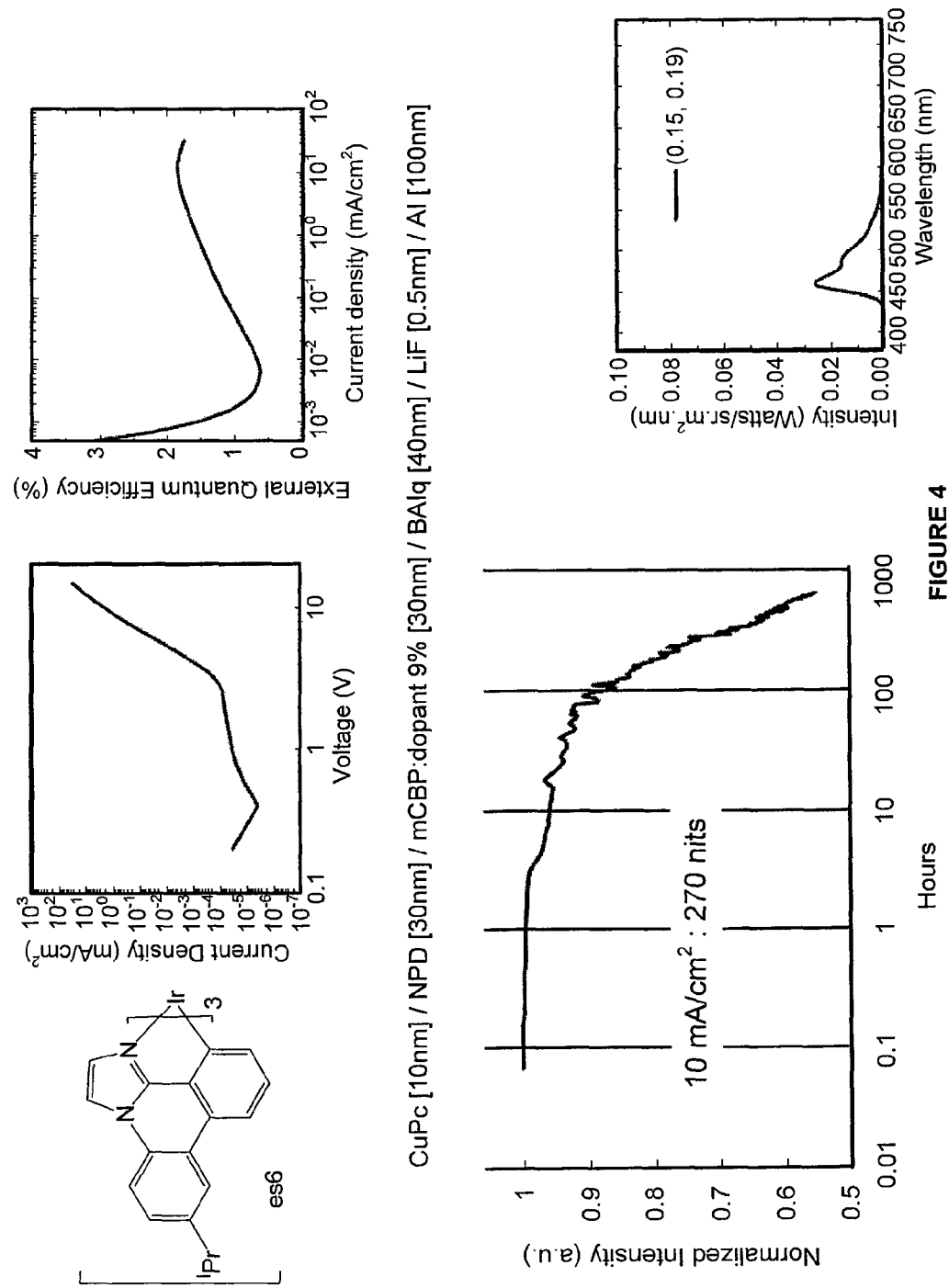
FIG. 4 shows IVL, spectral and lifetime data for a device comprising compound es6.
Figure 5:
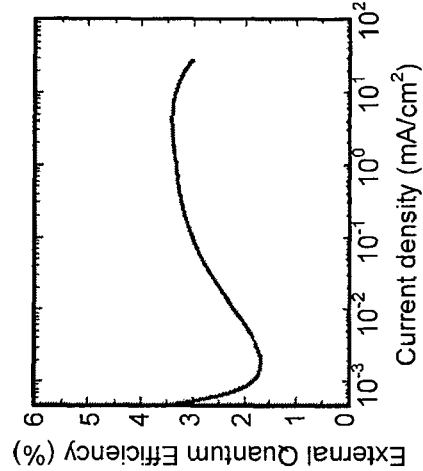
FIG. 5 shows IVL, spectral and lifetime data for a device comprising compound es8.
Figure 5:
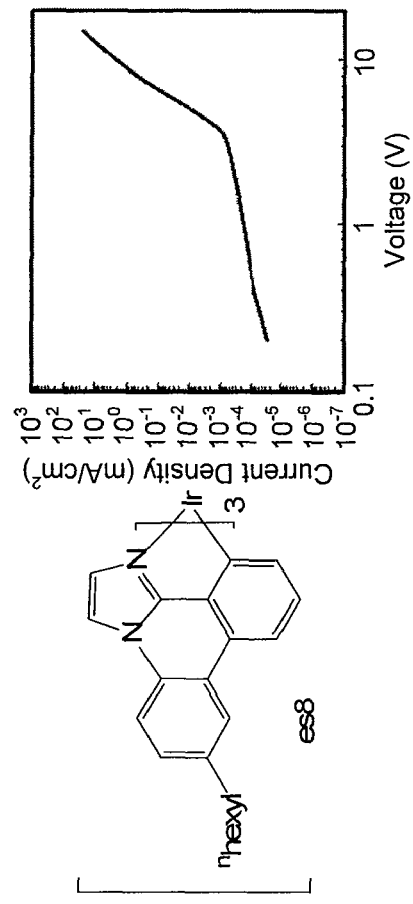
Figure 5:
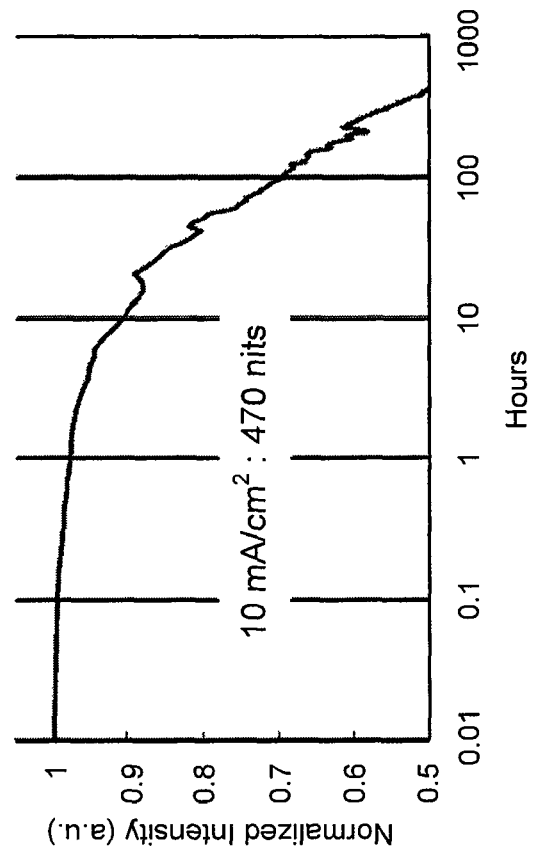
Figure 5:
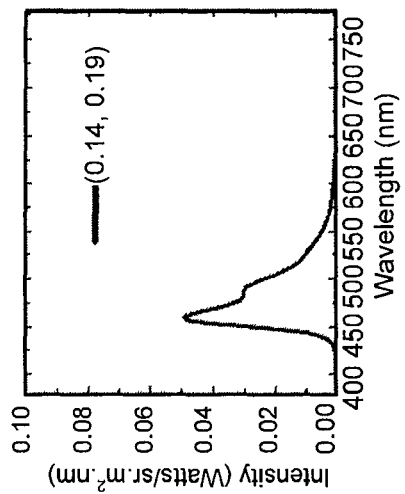
Figure 6:
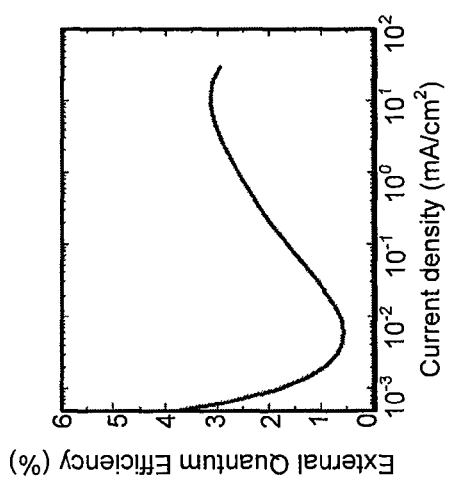
FIG. 6 shows IVL, spectral and lifetime data for a device comprising compound es9.
Figure 6:
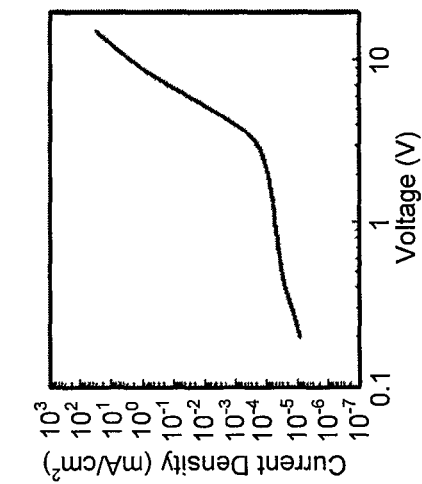
Figure 6:
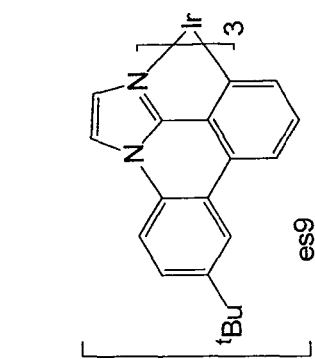
Figure 6:
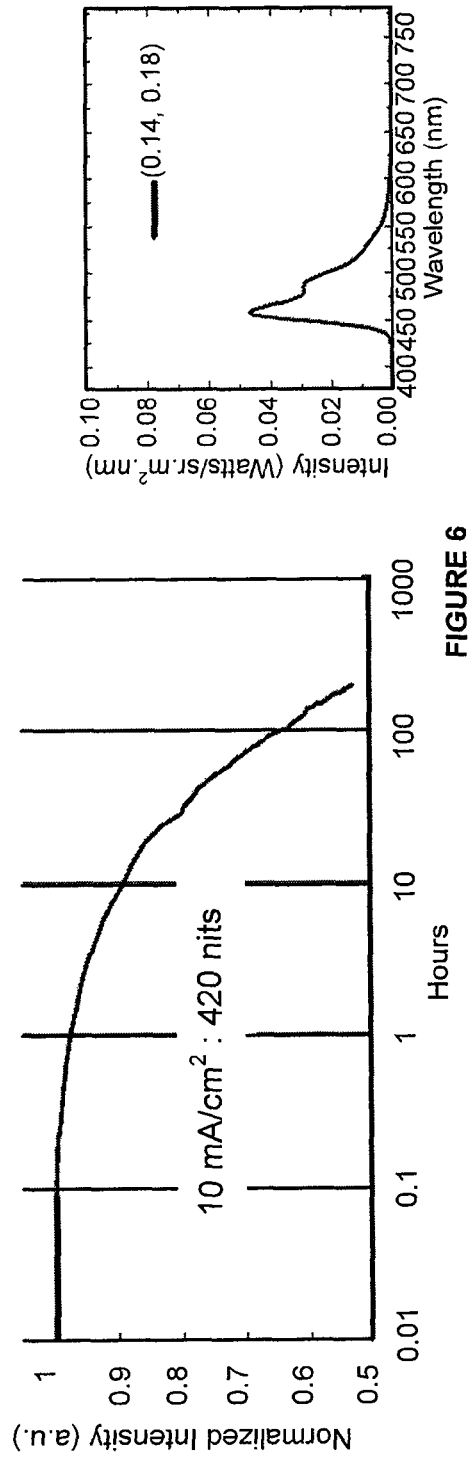
Figure 7:
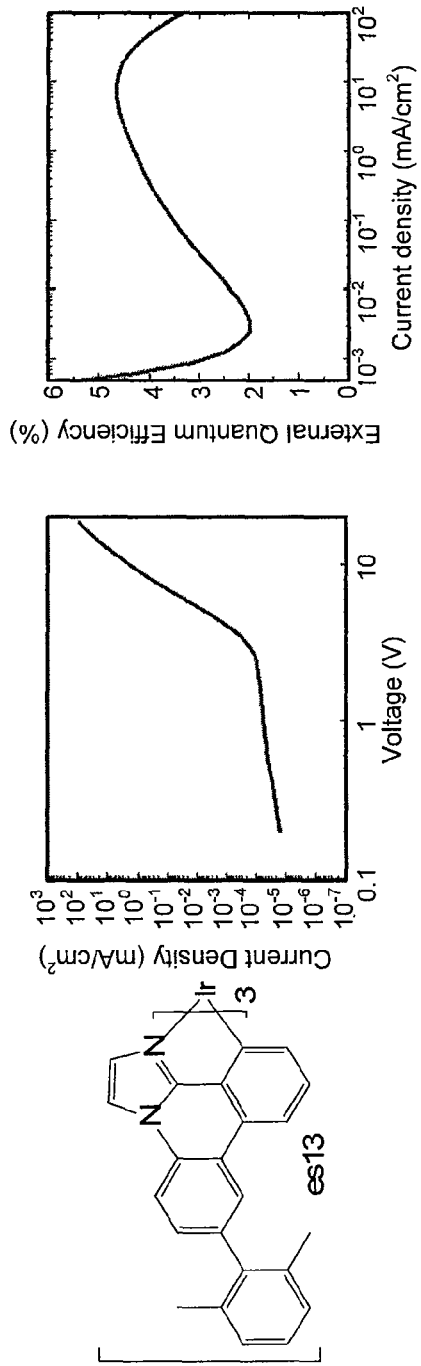
FIG. 7 shows IVL, spectral and lifetime data for a device comprising compound es13.
Figure 7:
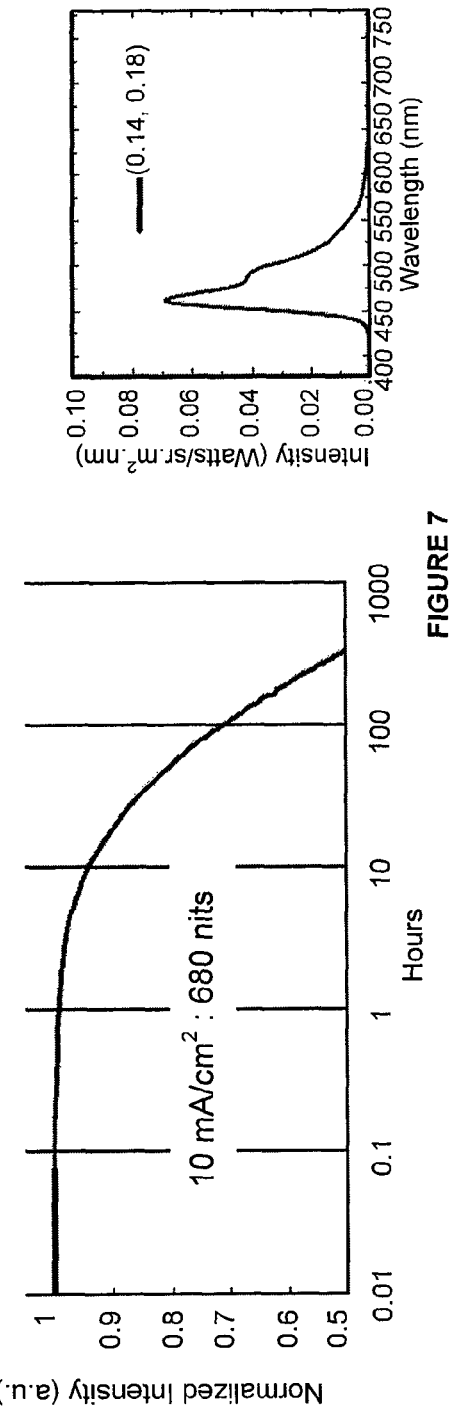
Figure 8:
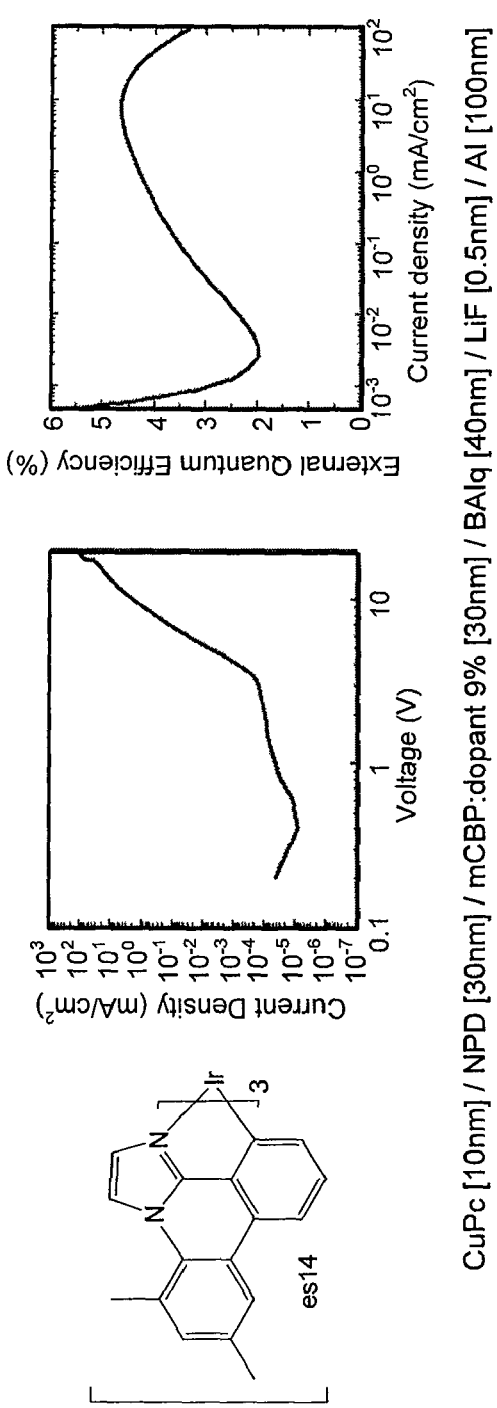
FIG. 8 shows IVL, spectral and lifetime data for a device comprising compound es14.
Figure 8:
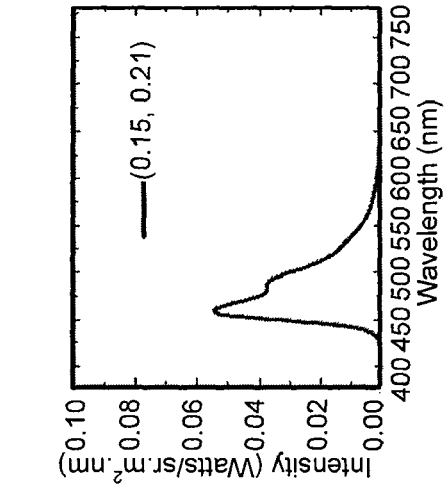
Figure 9:
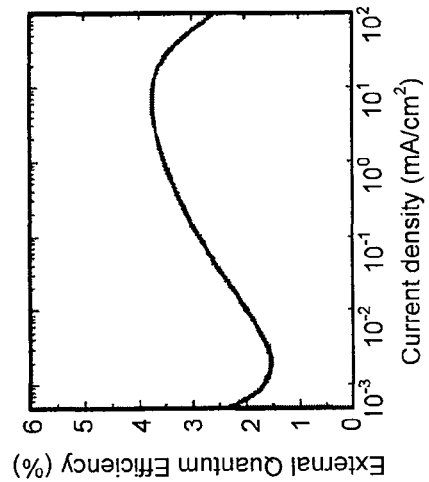
FIG. 9 shows IVL, spectral and lifetime data for a device comprising compound es16.
Figure 9:
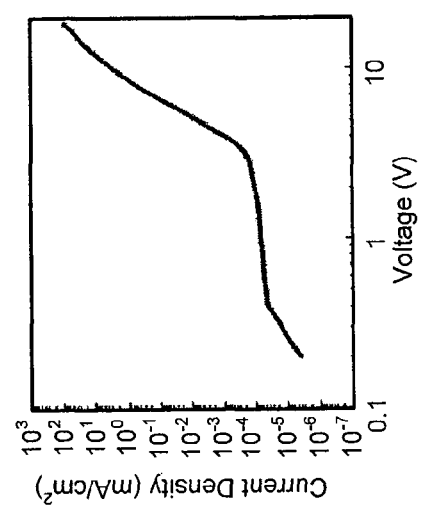
Figure 9:
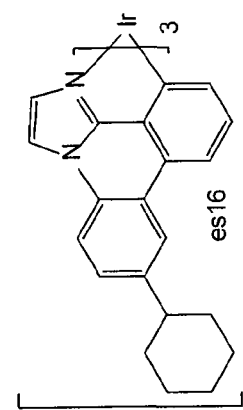
Figure 9:
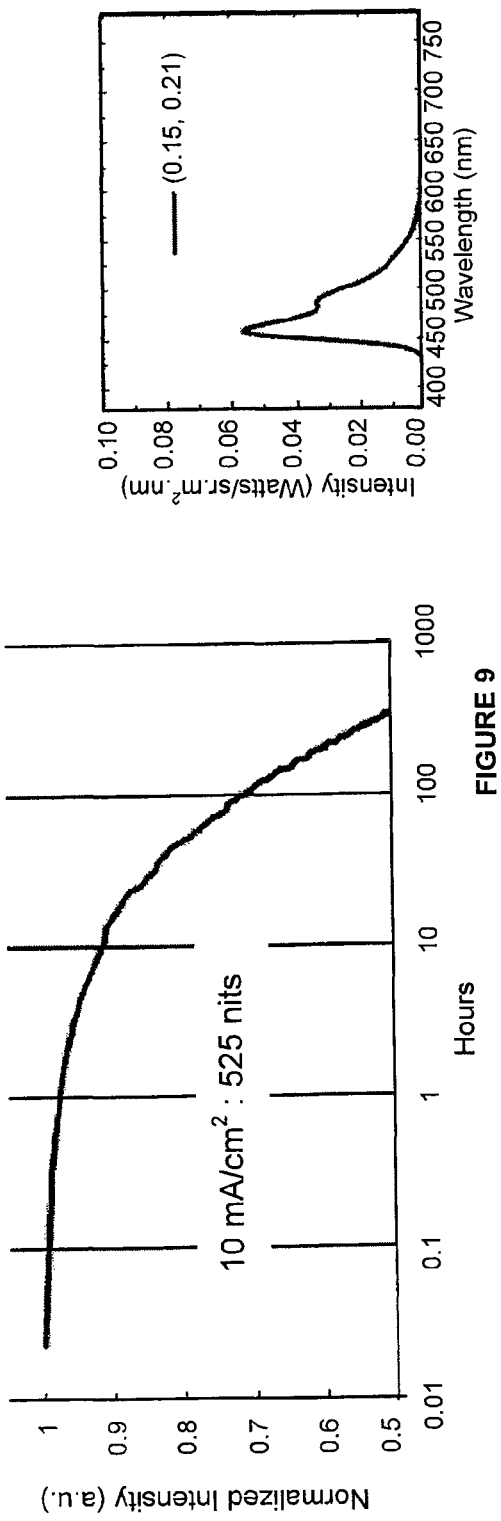
Figure 10:
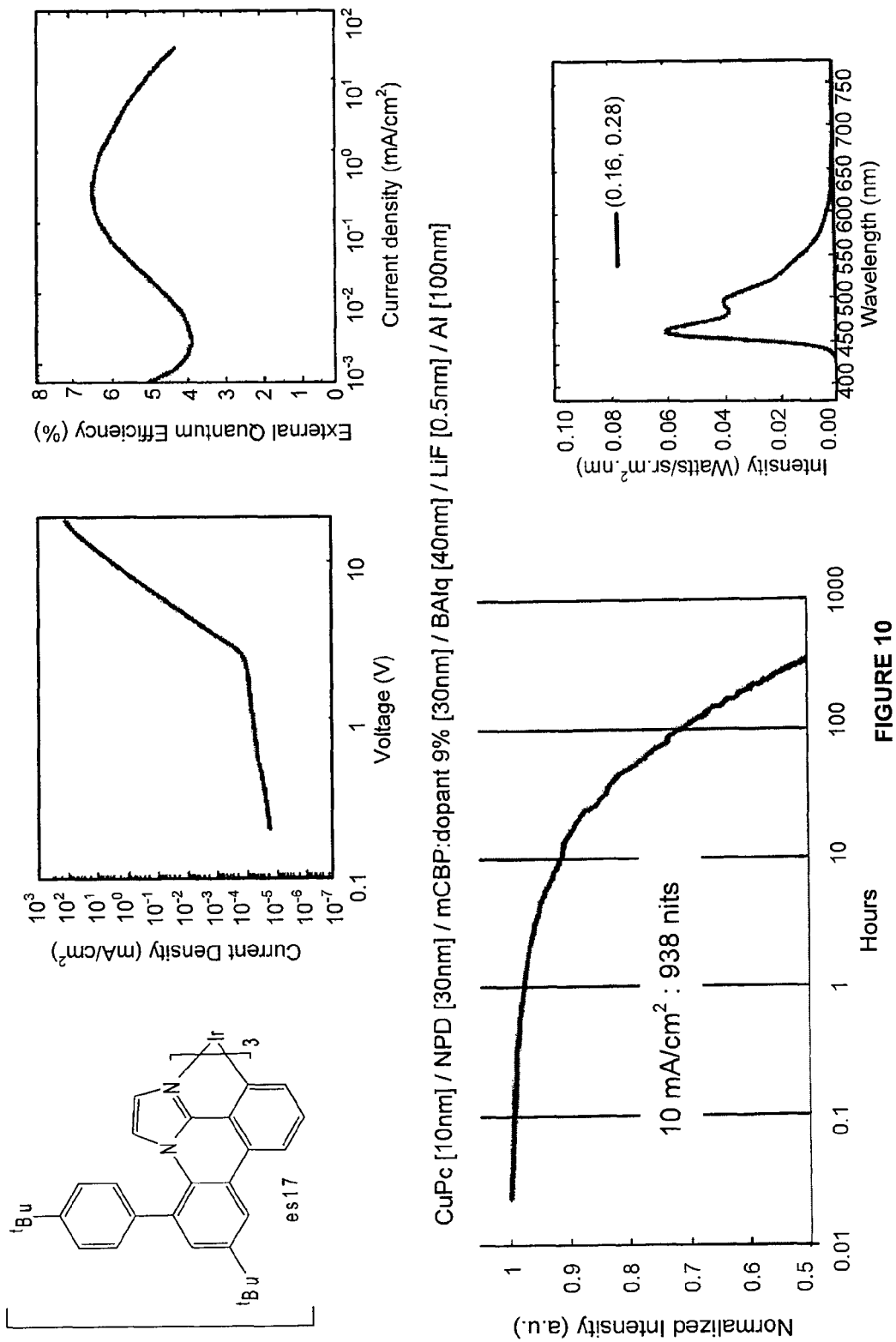
FIG. 10 shows IVL, spectral and lifetime data for a device comprising compound es17.
Figure 11:
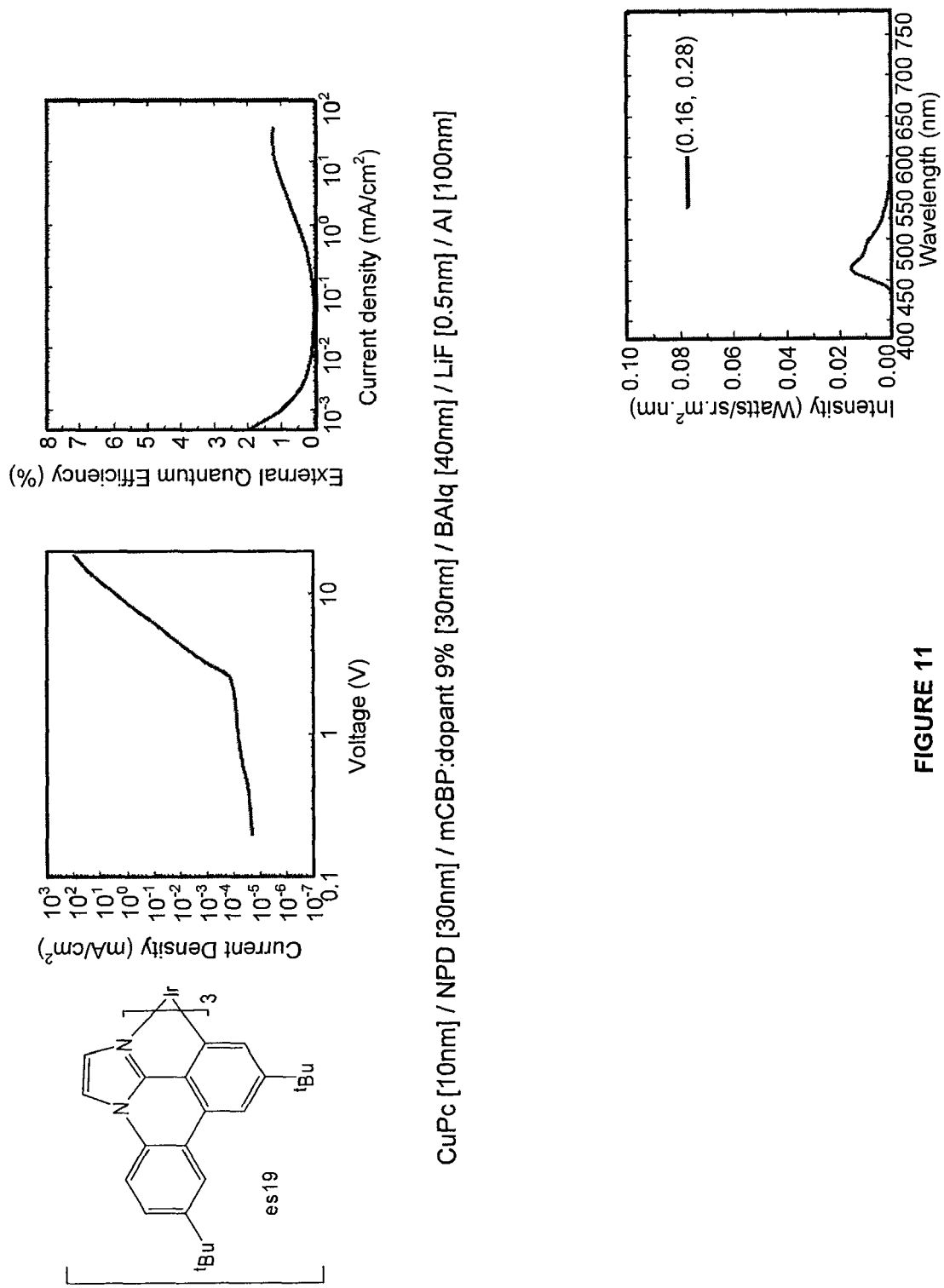
FIG. 11 shows IVL, and spectral data for a device comprising compound es19.
Figure 12:
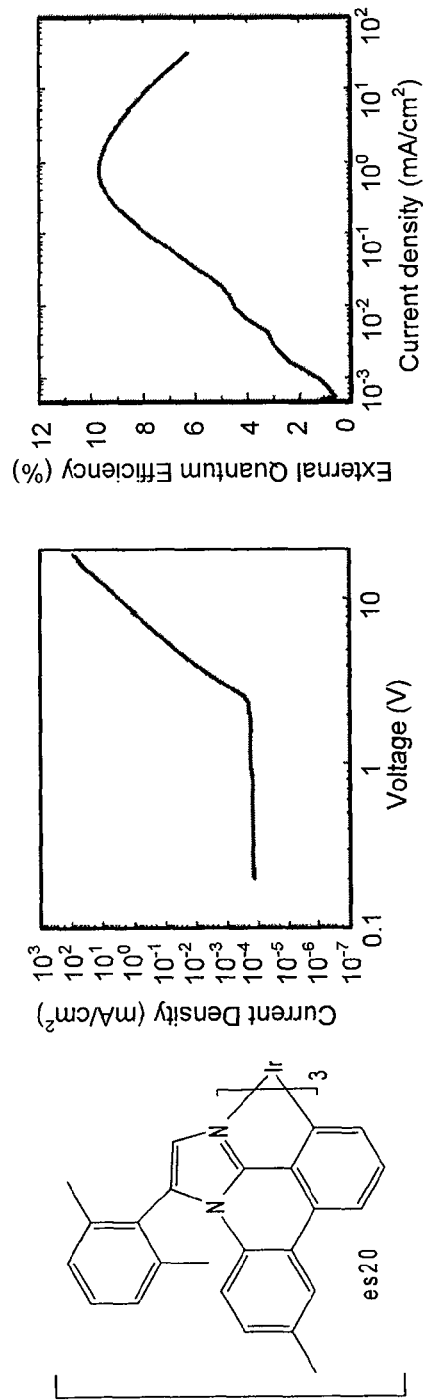
FIG. 12 shows IVL, spectral and lifetime data for a device comprising compound es20.
Figure 12:
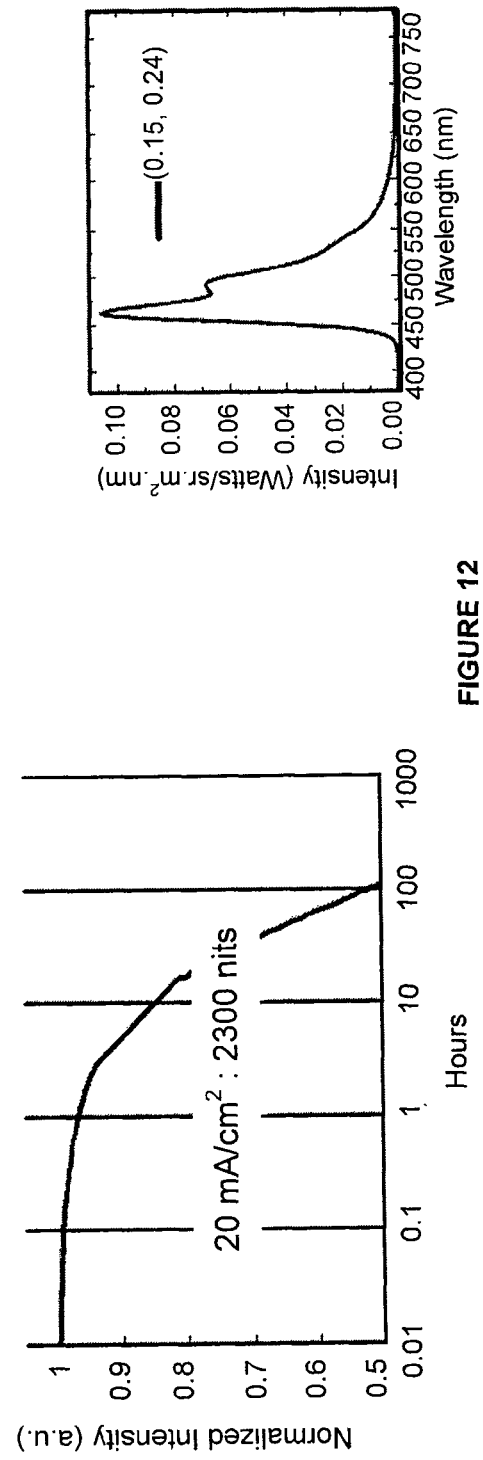
Figure 13:
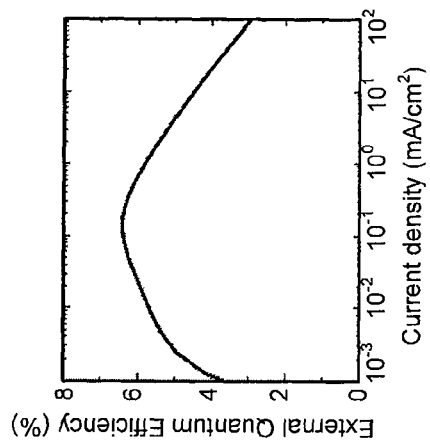
FIG. 13 shows IVL, spectral and lifetime data for a device comprising compound es4.
Figure 13:
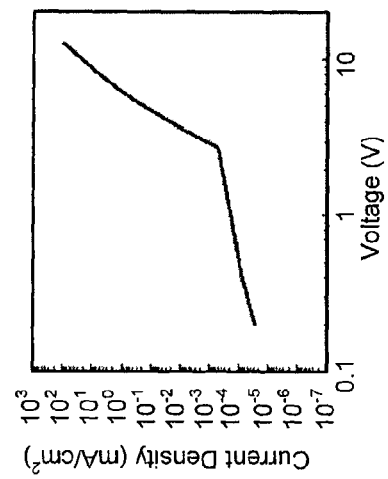
Figure 13:
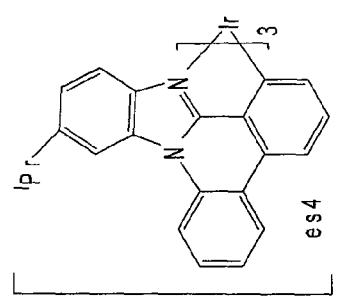
Figure 13:
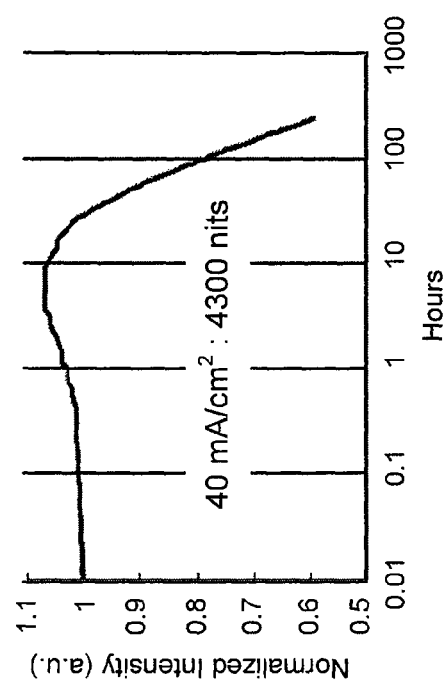
Figure 13:
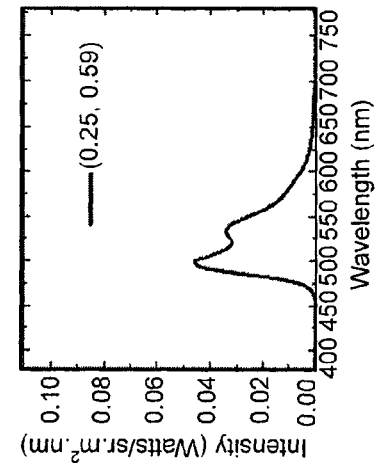
Figure 14:
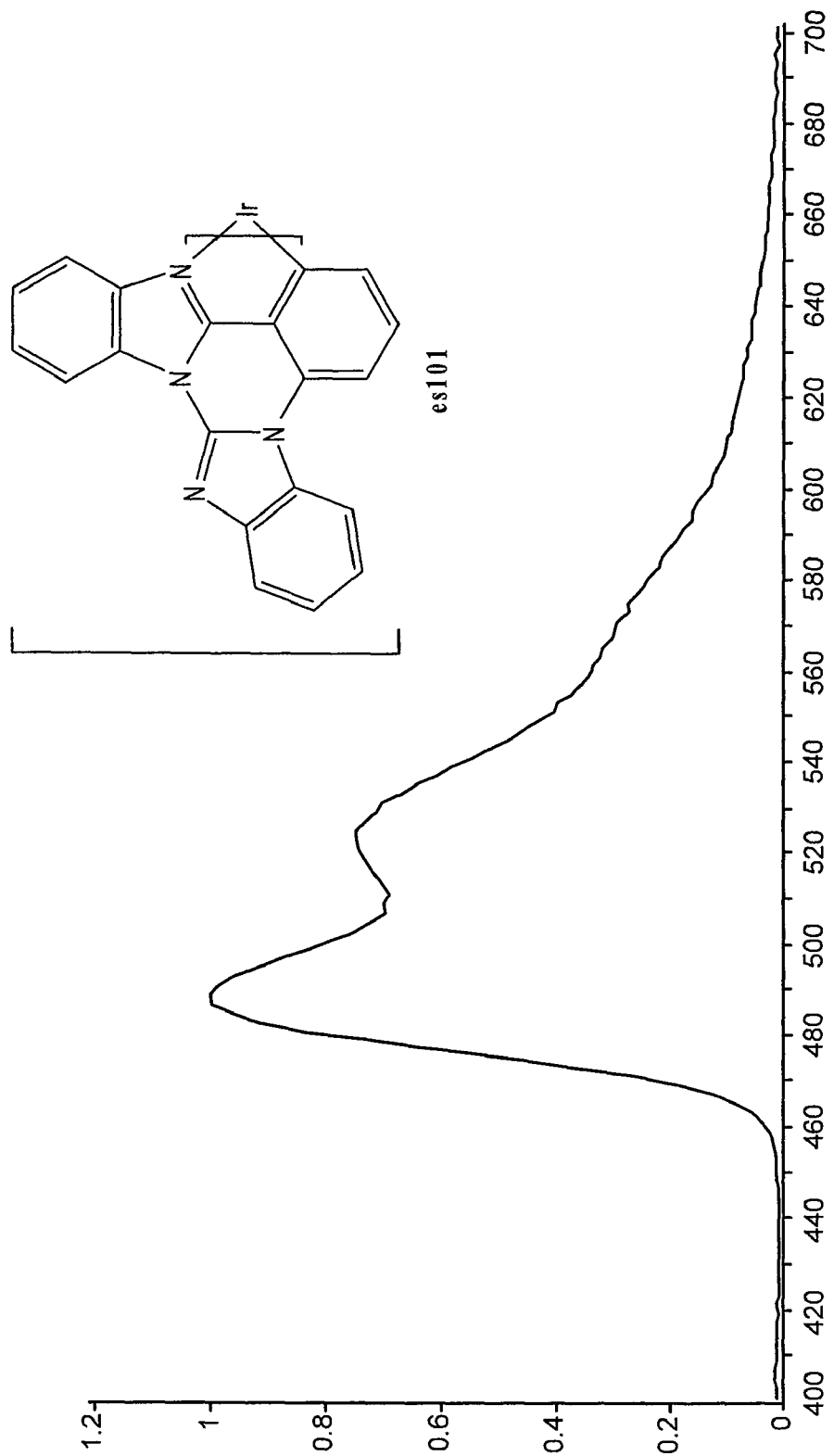
FIG. 14 shows the emission spectrum of es101 in methylene chloride solution.
Figure 15:
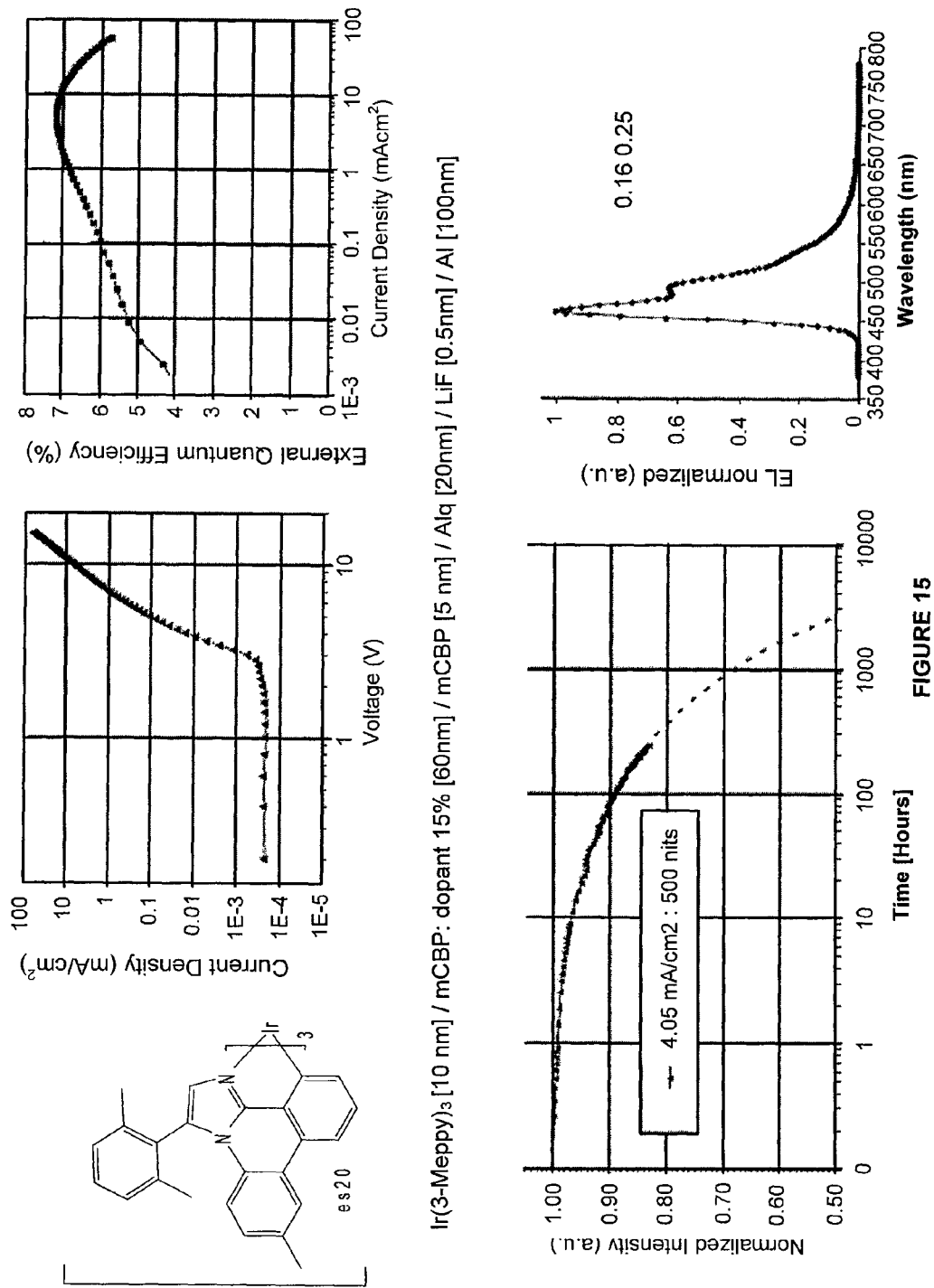
FIG. 15 shows IVL, spectral and lifetime data for a device comprising compound es20 as the emitter and Ir(3-Meppy)$_3$ as the hole injection layer material.
Figure 16:
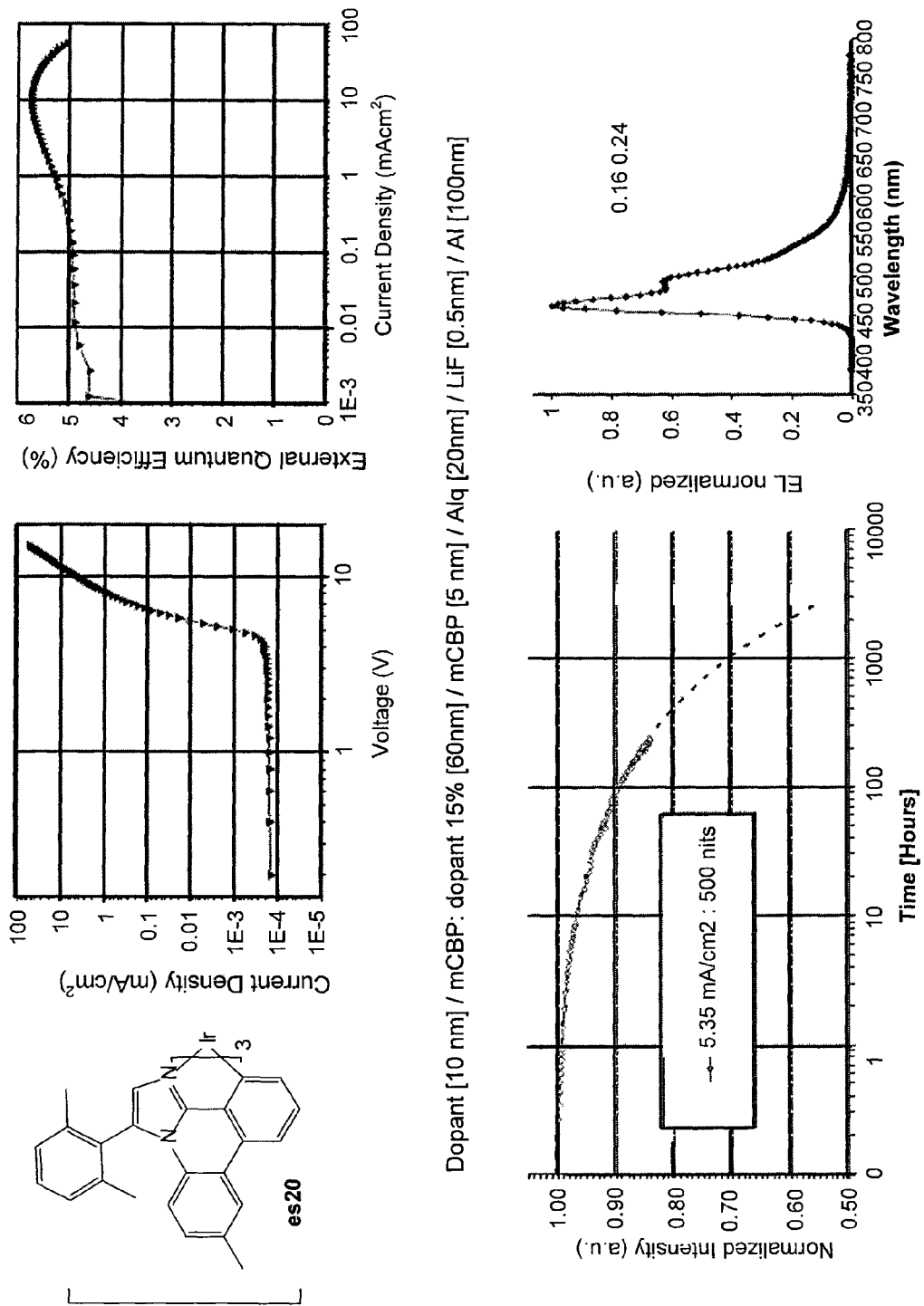
FIG. 16 shows IVL, spectral and lifetime data for a device comprising compound es20 as both emitter and hole injection layer material.
Figure 17:
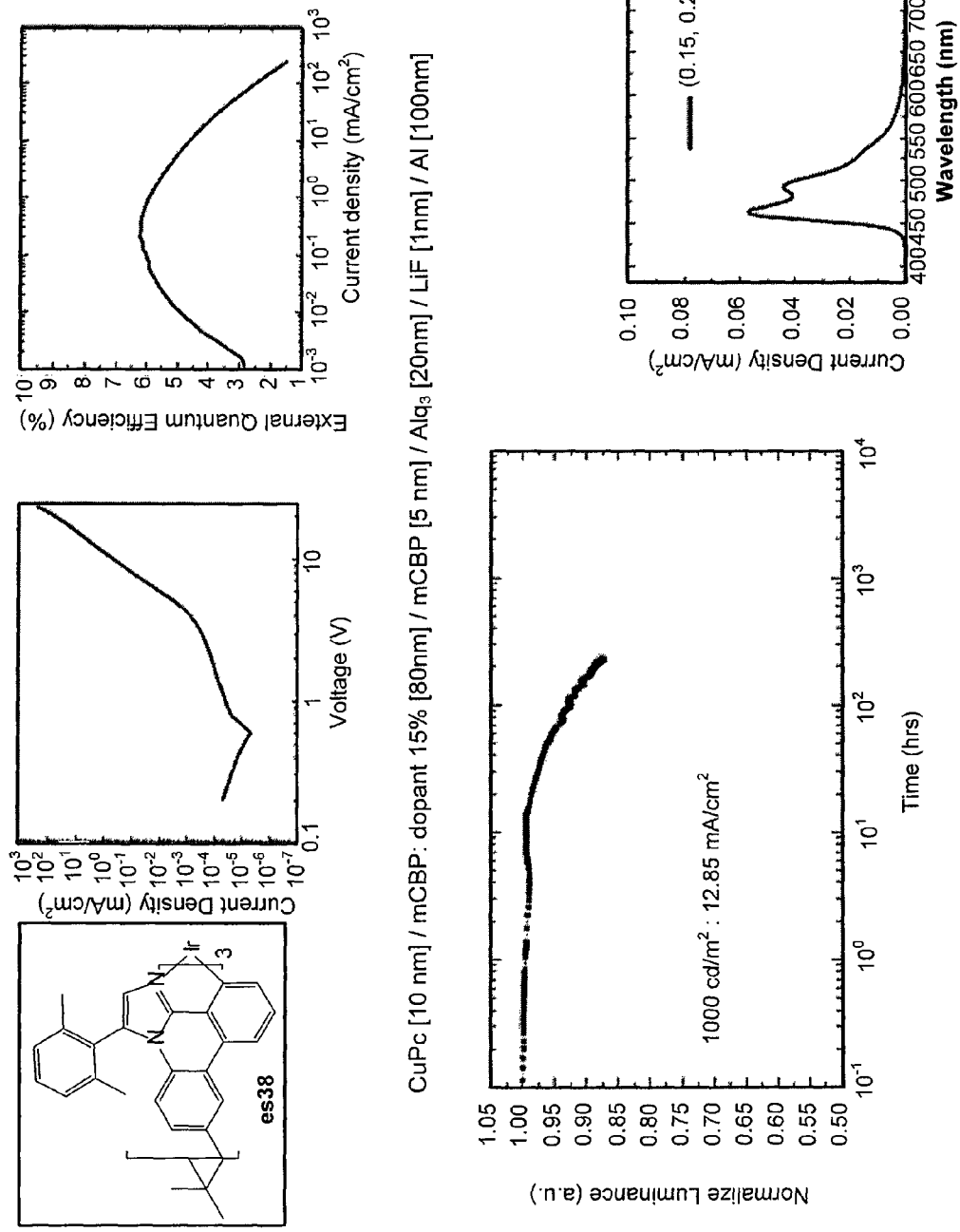
FIG. 17 shows IV, quantum efficiency, spectral and lifetime data for a device comprising compound es38 having an emissive layer 80 nm thick.
Figure 18:
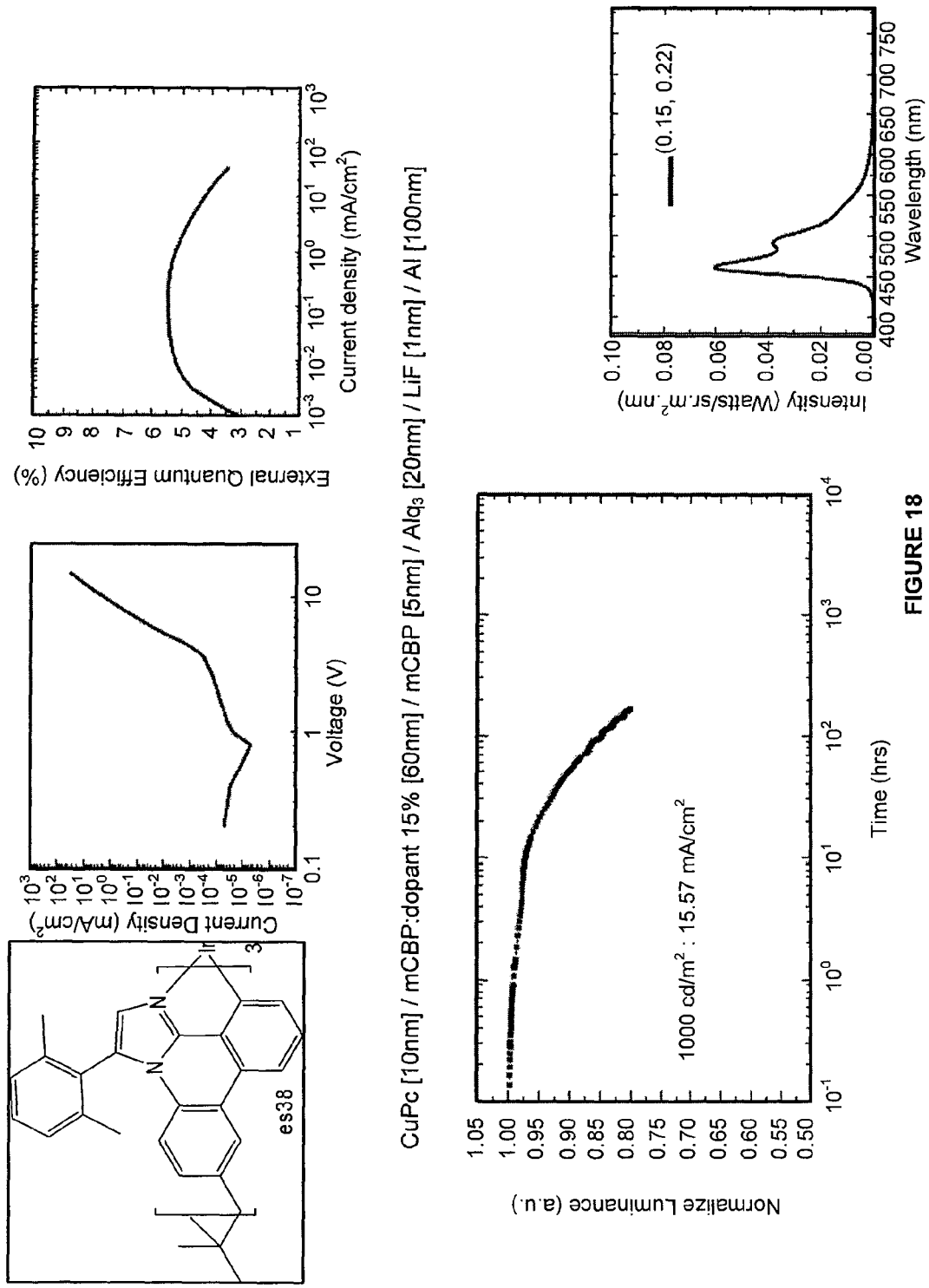
FIG. 18 shows IV, quantum efficiency, spectral and lifetime data for a device comprising compound es38 having an emissive layer 60 nm thick.
Figure 19:
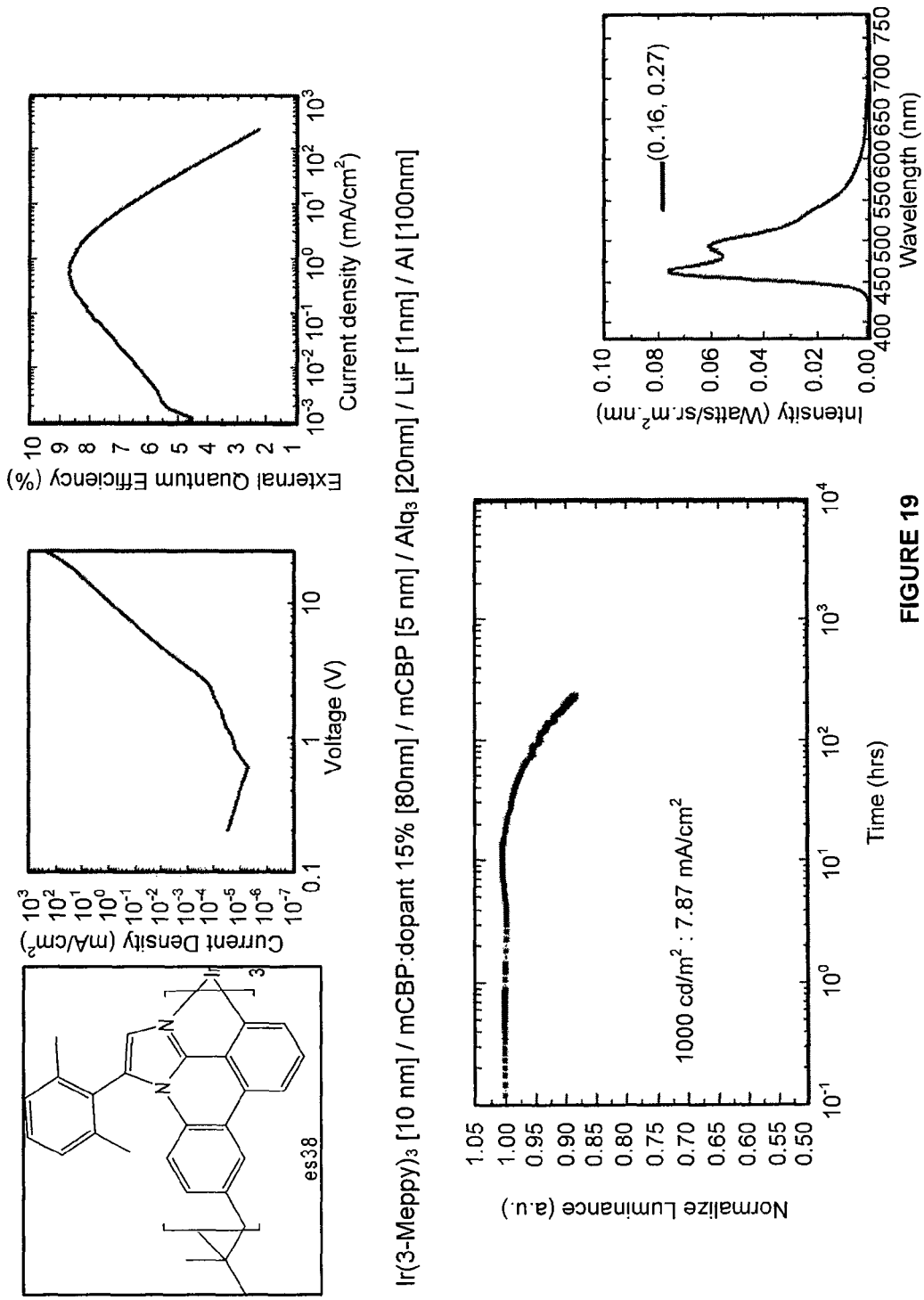
FIG. 19 shows IV, quantum efficiency, spectral and lifetime data for a device comprising compound es38 as the emitter and Ir(3-Meppy)$_3$ as the hole injection layer material, the device having an emissive layer 80 nm thick.
Figure 20:
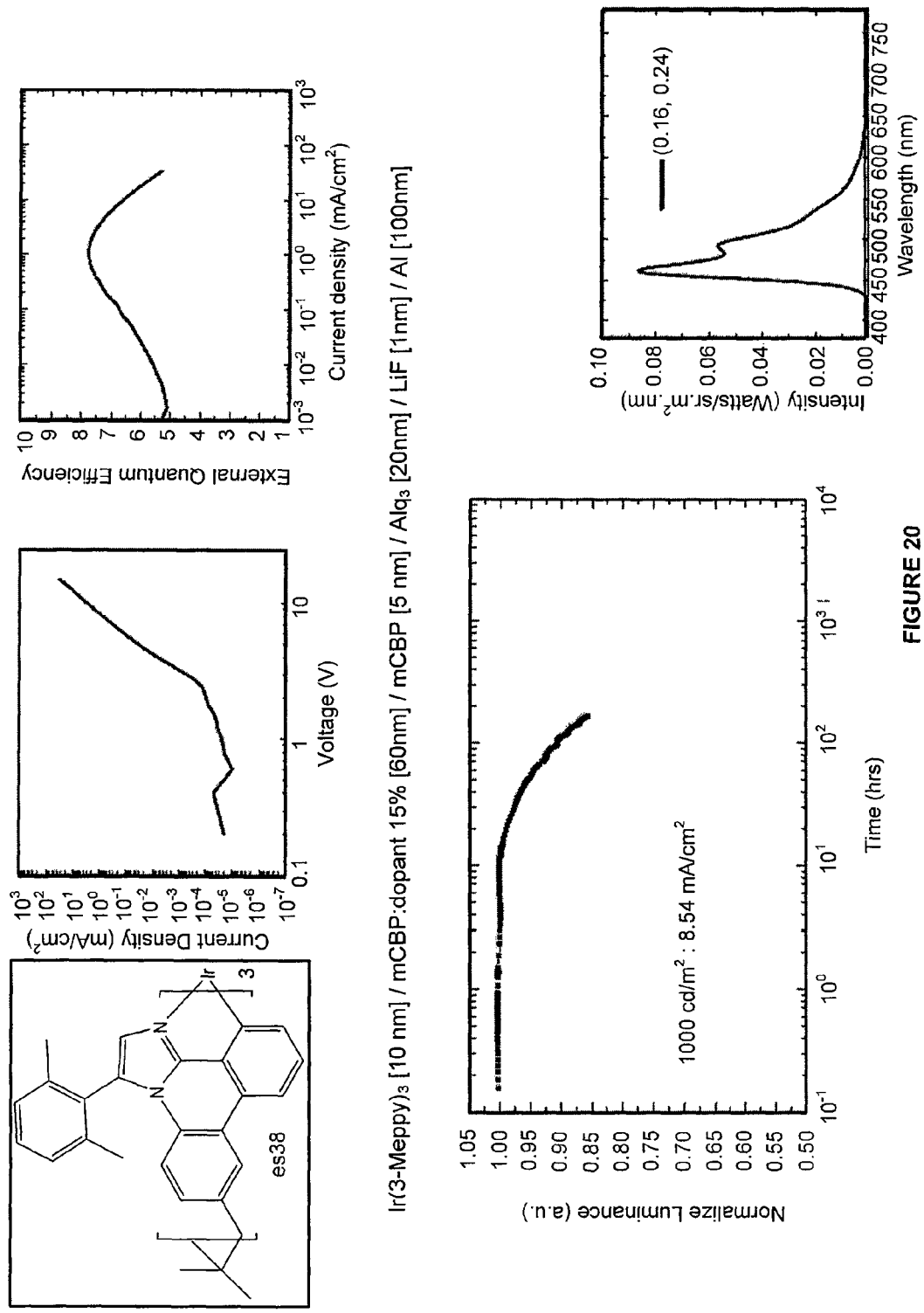
FIG. 20 shows IV, quantum efficiency, spectral and lifetime data for a device comprising compound es38 as the emitter and Ir(3-Meppy)$_3$ as the hole injection layer material, the device having an emissive layer 60 nm thick.
Figure 21:
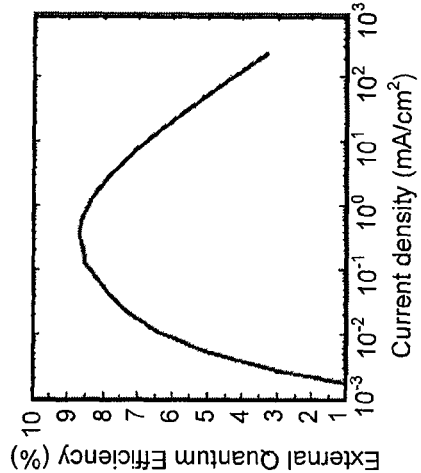
FIG. 21 shows IV, quantum efficiency, spectral and lifetime data for a device comprising compound es38 as the emitter and LG101 as the hole injection layer material, the device having an emissive layer 20 nm thick. LG101 was obtained from LG Chem. Ltd., Seoul, South Korea.
Figure 21:
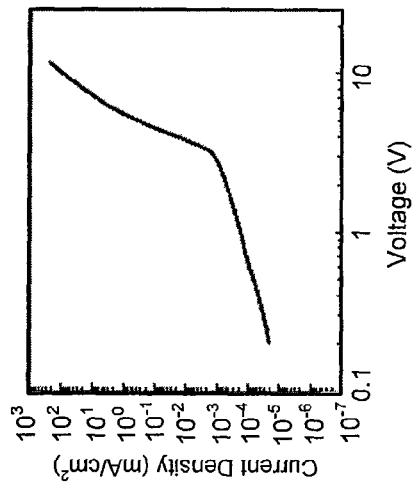
Figure 21:
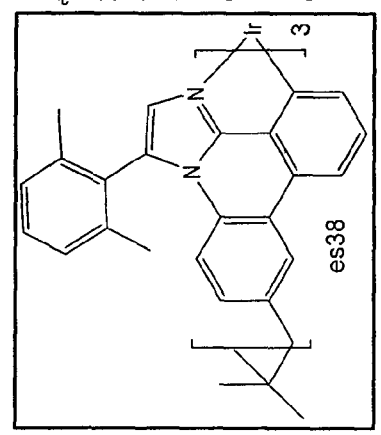
Figure 21:
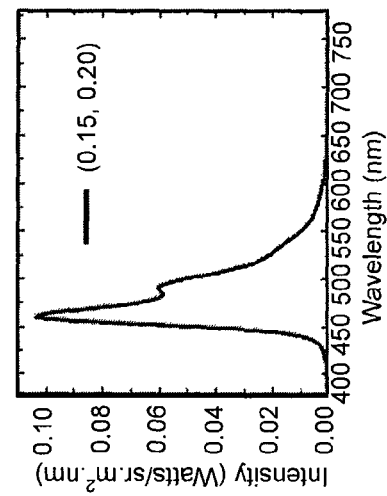
Figure 21:
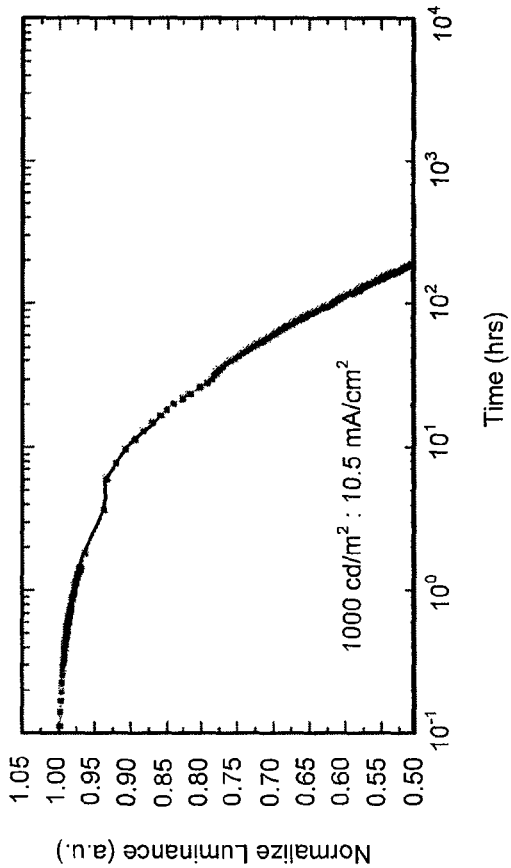

As a result, es43 illustrates a preferred substitution of a methyl group at the $R^{1a}$ position relative to es1. The color is not shifted much from the non-substituted version. However, the device incorporating es43 as the phosphorescent emitter, i.e., device example 19, has CIE of 0.15, 0.24, EQE of 12.2%, significantly improved from device example 1 (EQE=2.7%). Such EQE is very high in blue phosphorescent OLEDs to date. Presumably, as shown in the proposed energy diagram below, the higher MC state of the compound es43 may be less thermally populated during the device operation and lead to higher efficiency (FIG. 3).

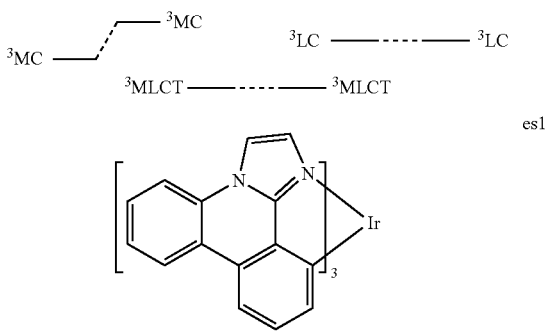

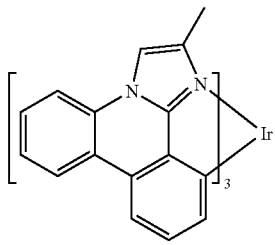

Proposed Energy Diagram of es1 and es43.

More generally, an electron donating group in the $R^{1a}$ position of complexes having Formula I is preferred for the same reasons that lead to superior results due to the methyl substitution in es43. Methyl is a preferred substituent $R^{1a}$ position based on ease of fabrication. es43 is a preferred compound. Other preferred compounds include es47, es48, es49, es50, es51, es52, es53, es54, and es55.

EXAMPLES

Unless otherwise indicated, the preparation and purification of the phosphorescent metal complexes described herein were carried out in dim room light or with yellow filters over the lights or using aluminum foil-wrapped glassware so as to minimize photo-oxidation of the metal complexes. The complexes vary considerably in their sensitivity. For example, some complexes such as es20 require only modest care and some complexes such as es1 are quite prone to light-induced decomposition in air and in certain halogenated solvents. Unless otherwise specified, the fac-isomers were isolated.

Example 1

Preparation of es1

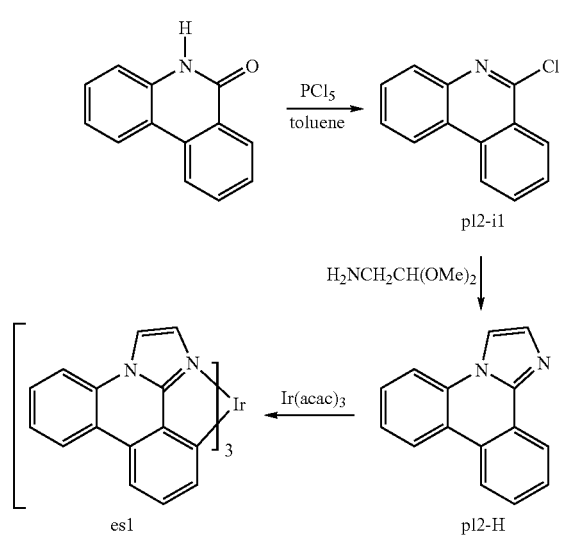

Step 1

Phenanthridinone (5.0 grams, 0.027 mole) was added to a reaction flask containing phosphorus pentachloride (6.1 grams, 0.29 mole) and 50 mL of phosphoryl chloride. The reaction mixture was refluxed for 1 hour, cooled to room temperature and diluted with toluene. The excess phosphoryl chloride and toluene were removed on a rotary evaporator. The residue was dissolved into ethyl acetate and washed with distilled water followed by brine. The solvent layer was dried over magnesium sulfate, filtered and concentrated to give pl2-i1 (5.5 grams, 96%) as an off-white solid. The product was confirmed by Mass Spectrometry and $^1$H NMR and used directly in the next step.

Step 2

Compound pl2-i1 from Step 1 (5.5 grams, 0.026 mole) was added to a reaction flask containing aminoacetaldehyde dimethylacetal (6.8 grams, 0.0646 mole) dissolved into 200 mL diglyme, heated to reflux and stirred under a nitrogen atmosphere. After 72 hours the reaction was complete as determined by TLC. The reaction mixture was cooled to room temperature and the excess solvent removed by distillation. The residue was taken up into methylene chloride and the insolubles were removed by vacuum filtration. The solvent was dried over magnesium sulfate filtered and concentrated. The crude product was purified by silica gel chromatography using 80% ethyl acetate and 20% methylene chloride as the eluents. The purified product was collected, washed with hexanes, and dried to give pl2-H (2.6 grams, 46% yield) as an off-white solid.

Step 3

Compound pl2-H (0.67 g, 3.1 mmol) from Step 2 above and iridium(III) acetylacetonate (0.38 gram, 0.77 mmol) were heated to 250° C. overnight under a nitrogen atmosphere. After the reaction was cooled, the residue was taken up into a 1:1 mixture of ethyl acetate and methylene chloride, filtered and purified by a first silica gel chromatography using 1:1 ethyl acetate:hexanes followed by a second silica gel column using 1:1 chloroform:hexanes to afford es1 (0.15 gram, 23% yield) as a beige solid. The high energy peak for the phosphorescence in dichloromethane solution was centered at 458 nm with CIE coordinates 0.18, 0.27.

Example 2

General Procedure A for Imidazophenanthridine Ligand Syntheses

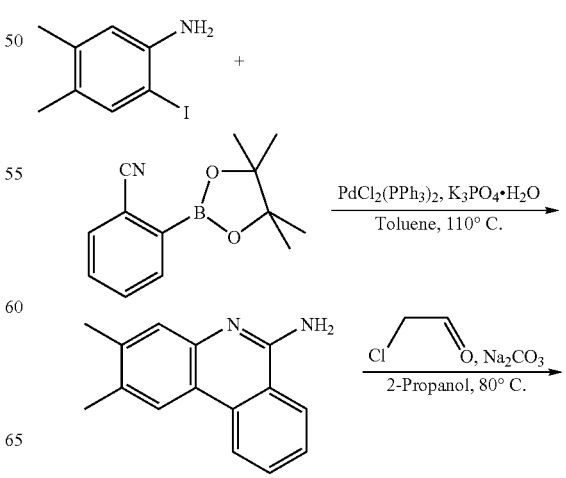

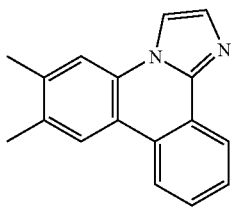

To a 1 L round flask was added 2-iodo-4,5-dimethylanaline (24.7 g, 100 mmol), 2-cyanophenylboronic acid, pinacol ester (27.5 g, 120 mmol), dichlorobis(triphenylphosphine)palladium(II) (3.51 g, 5 mmol), potassium phosphate tribasic monohydrate (46.0 g, 200 mmol), and 400 mL of toluene. The reaction was heated to reflux and stirred under a nitrogen atmosphere for 4 hours. After cooling, the precipitate formed was filtered and washed with toluene, hexanes and water. Yield was 14 g.

To a 1 L round flask was added the above intermediate, chloroacetaldehyde (50% wt. in water, 15.7 g, 100 mmol), sodium carbonate (15.9 g, 150 mmol), and 300 mL of 2-propanol. The mixture was heated to reflux for 2 hours. The solvents were removed and the residue was extracted with $CH_2Cl_2$ and further purified by a silica gel column. Yield was 13

Example 3

General Procedure for Tris(Bidentate Ligand)Iridium Complex Synthesis

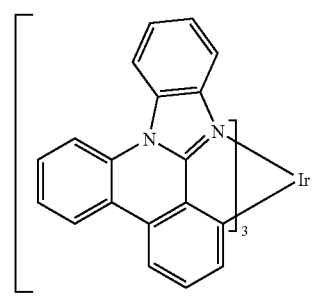

The following procedure was conducted in dim room light or using yellow filters over the light sources or with aluminum foil-wrapped glassware to minimize photo-oxidation of the metal complex. A 50 mL Schlenk tube flask was charged with 6,7-dimethylimidazo[1,2-f]phenanthridine (1.68 g, 6.8 mmol) and tris(acetylacetonate)iridium(III) (0.59 g, 1.4 mmol). The reaction mixture was stirred under a nitrogen atmosphere and heated in a sand bath at 240° C. for 48 hours. After cooling, the solidified mixture was dissolved in $CH_2Cl_2$ and further purified by a silica gel column to give es12 (0.30 g). The structure and purity was confirmed by $^1H$ NMR analysis. $\lambda_{max}$ emission=456, 486 nm (in $CH_2Cl_2$ solution at room temperature); CIE=(0.18, 0.23).

Example 4

Preparation of es3

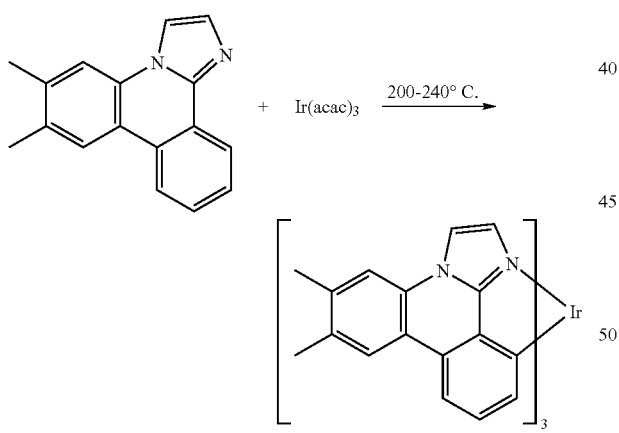

A 50 mL Schlenk tube flask was charged with 8b,13-diaza-indeno[1,2-f]phenanthrene (3.49 g, 13 mmol) and tris(acetylacetonate)iridium(III) (1.27 g, 2.6 mmol). The reaction mixture was stirred under a nitrogen atmosphere and heated in a sand bath at 240° C. for 48 hours. After cooling, the solidified mixture was dissolved in $CH_2Cl_2$ and further purified by a silica gel column to give es3 (1.4 g). $^1H$ NMR result confirmed the desired compound. $\lambda_{max}$ of emission=492, 524 nm ($CH_2Cl_2$ solution at room temperature), CIE=(0.23, 0.51).

Example 5

Preparation of es4

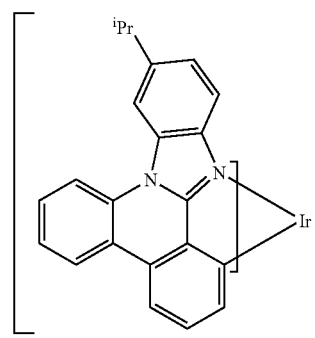

A 50 mL Schlenk tube flask was charged with 10-isopropyl-8b,13-diaza-indeno[1,2-f]phenanthrene (6.07 g, 19.6 mmol) and tris(acetylacetonate)iridium(III) (1.91 g, 3.92 mmol). The reaction mixture was stirred under a nitrogen atmosphere and heated in a sand bath at 240° C. for 48 hours. After cooling, the solidified mixture was dissolved in $CH_2Cl_2$ and further purified by a silica gel column to give es4 (0.7 g).

$^1$H NMR result confirmed the desired compound. $\lambda_{max}$ of emission=496 nm (CH$_2$Cl$_2$ solution at room temperature), CIE=(0.26, 0.57).

Example 6

Preparation of es7

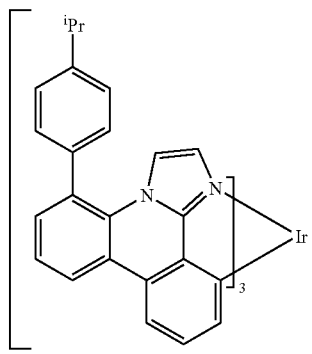

Step 1: Synthesis of 4-bromo-6-aminophenanthridine

A three neck 1 L round bottom flask was charged with 2,6-dibromoaniline (143.51 g, 0.57 mole), 2-cyanophenylboronic acid trimethylene ester (34.35 g, 0.19 mole), K$_3$PO$_4$·H$_2$O (43.89 g, 0.1906 mole), PdCl$_2$(PPh$_3$)$_2$ (6.67 g, 9.5 mmole) and anhydrous toluene (700 ml). The reaction mixture was heated to 100° C. under nitrogen for 6 hrs. The reaction mixture was then concentrated to dryness and subjected to column chromatography to obtain the title compound (19.11 g, 36.7%).

Step 2: Synthesis of 5-bromo-imidazo[1,2-f]phenanthridine

To a mixture of 4-bromo-6-aminophenanthridine (19.11 g, 69.91 mmole), sodium bicarbonate (12.3 g, 146 mmole) in 2-propanol (200 ml) was added chloroacetaldehyde (50% aqueous soln. 17.35 g). After the reaction mixture was heated at 75° C. for 5 hrs., the solvent was removed. The residue was redissolved in methylene chloride and washed with water. The organic fractions were combined, dried over sodium sulfate, filtered, and concentrated in vacuo. The crude mixture was purified by chromography on silica gel using hexane/ethyl acetate (80/20) to obtain the title compound (13 g, 62%).

Step 3: Synthesis of 5-(4-isopropylphenyl)-imidazo[1,2-f]phenanthridine

A three neck 1 L round bottom flask was charged with 5-bromo-imidazo[1,2-f]phenanthridine (4.55 g, 15.31 mmole), 4-isopropylphenylboronic acid (3.59 g, 21.89 mmole), potassium carbonate (2N aqueous soln., 27 ml), Pd(OAc)$_2$ (223 mg, 0.99 mmole), triphenylphosphine (1.044 g, 3.98 mmole) and 100 ml of 1,2-dimethoxyethane. The reaction mixture was heated to 80° C. under nitrogen for 17 hrs. The reaction mixture was diluted with methylene chloride and washed by brine. The organic fractions were combined, dried over sodium sulfate, filtered, and concentrated in vacuo. The crude mixture was purified by chromography on silica gel using hexane/ethyl acetate (80/20) to obtain pure 5-(4-isopropylphenyl)-imidazo[1,2-f]phenanthridine (4 g, 77%).

Step 4: Complexation

A 50 mL Schlenk tube flask was charged with 5-(4-isopropylphenyl)imidazo[1,2-f]phenanthridine (2.94 g, 8.74 mmol) and tris(acetylacetonate)iridium(III) (0.86 g, 1.75 mmol). The reaction mixture was stirred under a nitrogen atmosphere and heated in a sand bath at 240° C. for 48 hours. After cooling, the solidified mixture was dissolved in CH$_2$Cl$_2$ and further purified by a silica gel column to give es7 (0.7 g). $^1$H NMR result confirmed the desired compound. $\lambda_{max}$ of emission=496 nm (CH$_2$Cl$_2$ solution at room temperature), CIE=(0.26, 0.57).

Example 7

Preparation of es10

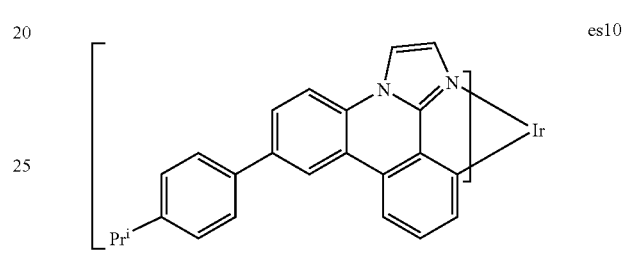

Step 1: Ligand Synthesis

To a 500 mL round flask was added 7-chloroimidazo[1,2-f]phenanthridine (3.8 g, 15 mmol, prepared from the general procedure A), 4-isopropylphenylboronic acid (3.7 g, 23 mmol), palladium(II) acetate (0.084 g, 0.38 mmol), 2-dicyclohexylphosphino-2',6'-dimethoxybiphenyl (S-Phos, 0.31 g, 0.75 mmol), potassium phosphate tribasic monohydrate (6.9 g, 30 mmol), and 200 mL of toluene. The reaction was heated to reflux and stirred under a nitrogen atmosphere for 12 hours. After cooling, the mixture was purified by a silica gel column. Yield was 3.8 g.

Step 2: Complexation

A 50 mL Schlenk tube flask was charged with 7-(4-isopropylphenyl)imidazo[1,2-f]phenanthridine (3.8 g, 11.3 mmol) and tris(acetylacetonate)iridium(III) (11.1 g, 2.26 mmol). The reaction mixture was stirred under a nitrogen atmosphere and heated in a sand bath at 240° C. for 48 hours. After cooling, the solidified mixture was dissolved in CH$_2$Cl$_2$ and further purified by a silica gel column to give es10 (1.2 g). $^1$H NMR result confirmed the desired compound. $\lambda_{max}$ of emission=464, 492 nm (CH$_2$Cl$_2$ solution at room temperature), CIE=(0.20, 0.32).

Example 8

Preparation of es16

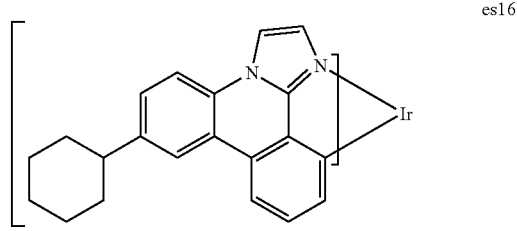

Step 1: Ligand Synthesis

To a 500 mL round flask was added 7-chloroimidazo[1,2-f]phenanthridine (5.2 g, 20.6 mmol, prepared from the general procedure A), tris(acetylacetonate)iron(III) (0.35 g, 1.0 mmol), 30 mL of NMP and 300 mL of dry THF. To this mixture with stirring, 15 mL of cyclohexylmagnesium chloride solution (2M in ether) was added dropwise at room temperature. The reaction was completed after the addition. The mixture was quenched by 1N HCl solution. After general work-up and purification by a silica gel column, yield was 3.4 g.

Step 2: Complexation

A 50 mL Schlenk tube flask was charged with 7-cyclohexylimidazo[1,2-f]phenanthridine (3.4 g, 11.2 mmol) and tris(acetylacetonate)iridium(III) (1.1 g, 2.25 mmol). The reaction mixture was stirred under a nitrogen atmosphere and heated in a sand bath at 240° C. for 48 hours. After cooling, the solidified mixture was dissolved in $CH_2Cl_2$ and further purified by a silica gel column to give es8 (1.5 g). $^1$H NMR result confirmed the desired compound. $\lambda_{max}$ of emission=462, 486 nm ($CH_2Cl_2$ solution at room temperature), CIE=(0.17, 0.27).

Example 9

Preparation of es18

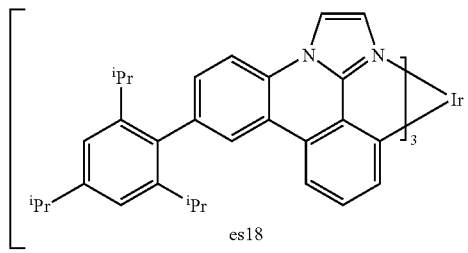

es18

Step 1: Ligand Synthesis

To a 500 mL round flask was added 7-chloroimidazo[1,2-f]phenanthridine (5.1 g, 20 mmol, prepared from the general procedure A), 2,4,6-triisopropylphenylboronic acid (9.9 g, 40 mmol), $Pd_2(dba)_3$ (0.92 g, 1.0 mmol), 2-dicyclohexylphosphino-2',6'-dimethoxybiphenyl (S-Phos, 1.64 g, 4.0 mmol), potassium phosphate tribasic (12.7 g, 60 mmol), and 200 mL of toluene. The reaction was heated to reflux and stirred under a nitrogen atmosphere for 72 hours. After cooling, the mixture was purified by a silica gel column. Yield was 2.6 g.

Step 2: Complexation

A 50 mL Schlenk tube flask was charged with 7-(2,4,6-triisopropylphenyl)imidazo[1,2-f]phenanthridine (2.6 g, 6.2 mmol) and tris(acetylacetonate)iridium(III) (0.61 g, 1.2 mmol). The reaction mixture was stirred under a nitrogen atmosphere and heated in a sand bath at 240° C. for 48 hours.

After cooling, the solidified mixture was dissolved in $CH_2Cl_2$ and further purified by a silica gel column to give es18 (0.3 g). $^1$H NMR result confirmed the desired compound. $\lambda_{max}$ of emission=464, 488 nm ($CH_2Cl_2$ solution at room temperature), CIE=(0.17, 0.29).

Example 10

Preparation of es20

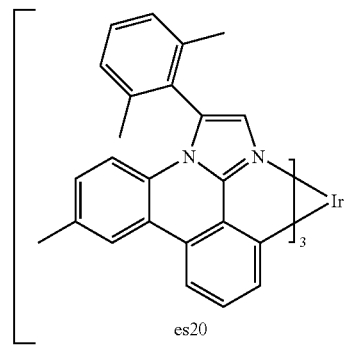

es20

Step 1

To a 1 L round flask was added 7-methylimidazo[1,2-f]phenanthridine (5.7 g, 24.5 mmol, prepared from the general procedure A), and 200 mL of dry DMF. To this mixture with stirring, 100 mL of N-bromosuccinimide DMF solution (4.6 g, 25.7 mmol) was added dropwise at room temperature in the dark. The reaction mixture was continued to stir overnight. Then the mixture was poured into 1 L of water with stirring. The precipitate was collected by filtration, and further washed with copious amount of water, and last with MeOH (50 mL×2), and then dried. Yield of 3-bromo-7-methylimidazo [1,2-f]phenanthridine was 6.5

Step 2

To a 500 mL round flask was added 3-bromo-7-methylimidazo[1,2-f]phenanthridine (6.2 g, 20 mmol), 2,6-dimethylphenylboronic acid (9.0 g, 60 mmol), $Pd_2(dba)_3$ (4.58 g, 5.0 mmol), 2-dicyclohexylphosphino-2',6'-dimethoxybiphenyl (S-Phos, 8.2 g, 20 mmol), potassium phosphate tribasic (17.0 g, 80 mmol), and 200 mL of toluene. The reaction was heated to reflux and stirred under a nitrogen atmosphere for 84 hours. After cooling, the mixture was purified by a silica gel column. Yield was 4.0 g.

Step 3

A 50 mL Schlenk tube flask was charged with 3-(2,6-dimethylphenyl)-7-methylimidazo[1,2-f]phenanthridine (3.3 g, 10 mmol) and tris(acetylacetonate)iridium(III) (0.98 g, 2.0 mmol). The reaction mixture was stirred under a nitrogen atmosphere and heated in a sand bath at 240° C. for 48 hours. After cooling, the solidified mixture was dissolved in $CH_2Cl_2$ and further purified by a silica gel column to give es20 (0.8 g). $^1$H NMR result confirmed the desired compound. $\lambda_{max}$ of emission=466, 492 nm ($CH_2Cl_2$ solution at room temperature), CIE=(0.17, 0.30).

Example 11

Preparation of es21

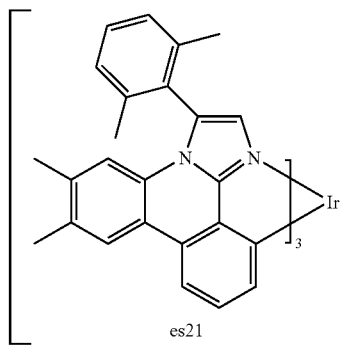

es21

Step 1

To a 1 L round flask was added 6,7-dimethylimidazo[1,2-f]phenanthridine (13.0 g, 52.8 mmol, prepared from the general procedure A), and 400 mL of dry DMF. To this mixture with stirring, 150 mL of N-bromosuccinimide DMF solution (10.3 g, 58 mmol) was added dropwise at room temperature in the dark. The reaction mixture was continued to stir overnight. Then the mixture was poured into 1 L of water with stirring. The precipitate was collected by filtration, and further washed with copious amount of water, and last with MeOH (50 mL×2), and dried. Yield of 3-bromo-6,7-dimethylimidazo[1,2-f]phenanthridine was 14.7 g.

Step 2

To a 500 mL round flask was added 3-bromo-6,7-dimethylimidazo[1,2-f]phenanthridine (6.5 g, 20 mmol), 2,6-dimethylphenylboronic acid (9.0 g, 60 mmol), Pd$_2$(dba)$_3$ (4.58 g, 5.0 mmol), 2-dicyclohexylphosphino-2',6'-dimethoxybiphenyl (S-Phos, 8.2 g, 20 mmol), potassium phosphate tribasic (17.0 g, 80 mmol), and 200 mL of toluene. The reaction was heated to reflux and stirred under a nitrogen atmosphere for 84 hours. After cooling, the mixture was purified by a silica gel column. Yield was 2.6 g.

Step 3

A 50 mL Schlenk tube flask was charged with 3-(2,6-dimethylphenyl)-6,7-dimethylimidazo[1,2-f]phenanthridine (2.6 g, 7.4 mmol) and tris(acetylacetonate)iridium(III) (0.73 g, 1.5 mmol). The reaction mixture was stirred under a nitrogen atmosphere and heated in a sand bath at 240° C. for 48 hours. After cooling, the solidified mixture was dissolved in CH$_2$Cl$_2$ and further purified by a silica gel column to give es21 (0.35 g). $^1$H NMR result confirmed the desired compound. $\lambda_{max}$ of emission=460, 490 nm (CH$_2$Cl$_2$ solution at room temperature), CIE=(0.16, 0.27).

Example 12

Preparation of es26

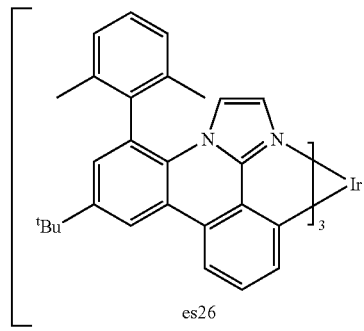

es26

Step 1

To a 500 mL round flask was added 5-bromo-7-tert-butyl-imidazo[1,2-f]phenanthridine (3.9 g, 11 mmol, prepared from general procedure A), 2,6-dimethylphenylboronic acid (3.5 g, 23 mmol), Pd$_2$(dba)$_3$ (0.51 g, 0.56 mmol), 2-dicyclohexylphosphino-2',6'-dimethoxybiphenyl (S-Phos, 0.91 g, 2.2 mmol), potassium phosphate tribasic (7.2 g, 34 mmol), and 60 mL of toluene. The reaction was heated to reflux and stirred under a nitrogen atmosphere for 48 hours. After cooling, the mixture was purified by a silica gel column. Yield was 1.2 g.

Step 2

A 50 mL Schlenk tube flask was charged with 5-(2,6-dimethylphenyl)-7-tert-butylimidazo[1,2-f]phenanthridine (0.40 g, 1.1 mmol) and tris(acetylacetonate)iridium(III) (0.10 g, 0.2 mmol). The reaction mixture was stirred under a nitrogen atmosphere and heated in a sand bath at 240° C. for 24 hours. After cooling, the solidified mixture was dissolved in CH$_2$Cl$_2$ and further purified by a silica gel column to give fac-tris iridium(III) (0.01 g). $^1$H NMR result confirmed the desired compound. $\lambda_{max}$ of emission=462, 488 nm (CH$_2$Cl$_2$ solution at room temperature).

Example 13

Preparation of es22

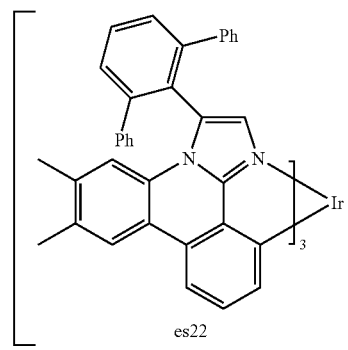

es22

Step 1

To a 500 mL round flask was added 3-bromo-6,7-dimethylimidazo[1,2-f]phenanthridine (8.2 g, 25.2 mmol), 2,6-dichlorophenylboronic acid (19.2 g, 100.9 mmol), Pd$_2$(dba)$_3$ (2.29 g, 2.5 mmol), 2-dicyclohexylphosphino-2',6'-dimethoxybiphenyl (S-Phos, 4.11 g, 10.0 mmol), potassium phosphate tribasic (26.7 g, 126 mmol), and 250 mL of toluene. The reaction was heated to reflux and stirred under a nitrogen atmosphere for 48 hours. After cooling, the mixture was purified by a silica gel column. Yield of 3-(2,6-dichlorophenyl)-6,7-dimethylimidazo[1,2-f]phenanthridine was 2.4 g.

Step 2

To a 500 mL round flask was added 3-(2,6-dichlorophenyl)-6,7-dimethylimidazo[1,2-f]phenanthridine (2.4 g, 6.1 mmol), phenylboronic acid (3.74 g, 30 mmol), Pd$_2$(dba)$_3$ (1.1 g, 1.2 mmol), 2-dicyclohexylphosphino-2',6'-dimethoxybiphenyl (S-Phos, 1.97 g, 4.8 mmol), potassium phosphate tribasic (7.64 g, 36 mmol), and 100 mL of toluene. The reaction was heated to reflux and stirred under a nitrogen atmosphere for 12 hours. After cooling, the mixture was purified by a silica gel column. Yield of 3-(2,6-diphenylphenyl)-6,7-dimethylimidazo[1,2-f]phenanthridine was 0.9 g.

Step 3

A 25 mL Schlenk tube flask was charged with 3-(2,6-diphenylphenyl)-6,7-dimethylimidazo[1,2-f]phenanthridine (0.095 g, 0.2 mmol) and tris(acetylacetonate)iridium(III) (0.025 g, 0.05 mmol). The reaction mixture was stirred under a nitrogen atmosphere and heated in a sand bath at 240° C. for 24 hours. After cooling, the solidified mixture was dissolved in CH$_2$Cl$_2$ and further purified by a silica gel column to give es22 (0.01 g). $^1$H NMR result confirmed the desired compound. $\lambda_{max}$ of emission=468, 496 nm (CH$_2$Cl$_2$ solution at room temperature), CIE=(0.19, 0.35).

Example 14

Preparation of es25

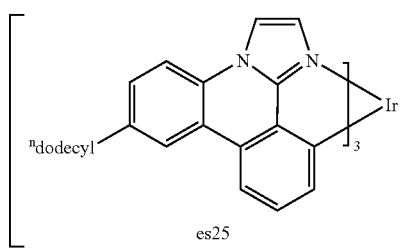

es25

A 50 mL Schlenk tube flask was charged with 7-n-dodecylimidazo[1,2-f]phenanthridine (3.66 g, 9.34 mmol prepared via general procedure A) and tris(acetylacetonate)iridium(III) (0.92 g, 1.87 mmol). The reaction mixture was stirred under a nitrogen atmosphere and heated in a sand bath at 240° C. for 48 hours. After cooling, the solidified mixture was dissolved in CH$_2$Cl$_2$ and further purified by a silica gel column to give es25 (1.5 g). $^1$H NMR result confirmed the desired compound.

Example 15

Preparation of es9

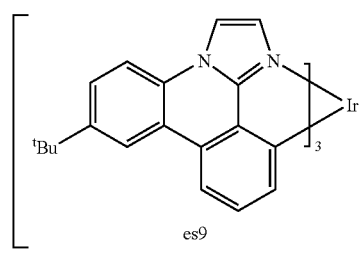

es9

Step 1: Synthesis of 2-(1,3,2-dioxaborinan-2-yl)benzonitrile 49.0 g (334 mmol) 2-cyanobenzeneboronic acid and 25.9 g (340 mmol) 1,3-propanediol were dissolved in 1 L CH$_2$Cl$_2$ with stirring in a 2 L round bottom flask for 20 h. The solution was then poured over a filter with suction to remove gummy solids. The filtrate was then dried with anhydrous MgSO$_4$ to remove residual water, filtered and evaporated of solvent to give light-colored oil. The oil was then dissolved in CH$_2$Cl$_2$ and purified on a silica gel plug using CH$_2$Cl$_2$ as eluent. The product fractions were evaporated down to give the product as clear oil (35.7 g, 57.2% yield).

Step 2: Synthesis of 2-(tert-butyl)-6-aminophenanthridine 35.7 g (190 mmol) 2-(1,3,2-dioxaborinan-2-yl)benzonitrile, 31.9 g (158 mmol) 2-bromo-4-(tertbutyl)aniline, 3.6 g (3.16 mmol) tetrakis(triphenylphosphine) palladium(0) and 59.0 g (427 mmol) K$_2$CO$_3$ were heated to reflux in a 2 L flask containing 400 ml toluene and 300 mL ethanol. The reaction mixture was heated for 19 hours under constant N$_2$ purge. HPLC of the reaction mixture indicated consumption of the starting aniline. The mixture was cooled and then filtered to remove the base. The base was washed with EtOAc to remove trace organic. The combined filtrate was evaporated down to give impure oil. The oil was purified on a column of silica using 95/5/0.05 CH$_2$Cl$_2$/MeOH/NH$_4$OH as eluent to obtain separation. The product fractions were evaporated of solvent and the resultant residue recrystallized from CH$_2$Cl$_2$/hexanes to yield 14.0 g of the target compound as white solids (35.5% yield, confirmed by GC-MS).

Step 3: Synthesis of es9 Ligand

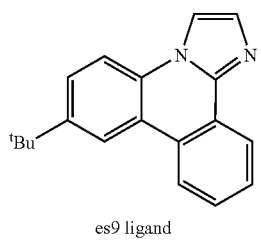

es9 ligand 13.0 g (52 mmol) 2-(tert-butyl)-6-aminophenanthridine, 12.3 g (78 mmol, 50% v/v in H$_2$O) chloroacetaldehyde, and 8.74 g (104 mmol) sodium bicarbonate were added to a 500 mL flask and refluxed in 200 mL 2-propanol for 35 hours under N$_2$ atmosphere. Upon completion, the mixture was cooled whereupon TLC and HPLC indicated complete consumption of the starting phenanthridine. The mixture was taken up in ethyl acetate and filtered to remove base. The filtrate was then evaporated to yield light amber oil. The oil was purified on a column of silica using 95/5/0.05 CH$_2$Cl$_2$/MeOH/NH$_4$OH as eluent. Alternatively, the ligand could be purified using automated chromatography with an Al$_2$O$_3$ column and a gradient of 2% EtOAc/hexanes—20% EtOAc/hexanes as eluent. The product fractions from these purifications were evaporated of solvent and recrystallized from methylene chloride/hexanes to yield a total of 10.8 g es9 ligand as a white solid (76.1% yield, NMR confirmed).

Step 4

10.6 g (38.7 mmol) es9 ligand and 4.76 g (9.7 mmol) Ir(acac)$_3$ were added to a 50 mL Schlenk tube equipped with a stirbar. 20 drops of tridecane were added, the tube was sealed with a septa and vacuum degassed thoroughly with N$_2$. The tube was submersed in a sand bath and heated at 245° C. for 72 hours under N$_2$ atmosphere. The cooled mixture was then taken up in CH$_2$Cl$_2$ with sonication to dissolve the impurities. The mixture was filtered in vacuo and the solids rinsed with CH$_2$Cl$_2$ and hexanes to give dark yellow solids in the amount of 8.5 g. The solids were then dissolved in 1 L boiling chlorobenzene and poured over a celite mat (hot) to remove impurities. The resultant filtrate was evaporated to 500 mL allowing the dopant to recrystallize as bright yellow solids (6.5 g, 66.4% yield, NMR confirmed, 99.3% HPLC assay). As a further method of purification, 3.5 g of the dopant was sublimed in a three zone sublimator at 370° C. and 1.0×10$^{-5}$ Torr vacuum to give 400 mg es9 as a bright yellow solid (100% HPLC assay).

Example 16

Preparation of es8

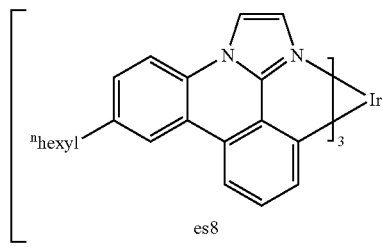

es8

Step 1: Synthesis of 2-(n-hexyl)-6-aminophenanthridine 13.1 g (69.8 mmol) 2-(1,3,2-dioxaborinan-2-yl)benzonitrile, 16.3 g (63.4 mmol) 2-bromo-4-hexylaniline, 1.62 g (1.40 mmol) tetrakis(triphenylphosphine) palladium(0), and 23.6 g (171 mmol) potassium carbonate where refluxed in 250 ml toluene and 100 ml EtOH under N$_2$ atmosphere for 20 hours. HPLC and TLC revealed almost complete consumption of the aniline. The reaction mixture was cooled and passed through a filter. The solids were washed with ethyl acetate to remove organics from the collected base. The filtrate was then evaporated down and dried on silica. The sample was purified using silica gel chromatography with 100% ethyl acetate as the eluent. The product fractions were then evaporated down to a minimal amount and hexanes added to crystallize the product as off white solids (7.05 g, 39.8% yield, GC-MS confirmed).

Step 2: Synthesis of es8 Ligand

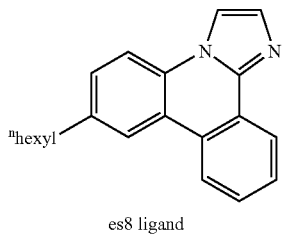

es8 ligand 7.02 g (25.2 mmol) 2-(n-hexyl)-6-aminophenanthridine, 2.99 g (37.8 mmol, 50% v/v in H$_2$O) chloroacetaldehyde, and 4.24 g (50.4 mmol) sodium bicarbonate were added to a 500 mL flask and refluxed in 150 mL 2-propanol for 20 hours under N$_2$ atmosphere. Upon completion, the mixture was cooled whereupon TLC and HPLC indicated complete consumption of the starting phenanthridine. The mixture was taken up in EtOAc and filtered to remove base. The filtrate was then evaporated to yield light amber oil. The oil was then dried on silica and purified on a column of silica using 70% ethyl acetate/hexanes→100% ethyl acetate as eluent. The product fractions from this purification were evaporated of solvent and recrystallized from ethyl acetate/hexanes to yield a total of 4.9 g es8 ligand as a white solid (55.1% yield, GC-MS confirmed).

Step 3

A 50 ml schlenk tube was charged with 2.9 grams (9.6 mmol) of es8 ligand, 0.94 g (1.9 mmol) iridium acetylacetonate, and 20 drops of tridecane. The reactor was evacuated and backfilled three times with nitrogen gas. The reaction was heated to 240° C. for 70 hours. The reaction was cooled and dichloromethane was added. The product was purified by column chromatography with dichloromethane as the eluent. The fractions containing the desired product were combined and the solvent was removed by rotary evaporation. The product was crystallized from toluene to yielded 300 mg es8, which was further purified by sublimation.

Example 17

Preparation of es13

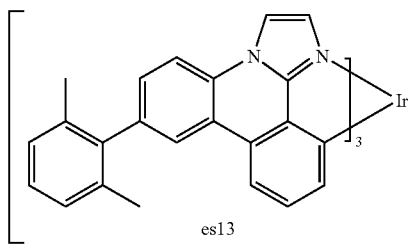
es13

Step 1: Synthesis of 2-Bromophenanthridinone 99.8 g (511 mmol) phenanthridinone was added to a 3 L multi-neck flask equipped with a stir arm and condenser. 1.2 L glacial acetic acid was added and the mixture was allowed to stir at 150 rpm and heated to reflux. 90 g (562 mmol) $Br_2$ suspended in 100 ml acetic acid was added to the refluxing solution dropwise over a period of 3 hours. After addition, the mixture was assayed and revealed to be ~80% complete. Based on this assay, an additional 20 g of $Br_2$ (in 30 mL acetic acid) was added dropwise to the mixture at reflux. After this addition, the assay was >90% complete. A final 20 g $Br_2$ (in 30 mL acetic acid) was added dropwise and the mixture allowed to stir for 1 hour after addition. The final assay was >97%. The mixture was cooled and 1 L of water was added and the mixture filtered. The wet solids were then stirred in aqueous sodium thiosulfate to destroy residual bromine and refiltered. These solids were rinsed with $H_2O$ and allowed to dry in vacuo to remove residual water. The solids were then recrystalllized from nitrobenzene (>2 liters) and collected on a funnel to give 128 g 2-bromophenanthridinone (90.8% yield).

Step 2: Synthesis of 2-Bromo-6-chlorophenanthridine 36.7 g (139 mmol) 2-bromophenanthridinone and 30.7 g (147 mmol) $PCl_5$ were added to a 1 L multi-neck flask (equipped with stir arm, condenser, and base trap) along with 350 mL $POCl_3$ and heated at 93° C. for 16 hours (note: evolution of HCl gas was predominant—destroyed by base trap). Afterwards, the mixture was assayed to determine complete consumption of 2-bromophenanthridinone. A dean stark trap was connected to the flask to remove the solvent by ½ volume. Subsequently, equal volumes of toluene were added and distilled off to remove majority of $POCl_3$. After the third addition of toluene, the volume was reduced to 300 mL's and the remainder of the solvent removed via rotary evaporation. The solids were then recrystallized from toluene and dried to give 30.8 g (78.6% yield, 98% assay) 2-bromo-6-chlorophenanthridine as off white solids (GC-MS confirmed).

Step 3: Synthesis of es13-i1

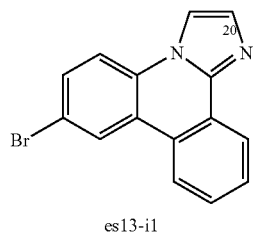
es13-i1

20 g 4A dried molecular sieves were added to a 2 L multi-neck flask equipped with a stir arm and condenser. 73.8 g (252 mmol) 2-bromo-6-chlorophenanthridine and 79.4 g (756 mmol) aminoacetaldehyde dimethylacetal were added to the flask along with 750 mL anhydrous diglyme. The mixture was heated at 135° C. using mechanical stirring for 18 hours under $N_2$ atmosphere. HPLC of the mixture revealed complete consumption of the starting material. The reaction was then cooled and enriched with ethyl acetate. The caked solids were removed from the flask side walls with scrapping. The mixture was then filtered in vacuo and the filtrate set aside. The solids from the funnel were then crushed (when dried) using a mortar and pestle and added to a 1 L flask and refluxed in 600 mL chlorobenzene. The chlorobenzene mixture was filtered and the filtrates combined. Solvent was then removed via rotary evaporation to give dark solids. The solids were then purified on a large column of silica using $CH_2Cl_2$ and $CH_2Cl_2$/MeOH as eluent (Note: when the $CH_2Cl_2$ solution of the product was put on top of the column, not all of the solids were solubilized. Through addition of extra eluent, the solids did eventually dissolve). After the lengthy chromatography, the product fractions were evaporated of solvent and the solids cleaned with $CH_2Cl_2$/hexanes. Filtration of the solids gave 62.0 grams of the title compound when dried (83.1% yield, NMR confirmed).

Step 4: Synthesis of es13 Ligand

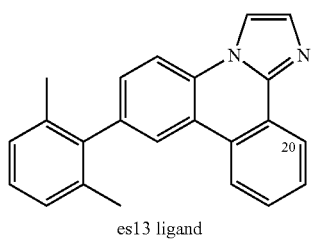
es13 ligand 3.12 g (10.5 mmol) 7-[bromo]-imidazo[1,2-f]phenanthridine, 3.93 g (26.2 mmol) 2,6-dimethylphenylboronic acid, 0.18 g (0.53 mmol) 2-(dicyclohexylphosphino)biphenyl, 0.13 g (0.14 mmol) $Pd_2(dba)_3$ and 6.68 g (31.5 mmol) potassium phosphate were added to a 50 mL air free flask equipped with a stir bar and vacuum degassed with $N_2$. 20 mL anhydrous m-xylene was added and the mixture set to 130° C. under $N_2$ atmosphere. HPLC of the mixture after 16 hours revealed complete consumption of the starting phenanthridine. The mixture was enriched with ethyl acetate and methylene chloride and filtered to remove the base. The filtrate was then pooled with 854-8741-076 (1 g scale rxn) and evaporated down to give a dark oil. The oil was dried on silica (using methylene chloride) and the product chromatographed using automated chromatography with a gradient of 5% EtOAc/hexanes→50% EtOAc/hexanes over a period of 1 hour. The pure fractions were evaporated down to give 3.40 g of a khaki colored solid (76.2% yield, 98% HPLC assay, NMR confirmed).

Step 5

3.40 g (10.6 mmol) 7-(2,6-dimethylphenyl)-imidazo[1,2-f]phenanthridine and 1.30 g (2.6 mmol) iridium(III) acetylacetonate were added to a 25 mL Schlenk tube equipped with a stir bar along with 12 drops of tridecane. The flask was sealed and vacuum degassed with $N_2$. The mixture was then submerged in a sand bath and heated at 250° C. under $N_2$ atmosphere for 96 hours. The mixture was then taken up in methylene chloride and purified on a column of silica using methylene chloride as the eluent. The product fractions were evaporated of solvent to give crude dopant. The solids were then recrystallized from methylene chloride/methanol to give 2.1 g of es13 as a yellow solid (68.9% yield, HPLC assay 99.5%, NMR confirmed).

Example 18

Preparation of es15

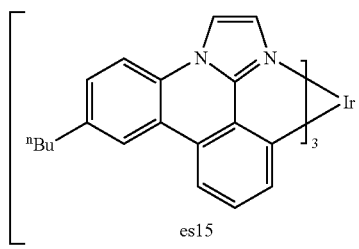

es15

Step 1: Preparation of 2-(n-butyl)-6-aminophenanthridine 20.0 g (87.7 mmol)2-(1,3,2-dioxaborinan-2-yl)benzonitrile, 13.7 g (73.1 mmol) 2-bromo-4-butylaniline, 1.70 g (1.46 mmol) tetrakis(triphenylphosphine)palladium(0), and 27.2 g (198 mmol) potassium carbonate where refluxed in 400 mL toluene and 200 mL ethanol under $N_2$ atmosphere for 20 h. HPLC and TLC revealed almost complete consumption of the aniline. An additional 1.8 g 2-(1,3,2-dioxaborinan-2-yl)benzonitrile was added and refluxed continued for an additional 18 h. The reaction mixture was cooled and passed through a filter. The solids were washed with ethyl acetate to remove organics from the collected base. The filtrate was then evaporated down and dried on silica. The sample was purified using silica gel chromatography with 100% ethyl acetate as the eluent. The product fractions were then evaporated down to a minimal amount and the product recrystallized from EtOAc/hexanes to give 12.0 g of the title compound as light yellow solids (65.9% yield, GC-MS confirmed).

Step 2: Synthesis of es15 ligand

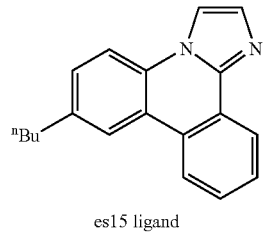

es15 ligand 12.0 g (48.0 mmol)2-(n-butyl)-6-aminophenanthridine, 11.4 g (72.0 mmol, 50% v/v in $H_2O$) chloroacetaldehyde, and 8.06 g (96.0 mmol) sodium bicarbonate were added to a 500 mL flask and refluxed in 200 mL 2-propanol for 20 hours under $N_2$ atmosphere. Upon completion, the mixture was cooled whereupon TLC and HPLC indicated complete consumption of the starting phenanthridine. The mixture was taken up in EtOAc and filtered to remove base. The filtrate was then evaporated to yield brown oil. The oil was then dried on silica and purified on a column of silica using 70% ethyl acetate/hexanes ~100% ethyl acetate as eluent. The product fractions from this purification were evaporated of solvent and recrystallized from ethyl acetate/hexanes to yield a total of 5.22 g es15 ligand as an off-white solid (40.5% yield, NMR confirmed).

Step 3

5.2 g (21.0 mmol) es15 ligand and 2.58 g (5.25 mmol) iridium(III) acetylacetonate were added to a 25 mL Schlenk tube equipped with a stirbar. 10 drops of tridecane were added, the tube was sealed with a septa and vacuum degassed thoroughly with $N_2$. The tube was submersed in a sand bath and heated at 250° C. for 72 h under a $N_2$ atmosphere. The cooled mixture was then taken up in $CH_2Cl_2$ with sonication to dissolve the impurities. The mixture was filtered in vacuo and the solids rinsed with $CH_2Cl_2$ and hexanes to give yellow solids in the amount of 2.74 g. The solids were then dissolved in 130 mL boiling chlorobenzene and poured over a celite mat (hot) to remove impurities. The resultant filtrate was evaporated to dryness. The residue was taken up in methylene chloride and the contents purified on a silica gel column using methylene chloride and flash. The product fractions were evaporated of solvent and the solids recrystallized from chlorobenzene to yield 1.52 g of es15 as a yellow solid (29.6% yield, NMR confirmed, 96.3% HPLC assay), 1.5 g of which was further purified by sublimation in a three zone sublimator at 360° C. and $1.0 \times 10^{-5}$ Torr vacuum to give 160 mg of es15 as a bright yellow solid.

Example 19

Preparation of es6

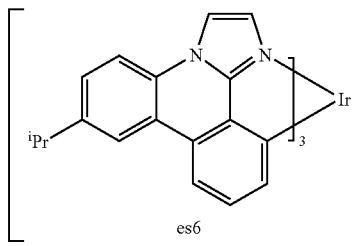

es6

Step 1: Synthesis of 2-isopropyl-phenanthridin-6-ylamine

A 500 ml round bottom flask was charged with 12.2 grams (65.4 mmol) of 2-cyanophenylboronic acid propanediol ester, 14.0 g (65.4 mmol) of 2-bromo-4-isopropylaniline, 2.27 (2 mmol) tetrakis(triphenylphosphine)palladium, 18.0 g (131 mmol) of potassium carbonate, 150 ml toluene, and 50 ml ethanol. The reaction was heated to reflux under $N_2$ for 18 hours. After cooling to room temperature the reaction was extracted with ethyl acetate and water. The organic was washed with brine and then dried with magnesium sulfate. The solids were collected by filtration and the solvent removed from filtrate. The product was purified by silica gel chromatography using 94.5% dichloromethane, 5% methanol, 0.5% ammonium hydroxide as the eluent. The fractions containing the desired product were combined and the solvent removed. The product was confirmed by NMR and mass spectroscopy.

Step 2: Synthesis of es6 Ligand

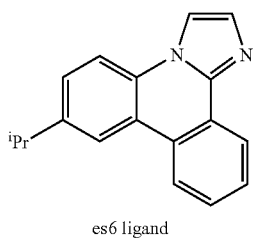

es6 ligand

A 250 ml round bottom flask was charged with 5 grams (21.2 mmol) 2-Isopropyl-phenanthridin-6-ylamine, 5 grams (31.8 mmol, 50% solution in water) chloroacetaldehyde, 3.56 grams (42.4 mmol) sodium bicarbonate, and 150 ml isopropanol. The mixture was heated to reflux for 18 hours and then cooled to room temperature. Dichloromethane was added and the solids filtered. The solvent was removed by rotary evaporation and the product purified by column chromatography with 40% hexane/ethyl acetate as the eluent. The fractions containing the desired product were combined and the solvent removed. The product was further purified by Kugelrohr distillation. Collected 5.8 grams of es6 ligand.

Step 3

A 50 ml schlenk tube was charged with 2.8 grams (10.8 mmol) of 7-Isopropyl-imidazo[1,2-f]phenanthridine and 1.05 g (2.2 mmol) iridium acetylacetonate. The reactor was evacuated and backfilled three times with nitrogen gas. The reaction was heated to 250° C. for 24 hours. The reaction was cooled and dichloromethane was added and then the solids were filtered to yield 1.5 grams of a yellow solid. The solids were dissolved in hot 1,2-dichlorobenzene. The mixture was cooled and the solids filtered to yield 0.4 grams of es6 as a yellow solid. The material was further purified by sublimation.

Example 20

Preparation of es8

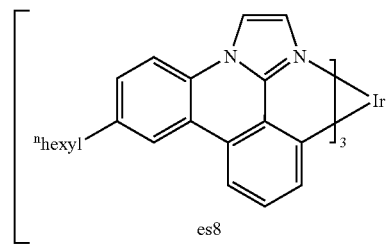

es8

A 50 ml schlenk tube was charged with 2.9 grams (9.6 mmol) of es8 ligand, 0.94 g (1.9 mmol) iridium acetylacetonate, and 20 drops of tridecane. The reactor was evacuated and backfilled three times with nitrogen gas. The reaction was heated to 240° C. for 70 hours. The reaction was cooled and dichloromethane was added. The product was purified by column chromatography with dichloromethane as the eluent. The fractions containing the desired product were combined and the solvent was removed by rotary evaporation. The product was crystallized from toluene to yielded 300 mg of es8, which was further purified by sublimation.

Example 21

Preparation of es5

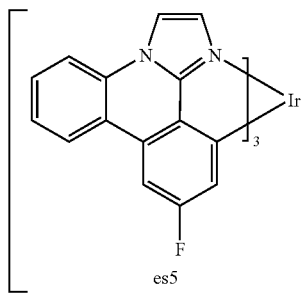

es5

Step 1: Synthesis of 9-fluoro-6-phenanthridinamine

To a solution of 2-chloro-4-fluorobenzonitrile (1.0 g, 6.42 mmol), 2-aminophenylboronic acid pinacol ester (1.6 g, 7.1 mmol), palladium(II) acetate (0.07 g, 0.32 mmol), amantadine hydrochloride (0.24 g, 1.3 mmol) and cesium carbonate (4.6 g, 14.1 mmol) were added to dioxane previously deaerated with nitrogen and heated to reflux for 17 hours. After cooling, both distilled water and methylene chloride (50 mL) were added to the reaction mixture. The solvent layer was separated and concentrated to give a crude oil that was purified by column chromatography by first using 1:1 ethyl acetate and hexanes ratio followed by 4:1 ethyl acetate/hexanes as the eluants. The pure product was collected to give 9-fluoro-6-phenanthridinamine (42 g, 32% Yield) whose NMR spectrum is consistent with the proposed structure.

Step 2: Synthesis of 10-fluoro-imidazo[1,2-f]phenanthridine)

9-Fluoro-6-Phenanthridinamine (0.8 g, 3.7 mmol), and a 50% solution of acetyl chloride (0.4 g, 5.66 mmol) in water containing sodium bicarbonate (0.6 g, 7.54 mmol) was dissolved in isopropyl alcohol (25 mL). The reaction mixture was refluxed for 17 hours under a nitrogen pad. The reaction mixture was cooled to room temperature and the precipitate vacuum filtered and washed with methylene chloride. The crude product was purified by column chromatography using a 1:1 ratio of ethyl acetate and hexanes as the eluants followed by distillation to give 10-fluoro-imidazo[1,2-f]phenanthridine) (0.46 g, 52% yield).

Step 3

A 50 ml schlenk tube was charged with 2.1 grams (9.6 mmol) of 10-fluoro-imidazo[1,2-f]phenanthridine, 0.87 g (1.9 mmol) iridium acetylacetonate, and 15 drops of tridecane. The reactor was evacuated and backfilled three times with nitrogen gas. The reaction was heated to 230° C. for 40 hours. The reaction was cooled and dichloromethane was added. The product was purified by column chromatography with dichloromethane as the eluent. The fractions containing the desired product were combined and the solvent was removed by rotary evaporation. The product was crystallized from a dichloromethane/hexane mixture to yield 500 mg of es5, which was further purified by sublimation.

Example 22

Preparation of es19

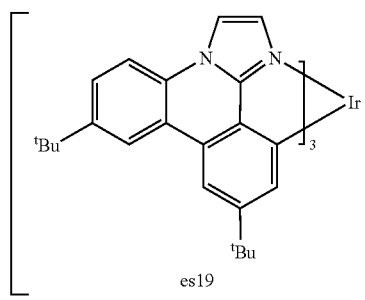

es19

Step 1: Synthesis of 3-tert-butylphenylboronic acid

To a solution of dry THF (10 mL) was added magnesium (1.25 g, 52 mmol), 3-t-butyl bromobenzene (2.0 g, 9.4 mmol) and a crystal of iodine. The reaction was first heated slightly until the reaction started and then removed. The remaining 3-t-butyl bromobenzene (8.0 g, 37.7 mmol) was added via an addition funnel until the spontaneous refluxing stopped. The reaction mixture was heated to reflux for 2 hours. The Grignard was transferred via a syringe into a cooled solution (−40° C.) of trimethyl borate dissolved in THF and added over a 10 minute period. The reaction mixture was warmed to room temperature overnight. Ethyl acetate and distilled water were added to the reaction mixture and the layers separated. The organics were washed with brine and dried over magnesium sulfate. The solvent was concentrated and the product purified by a silica gel column using 10% ethyl acetate and hexanes as the eluants to give 3-t-butylphenyl boronic acid (4.0 g, 46% yield) as a white solid. The product was confirmed by GCMS and was used directly in the next step.

Step 2: Synthesis of 2-amino-3',5-di-tert-butyl biphenyl

Added together were 3-t-butylphenylboronic acid (4.0 g, 22.4 mmol), 2-bromo-4-t-butyl aniline (4.3 g, 18.7 mmol), palladium(II)acetate (0.11 g, 0.468 mmol), triphenyl phosphine (0.5 g, 1.8 mmol), and 25 mL of a 2 M solution of potassium carbonate in 36 mL of ethylene glycol dimethyl ether. The reaction mixture was heated at reflux for 18 hours. The reaction was cooled to room temperature and the aqueous phase was separated from the organic phase. The aqueous phase was extracted with ethyl acetate. The organic extractions were combined, dried over magnesium sulfate filtered and concentrated. The crude product was purified by column chromatography using 20% ethyl acetate and hexanes as the eluants. The pure product 2-amino-3',5-di-tert-butyl biphenyl (3.0 g, 57% yield) was collected as a white solid whose NMR was consistent with the proposed structure.

Step 3: Synthesis of N-formyl-2-amino-3',5-di-tert-butyl biphenyl

Added 2-amino-3',5-di-t-butyl biphenyl (2.0 g, 7.11 mmol) to a solution of formic acid and heated to reflux for 16 hours. After cooling, water (25 mL) was added the product and the precipitate collected by vacuum filtration. The crude product was dissolved into ethyl acetate, washed with water. The organics were dried over magnesium sulfate and concentrated and purified by column chromatography using 10% ethyl acetate and hexanes as the eluants to give the pure N-formyl-2-amino-3',5-di-t-butyl biphenyl (1.8 g, 82% yield) as determined by GCMS.

Step 4: Synthesis of 2,9-di-tert-butylphenanthridinone

The above compound, N-formyl-2-amino-3',5-di-t-butyl biphenyl (6.5 g, 21 mmol) was dissolved into 50 mL of chlorobenzene to which 5 equivalents of di-t-butyl peroxide was added. The reaction mixture was heated to 110° C. for 72 hours. The reaction mixture was concentrated in half and cooled to 0° C. The precipitate that formed was collected by vacuum filtration. The off-white solid was washed with hexanes to give 2,9-di-tert-butylphenanthridinone as determined by GCMS and not purified any further.

Step 5: Synthesis of 2,9-di-tert-butyl-6-chlorophenanthridine

The above 2,9-di-t-butylphenanthridinone (3.0 g, 9.7 mmole) was added to a reaction flask containing phosphorus pentachloride (3.0 g, 14.6 mmole) and 50 mL of phosphoryl chloride. The reaction mixture was refluxed overnight, cooled to room temperature and diluted with toluene. The excess phosphoryl chloride and toluene were removed by a rotary evaporator. The residue was dissolved into ethyl acetate and washed with distilled water followed by brine. The solvent layer was dried over magnesium sulfate, filtered and concentrated to give the desired 2,9-di-tert-butyl-6-chlorophenanthridine (3.0 grams, 98%) as an off white solid. The product was confirmed by GC Mass Spec and not purified further but used directly in the next step.

Step 5: Synthesis of
7,10-di-tert-butyl-imidazo[1,2-f]phenanthridine 2,9-Di-t-butyl-6-chlorophenanthridine (3.7 grams, 11.0 mmole) was added to a reaction flask containing aminoacetaldehyde dimethylacetal (2.4 grams, 23 mmole) dissolved into 200 mL of diglyme, heated to reflux and stirred under a nitrogen atmosphere. After 96 hours the reaction was complete as determined by TLC. The reaction mixture was cooled to room temperature and the excess solvent removed by distillation. The residue was taken up into methylene chloride. The solvent was dried over magnesium sulfate filtered and concentrated. The crude product was purified by silica gel chromatography using 10% ethyl acetate and 90% methylene chloride as the eluents. The purified product was collected, washed with hexanes, and dried to give 7,10-di-tert-butyl-imidazo[1,2-f]phenanthridine (2.0 grams, 56% yield) as a white solid.

Step 6

A 50 ml schlenk tube was charged with 2.0 grams (6.1 mmol) of 10-fluoro-imidazo[1,2-f]phenanthridine, 0.84 g (1.7 mmol) iridium acetylacetonate, and 10 drops of tridecane. The reactor was evacuated and backfilled three times with nitrogen gas. The reaction was heated to 240° C. for 18 hours. The reaction was cooled and dichloromethane was added. The product was purified by column chromatography with dichloromethane as the eluent. The fractions containing the desired product were combined and the solvent was removed by rotary evaporation. The product was crystallized from a dichloromethane/hexane mixture to yield 0.6 g of es19, which was further purified by sublimation.

Example 23

Preparation of es14

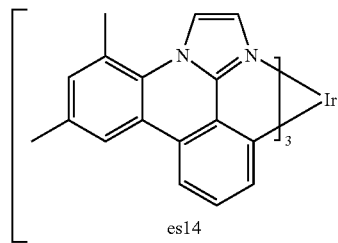

es14

Step 1: Synthesis of
3,5-dimethyl-6-phenanthridinamine

Added together 2-cyanophenylboronic acid pinacol ester (13.7 g, 60 mmol), 2-bromo-4,6-dimethylaniline (10.0 g, 50 mmol), tetrakis(triphenylphosphine)palladium(0) (2.3 g, 2.0 mmol) and potassium carbonate (18.6 g, 138.21 mol) to a 125 mL of a 95/5 mixture of toluene/methanol. The solvents were degassed and the reaction mixture heated to reflux for 48 hours. After cooling, the reaction mixture was vacuum filtered and the organics evaporated and crude product was purified using silica gel column chromatography treated with triethylamine and 1:9 ethyl acetate and methylene chloride mixture as the eluants. The pure product was collected and concentrated to give 3,5-dimethyl-6-phenanthridinamine (9.1 g, 82% Yield).

Step 2: Synthesis of
5,7-dimethyl-imidazo[1,2-f]phenanthridine)

3,5-Dimethyl-6-phenanthridinamine (8.6 g, 39 mmol), a 50% solution of acetyl chloride (4.6 g, 58 mmol) in water, sodium bicarbonate (6.5 g, 77.4 mmol) in 258 mL of isopropyl alcohol were heated to reflux for 40 hours. After cooling the crude product was dissolve into methylene chloride and vacuum filtered. The filtrate was concentrated and the crude product was crystallized in methylene chloride and ethyl acetate mixture. The pure product was collected by vacuum filtration to give 5,7-dimethyl-imidazo[1,2-f]phenanthridine) (3.8 g, 40% yield) as determined by NMR.

Step 3

3.7 g (15.0 mmol) 5,7-dimethyl(imidazo[1,2-f]phenanthridine) and 1.85 g (3.76 mmol) Ir(acac)$_3$ were added to a 50 mL Schlenk tube equipped with a stirbar. 12 drops tridecane was added and the tube sealed and vacuum degassed with N$_2$. The tube was then immersed in a sand bath and heated to 250° C. for 72 hours. The reaction mixture was cooled and the contents sonicated with CH$_2$Cl$_2$ to dissolve. The yellow solids were filtered and heated in chlorobenzene. The solution was filtered through Celite and concentrated to induce crystallization. The solids were filtered to yield 600 mg es14 as a yellow solid that was further purified by sublimation.

Example 24

Preparation of es27

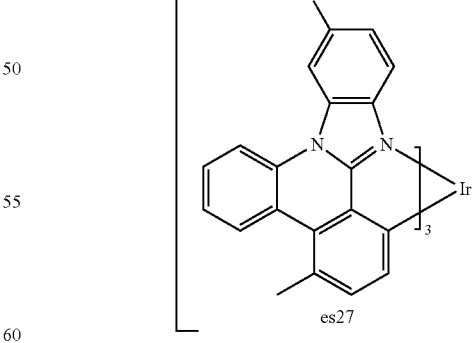

es27

Step 1: Synthesis of 2-amino-2'-methyl-biphenyl

Added together 2-methylphenyl boronic acid (24.7 g, 181 mmol), 2-bromo aniline (25.7 g, 151 mmol), palladium(II) acetate (0.85 g, 3.78 mmol), triphenylphosphine (4.0 g, 15.1 mmol), a 2 M solution of potassium carbonate (204 mL) and ethylene glycol dimethyl ether (223 mL) and heated the reaction mixture at reflux for 18 hours. After the reaction was cooled to room temperature, the aqueous phase was separated from the organic phase. The aqueous phase was extracted with ethyl acetate and the organic extractions were combined, dried over magnesium sulfate and filtered. The crude product was purified by silica gel column chromatography using 10% ethyl acetate in hexanes as the eluants. The pure fractions were collected, combined and concentrated to give 2-amino-2'-methyl-biphenyl (23.5 g, 84.8% yield) whose structure was confirmed by GCMS and NMR.

Step 2: Synthesis of
N-ethoxycarbonyl-2-amino-2'methyl biphenyl

The above compound, 2-amino-2'-methyl-biphenyl (11.0 g, 60 mmol) was added to dry toluene (250 mL) containing triethyl amine (24 g, 24 mmol) and stirred under a nitrogen pad. Ethyl chloroformate (26 g, 240 mmol) was slowly added to the stirred solution via a syringe. The reaction mixture was washed with brine and the organics separated, dried over magnesium sulfate and concentrated to give N-ethoxycarbonyl-2-amino-2'methyl biphenyl as a colorless oil (7.0 g, 46% yield) whose structure was confirmed by GCMS and NMR.

Step 3: Synthesis of 10-methyl-phenanthridinone

The above compound, N-ethoxycarbonyl-2-amino-2'methyl biphenyl (6.7 g, 26 mmol) was added to polyphosphoric acid (15 g) and heated to 170° C. overnight. After cooling, water was added and the white precipitate collected by vacuum filtration to give the 10-methyl-phenanthridinone (3.5 g, 65% yield) whose structure was consistent with CGMS and NMR.

Step 4: Synthesis of
6-chloro-10-methylphenanthridine

The above compound, 10-methyl-phenanthridinone (4.0 grams, 19 mmole) was added to a reaction flask containing phosphorus pentachloride (6.0 grams, 0.29 mole) and phosphoryl chloride (50 mL). The reaction mixture was refluxed for 4 hours, cooled to room temperature and diluted with toluene. The excess phosphoryl chloride and toluene were removed by a rotary evaporator. The residue was dissolved into ethyl acetate and washed with distilled water followed by brine. The solvent layer was dried over magnesium sulfate, filtered and concentrated to give 6-chloro-10-methylphenanthridine (4.1 grams, 95%) as an off-white solid. The product was confirmed by Mass Spec and NMR and not purified further but used directly in the next step.

Step 5: Synthesis of es27i-1

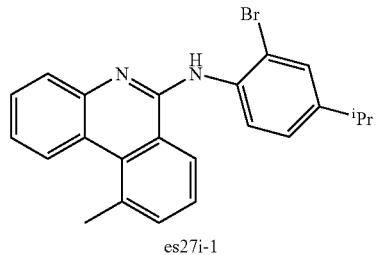

es27i-1

To a solution of diglyme (100 mL) was added the above 6-chloro-10-methyl-phenanthridine (1.8 g, 7.9 mmol) and 2-bromo-4-isopropylanaline (3.4 g, 15.8 mmol). The reaction mixture was stirred under a nitrogen pad for 3 hours at 160° C. After cooling, the precipitate was vacuum filtered, washed with ethyl acetate followed by hexanes to give es27i-1 (2.5 g, 78% yield) as a beige solid.

Step 6: Synthesis of 10-isopropyl-3-methyl-8b,13-diaza-indeno[1,2-f]phenanthrene The above compound, (3.5 g, 8.7 mmol) was dissolved into toluene containing triphenylphosphine (0.45 g, 1.7 mmol), palladium acetate (0.12 g, 0.5 mmol), potassium carbonate (3.6 g, 26 mmol). The reaction mixture was refluxed overnight under a nitrogen pad. The reaction mixture was cooled to room temperature and washed with distilled water followed by brine. After separating the organic layers, the es27 ligand product was purified on a silica gel column.

Step 7

A 50 ml round bottom flask was charged with 1.8 g (5.5 mmol) of 10-isopropyl-3-methyl-8b,13-diaza-indeno[1,2-f] phenanthrene, 0.67 g (1.4 mmol) iridium acetylacetonate and 20 ml ethylene glycol. The reaction was heated to reflux under nitrogen for 24 hours. The reaction was cooled and methanol was added followed by filtration of the yellow solids. The solids were dissolved in dichloromethane and purified by column chromatography with dichloromethane as the eluent. The fractions containing the desired product were combined and the solvent was removed by rotary evaporation. The product was crystallized from chlorobenzene to yield 0.3 g of es27.

Example 25

Preparation of es17

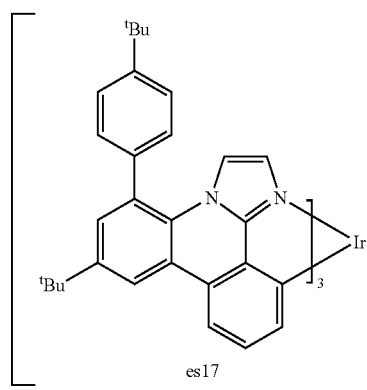

es17

Step 1: Synthesis of es17i-1

A three neck 1 L round bottom flask was charged with 2,6-dibromo-4-tert-butyl aniline (38 g, 0.124 mole), 2-cyanophenylboronic acid pinacol ester (10 g, 0.044 mole), K₃PO₄·H₂O (35.4 g, 0.154 mole), PdCl₂(PPh₃)₂ (1.8 g, 2.6 mmole) and anhydrous toluene (500 ml). The reaction mixture was heated to 100° C. under nitrogen for 6 hrs. The reaction mixture was then concentrated to dryness and subjected to column chromography to get es17i-1 (5.65 g, 39%).

Step 2: Synthesis of es17i-2

To a mixture of es17i-1 (2.75 g, 8.4 mmole), sodium bicarbonate (1.4 g, 16.7 mmole) in 2-propanol (75 ml) was added chloroacetaldehyde (50% aqueous soln. 1.96 g). After the reaction mixture was heated at 75° C. for 5 hrs., the solvent was removed. The residue was redissolved in methylene chloride and washed with water. The organic fractions were combined, dried over sodium sulfate, filtered, and concentrated in vacuo. The crude mixture was purified by chromatography on silica gel using hexane/ethyl acetate (80/20) to give pure es17i-2 (2.52 g, 85%)

Step 3: Synthesis of es17i-2

A three neck 1 L round bottom flask was charged with es17i-2 (4.5 g, 12.7 mmol), 4-tert-butylphenylboronic acid (5.09 g, 29 mmol), sodium carbonate (9.22 g, 87 mmol), Pd(PPh)₄ (0.99 g, 0.86 mmol), 50 ml of water and 400 ml of toluene. The reaction mixture was heated to 100° C. under nitrogen for 17 hrs. The reaction mixture was diluted with methylene chloride and washed by brine. The organic fractions were combined, dried over sodium sulfate, filtered, and concentrated in vacuo. The crude mixture was purified by chromogry on silica gel using hexane/ethyl acetate (80/20) to give pure es17i-3 (5.05 g, 97%).

Step 4

A 25 ml 2 neck flask was charged with es17i-3 (3.41 g, 8.38 mmol), Ir(acac)₃ (821.24 mg, 1.67 mmol) and 30 drops of tridecane. The flask was vacuum and back refilled with nitrogen for three times and then heat to 220° C. for 65 hrs. The reaction mixture was dissolved in methylene chloride and subjected to column chromatography to obtain es17 (1 g, 42% yield).

Example 26

Preparation of es23

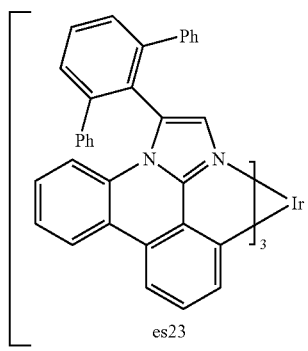

es23

Step 1: Synthesis of 3-(tributyltin)-imidazol[1,2-f]phenanthridine

A three neck round bottom flask was charged with imidazo [1,2-f]phenanthridine (11.6 g, 53.21 mmol) and 600 mL of anhydrous THF. A solution of n-butyl lithium (2 M solution in cyclohexane, 39.9 mL, 79.8 mmol) was added to the reaction mixture at −78° C. After stirring at −78° C. for 2 hrs; tributyltin chloride (25.97 g, 79.8 mmol) was added at −78° C. The reaction mixture was stirred at −78° C. for two hours. The reaction mixture was concentrated under vacuum to dryness and subjected to column chromatography (Silica gel pretreated with triethylamine, 50% EtOAC in hexanes) to obtain the title compound (24.61 g, 91% yield).

Step 2: Synthesis of 3-(2,6-dichlorophenyl)-imidazo [1,2-f]phenanthridine

A 250 ml round bottom flask was charged with 3-(tributyl-tin)-imidazo[1,2-f]phenanthridine (23.87 g, 47 mmol), 2,6-dichloroiodobenzene (12.84 g, 47.08 mmol), PdCl₂(PPh₃)₂ (1.97 g, 2.82 mmol) and 170 ml of anhydrous para-xylene. The reaction mixture was heated to 120° C. under nitrogen for 17 hrs. The reaction mixture was diluted with methylene chloride and washed by saturated KF aqueous solution. The precipitation was filtered off and the filtrate was subjected to column chromography. (Silica gel, methylene chloride) to obtain the title compound (10.35 g, 60.8% yield).

Step 3: Synthesis of 3-(2,6-diphenylphenyl)-imidazo [1,2-f]phenanthridine

A 200 ml round bottom flask was charged with 3-(2,6-dichlorophenyl)-imidazo[1,2-f]phenanthridine (2.1 g, 5.8 mmol), phenyl boronic acid (2.828 g, 23.4 mmol), Pd(OAc)₂ (1.127 g, 5.02 mmol), 2-Dicyclohexylphosphino-2',6'-dimethoxybiphenyl (4.11 g, 10.03 mmol), K₃PO₄ and 70 ml of anhydrous toluene. The reaction mixture was heated to 100° C. under nitrogen for 22 hrs. The reaction mixture was concentrated to dryness and subjected to column chromatography to obtain the title compound (1.62 g, 62% yield).

Step 4

A 25 ml 2-neck flask was charged with 3-(2,6-diphenylphenyl)-imidazo[1,2-f]phenanthridine (2.93 g, 6.56 mmol), Ir(ACAC)₃ (0.643 g, 1.31 mmol) and 30 drops of tridecane. The flask was vacuum and back refilled with nitrogen for three times and then heat to 220° C. for 65 hrs. The reaction mixture was dissolved in methylene chloride and subjected to column chromatography to obtain es23 (560 mg, 28% yield).

Example 27

Preparation of es101

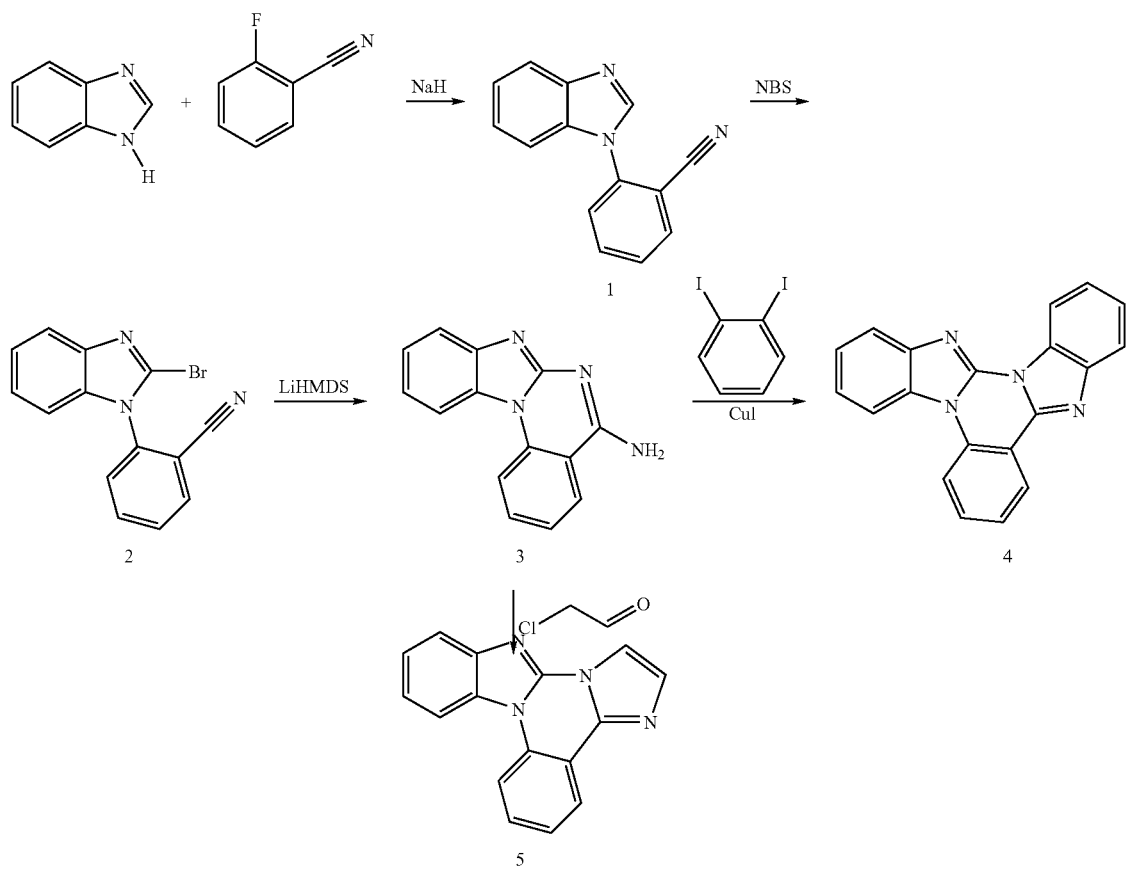

Step 1: 2-(1H-benzo[d]imidazol-1-yl)benzonitrile 1

Benzimidazole (2.00 grams, 16.9 mmol) was dissolved in 30 mL of anhydrous dimethylformamide. To this was added sodium hydride (0.68 grams 60%, 16.9 mmol). This was stirred at ambient temperature for 30 min. before addition of 1.80 mL (16.9 mmol) of 2-fluorobenzonitrile. The reaction was stirred at 50° C. for 18 hours after which time the mixture was cooled in an ice-water bath and diluted with 100 mL of water. The product was extracted with ethyl acetate. The organic layer was washed with water, dried over sodium sulfate and evaporated in vacuo giving the title compound. Mass spectral and NMR data agree with the structure. Also synthesized analogously was the 5,6-dimethyl benzimidazole analog.

Step 2: 2-(2-bromo-1H-benzo[d]imidazol-1-yl)benzonitrile 2

Compound 1 (25.75 grams, 117.5 mmol) was dissolved in dioxane (400 mL). To this was added N-bromosuccinimide (20.91 grams, 117.5 mmol). This was stirred at reflux for 3 hours after which time the mixture was poured into water and the product was extracted with ethyl acetate. The organic layer was dried over sodium sulfate, concentrated in vacuo and chromatographed (silica gel) using a mobile phase of dichloromethane-ethyl acetate 5:1 (v/v) to provide the title compound. Mass spectral and NMR data confirm the structure. Also synthesized analogously was the 5,6-dimethylbenzimidazole analog.

Step 3: Synthesis of 3

Compound 2 (4.86 grams, 16.3 mmol) was stirred in 20 mL of anhydrous tetrahydrofuran. To this was added 25 mL of a 1 N solution of lithium hexamethyldisilazane in tetrahydrofuran. The reaction was stirred at 65° C. for 2.5 hours. The reaction mixture was then cooled to ambient temperature and quenched with water. Aqueous hydrochloric acid (25 mL of 1 N solution) was added and this was stirred for 10 minutes before being neutralized with aqueous ammonium hydroxide. The resulting brown solid was collected by filtration and dried under vacuum. Structure confirmed by mass spectral and NMR data.

Step 4: Synthesis of 4

Compound 3 (2.15 grams, 9.18 mmol) was placed in a 200 mL round bottom flask. To this was added 1,2-diiodobenzene (1.20 mL, 9.18 mmol), Copper iodide (0.52 grams, 2.75 mmol), 1,10-phenanthroline (0.50 grams, 2.75 mmol) and potassium carbonate (2.66 grams, 19.28 mmol). The flask was degassed and backfilled with nitrogen before addition of 40 mL of anhydrous dimethylformamide. The reaction was stirred at 150° C. for 18 hours before being cooled and poured into water. The crude solid was filtered and chromatographed (silica gel) using a mobile phase of dichloromethane-methanol 19:1 to give the product 4. LCMS 309.2 (ES+), 309.2 (AP+); $^1$H NMR (CDCl$_3$) δ 8.75 (m, 2H), 8.36 (d, 1H), 8.15 (d, 1H), 7.95 (m, 2H), 7.81 (m, 1H), 7.56 (m, 3H), 7.44 (m, 2H).

Step 5

A 25 mL 2 neck flask was charged with 4 (0.6 g, 1.945 mmol), Ir(acac)$_3$ (0.19 g,

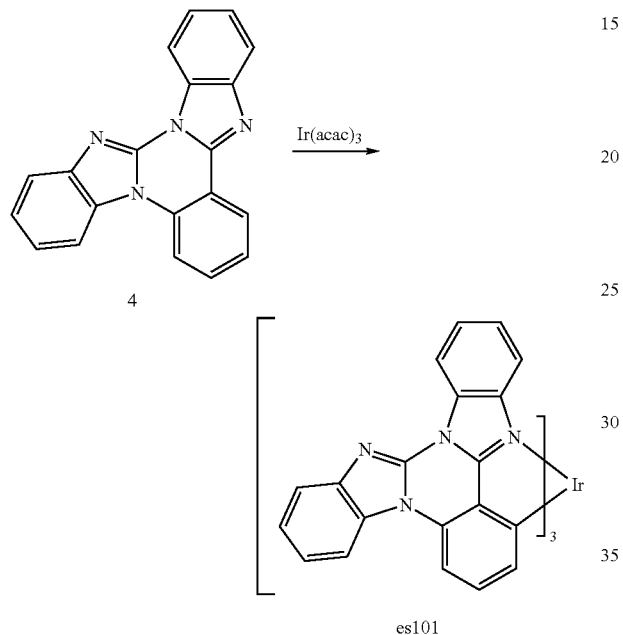

0.389 mmol) and 30 drops of tridecane. The flask was evacuated and re-filled refilled with nitrogen three times and then heated to 240 C for 26 h. The resultant mixture was dissolved in methylene chloride and subjected to silica gel column chromatography to afford es101, the structure of which was confirmed by mass spectrometry.

Example 28

Preparation of Compound 5

Compound 3 (0.59 grams, 2.52 mmol) was stirred in 15 mL of isopropanol. To this was added sodium bicarbonate (0.42 grams, 5.04 mmol) and chloroacetaldehyde (0.50 mL 50% solution, 3.78 mmol). This was stirred at reflux for 7 hours before being cooled, diluted with water and extracted with dichloromethane. The product was purified using column chromatography (silica gel) eluted with dichloromethane-methanol 19:1. LCMS 258.7 (AP+), 259.3 (ES+); $^1$H NMR (DMSO d$_6$) δ 8.66 (d, 1H), 8.55 (m, 1H), 8.46 (dd, 1H), 8.28 (d, 1H), 7.84 (m, 2H), 7.62 (m, 2H), 7.47 (m, 2H).

Example 29

Preparation of
2-(2,4-dimethyl-1H-imidazol-1-yl)benzonitrile 6

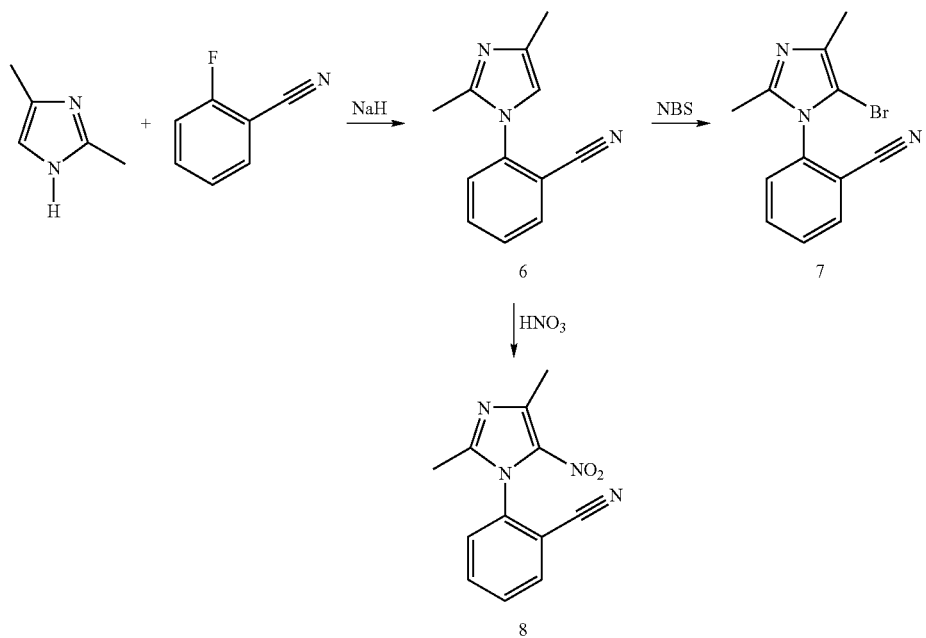

Sodium hydride (8.65 grams 60%, 0.216 mol) was stirred in 75 mL of anhydrous dimethylformamide. To this was added dropwise a solution of 2,4-dimethylimidazole (20.75 grams, 0.216 mol) in 100 mL of DMF. After stirring at ambient temperature for 1 hour a solution of 2-fluorobenzonitrile (23.0 mL, 0.216 mol) in 75 mL of DMF was added dropwise. This was stirred at 50° C. for 2 hours and then at ambient temperature for 16 hours. The mixture was then poured into water and the product extracted with ethyl acetate. The organic layer was washed with water and dried over sodium sulfate. The crude product was chromatographed (silica gel) and eluted with 19:1 dichloromethane-methanol then 9:1 dichloromethane-methanol to afford the product as a solid. LCMS data confirmed structure.

Example 30

Preparation of 2-(5-bromo-2,4-dimethyl-1H-imidazol-1-yl)benzonitrile 7

Compound 6 (5.18 grams, 26.0 mmol) was dissolved in acetonitrile (150 mL). To this was added N-bromosuccinimide (4.67 grams, 26.0 mmol). This was stirred at reflux for 1 hour before being evaporated in vacuo. The residue was dissolved in dichloromethane and washed with water. The organic layer was evaporated in vacuo to give the title compound as a yellow solid. NMR confirmed structure.

Example 31

Preparation of 2-(2,4-dimethyl-5-nitro-1H-imidazol-1-yl)benzonitrile 8

Compound 6 (6.82 grams, 34.5 mmol) was added in portions to trifluoroacetic anhydride (50 mL) cooled to 0° C. After 15 minutes the sodium chloride ice water bath was replaced with a dry ice acetone bath and nitric acid (6.0 mL 70%) was added drop wise. This was stirred to ambient temperature for 16 hours after which time it was pored into ice-water and neutralized with solid sodium bicarbonate. The product was extracted with dichloromethane and purified on a silica gel flash column eluted with 49:1 dichloromethane-methanol to give the desired product as an orange paste. LCMS data supported the structure.

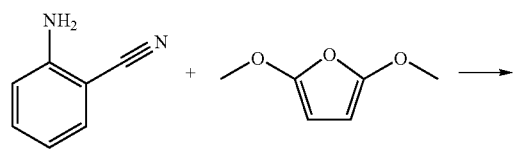

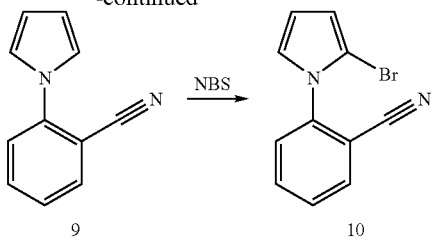

Example 32

Preparation of 2-(1H-pyrrol-1-yl)benzonitrile 9

Anthranilonitrile (10.0 grams, 85.0 mmol) was dissolved in 350 mL of acetic acid. To this was added 2,5-dimethoxytetrahydrofuran (11.0 mL, 85.0 mmol). This was stirred at reflux for 2 hours after which time the reaction mixture was pored into water and the product extracted with dichloromethane. The organic layer was washed with water, dried over sodium sulfate and chromatographed on a silica gel column using a mobile phase of 1:1 dichloromethane-hexane to afford the title compound as a white solid. NMR confirms structure.

Example 33

Preparation of 2-(1H-2-bromo-pyrrol-1-yl)benzonitrile 10

Compound 9 (12.07 grams, 72.0 mmol) was dissolved in 250 mL of anhydrous dimethylformamide. This was cooled in an ice water bath. To this was added N-bromosuccinimide (12.77 grams, 72.0 mmol). The reaction mixture was stirred at 0° C. for 3 hours before being poured into water. The product was extracted with dichloromethane. The organic layer was washed with water, dried over sodium sulfate and concentrated in vacuo. The crude product was column chromatographed (silica gel) using a mobile phase of 1:1 dichloromethane-hexane to give compound 10 as a colorless oil. NMR and LCMS data confirmed the structure.

Example 34

Preparation of es33

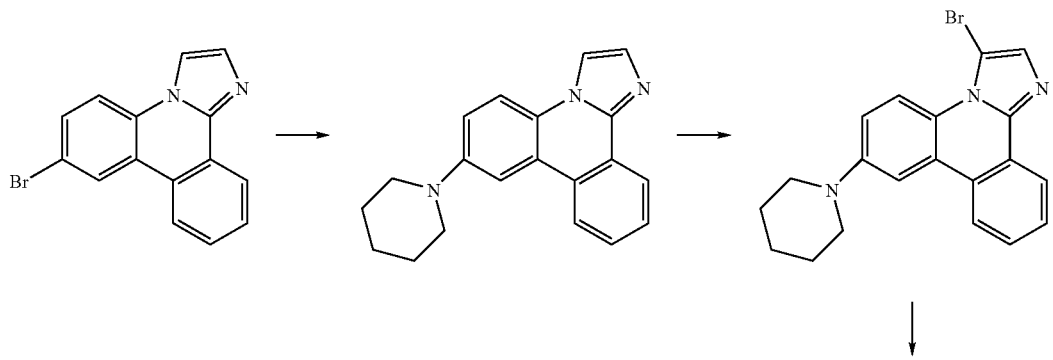

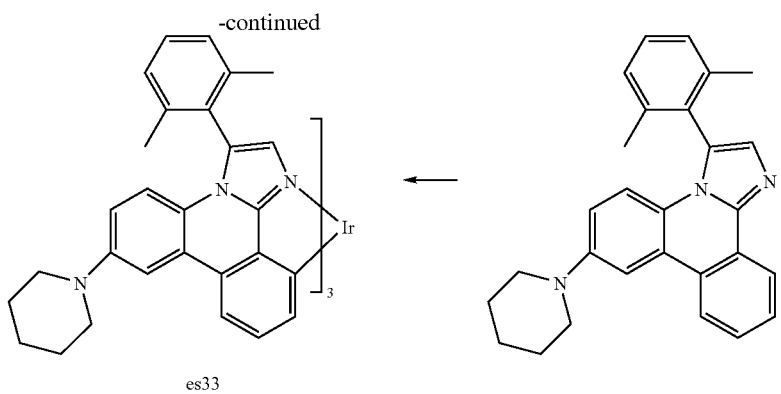

es33

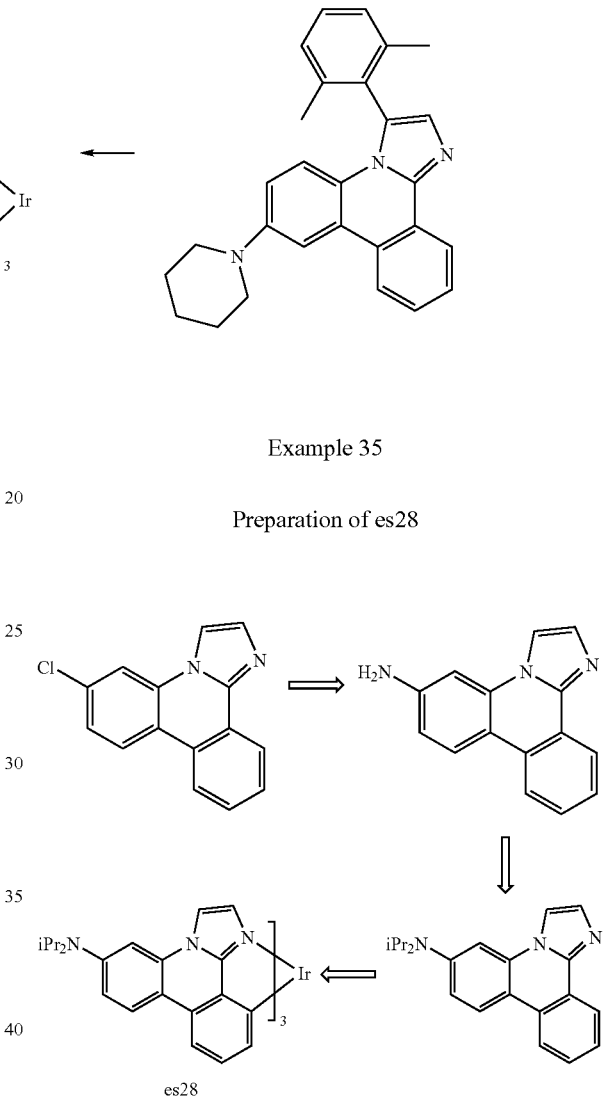

Step 1

To a 1 L round bottom flask was added 7-bromoimidazo[1,2,-f]phenanthridine (10 g, 33.89 mmol, prepared via the general procedure), piperidine (8.66 g, 101 mmol), palladium acetate (532 mg, 2.37 mmol), di-tert-butylbiphenylphosphine (1.41 g, 4.74 mmol), sodium tert-butoxide (4.56 g, 47.45 mmol) and 200 mL of anhydrous toluene. The reaction mixture was heated to 100° C. for 14 h. After cooling, the reaction mixture was purified by chromatography on an aluminum oxide column. Yield: 3.19 g.

Step 2

To a 1 L round bottom flask was added 7-piperidine-imidazo[1,2,-f]phenanthridine (2.9 g, 33.89 mmole, prepared from step 1), and 200 ml of dry DMF. To this mixture with stirring, 100 mL of N-bromosuccinimide DMF solution (1.79 g, 10.08 mmole) was added dropwise at room temperature in the dark. The reaction mixture was continued to stir overnight. Then the mixture was poured into 1 L of water with stirring. The precipitate was collected by filtration, and further washed with copious amount of water, and last with MeOH (50 mL×2), and then dried. Yield of 3-bromo-7-piperidenyl-imidazo[1,2-f]phenanthridine was 3.5 g.

Step 3

To a 500 mL round flask was added 3-bromo-7-piperidenyl-imidazo[1,2-f]phenanthridine (3.5 g, 9.2 mmol), 2,6-dimethylphenylboronic acid (8.28 g, 55.2 mmol), $Pd_2(dba)_3$ (4.21 g, 4.6 mmol), 2-dicyclohexylphosphino-2',6'-dimethoxybiphenyl (S-Phos, 7.55 g, 18.40 mmol), potassium phosphate tribasic (15.6 g, 73.6 mmol), and 200 mL of xylene. The reaction was heated to reflux and stirred under a nitrogen atmosphere for 84 hours. After cooling, the mixture was purified by a silica gel column. Yield was 2.25 g.

Step 4

A 50 mL Schlenk tube flask was charged with 3-(2,6-dimethylphenyl)-7-piperidenyl-imidazo[1,2-f]phenanthridine (1.75 g, 4.32 mmol) and tris(acetylacetonate)iridium (III) (0.5 g, 1 mmol). The reaction mixture was stirred under a nitrogen atmosphere and heated in a sand bath at 240° C. for 48 hours. After cooling, the solidified mixture was dissolved in $CH_2Cl_2$ and further purified by a silica gel column to give the desired compound (0.38 g)

Example 35

Preparation of es28

Step 1

To a 300 ml round bottom flask was added 6-chloroimidazo[1,2,-f]phenanthridine (5 g, 19.78 mmole, prepared from the general procedure), $pd_2(dba)_3$ (1.08 g, 1.18 mmol), 2-(di-cyclohexyl)phosphinobiphenyl (998 mg, 2.84 mmol), lithium bis(trimethylsilyl)amide in THF (23.75 ml, 1 M, 23.74 ml) were added via syringe. The reaction flask was evacuated and back-filled with nitrogen. The reaction mixture was heated to 65° C. for overnight. The reaction was allowed to cool to room temperature, aqueous 1 M HCl (100 ml) was added and the reaction was stirred at room temperature for 5 min. Then the solution was neutralized by the addition of aqueous NaOH solution. The aqueous phase was extracted with dichloromethane three times. The organic layers were combined, concentrated in vacuum. The residue was purified by flash chromatography. Yield was 1.56 g.

Step 2

To a 100 ml round bottom flask was added 6-amino-imidazo[1,2,-f]phenanthridine (100 mg, 0.42 mmol, prepared from step 1), butyl aldehyde (61.84 mg, 0.85 mmol), sodium triacetoxyborohydride (272 mg, 1.28 mmol) and 50 ml of methylene chloride. The reaction mixture was stirred at room temperature for overnight. The reaction mixture was quenched by adding aqueous saturated NaHCO₃, and the product was extracted with EtOAC. The EtOAC layer was concentrated and yield desired product (140 mg)

Step 4

A 50 mL Schlenk tube flask was charged with 6-N,N-diisopropyl-imidazo[1,2-f]phenanthridine (0.45 g, 1.14 mmol) and tris(acetylacetonate)iridium(III) (0.138 g, 0.28 mmol). The reaction mixture was stirred under a nitrogen atmosphere and heated in a sand bath at 240° C. for 48 hours. After cooling, the solidified mixture was dissolved in CH₂Cl₂ and further purified by a silica gel column to give the desired compound (0.1 g)

Example 36

Preparation of es36

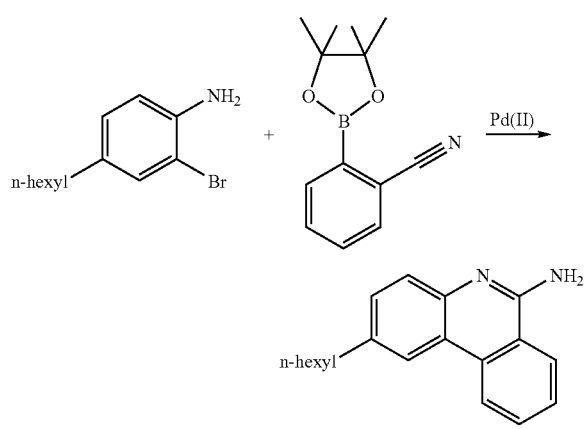

Into a 500 mL 2-necked round bottom flask was placed 2-bromo-4-n-hexylaniline (8.87 grams, 0.035 mol), 2-cyanophenylboronic acid pinacol ester (8.82 grams, 0.039 mol), dichlorobis(triphenylphosphine) palladium(II) (0.98 grams, 4%) and potassium phosphate tribasic monohydrate (12.1 grams, 0.053 mol). The flask was degassed and backfilled with nitrogen before addition of toluene (120 mL) via syringe. The reaction was stirred at reflux for three hours after which time the mixture was cooled to ambient temperature. Dichloromethane (200 mL) was added and the mixture was washed with water. The organic layer was dried over sodium sulfate, concentrated in vacuo and chromatographed (silica gel). Elution with dichloromethane-methanol 9:1 v/v yielded the desired product as a tan solid. NMR, MS confirmed structure.

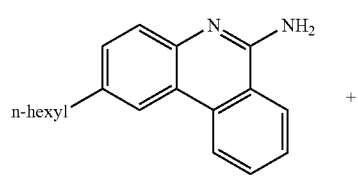

-continued

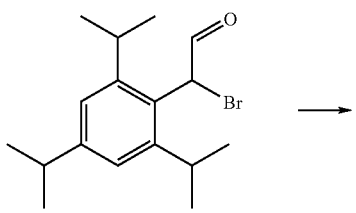

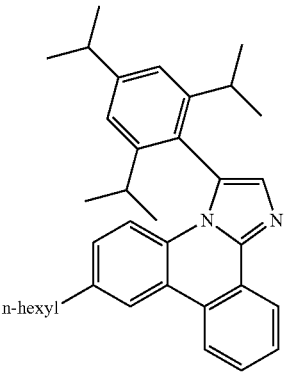

Into a 250 mL round bottom flask was placed 2-hexylphenanthridine-6-amine (6.17 grams, 0.022 mol), 2,4,6-triisopropylphenylbromoacetaldehyde (7.93 grams, 0.024 mol prepared via general procedure B) and isopropanol (50 mL). This was stirred at reflux for 2 hours before addition of sodium bicarbonate (3.7 grams, 0.044 mol). This was stirred at reflux for an additional 18 hours. Water (100 mL) and dichloromethane (100 mL) were added. The layers were separated. The organic layer was dried over sodium sulfate, concentrated in vacuo and chromatographed (silica gel). Elution with ethyl acetate-dichloromethane 1:1 v/v afforded the desired product as an orange oil which solidified on standing. ¹H NMR (CDCl₃) δ8.72 (d, 1H), 8.37 (d, 1H), 7.64 (m, 2H), 7.36 (s, 1H), 7.19 (m, 1H), 7.14 (s, 2H), 7.00 (d, 1H), 3.00 (p, 1H), 2.69 (t, 2H), 2.59 (p, 2H), 1.36 (d, 6H), 1.09 (d, 6H), 0.93 (d, 6H), 0.83 (t, 3H); GC MS 504.

-continued

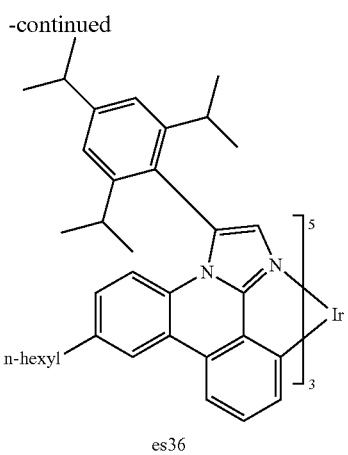

es36

A 50 mL Schlenk tube flask was charged with 7-hexyl-3-(2,4,6-triisopropylphenyl)imidazo[1,2-f]phenanthridine (3.9 g, 7.72 mmol) and tris(acetylacetonate)iridium(III) (0.757 g, 1.54 mmol). The reaction mixture was stirred under a nitrogen atmosphere and heated in a sand bath at 240° C. for 48 hours. After cooling, the solidified mixture was dissolved in CH$_2$Cl$_2$ and further purified by a silica gel column to give the desired compound (0.732 g)

Example 37

General Procedure B for Imidazophenanthridine Ligand Syntheses

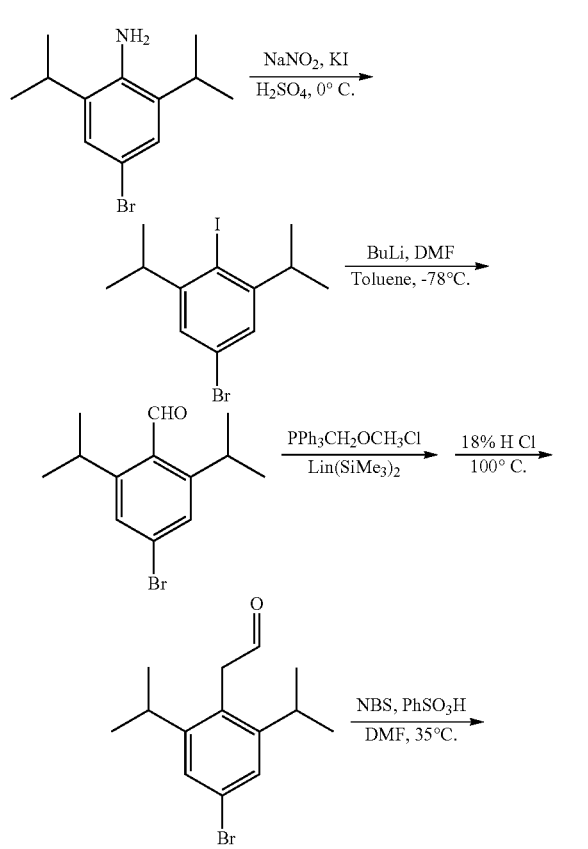

-continued

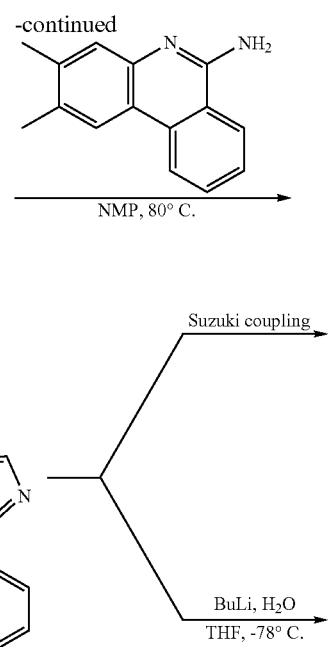

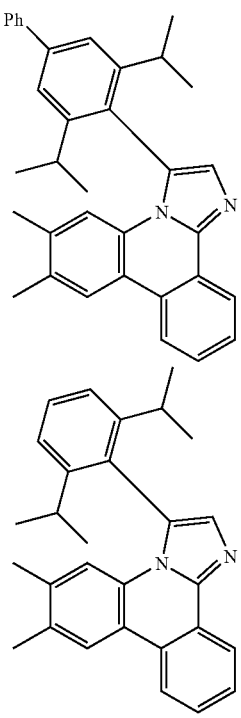

To a 2 L 3-neck flask, equipped with mechanical stirrer, thermometer, and additional funnel, added 300 g of ice and 300 mL of H$_2$SO$_4$. 2,6-diisopropyl-4-bromoaniline (46.0 g, 0.18 mol) in 200 mL of CH$_3$CN was added dropwise to this mixture while the temperature was maintained under 5° C. Then sodium nitrite (22.5 g, 0.32 mol) in 180 mL of ice cold water was added dropwise while the temperature was maintained around 0° C. The resulting clear solution was slowly poured into the solution of potassium iodide (105 g, 0.63 mol) in 300 ml of water at room temperature. The mixture was stirred for 1 h. After regular work up, the crude product was distilled at 170° C. under vacuum to afford 1-iodo-2,6-diisopropyl-4-bromobenzene (60 g) as light brown soft solid upon cooling.

A 150 mL of dry toluene solution of 1-iodo-2,6-diisopropyl-4-bromobenzene (17.6 g, 0.048 mol) was treated with n-BuLi (1.6 M in hexane, 75 mL) at −78° C. in 30 minutes. After stirring for 15 minutes, dry DMF (20 mL) in 50 mL of toluene was added dropwise. The resulting mixture was slowly warmed up to room temperature. After regular work up, the crude product was distilled at 140° C. under vacuum to afford 2,6-diisopropyl-4-bromobenzaldehyde (11.5 g).

Methoxymethyl triphenylphosphonium chloride (18.68 g, 54.5 mmol) was suspended in 200 mL of THF at −78° C. Lithium hexamethyldisilazide (1.0 M in THF, 50 mL) was added dropwise. The resulting mixture was warmed up to 0° C. with stirring. After cooling the solution to −78° C., 2,6-diisopropyl-4-bromobenzaldehyde (11.5 g, 42.7 mmol) in 20 mL of THF was added dropwise. The mixture was slowly warmed up to room temperature and continually stirred overnight. After regular work up, the crude product was distilled at 165° C. under vacuum to afford 2,6-diisopropyl-4-bromo-β-methoxystyrene (10 g). This product was dissolved in 20 mL of dioxane and 100 mL of 18% HCl solution and refluxed at 100° C. for 6 h. After regular work up, the crude product was distilled at 160° C. under vacuum to afford 2,6-diisopropyl-4-bromophenylacetaldehyde (7.5 g).

To a dry DMF solution of 2,6-diisopropyl-4-bromophenylacetaldehyde (7.3 g, 25.8 mmol) at 0° C. was added 2,6-ditert-butyl-4-methylphenol (0.056 g, 0.26 mmol), followed by NBS (4.59 g, 25.8 mmol). After stirring for few minutes, benzenesulfonic acid (8.16 g, 51.6 mmol) was added. The resulting mixture was stirred at 35° C. for 12 h under nitrogen. After regular work up, the crude product was purified by column chromatography to afford 2-(2,6-diisopropyl-4-bromophenyl)propionaldehyde (5.4 g).

To a 500 mL round flask was added the above intermediate, 2,3-dimethyl-6-aminophenanthridine (6.6 g, 30 mmol), and 100 mL of NMP. The mixture was stirred at 80° C. for 48 hours. After regular work up, the crude product was purified by a silica gel column. Yield was around 1 to 2 g in different runs.

Example 38

Preparation of es32

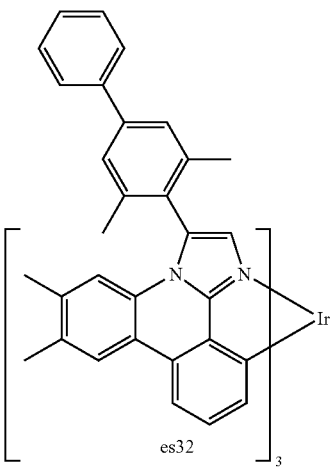

Each step of the following procedure should be protected from light. A 50 mL Schlenk tube flask was charged with 3-(2,6-dimethyl-4-phenylphenyl)-6,7-dimethylimidazo[1,2-f]phenanthridine (1.90 g, 4.46 mmol, obtained from 3-(2,6-dimethyl-4-bromophenyl)-6,7-dimethylimidazo[1,2-f]phenanthridine through general method B followed by Suzuki coupling and tris(acetylacetonate)iridium(III) (0.48 g, 0.99 mmol). The reaction mixture was stirred under a nitrogen atmosphere and heated in a sand bath at 240° C. for 48 hours. After cooling, the solidified mixture was dissolved in $CH_2Cl_2$ and further purified by a silica gel column to give es32 (0.60 g). $^1H$ NMR result confirmed the desired compound. $\lambda_{max}$ of emission=468, 490 nm ($CH_2Cl_2$ solution at room temperature), CIE=(0.17, 0.33).

Example 39

Preparation of es24

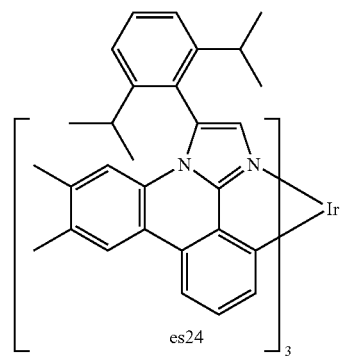

Each step of the following procedure should be protected from light. A 50 mL Schlenk tube flask was charged with 3-(2,6-diisopropylphenyl)-6,7-dimethylimidazo[1,2-f]phenanthridine (2.10 g, 5.17 mmol, obtained from 3-(2,6-diisopropyl-4-bromophenyl)-6,7-dimethylimidazo[1,2-f]phenanthridine through general method B followed by treating this THF solution with n-BuLi and quenched by water at −78° C.) and tris(acetylacetonate)iridium(III) (0.56 g, 1.15 mmol). The reaction mixture was stirred under a nitrogen atmosphere and heated in a sand bath at 240° C. for 48 hours. After cooling, the solidified mixture was dissolved in $CH_2Cl_2$ and further purified by a silica gel column to give es24 (0.54 g). $^1H$ NMR result confirmed the desired compound. $\lambda_{max}$ of emission=458, 488 nm ($CH_2Cl_2$ solution at room temperature), CIE=(0.17, 0.25).

Example 40

Preparation of es37

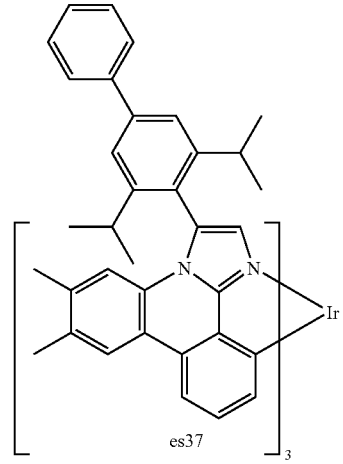

Each step of the following procedure should be protected from light. A 50 mL Schlenk tube flask was charged with 3-(2,6-diisopropyl-4-phenylphenyl)-6,7-dimethylimidazo[1,2-f]phenanthridine (1.75 g, 3.60 mmol, obtained from 3-(2,6-diisopropyl-4-bromophenyl)-6,7-dimethylimidazo[1,2-f]phenanthridine through general method B followed by Suzuki coupling and tris(acetylacetonate)iridium(III) (0.40 g, 0.80 mmol). The reaction mixture was stirred under a nitrogen atmosphere and heated in a sand bath at 240° C. for 48 hours. After cooling, the solidified mixture was dissolved in CH$_2$Cl$_2$ and further purified by a silica gel column to give es37 (0.54 g). $^1$H NMR result confirmed the desired compound. $\lambda_{max}$ of emission=456, 488 nm (CH$_2$Cl$_2$ solution at room temperature), CIE=(0.17, 0.24).

Example 41

Preparation of es31

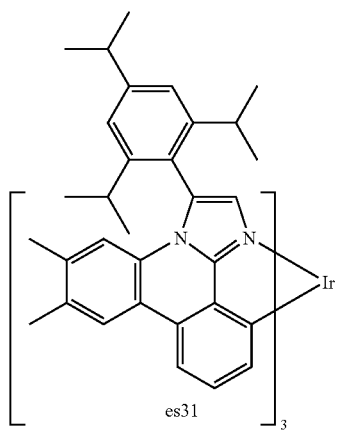

Each step of the following procedure should be protected from light. A 50 mL Schlenk tube flask was charged with 3-(2,4,6-triisopropylphenyl)-6,7-dimethylimidazo[1,2-f]phenanthridine (1.95 g, 4.35 mmol, obtained from general method B by using 2,4,6-triisopropylbenzadelhyde as starting material) and tris(acetylacetonate)iridium(III) (0.43 g, 0.96 mmol). The reaction mixture was stirred under a nitrogen atmosphere and heated in a sand bath at 240° C. for 48 hours. After cooling, the solidified mixture was dissolved in CH$_2$Cl$_2$ and further purified by a silica gel column to give es31 (0.52 g). $^1$H NMR results confirmed the desired compound. $\lambda_{max}$ of emission=460, 490 nm (CH$_2$Cl$_2$ solution at room temperature), CIE=(0.16, 0.25).

Example 42

Fabrication of an OLED Device Comprising es101

An OLED device comprising es101 as the emissive compound is fabricated according to procedures described by Lin et al. in U.S. patent application Ser. No. 11/241,981 and by Tung et al. in U.S. patent application Ser. No. 11/242,025 and emits blue-green light when a 10 mA/cm$^2$ current is passed through the device.

Example 43

OLED Devices

OLED devices comprising dopants of the present invention were fabricated according to procedures described by Lin et al. in U.S. patent application Ser. No. 11/241,981 and by Tung et al. in U.S. patent application Ser. No. 11/242,025 and gave rise to the data detailed in FIGS. 3-13, 15 and 16.

Example 44

Preparation of es38

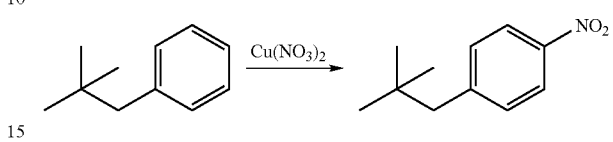

Neopentylbenzene (43.17 grams, 0.29 mol) was charged into a 1 liter round bottom flask. To this was added acetic anhydride (400 mls). The flask was then placed into an ice-water bath and copper (II) nitrate hydrate (54.4 grams, 0.29 mol) was added. The reaction was stirred for one hour at 0-5° C. The ice bath was then removed and the reaction stirred to ambient temperature for one additional hour after which time the mixture was poured into ice-water. The pH was adjusted to 7 using aqueous ammonium hydroxide. The product was then extracted with ethyl acetate. The organic layer was sequentially washed with aqueous sodium carbonate and brine and dried over sodium sulfate. Evaporation of solvents in vacuo gave an oil (55.9 grams, >99%) which was used without further purification.

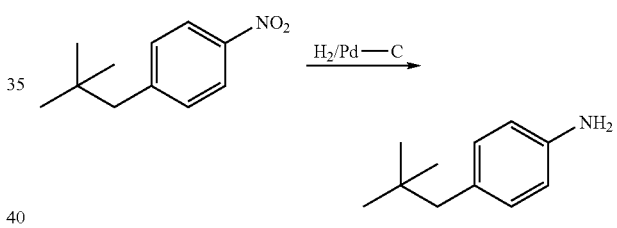

The 4-nitro neopentylbenzene from the above reaction (55.9 grams) was hydrogenated approximately 10 grams at a time in ethyl acetate (100 mls) using Pd—C 10% (1 gram) and H$_2$ (40 psi) for 20 minutes. The crude product was then filtered through a bed of celite and concentrated in vacuo. When all of the hydrogenations were complete the product was purified on a silica gel column eluting first with 9:1 hexane-ethyl acetate then 4:1 hexane—ethyl acetate. The undesired isomer elutes first. The desired isomer elutes second and is obtained as a white solid $^1$H nmr (CDCl$_3$) δ 6.91 (d, 2H), 6.61 (d, 2H), 2.38 (s, 2H), 0.87 (s, 9H).

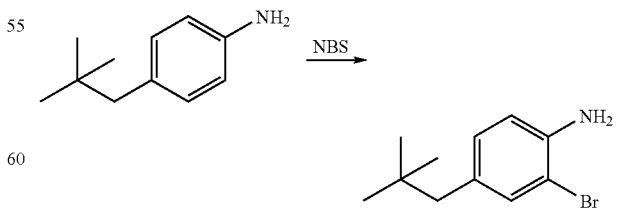

4-neopentyl aniline (18.38 grams, 0.112 mol) was dissolved in 200 mls of anhydrous dimethyl formamide. To this was added (dropwise) N-bromosuccinimide (20.0 grams, 0.112 mol) dissolved in 80 mls of dimethyl formamide. The reaction was stirred at ambient temperature over night. The reaction was then poured into water and neutralized with sodium bicarbonate. The product was extracted with ethyl acetate. The organic layer was then washed with water, dried over sodium sulfate and evaporated in vacuo to give the crude product which was purified using silica gel chromatography. Elution with 19:1 hexane-ethyl acetate gave the desired product (22.18 grams, 82%) as a light orange solid. $^1$H nmr (CD$_2$Cl$_2$) δ 7.25 (s, 1H), 6.86 (d, 1H), 6.68 (d, 1H), 2.33 (s, 2H), 0.85 (s, 9H).

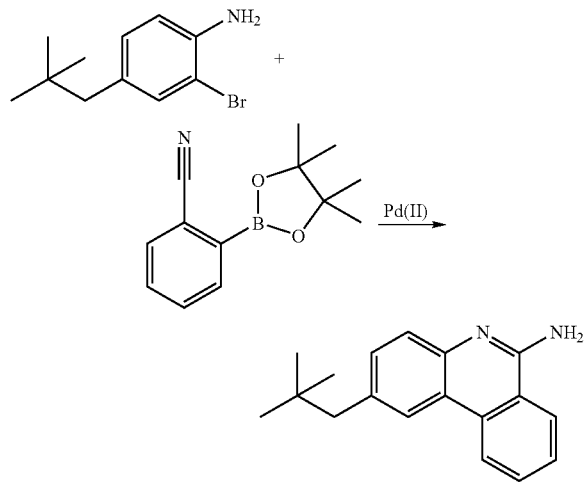

2-bromo-4-neopenyl aniline (22.12 grams, 0.091 mol) was placed into a 500 ml round bottom flask. To this was added the 2-cyanophenyl boronic ester (20.93 grams, 0.091 mol), bis(triphenylphosphine) palladium(II) dichloride 6.3 grams (10%), potassium phosphate monohydrate (31.4 grams, 0.14 mol), water (1.8 mls, 0.1 mol) and toluene (200 mls). The reaction was evacuated and backfilled with nitrogen twice before being stirred at reflux for 5 hours. The reaction was cooled to ambient temperature and filtered. The crude solid was washed with hexane and partitioned between water and dichloromethane. The organic layer was dried over sodium sulfate and evaporated to give 10.56 grams of product. The filtrate was chromatographed (silica gel) eluting first with 1:1 ethyl acetate-dichloromethane and then 9:1 dichloromethane-methanol to afford 6.32 additional grams of product. Total yield 16.88 grams, 70%. Beige solid. $^1$H nmr (DMSO d6) δ 8.61 (d, 1H), 8.30 (d, 1H), 8.15 (s, 1H), 7.78 (t, 1H), 7.63 (t, 1H), 7.43 (d, 1H), 7.27 (d, 1H), 2.61 (s, 2H), 0.91 (s, 9H). LCMS (ES+) 265.1

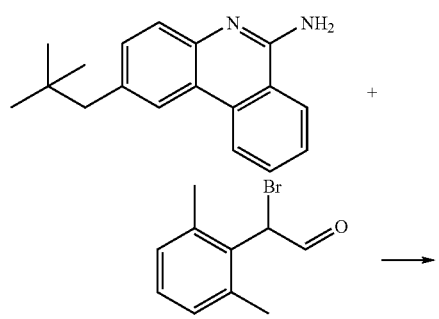

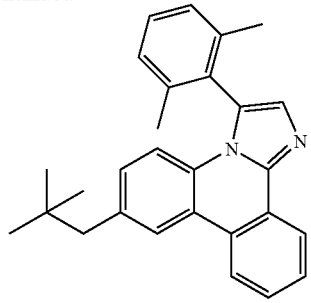

Into a 500 ml round bottom flask was placed the amidine (7.13 grams, 0.027 mol) and the 2,6-dimethyl bromophenyl acetaldehyde (6.13 grams, 0.027 mol) and isopropanol (200 mls). This was stirred at reflux for 2 hours before addition of sodium bicarbonate (4.54 grams, 0.054 mol). This was stirred at reflux for 8 additional hours before being evaporated in vacuo. The crude residue was partitioned between water and dichloro methane. The organic layer was dried (sodium sulfate) and chromatographed (silica gel). Elution with 49:1 hexane-ethyl acetate then 9:1 hexane-ethyl acetate gave the product as a white solid. (6.58 grams, 62%). $^1$H nmr (CD$_2$Cl$_2$) d 8.75 (m, 1H), 8.38 (d, 1H), 8.19 (s, 1H), 7.66 (m, 2H), 7.36 (m, 2H), 2.60 (s, 2H), 2.08 (s, 6H), 0.93 (s, 9H).

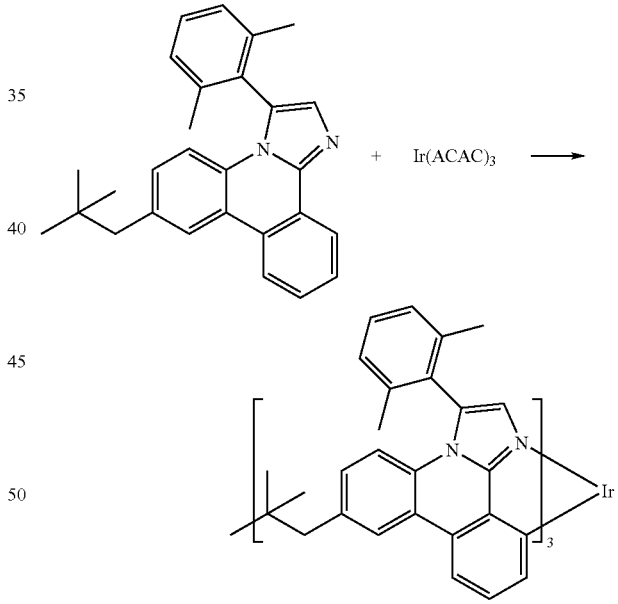

Each step of the following procedure should be protected from light. A 50 mL Schlenk tube flask was charged with 3-(2,6-dimethylphenyl)-7-neopentylimidazo[1,2-f]phenanthridine (4.69 g, 11.96 mmol) and tris(acetylacetonate)iridium(III) (1.17 g, 2.39 mmol). The reaction mixture was stirred under a nitrogen atmosphere and heated in a sand bath at 240° C. for 48 hours. After cooling, the solidified mixture was dissolved in CH$_2$Cl$_2$ and further purified by a silica gel column to give desired compound (2.3 g). $^1$H NMR confirmed the structure. Emission maximum=464, 490 nm (CH$_2$Cl$_2$ solution at room temperature), CIE=(0.17, 0.30).

Example 45

Preparation of es38

Example 45 provides a method of preparing es38 that is improved relative to Example 44.

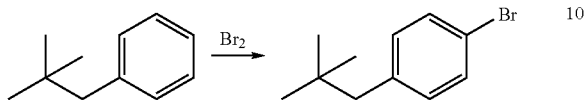

A one liter 3-necked flask was equipped with an overhead stirrer and nitrogen inlet. To this was added neopentyl benzene (20.0 grams, 0.13 mol) and neutral alumina (50 grams). This was stirred to assure complete adsorption. In a beaker were added bromine (22.5 grams, 0.14 mol) and neutral alumuna (50 grams). This was stirred with a spatula and then added portion wise to the neopentyl benzene with stirring. The mixture goes from dark orange to a cream color within a few minutes. The alumina was then placed on a silica gel column and eluted with dichloro methane to give 28.6 grams of product as an oil which was used without further purification.

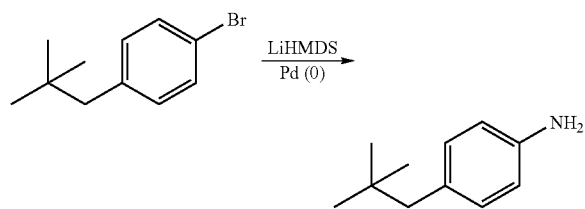

The oil, 4-neopentylphenyl bromide (28.6 grams) was placed into a 1 liter 3-necked flask equipped with a thermocouple, addition funnel and a reflux condenser. To this was added tris (dibenzylideneacetone) di palladium (0) (3.5 grams, 3 mol %) and (2-biphenyl)dicyclohexyl phosphine (2.2 grams, 5 mol %). The flask was evacuated and back filled with nitrogen twice before addition of 200 mls of 1 N sol'n of lithium bis trimethylsilyl amide in THF. The reaction was stirred at 65° C. for 24 hours before removal of heat and careful quenching with water. Next 150 mls of 1N HCl was added and this was stirred for 30 minutes before addition of 10% NaOH to bring the pH to 7. The product was extracted with dichloromethane (3×100 mls). The combined organic layers were washed with brine (100 mls), dried over sodium sulfate, concentrated in vacuo and chromatographed (silica gel) eluting first with 9:1 hexane-ethyl acetate then with 4:1 hexane-ethyl acetate to give 13.4 grams of product as a white solid.

Example 46

Preparation of es45

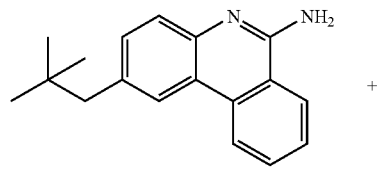

+

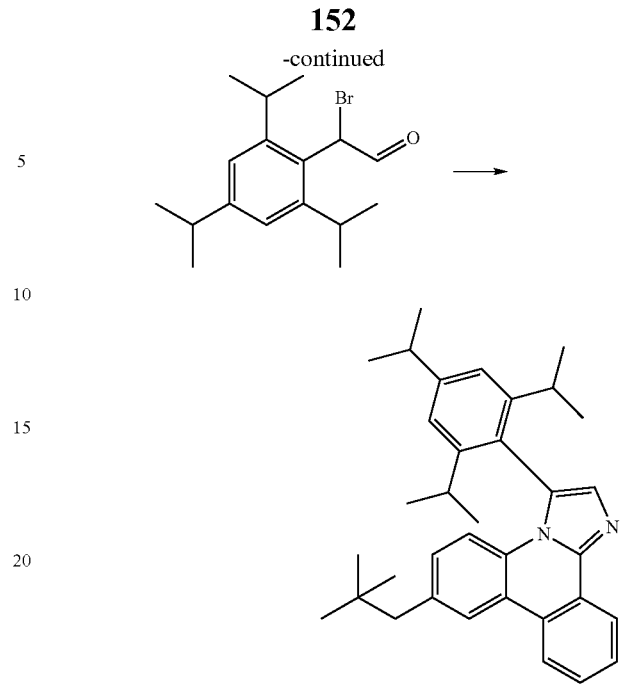

10.82 g (0.041 moles) of the neopentyl amidine intermediate was dissolved in 200 ml of isopropanol. To this solution, 13.27 g (0.041 moles) of the triisopropylphenyl acetyl bromide intermediate was added all at once. This solution was heated at 85° C. for three hours. At this point, the reaction mixture was allowed to cool to just under the reflux temperature of isopropanol. Sodium bicarbonate 6.89 g (0.082 moles) was added portion wise over a 5 minute period to the reaction mixture. The reaction mixture was then heated back up to 85 C and was held at this temperature for 18 hours. The reaction mixture was diluted with 300 mls. of water. This mixture was filtered. The filtrate was extracted 2×250 mls ethyl acetate. These ethyl acetate extracts were combined and washed 1×100 mls aqueous 10% LiCl. These extracts were then dried over magnesium sulfate, filtered and stripped under vacuum.

The crude product from the work-up was passed through a silica gel column. The column was eluted with 5-25% ethyl acetate/methylene chloride. The cleanest fractions were combined and stripped under vacuum yielding 4.5 g of product. $^1$H nmr (CDCl$_3$) δ 3.05 (m, 1H), 2.60 (m, 4H), 1.37 (d, 6H), 1.11 (d, 6H), 0.92 (m, 15H).

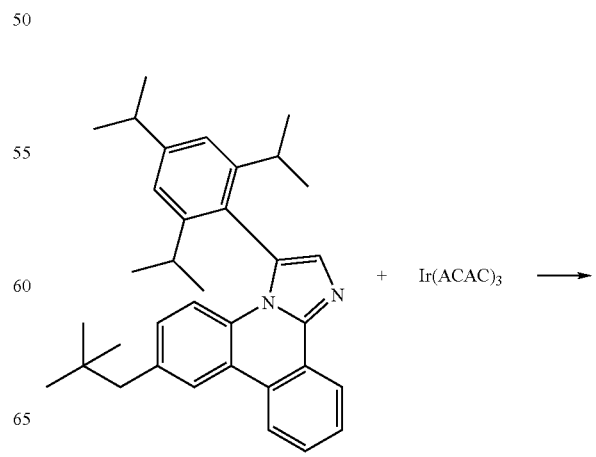

+ Ir(ACAC)$_3$ →

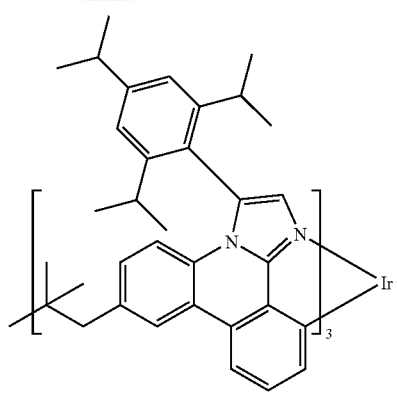

To a 50 mL Schlenk tube were added ligand (3.77 g, 8.16 mmol), tris(acetylacetonate)iridium (III) (0.8 g, 1.63 mmol, which was purified by an Al$_2$O$_3$ column with CH$_2$Cl$_2$ as eluent) and tridecane (50 drops). The mixture was degassed and back filled with nitrogen before being heated in a sand bath (outside sand bath temperature was 240-250° C.) with stirring under a nitrogen atmosphere for 72 h. After cooling, the reaction mixture was sonicated with a mixture of solvent (CH$_2$Cl$_2$: Hexanes=10 ml: 90 ml). A dark yellow suspension was obtained. A yellow solid was collected by filtration. The solid was purified by flash column chromatography (SiO2; CH$_2$Cl$_2$). The solid after column chromatography was recrystallized from Ethyl Acetate. The yield after crystallization is 0.8 g. Structure was confirmed by proton nmr.

Example 47

Preparation of es39 (Prophetic Example)

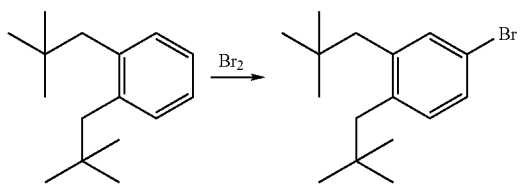

O-dineopentyl benzene can be synthesized using the methodology of Nakayama et. al. J. Org. Chem. 1998, 63, 4912-4924. The O-dineopentyl benzene could be brominated using bromine and neutral alumina as described in example 45.

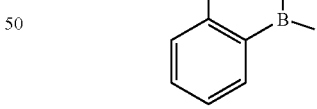

The 3,4-dineopentylbromobenzene could be aminated using lithium hexamethyldisilazane and a palladium (0) catalyst as described in example 45.

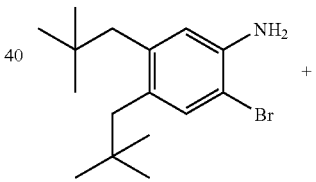

The 3,4-dineopentylaniline could be brominated using N-bromosuccinimide in dimethylformamide as demonstrated in example 44.

The 2-bromo-4,5-dineopentylaniline could be reacted with the 2-cyanophenyl boronic acid pinacol ester using the conditions described in example 44 to give the amidine intermediate.

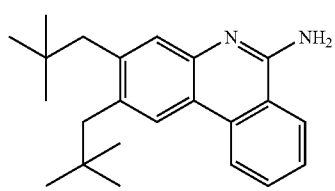

+

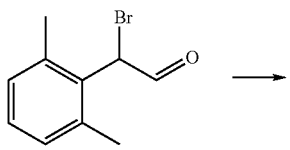

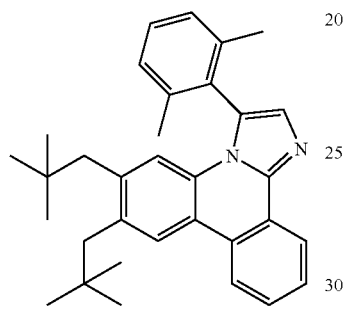

The amidine intermediate can be reacted with the 2-bromo-2-(2,6-dimethylphenyl)acetaldehyde as described in example 44 to give the ligand.

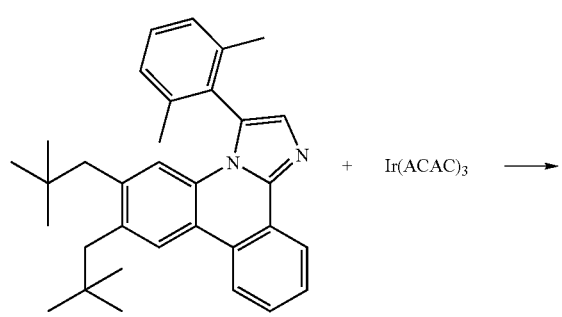 + Ir(ACAC)$_3$ →

The ligand can be reacted with tris(acetylacetonate)iridium (III) at a temperature of 250° C. as described in example 44 to give the emitter.

Example 48

Preparation of es40 (Prophetic Example)

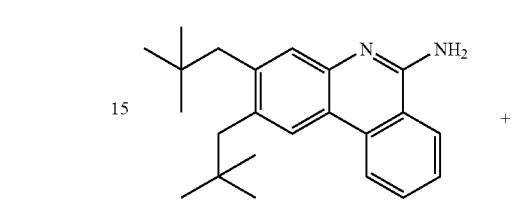

+

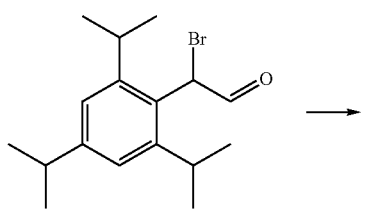

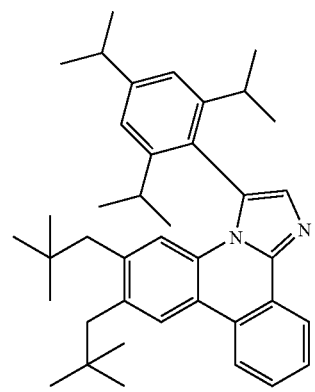

The amidine intermediate can be reacted with 2-bromo-2-(2,4,6-triisopropyl)acetaldehyde in isopropanol as described in example 46 to give the ligand.

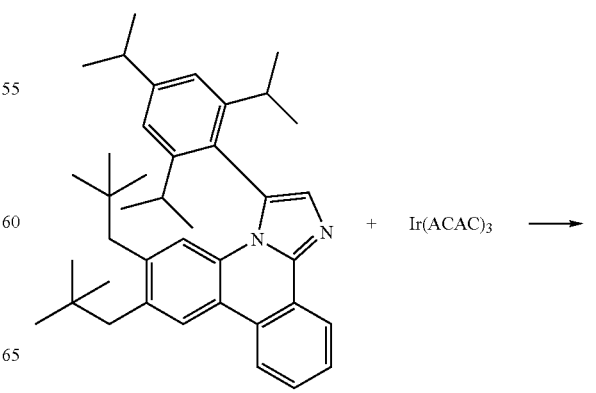 + Ir(ACAC)$_3$ →

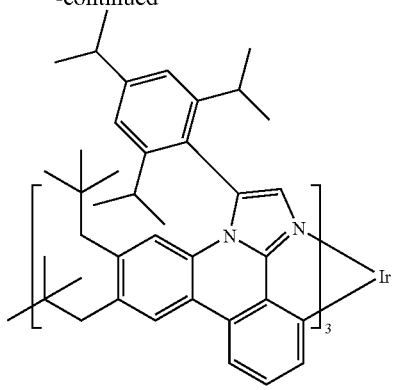

The ligand can be ligated with tris(acetylacetonate)iridium (III) at 250° C. as described in example 46 to give the emitter.

Example 49

Preparation of es41 (Prophetic Example)

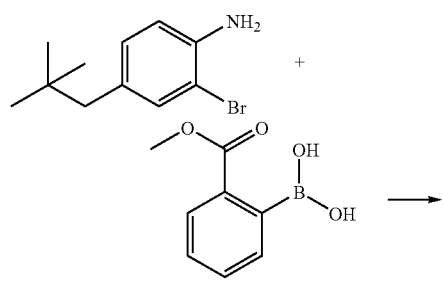

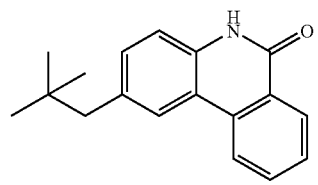

The 2-bromo-4-neopentyl aniline described in example 44 can be reacted with the ester substituted phenyl boronic acid in a solvent such as toluene and using a palladium catalyst such as bis(triphenylphosphine)palladium dichloride to give the phenanthridinone.

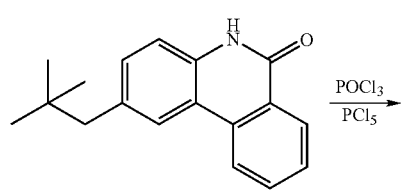

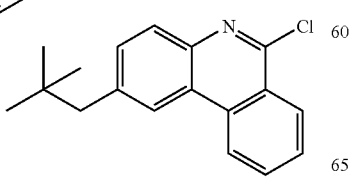

The phenanthridinone can be stirred at reflux in phosphorus oxychloride with phosphorus pentachloride to give the chlorophenanthridine.

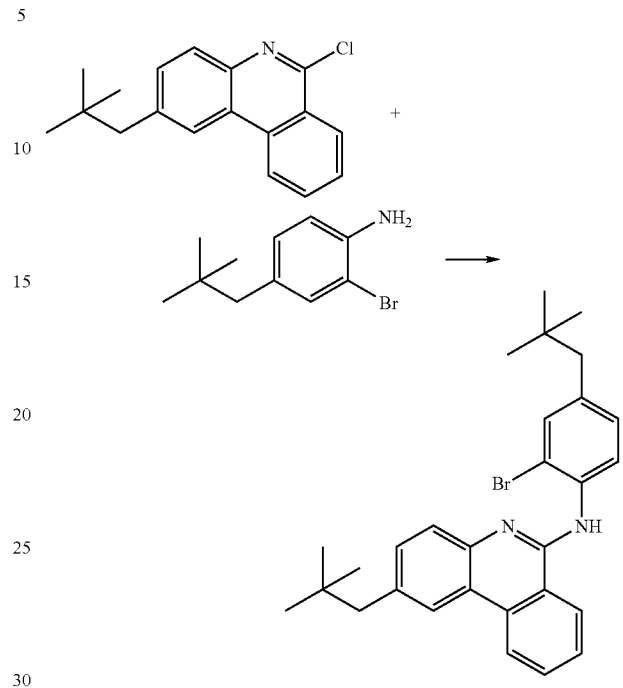

The chlorophenanthridine can be reacted with the 2-bromo-4-neopentyl aniline at reflux in a solvent such as diglyme (di-ethyleneglycol dimethyl ether) to give the phenylamino substituted phenanthridine shown.

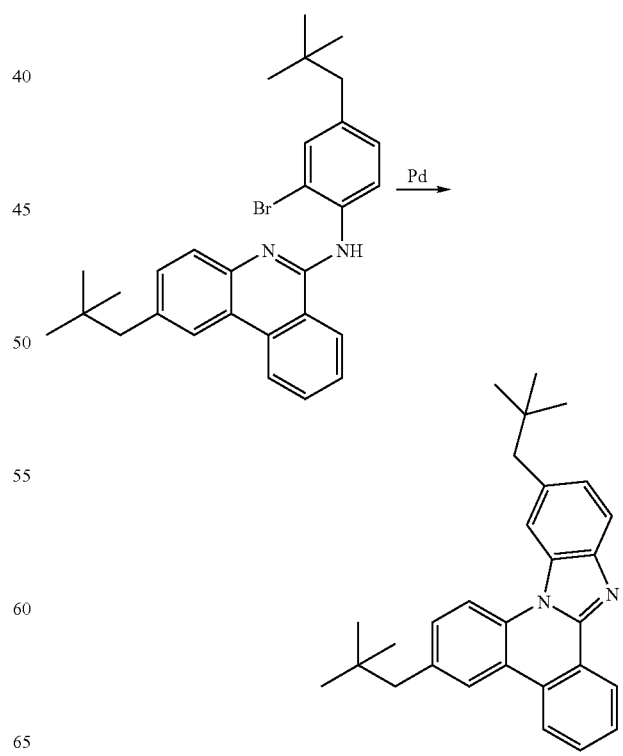

The phenylamino substituted phenanthridine can be with a palladium catalyst such as palladium acetate in a solvent such as toluene to give the benzannulated ligand.

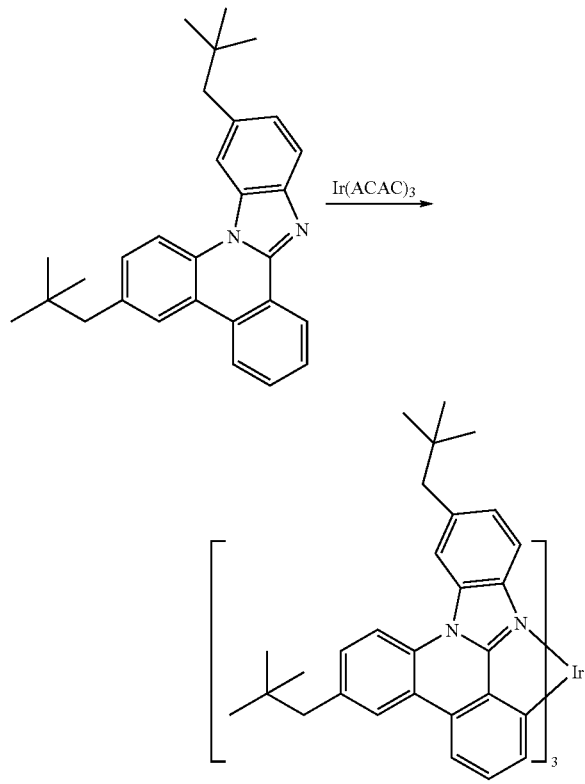

Treatment of the ligand with tris(acetylacetonate)iridium (III) at 250° C. would afford the emitter.

Example 50

Preparation of es56 (Prophetic Example)

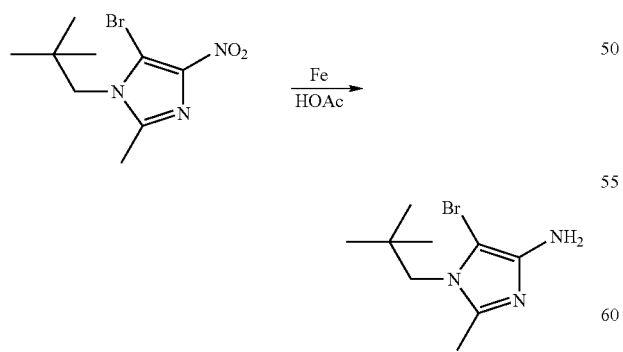

The Brominated nitro imidazole can be prepared using the synthetic procedures reported by Singh et. al. J. Org. Chem. 1992, 57, pp 3240-3242. Treatment of the imidazole with iron powder in acetic acid would yield the amino imidazole.

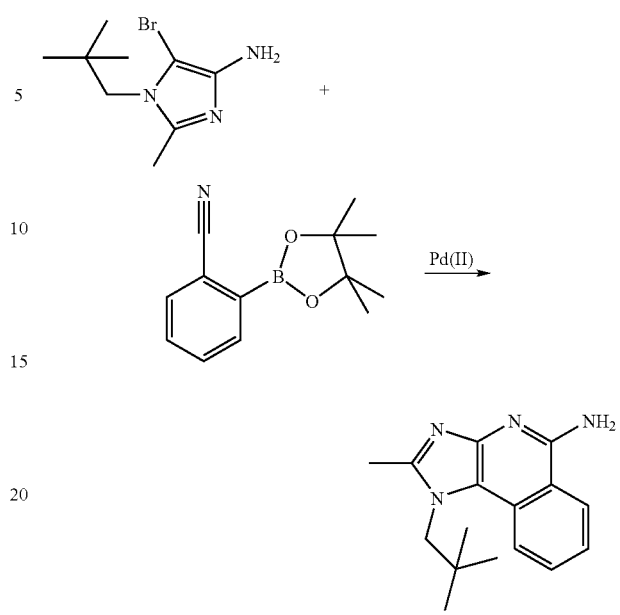

The amino imidazole can be reacted with 2-cyano phenyl-boronic acid pinacol ester in a Suzuki coupling reaction analogous to that described in example 44 to give the amidine intermediate.

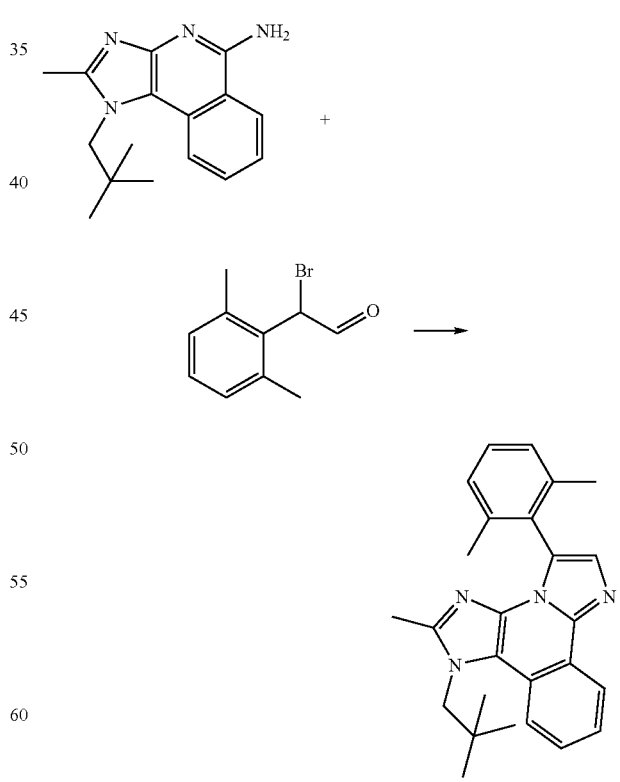

The amidine intermediate can be reacted with the 2-bromo-2-(2,6-dimethylphenyl)acetaldehyde as described in example 44 to give the target ligand.

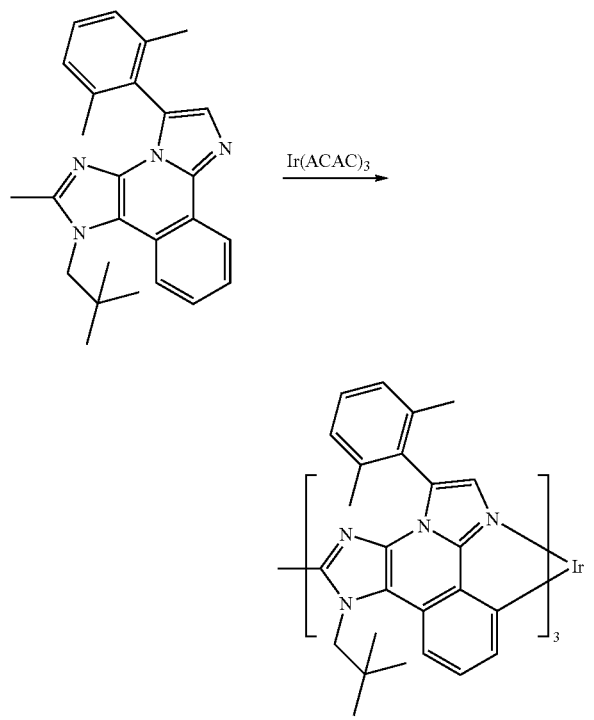

The ligand can be treated with tris(acetylacetonate)iridium (III) at 250° C. to give the desired emitter.

Example 51

Preparation of es57 (Prophetic Example)

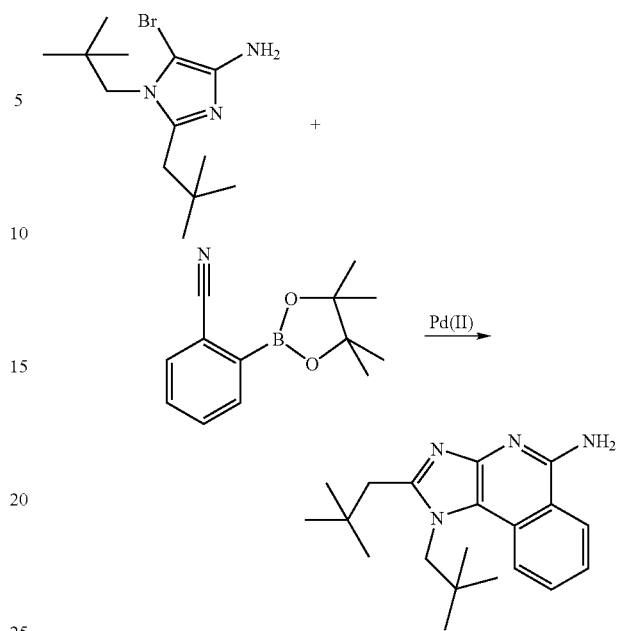

The amino imidazole can be reacted with 2-cyanophenyl boronic acid pinacol ester in a Suzuki reaction analogously to the reaction described in example 44 to give the amidine.

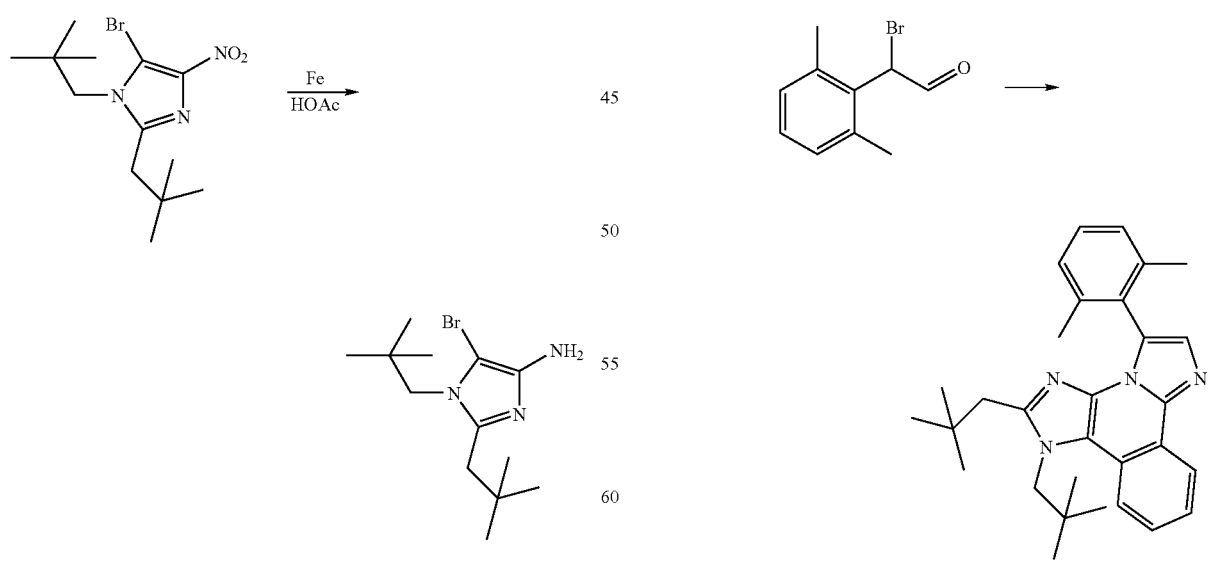

The starting imidazole can be prepared by the same reference as in Example 50. Reduction of the nitro group using iron powder in acetic acid would provide the amino imidazole.

The amidine can be reacted with 2-bromo-2-(2,6-dimethylphenyl)acetaldehyde in a solvent such as isopropanol as described in example 44 to afford the ligand.

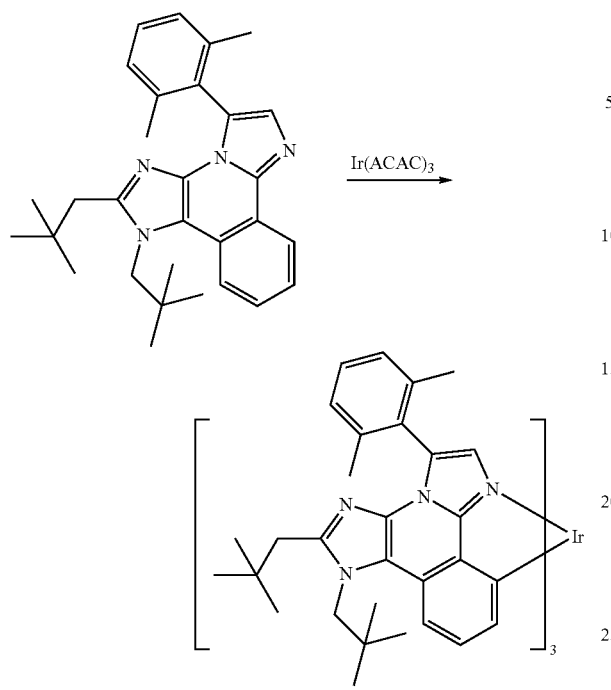

The ligand can be treated with tris(acetylacetonate)iridium (III) at 250° C. as described in example 46 to give the target emitter.

Example 52

Preparation of es58 (Prophetic Example)

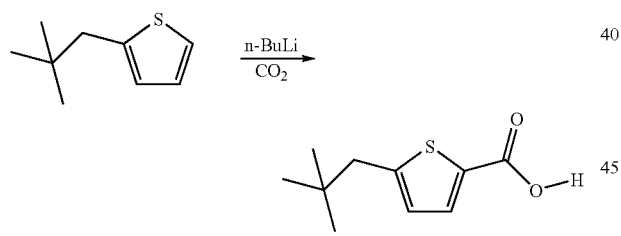

Neopentyl thiophene can be lithiated upon treatment with n-butyllithium in a solvent such as tetrahydrofuran. Treatment of the lithiated specie with dry ice ($CO_2$) would give the carboxylic acid.

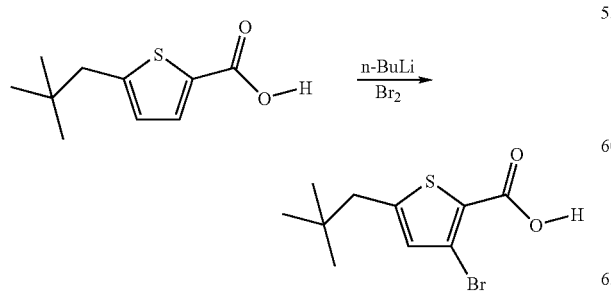

Reaction of the starting carboxylic acid with n-butyllithium followed by addition of bromine would afford the Brominated intermediate.

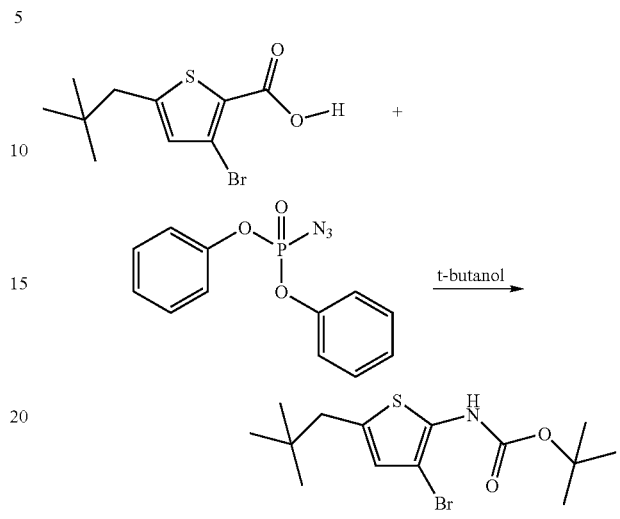

The starting thiophene carboxylic acid can be reacted with the commercially available diphenoxyphosphoryl azide in tertiary butanol at reflux temperature for approximately 15 hours to give the protected amine. This follows the general procedure of Yang et. al. *Chemica Scripta* 1988, 28, pp 275-279.

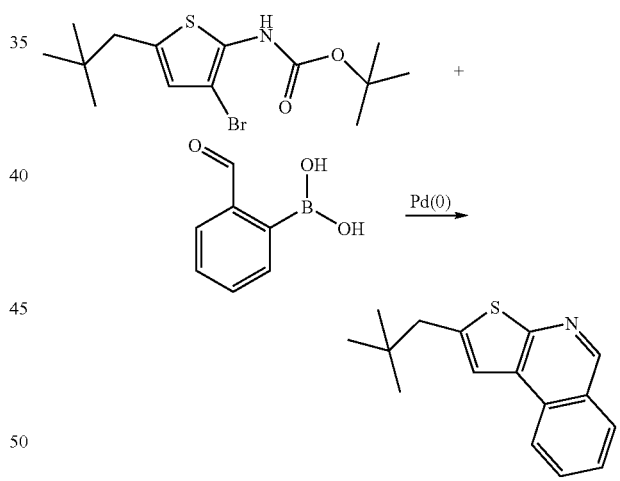

The starting thiophene can be reacted with 2-formylphenyl boronic acid using an adaptation of Gronowitz et. al. *J Heterocyclic Chem.*, 26, pp 865-868 (1989) to give the resulting thienoisoquinoline.

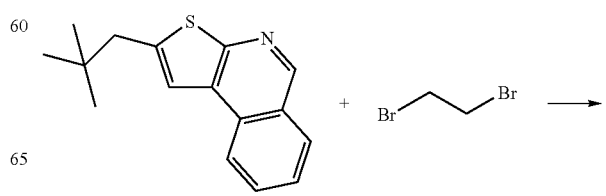

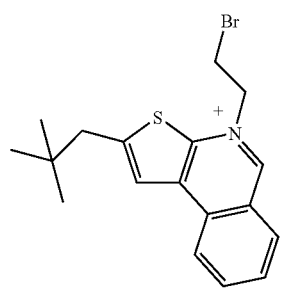

The thienoisoquinoline can be reacted with ethylene dibromide as the solvent to give the salt.

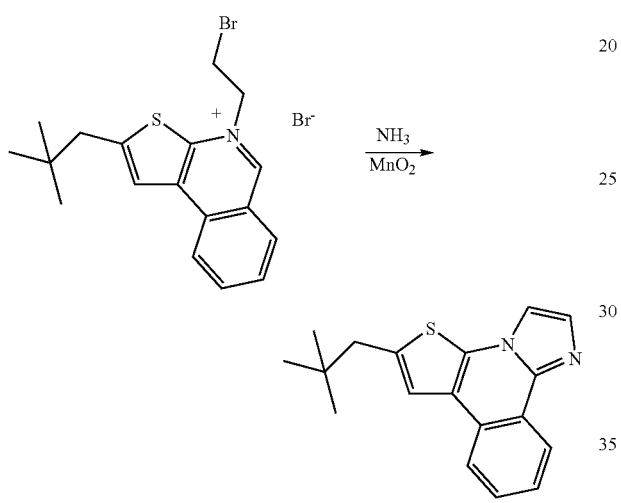

The salt can be reacted first with ammonia in toluene and the manganese dioxide using the general procedure of Cronin et. al. *Organic Letters* vol 9 (12) pp 2253-2256 (2007).

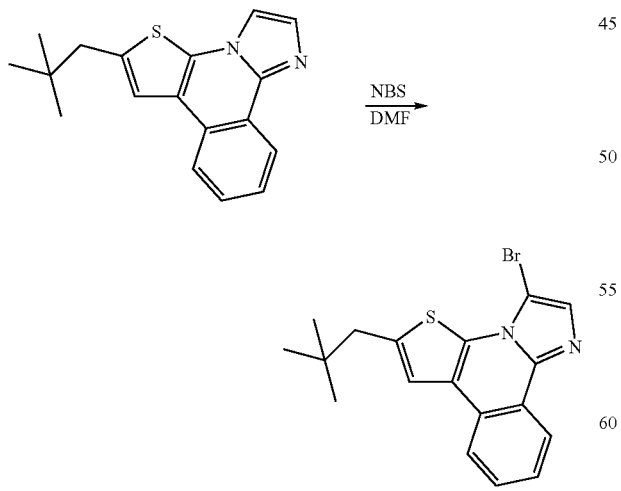

The imidazole ring can be selectively Brominated at the indicated position using n-bromo succinimide in dimethylformamide at ambient temperature.

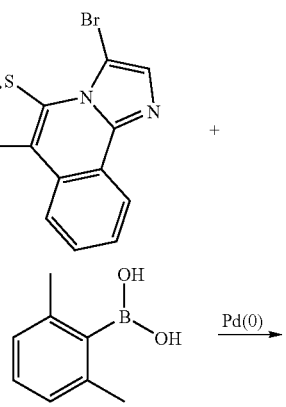

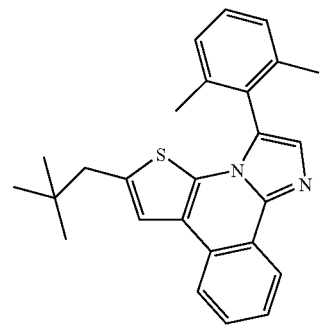

The Brominated intermediate can be reacted with the commercially available 2,6-dimethylphenyl boronic acid in toluene using a palladium catalyst such as tris(dibenzylidene) dipalladium to provide the ligand.

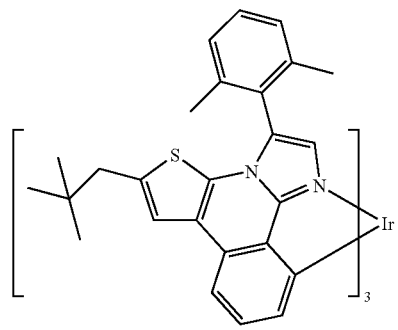

Example 53

Preparation of es42 (Prophetic Example)

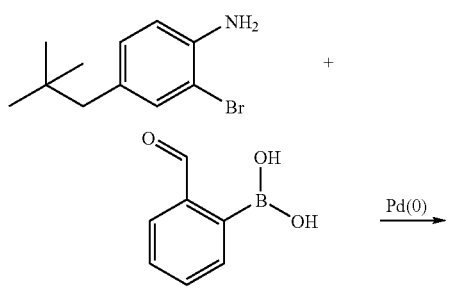

The 2-bromo-4-neopentyl aniline can be reacted with the commercially available 2-formylphenyl boronic acid in a Suzuki reaction employing a palladium (0) catalyst such as the commercially available tetrakis(triphenylphosphine)palladium (0) to give the neopentyl substituted phenanthridine.

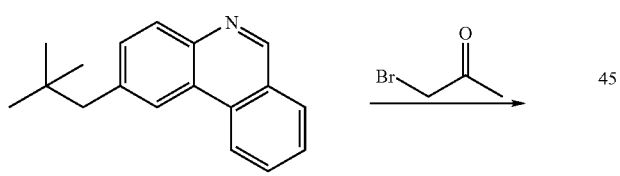

The phenanthridine can be reacted with bromoacetone in a refluxing solvent such as acetonitrile using an adaptation of Cronin et. Al. *Organic Letters* vol 9 (12) pp 2253-2256 (2007) to provide the quaternary salt.

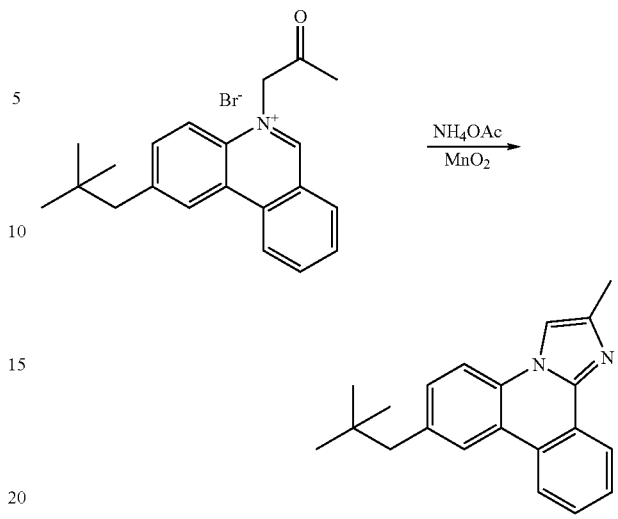

The quaternary salt can be treated with ammonium acetate and manganese dioxide to give the ligand shown above.

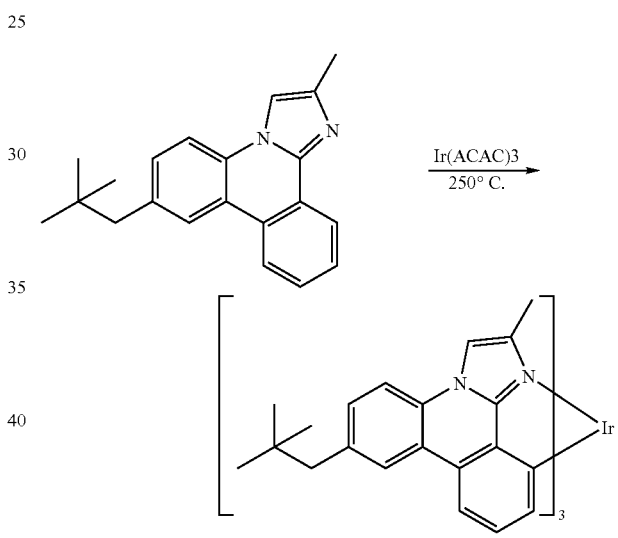

The ligand can be treated with tris(acetylacetonate)iridium (III) at 250° C. to give the desired dopant.

Example 54

Preparation of es59 (Prophetic Example)

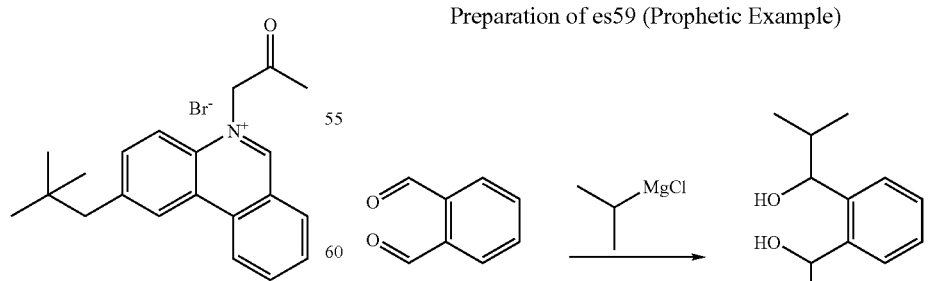

Following an adaptation of Garg et. al. SYNLETT pp 310-312 (1998), the commercially available phthaldialdehyde (8.85 grams, 0.066 mol) was dissolved in 100 mls of anhydrous tetrahydrofuran. This solution was cooled to ⁻40° C. in a dry ice acetonitrile bath. Isopropyl magnesium chloride (100 mls of 2N solution in THF) was added via addition funnel. Following addition of the Grignard reagent the mixture was allowed to stir to ambient temperature over night. The reaction was then quenched with water then aqueous ammonium chloride. The crude material was then filtered through celite and the filtrate was diluted with ethylacetate (100 mls) and was then washed with 1N HCl. The layers were separated and the organic layer was washed with water, dried over sodium sulfate and evaporated in vacuo. Final purification was achieved by silica gel column chromatography using a mobile phase of hexane:ethyl acetate 3:2 to afford the diol as a viscous yellow oil. $^1$H NMR (CDCl$_3$) δ 4.63 (d, 2H, CHOH), 2.04 (m, 2H, isopropyl CH), 1.06 (d, 6H, CH$_3$), 0.76 (d, 6H, CH$_3$).

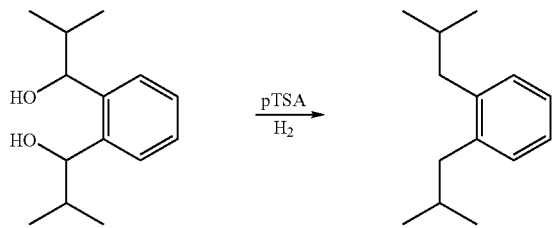

The diol can be dissolved in a solvent such as methanol with a catalytic amount of p-toluene sulfonic acid and a catalyst such as palladium on carbon and hydrogenated to give the di-isobutyl benzene.

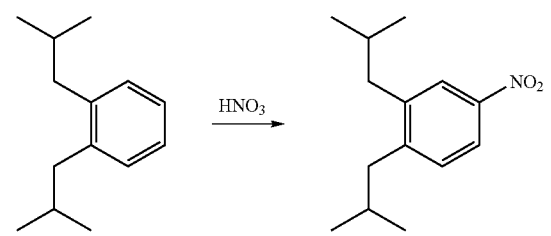

Di-isobutyl benzene can be nitrated using nitric acid or fuming nitric acid to provide the nitrated intermediate shown above.

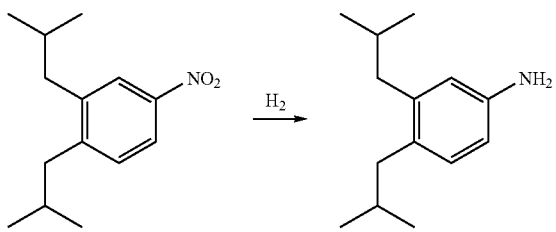

The 3,4-di-isobutylnitrobenzene can be hydrogenated in a solvent such as ethyl acetate using palladium on carbon to afford the aniline.

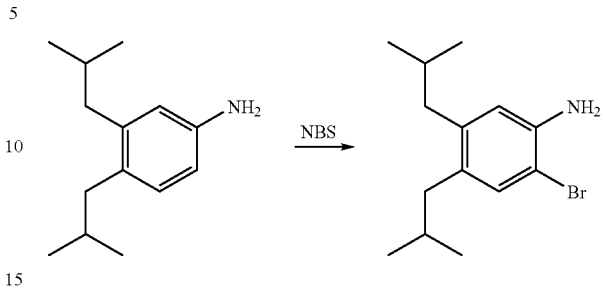

The 3,4-di-isobutyl aniline could be brominated in dimethylformamide using n-bromosuccinimide at ambient temperature to yield the Brominated product.

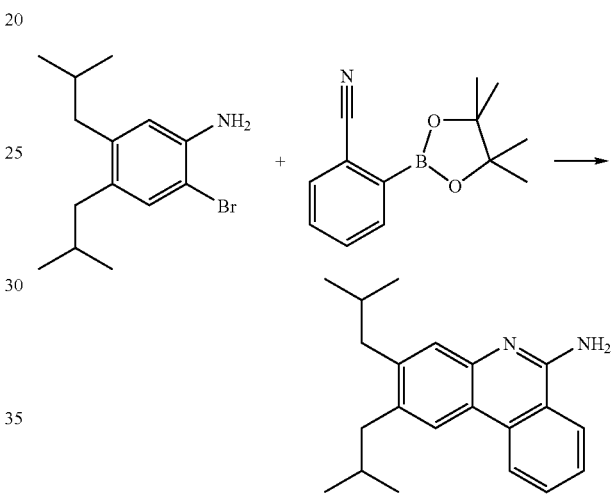

The 2-bromo-4,5-di-isobutyl aniline can undergo a Suzuki reaction with the commercially available 2-cyanophenyl boronic acid pinacol ester in a solvent such as toluene or dioxane and using a catalyst such as bis(triphenyl phosphine) palladium (II) dichloride to provide the desired amino phenanthridine.

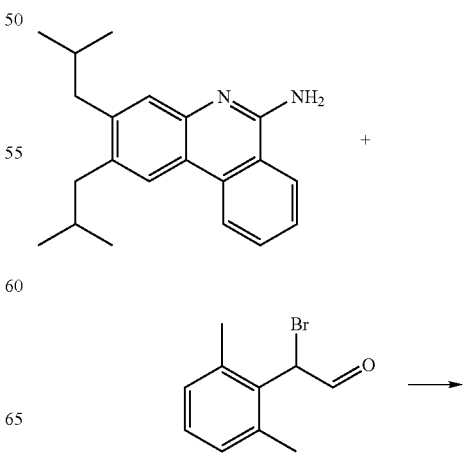

-continued

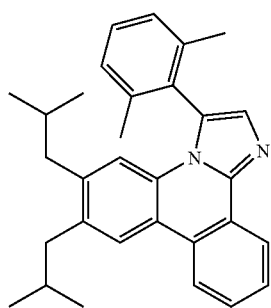

The amino phenanthridine can be reacted with the (2,6-dimethyl)phenylbromoacetaldehyde in isopropanol to give the ligand.

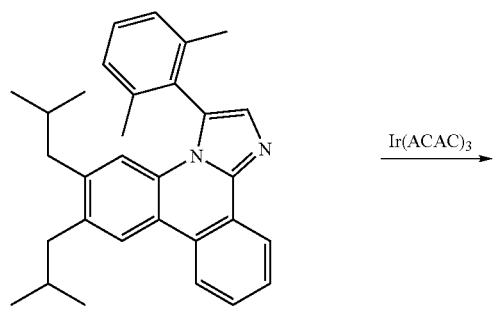

The ligand can be treated with tris (acetylacetonate) iridium (III) and tridecane at 250° C. for 48-72 hours to give the desired emitter.

Example 55

Preparation of es60 (Prophetic Example)

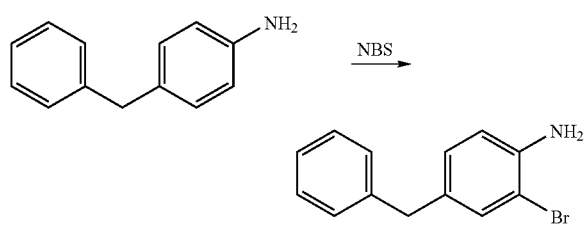

The commercially available 4-benzyl aniline can be selectively brominated at the ortho position using n-bromosuccinimide in dimethylformamide to give the desired 2-bromo-4-benzyl aniline.

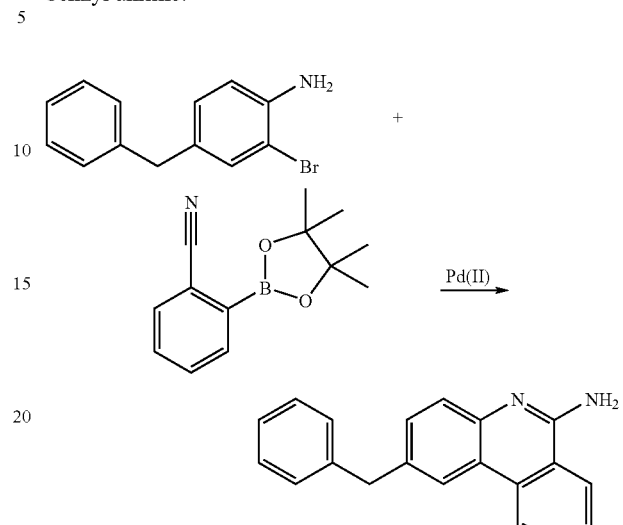

The 2-bromo-4-benzyl aniline can be reacted with the 2-cyano phenyl boronic acid pinacol ester in a Suzuki reaction using a palladium (II) catalyst to give the desired amino phenanthridine.

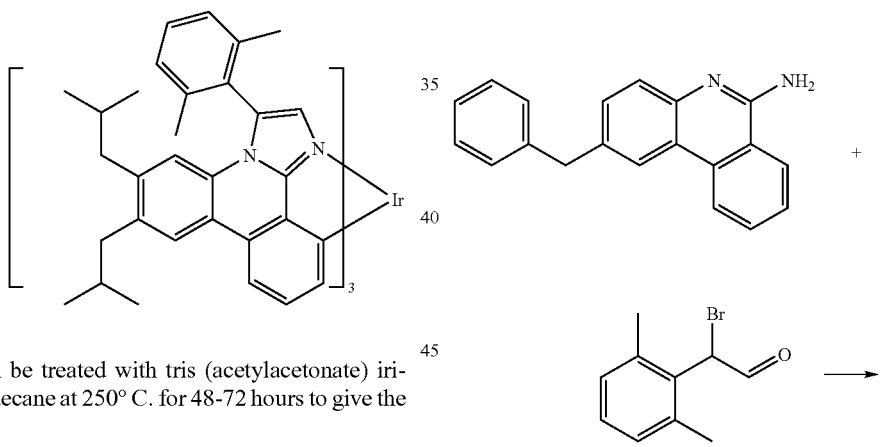

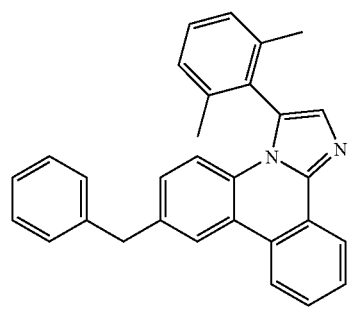

The amino phenanthridine can be reacted with (2,6-dimethyl)phenyl bromoacetaldehyde in isopropanol using sodium carbonate as base to yield the desired ligand.

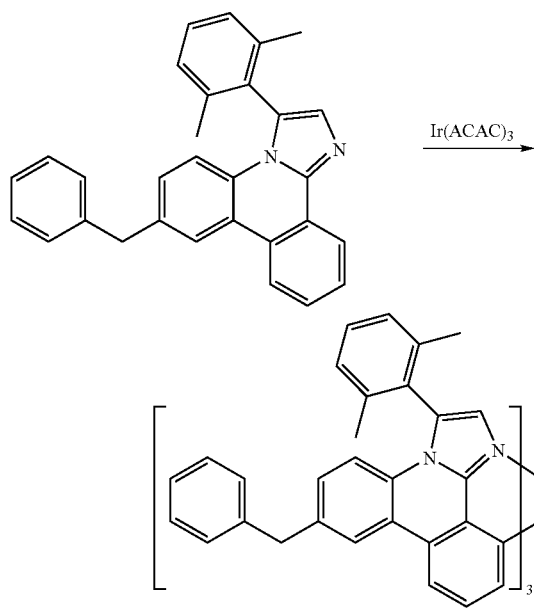

The ligand can be treated with tris (acetylacetonate) iridium (III) and tridecane at 250° C. for 48-72 hours to give the desired emitter.

Example 56

Preparation of es61 (Prophetic Example)

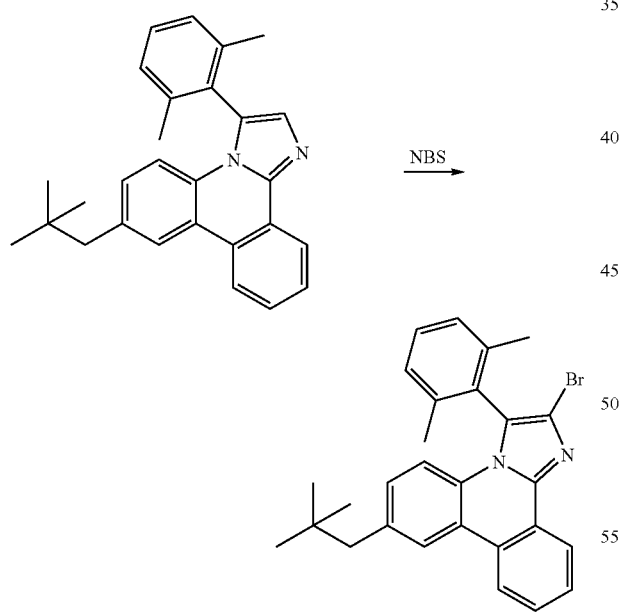

The starting imidazophenanthridine (5.0 grams, 0.013 mol) was dissolved in 75 mls of dimethylformamide. To this was added dropwise, a solution of n-bromo succinimide (3.07 grams, 0.017 mol) in dimethylformamide (15 mls). The solution was stirred under nitrogen at ambient temperature for 48 hours before being diluted with water (200 mls). The mixture was made basic by addition of sodium bicarbonate. The product was extracted with ethyl acetate (2×150 mls). The combined extracts were washed with 10% aqueous lithium chloride, dried over magnesium sulfate and concentrated in vacuo. The product was purified by column chromatography (neutral, deactivated alumina) using a mobile phase of 40-60% dichloromethane in hexane to give the desired product (4.6 grams, 76%) as a tan solid. LCMS 472.8 (ES+).

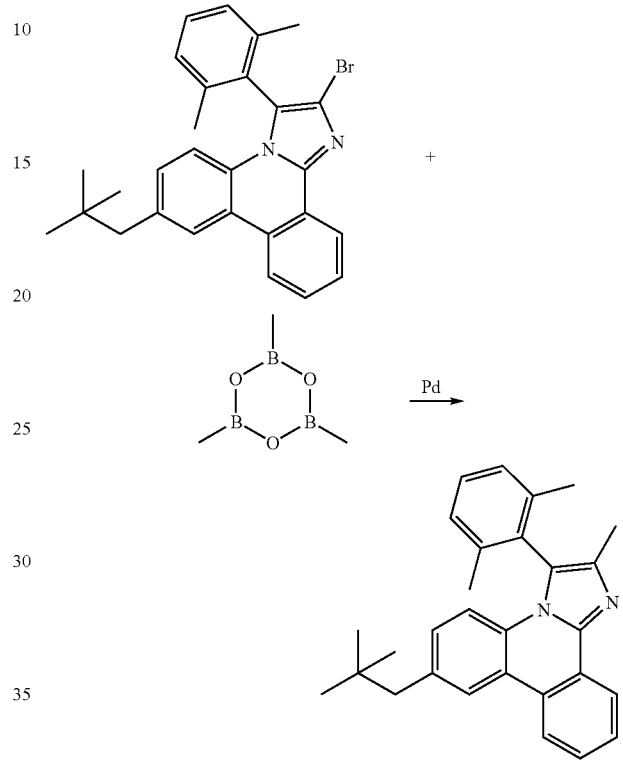

Into a 100 ml round bottom flask was placed bromo-imidazophenanthridine (0.45 grams, 0.96 mmol), trimethylboroxine 0.93 grams, 7.4 mmol), Palladium (II) acetate (0.018 grams, 0.08 mmol), 2-dicyclohexylphosphino-2',6'-dimethoxy biphenyl (S-Phos) (0.17 grams, 0.42 mmol), toluene (20 mls) and potassium phosphate tribasic (0.88 grams 3.8 mmol dissolved in 5 mls of water). The flask was evacuated and backfilled with nitrogen and then stirred at reflux for 16 hours after which time the layers were separated and the organic layer was dried over MgSO$_4$, concentrated in vacuo and chromatographed (silica gel) eluting with 15% ethyl acetate in dichloromethane to give the desired product (0.32 grams, 82%) as a white solid. LC MS (ES$^+$) 407.0

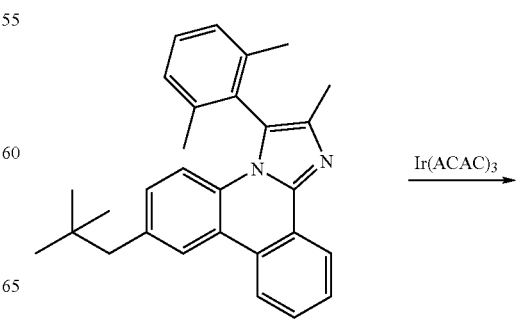

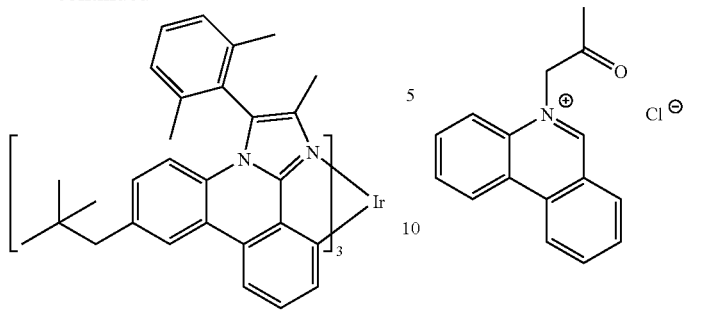

To a 50 mL Schlenk tube were added ligand (3.77 g, 9.27 mmol), tris(acetylacetonate)iridium (II) (0.91 g, 1.85 mmol, which was purified by an Al₂O₃ column with CH₂Cl₂ as eluent) and tridecane (50 drops). The mixture was degassed and back filled with nitrogen before being heated in a sand bath (outside sand bath temperature was 235° C.) with stirring under a nitrogen atmosphere for 116 h. After cooling, the reaction mixture was sonicated with a mixture of solvent. (30% methylene chloride in hexanes) A dark yellow suspension was obtained. A yellow solid was collected by filtration. The solid was washed extensively with hot acetonitrile to get desired compound. (1.97 g; 75%).

Example 57

Preparation of es43

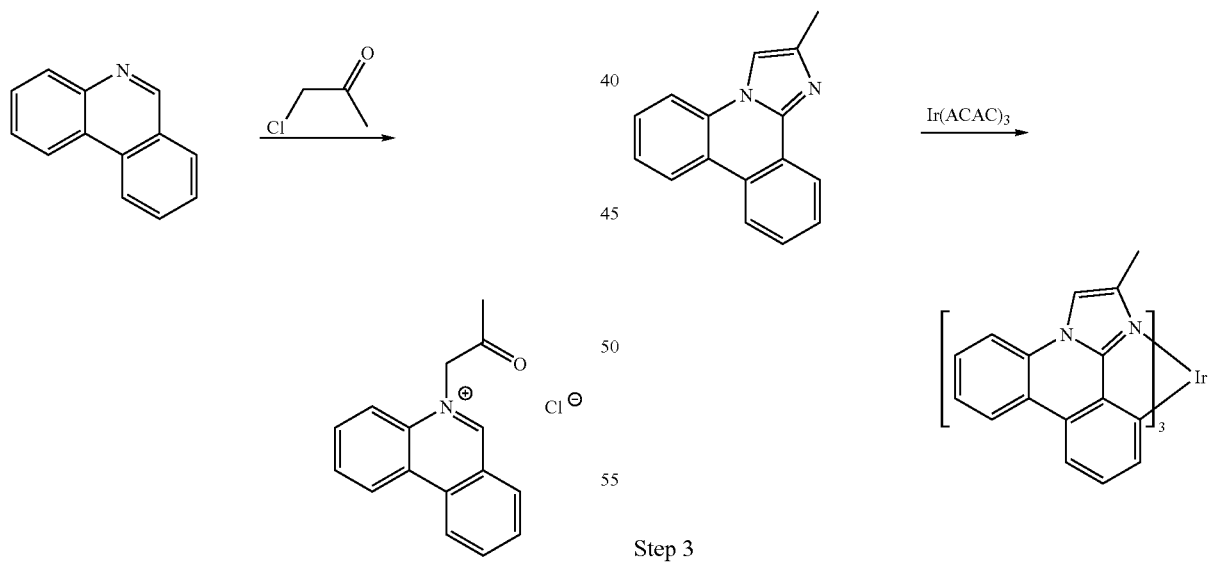

Step 1

A 500 ml round bottom flask was charged with phenanthridine (15 g, 83.69 mmole), chloroacetone (277 g). The reaction mixture was heated at 50° C. for 2 days. The reaction mixture was cooled to room temperature and diluted with ether to induce the precipitation. The precipitation was filtered off to yield the desired product (6.74 g, 30%)

Step 2

To a stirred suspension of the product from step 1 (6.74 g, 24.8 mmole) in dioxane (240 ml) at room temperature, were added ammonium acetate (7.64 g, 99.1 mmole), followed by MnO₂ (21.54 g, 248 mmole). The reaction mixture was refluxed for 4 hours before adding 10 equivalents of Na₂CO₃ (26.27 g, 248 mmole). The suspension was then cooled down to room temperature and filtered on glass frit and then the residue was rinsed extensively with acetone. Finally, the mother liquid was concentrated to dryness and subjected to column chromatography (SiO₂, 1% methanol in CH₂Cl₂) to yield desired compound (5 g, 87%).

Step 3

To a 50 mL Schlenk tube were added ligand from step 2 (2.3 g, 9.9 mmol), tris(acetylacetonate)iridium (III) (0.97 g, 1.98 mmol, which was purified by an Al₂O₃ column with CH₂Cl₂ as eluent) and tridecane (50 drops). The mixture was degassed and back filled with nitrogen before being heated in a sand bath (outside sand bath temperature was 235° C.) with stirring under a nitrogen atmosphere for 67 h. After cooling, the reaction mixture was sonicated with a CH₂Cl₂. A dark yellow suspension was obtained. A yellow solid was collected by filtration. The solid was washed extensively with hot ethyl acetate to get desired compound. (919 mg; 53%).

Example 58

Preparation of es46

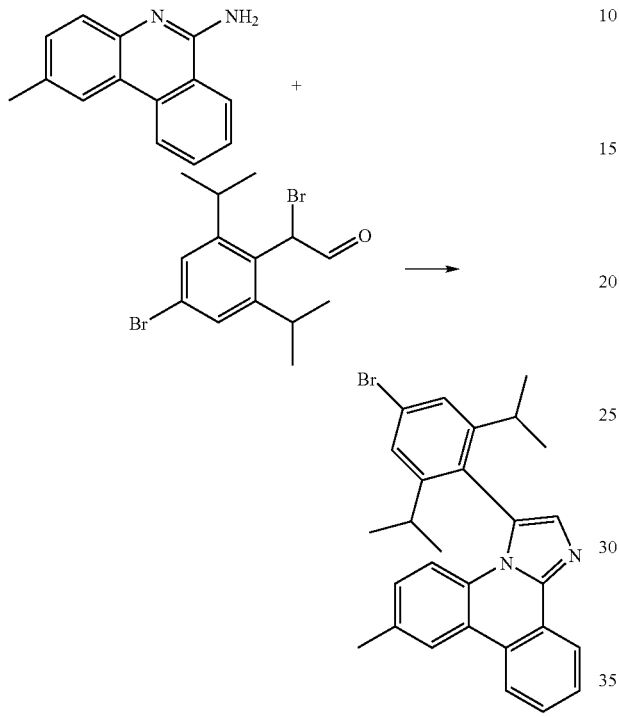

Into a 250 ml round bottom flask was placed the aminophenanthridine (2.88 grams, 14.0 mmol) and isopropanol (100 mls). The bromophenyl acetaldehyde (5.0 grams, 14.0 mmol) was dissolved in 50 mls of isopropanol and added to the reaction mixture dropwise. This was then stirred at reflux for 16 hours after which time the reaction mixture was cooled to 70° C. and sodium bicarbonate (2.35 grams, 28.0 mmol) was added. The reaction was heated to reflux and stirred for an additional 16 hours. The reaction mixture was then cooled to ambient temperature and filtered. The filtrate was concentrated in vacuo and column chromatographed (silica gel) eluting with 10-20% ethyl acetate in hexane to give the product as a solid. GC MS 472.

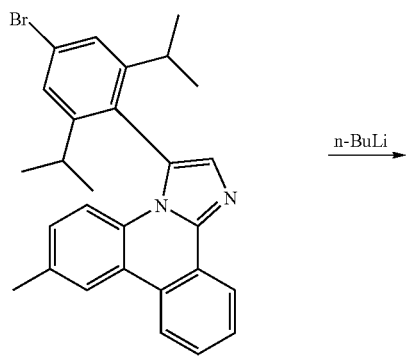

-continued

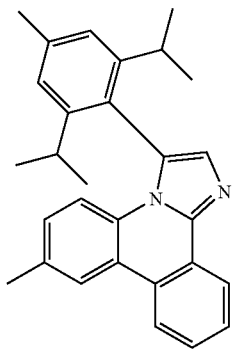

The imidazophenanthridine (4.0 grams, 8.48 mmol) was dissolved in tetrahydrofuran (100 mls) and cooled to −78° C. N-butyllithium (8.5 mls of 1.6 N sol'n) was added dropwise. The reaction continued to stir at −78° C. for one additional hour before addition of water (2 mls). The reaction was stirred to ambient temperature before being diluted with brine (100 mls) and ethyl acetate (100 mls). The organic layer was dried over MgSO$_4$ and concentrated in vacuo. The product was purified on an alumina column eluted with 10-50% dichloromethane in hexane to give the product as a solid. GC MS 392.

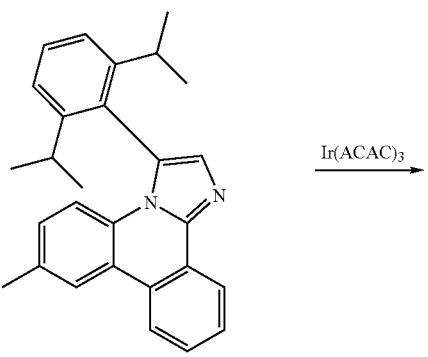

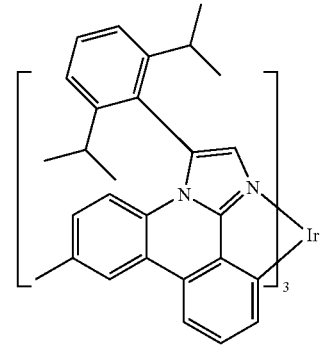

A 50 mL Schlenk tube flask was charged with 3-(2,6-diisopropylphenyl)-7-methylimidazo[1,2-f]phenanthridine (1.80 g, 4.58 mmol) and tris(acetylacetonate)iridium(III) (0.49 g, 1.00 mmol). The reaction mixture was stirred under a nitrogen atmosphere and heated in a sand bath at 240° C. for 48 hours. After cooling, the solidified mixture was dissolved in CH$_2$Cl$_2$ and further purified by a silica gel column eluted with dichloromethane to give (0.70 g). $^1$H NMR result confirmed the desired compound. $\lambda_{max}$ of emission=462, 492 nm ($CH_2Cl_2$ solution at room temperature), CIE=(0.17, 0.30).

Example 59

Preparation of es49

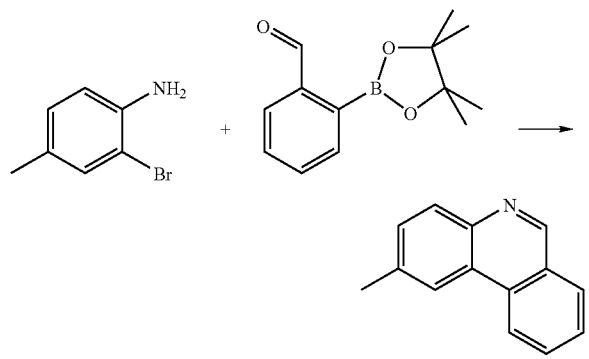

A 500 ml round bottom flask was charged with 2-formyl boronic acid (9.40 grams, 0.063 mol), 2-bromo-4-methyl aniline (5.0 mls, 0.040 mol), bis(triphenylphosphine) palladium dichloride (2.81 grams, 0.004 mol), tripotassium phosphate (19.1 grams, 0.090 mol), toluene (200 mls) and water (2 mls). This was refluxed for 18 hours. The mixture was filtered through celite. The filtrate was concentrated in vacuo and purified on a silica gel column eluted with 4:1 dichloromethane-ethyl acetate to give the product as a red solid. $^1$H nmr ($CDCl_3$) $\delta$ 9.23 (s, 1H), 2.63 (s, 3H).

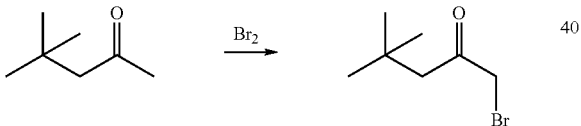

To a solution of 4,4-dimethyl-2-pentanone (10 g, 0.0867 mole) in 150 ml methanol; cooled to −5° C. in a ice/salt batch; was added bromine (14.7 g, 0.092 mole) in a rapid stream through an additional funnel. Reaction was stirred in the ice bath for 3 hours while the temperature maintained below 5° C. The ice bath was removed and reaction proceeded at room temperature for 2 hours. The reaction mixture was diluted with 250 ml of water and extracted with 3×75 ml of ether. The ether extract were washed with 10% $Na_2CO_3$ and water; dried over $Na_2SO_4$; evaporated to yield desired product. (15.18 g, 90%)

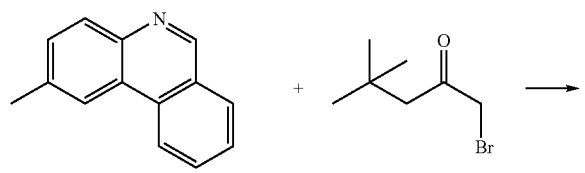

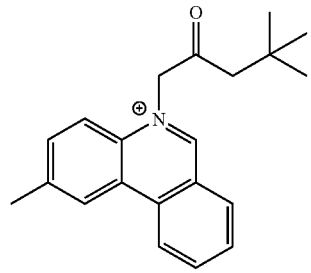

A 500 ml round bottom flask was charged with 2-methyl phenanthridine (1 g, 5.2 mmole), 1-bromo-4,4-dimethylpentan-2-one (1.2 g, 6.2 mmole) and 10 mls of dioxane. The reaction mixture was heated to reflux for over night. The reaction mixture was cooled to room temperature and diluted with ether to induce the precipitation. The precipitation was filtered off to yield the desired product (1.8 g)

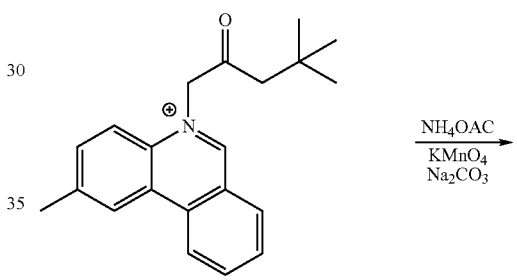

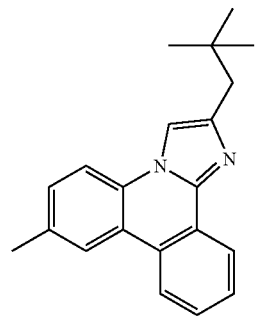

To a stirred suspension of the product from step 3 (19.6 g, 50 mmole) in dioxane (0.7 L) at room temperature, were added ammonium acetate (15.64 g, 200 mmole), followed by $MnO_2$ (43.4 g, 580 mmole). The reaction mixture was refluxed for 4 hours before adding 10 equivalents of $Na_2CO_3$ (53 g, 500 mmole). The suspension was then cooled down to room temperature and filtered on glass frit and then the residue was rinsed extensively with acetone. Finally, the mother liquid was concentrated to dryness and subjected to column chromatography ($SiO_2$, 5% methanol in $CH_2Cl_2$) to yield desired compound (11.4 g)

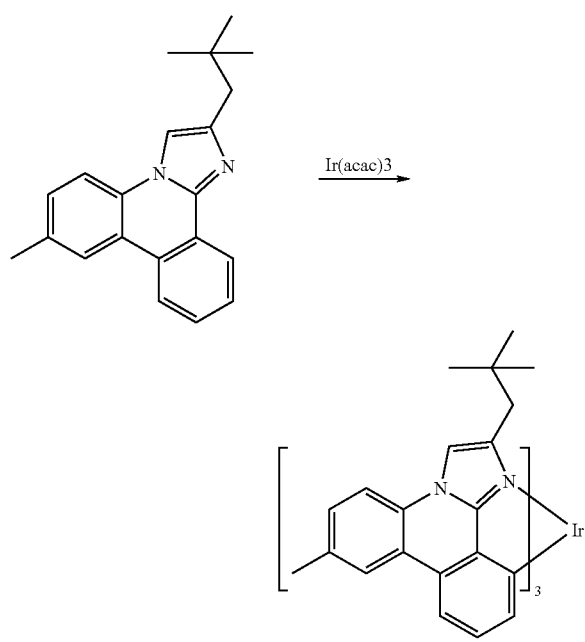

To a 50 mL Schlenk tube were added ligand from step 4 (2.72 g, 8.99 mmol), tris(acetylacetonate)iridium (III) (0.885 g, 1.79 mmol, which was purified by an Al$_2$O$_3$ column with CH$_2$Cl$_2$ as eluent) and tridecane (50 drops). The mixture was degassed and back filled with nitrogen before being heated in a sand bath (outside sand bath temperature was 235° C.) with stirring under a nitrogen atmosphere for 67 h. After cooling, the reaction mixture was dissolved with a mixture of CH$_2$Cl$_2$ and hexanes (4:6) and subjected to column chromatography (SiO$_2$, 40% CH$_2$Cl$_2$ in hexanes) and yielded desired compound (0.58 g; 30%).

Example 60

Preparation of es44

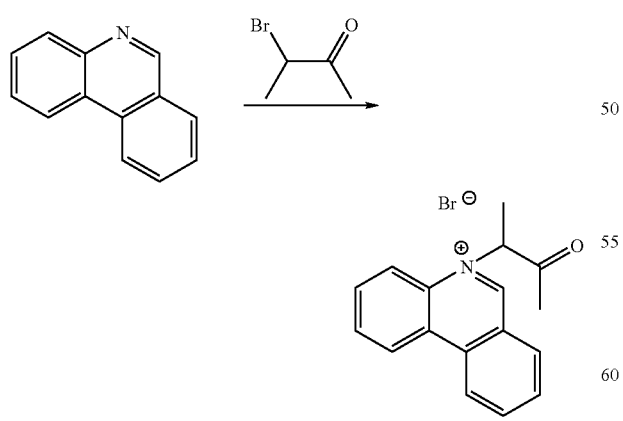

A 500 ml round bottom flask was charged with phenanthridine (14.8 g), 3-bromo-2-butanone (15.16 g) and 50 ml of dioxane. The reaction mixture was heated to reflux for over night. The reaction mixture was cooled to room temperature and diluted with ether to induce the precipitation. The precipitation was filtered off to yield the desired product (25.2 g)

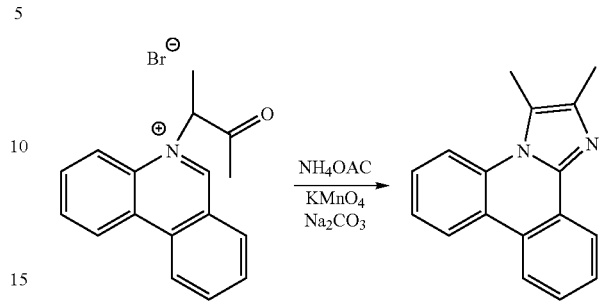

To a stirred suspension of the product from step 1 (25.2 g, 88 mmole) in dioxane (1 L) at room temperature, were added ammonium acetate (27.1 g, 350 mmole), followed by MnO$_2$ (76.5 g, 880 mmole). The reaction mixture was refluxed for 4 hours before adding 10 equivalents of Na$_2$CO$_3$ (93.27 g, 880 mmole). The suspension was then cooled down to room temperature and filtered on glass frit and then the residue was rinsed extensively with acetone. Finally, the mother liquor was concentrated to dryness and subjected to column chromatography (SiO$_2$, 1% methanol in CH$_2$Cl$_2$) to yield desired compound (14.9 g, 69%).

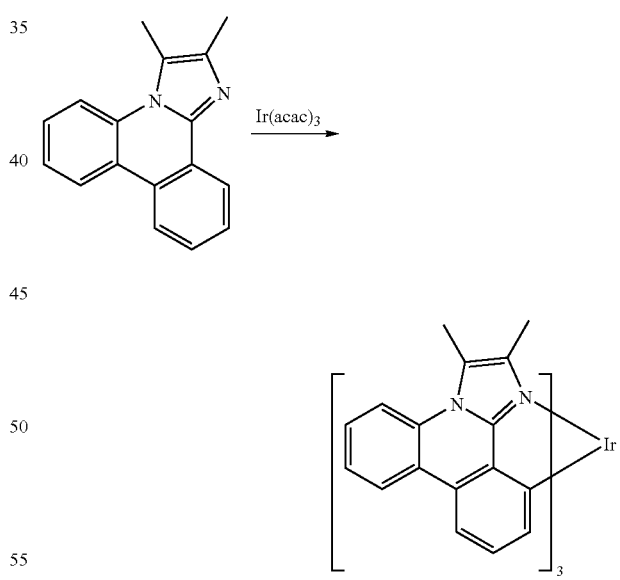

To a 50 mL Schlenk tube were added ligand from step 2 (4 g, 16.24 mmol), tris(acetylacetonate)iridium (III) (1.6 g, 3.24 mmol, which was purified by an Al$_2$O$_3$ column with CH$_2$Cl$_2$ as eluent) and tridecane (50 drops). The mixture was degassed and back filled with nitrogen before being heated in a sand bath (outside sand bath temperature was 235° C.) with stirring under a nitrogen atmosphere for 67 h. After cooling, the reaction mixture was sonicated with a CH$_2$Cl$_2$. A dark yellow suspension was obtained. A yellow solid was collected by filtration. The solid was washed extensively with hot Ethyl Acetate to get desired compound. (2.17 g; 72%).

Example 61

Preparation of es45

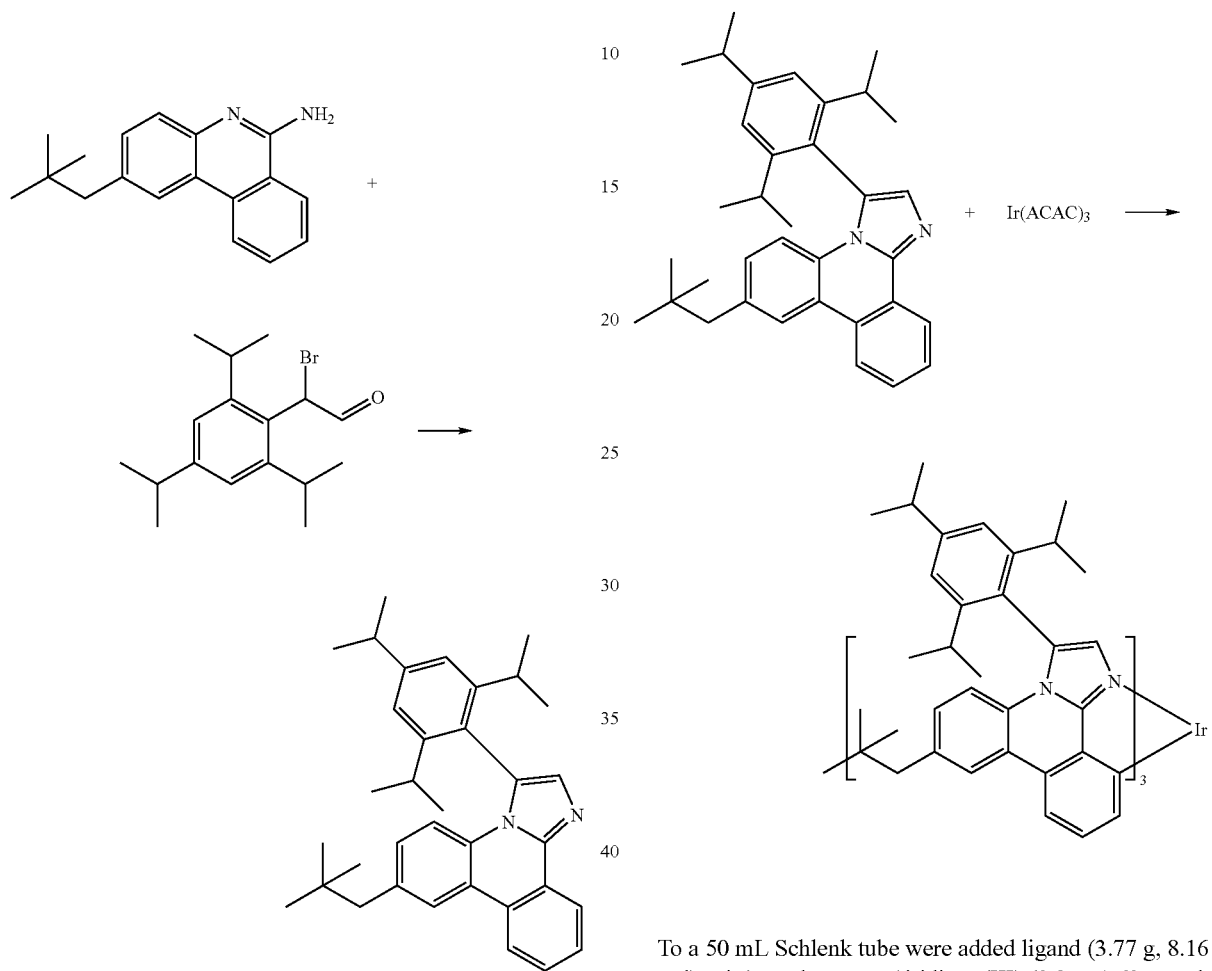

10.

82 g (0.041 moles) of the neopentyl amidine intermediate was dissolved in 200 ml of isopropanol. To this solution, 13.27 g (0.041 moles) of the triisopropylphenyl acetyl bromide intermediate was added all at once. This solution was heated at 85° C. for three hours. At this point, the reaction mixture was allowed to cool to just under the reflux temperature of isopropanol. Sodium bicarbonate 6.89 g (0.082 moles) was added portion wise over a 5 minute period to the reaction mixture. The reaction mixture was then heated back up to 85 C and was held at this temperature for 18 hours. The reaction mixture was diluted with 300 mls. of water. This mixture was filtered. The filtrate was extracted 2×250 mls ethyl acetate. These ethyl acetate extracts were combined and washed 1×100 mls aqueous 10% LiCl. These extracts were then dried over magnesium sulfate, filtered and stripped under vacuum. The crude product from the work-up was passed through a silica gel column. The column was eluted with 5-25% ethyl acetate/methylene chloride. The cleanest fractions were combined and stripped under vacuum yielding 4.5 g of product. $^1$H nmr (CDCl$_3$) δ 3.05 (m, 1H), 2.60 (m, 4H), 1.37 (d, 6H), 1.11 (d, 6H), 0.92 (m, 15H).

To a 50 mL Schlenk tube were added ligand (3.77 g, 8.16 mmol), tris(acetylacetonate)iridium (III) (0.8 g, 1.63 mmol, which was purified by an Al$_2$O$_3$ column with CH$_2$Cl$_2$ as eluent) and tridecane (50 drops). The mixture was degassed and back filled with nitrogen before being heated in a sand bath (outside sand bath temperature was 240-250° C.) with stirring under a nitrogen atmosphere for 72 h. After cooling, the reaction mixture was sonicated with a mixture of solvent (CH$_2$Cl$_2$: Hexanes=10 ml: 90 ml). A dark yellow suspension was obtained. A yellow solid was collected by filtration. The solid was purified by flash column chromatography (SiO$_2$; CH$_2$Cl$_2$). The solid after column chromatography was re-crystallized from Ethyl Acetate. The yield after crystallization is 0.8 g. Structure was confirmed by proton nmr.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

The invention claimed is:

1. An iridium complex of the formula

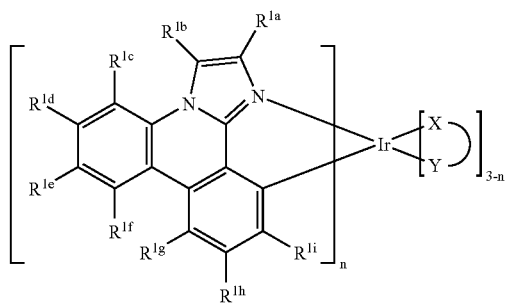

wherein n=1, 2 or 3;

$R^{1a}$, $R^{1b}$, $R^{1c}$, $R^{1d}$, $R^{1e}$, $R^{1f}$, $R^{1g}$, $R^{1h}$, and $R^{1i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a-c}$ are each, independently, hydrocarbyl or heteroatom substituted hydrocarbyl, and where any two of $R^{1a-i}$ and $R^{2a-c}$ may be linked to form a saturated or unsaturated, aromatic or non-aromatic ring; and X-Y is an ancillary ligand.

2. The complex of claim 1, wherein at least one of $R^{1a}$, $R^{1b}$, $R^{1c}$, $R^{1d}$, $R^{1e}$, $R^{1f}$, $R^{1g}$, $R^{1h}$, and $R^{1i}$ is a branched alkyl containing at least 4 carbon atoms and wherein the branching occurs at a position further than the benzylic position.

3. The complex of claim 2, wherein at least one of $R^{1a}$, $R^{1b}$, $R^{1c}$, $R^{1d}$, $R^{1e}$, $R^{1f}$, $R^{1g}$, $R^{1h}$, and $R^{1i}$ is neopentyl.

4. The complex of claim 2, wherein $R^{1e}$ is a branched alkyl containing at least 4 carbon atoms and wherein the branching occurs at a position further than the benzylic position.

5. The complex of claim 4, wherein the complex includes a ligand selected from the group consisting of:

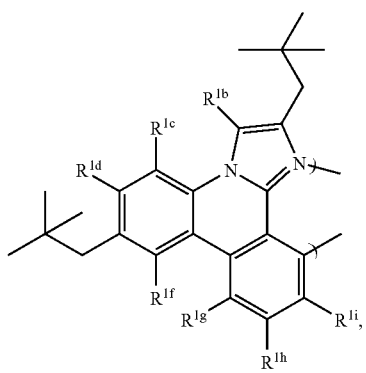

gs1-32

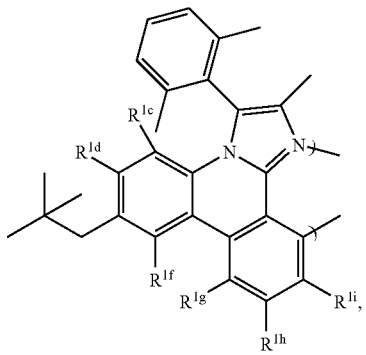

gs1-33

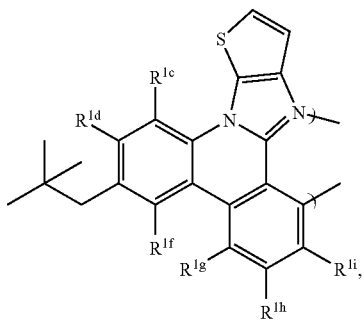

gs1-34

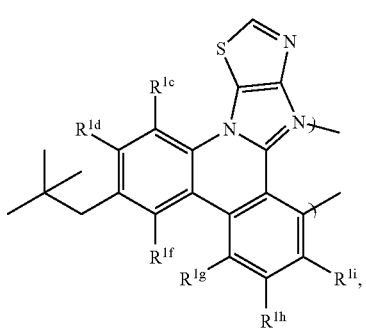

gs1-35

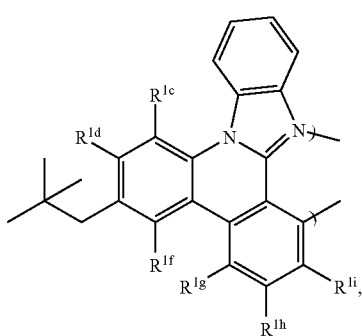

gs1-36 gs1-37
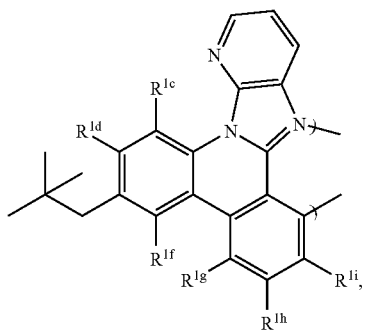
gs1-38
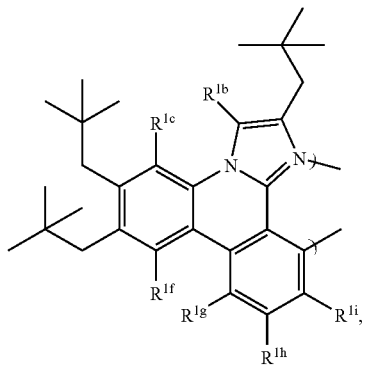
gs1-39
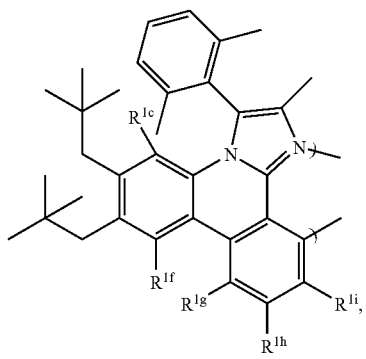
gs1-40
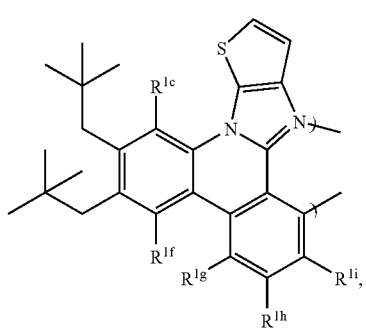
ga1-41
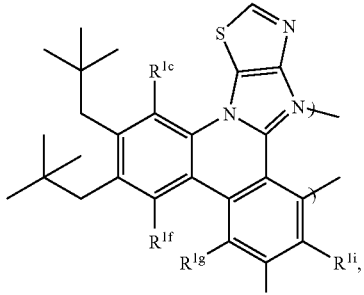
gs1-42
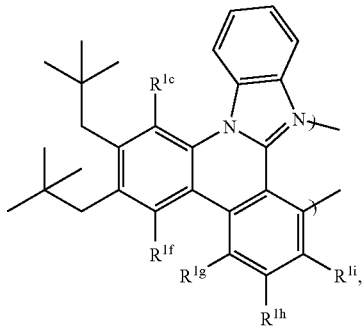
gs1-43
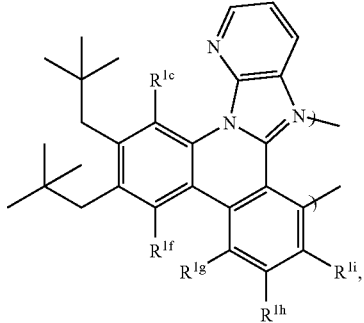
gs1-44
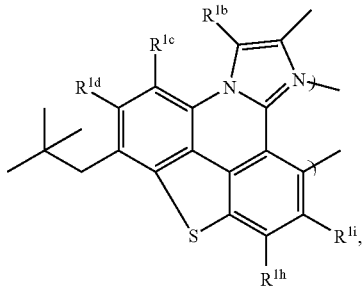
gs1-45
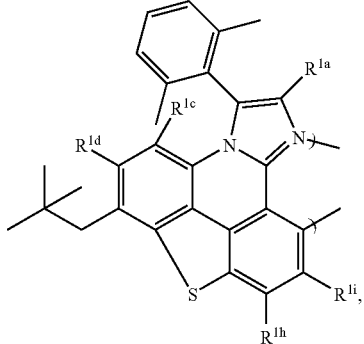

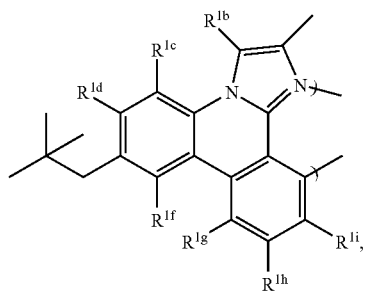
gs1-46
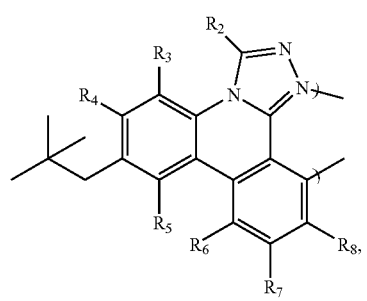
gs1-47
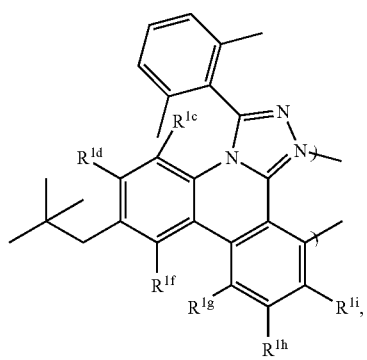
gs1-48
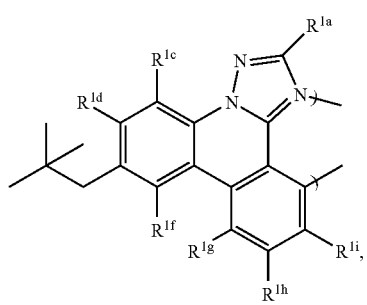
gs1-49
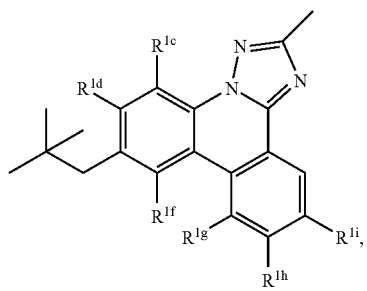
gs1-50
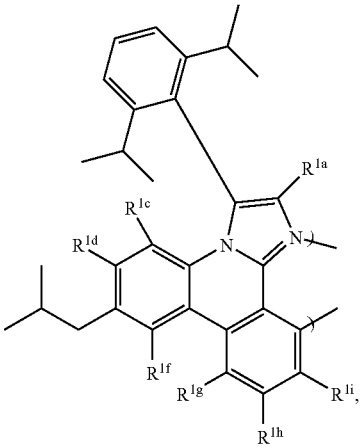
gs1-51
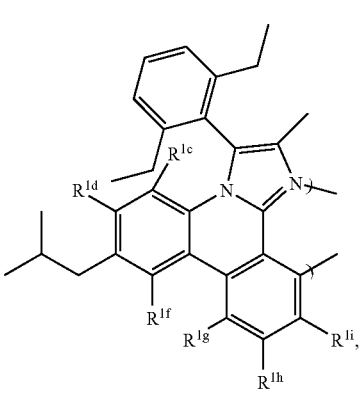
gs1-52
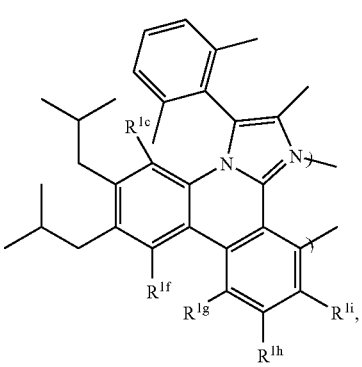
gs1-53
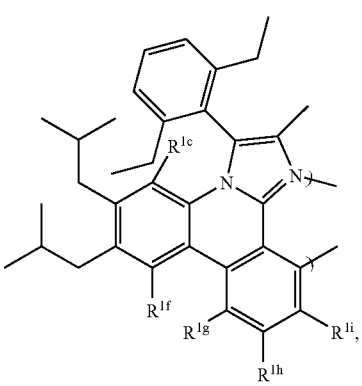
gs1-54

-continued gs1-55
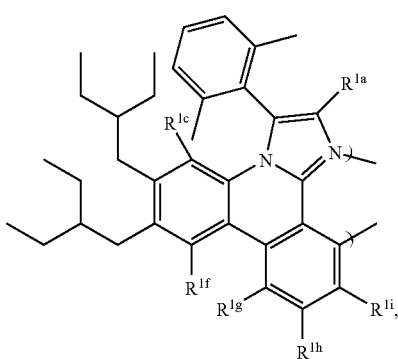

gs1-56
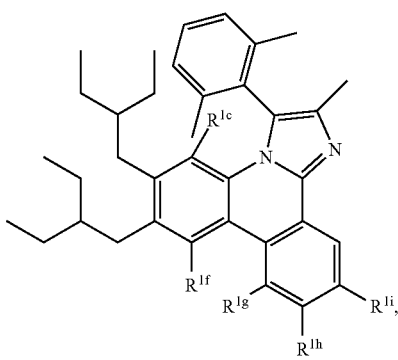

gs1-59
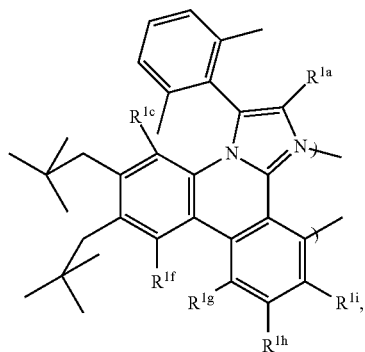

gs1-60
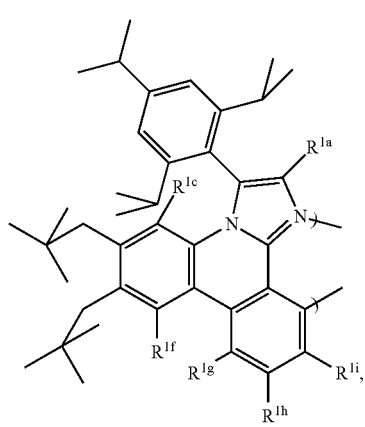

-continued gs1-61
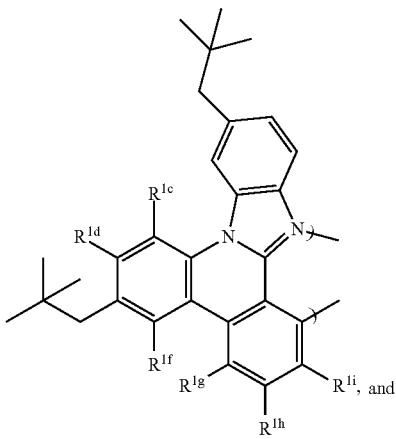
, and gs1-62
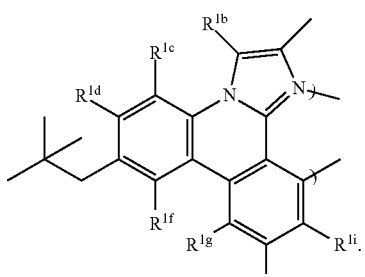

6. The complex of claim 5, where $R^{1a}$, $R^{1b}$, $R^{1c}$, $R^{1d}$, $R^{1f}$, $R^{1g}$, $R^{1h}$, and $R^{1i}$, are all H.

7. The complex of claim 1, wherein $R^{1b}$ is an aryl group having the structure:

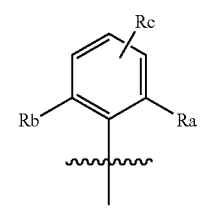

wherein Ra, Rb and Rc are independently H, alkyl or aryl; at least one of Ra and Rb is an alkyl or aryl; and Ra, Rb and Rc can join to form fused rings.

8. The complex of claim 7, at least one of Ra and Rb is an alkyl.

9. The complex of claim 7, wherein $R^{1b}$ is an aryl group with a dihedral angle of more than 70 degrees from the imidazole ring.

10. The complex of claim 7, wherein Ra and Rb are both alkyl.

11. The complex of claim 10, wherein Ra and Rb are both methyl.

12. The complex of claim 10, wherein the Ra and Rb are both isopropyl.

13. The complex of claim 7, wherein $R^{1b}$ is an aryl group with a dihedral angle of more than 70 degrees from the imidazole ring and $R^{1a}$ is alkyl.

14. The complex of claim 7, wherein the complex is:
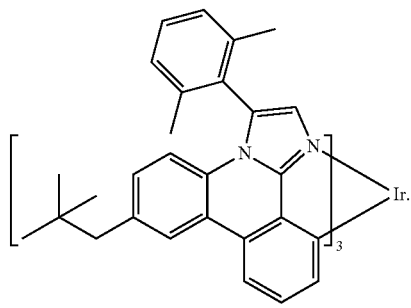
15. The complex of claim 7, wherein the complex is:
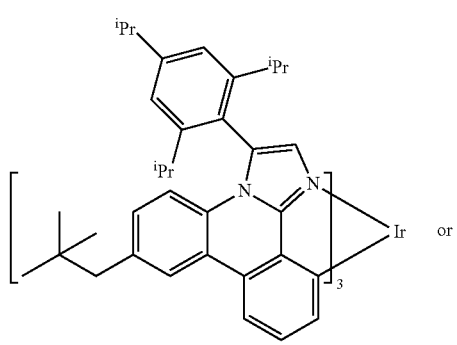
16. The complex of claim 7, wherein the complex is:
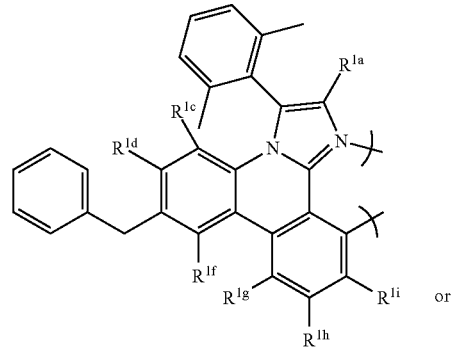
gs1-57
or
gs1-58
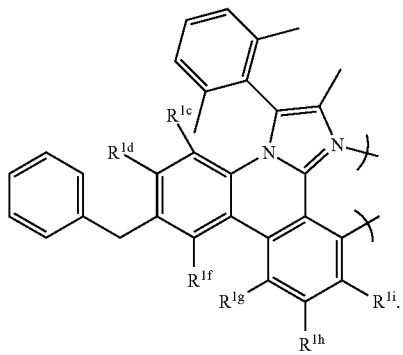
17. The complex of claim 1, wherein $R^{1a}$ is an electron donating group.
18. The complex of claim 17, wherein $R^{1a}$ is methyl.
19. The complex of claim 17, wherein the complex is:
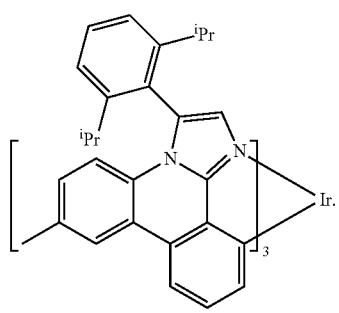
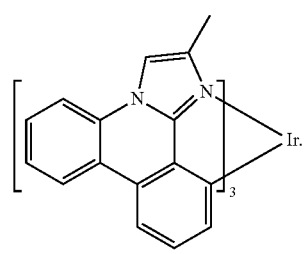

20. The complex of claim 17, wherein the complex is selected from the group consisting of:
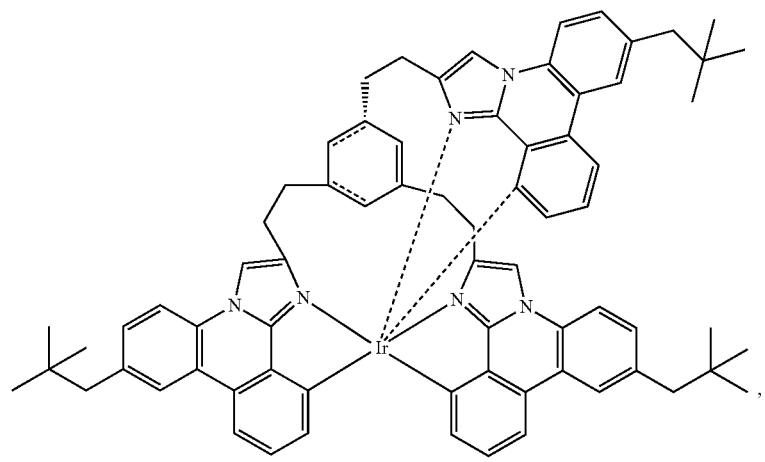
,
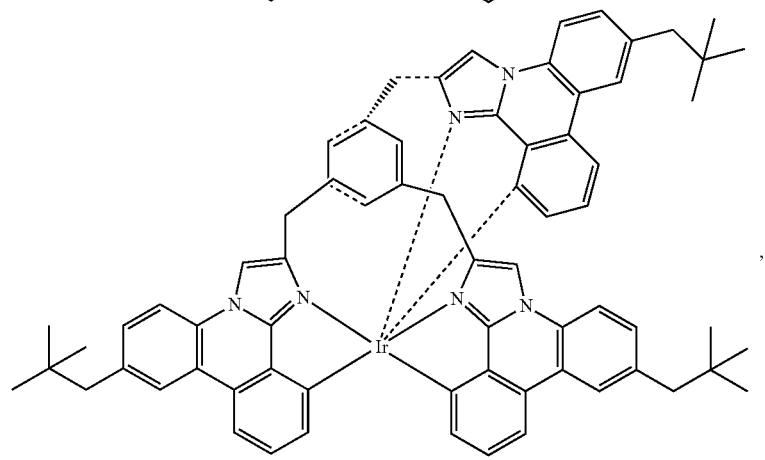
,
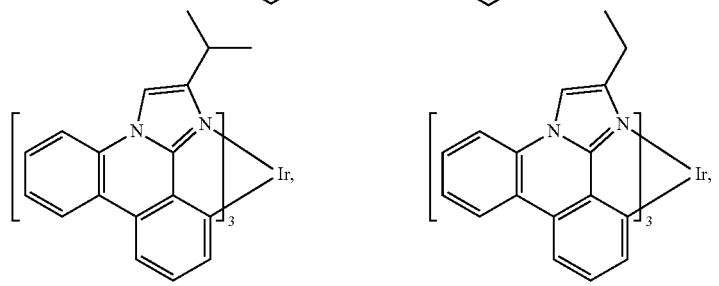
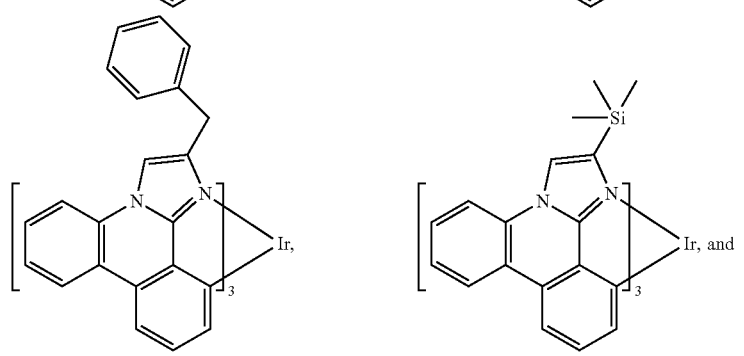
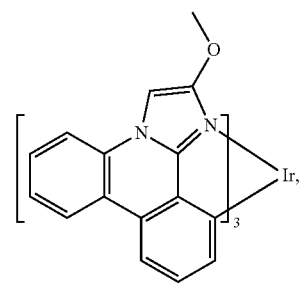
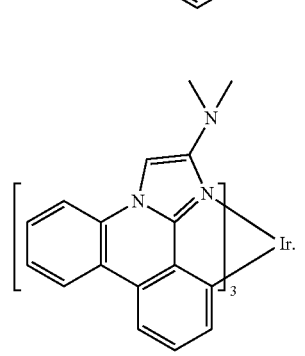
21. A device, comprising:
an anode;
a cathode; and
an organic emissive layer, disposed between the anode and the cathode, the organic layer further comprising an emissive complex having the formula:

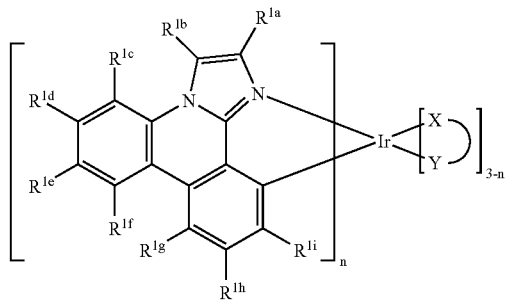

wherein n=1, 2 or 3;

$R^{1a}$, $R^{1b}$, $R^{1c}$, $R^{1d}$, $R^{1e}$, $R^{1f}$, $R^{1g}$, $R^{1h}$, and $R^{1i}$ are each, independently, H, hydrocarbyl, heteroatom substituted hydrocarbyl, cyano, fluoro, $OR^{2a}$, $SR^{2a}$, $NR^{2a}R^{2b}$, or $SiR^{2a}R^{2b}R^{2c}$, where $R^{2a\text{-}c}$ are each, independently, hydrocarbyl or heteroatom substituted hydrocarbyl, and where any two of $R^{1a\text{-}i}$ and $R^{2a\text{-}c}$ may be linked to form a saturated or unsaturated, aromatic or non-aromatic ring; and X-Y is an ancillary ligand.

22. The device of claim 21, wherein the organic emissive layer further comprises a host, wherein the host is an organic material that contains a carbazole group.

23. The device of claim 22, wherein the host is mCBP.

24. The device of claim 21, wherein at least one of $R^{1a}$, $R^{1b}$, $R^{1c}$, $R^{1d}$, $R^{1e}$, $R^{1f}$, $R^{1g}$, $R^{1h}$, and $R^{1i}$ is a branched alkyl containing at least 4 carbon atoms and wherein the branching occurs at a position further than the benzylic position.

25. The device of claim 24, wherein the organic emissive layer further comprises a host, wherein the host is an organic material that contains a carbazole group.

26. The device of claim 25, wherein the host is mCBP.

27. The device of claim 24, wherein the complex includes a ligand selected from the group consisting of:

gs1-32

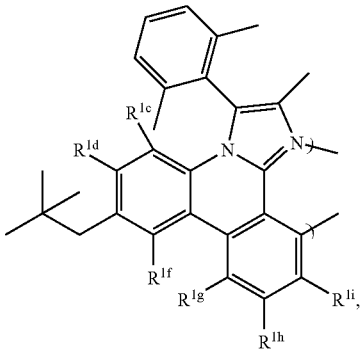

gs1-33

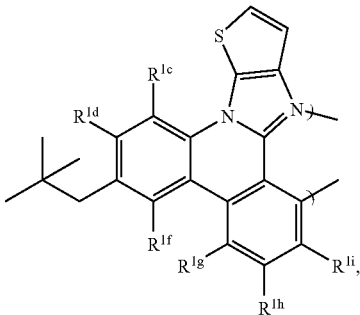

gs1-34

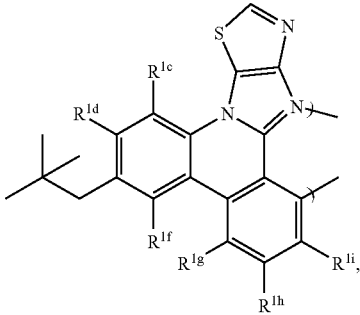

gs1-35

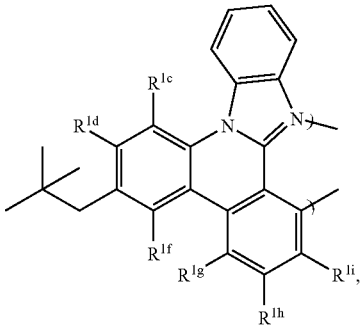

gs1-36 gs1-37

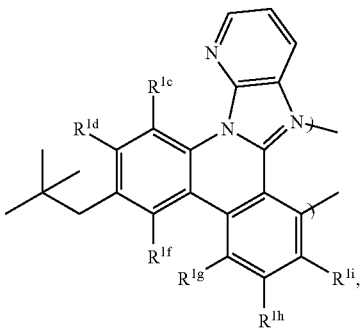

gs1-38
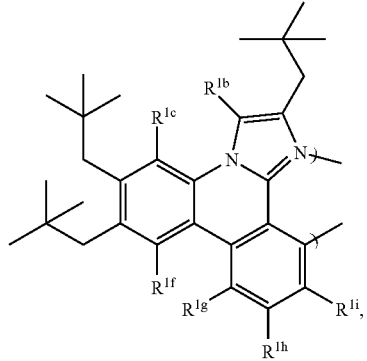
gs1-39
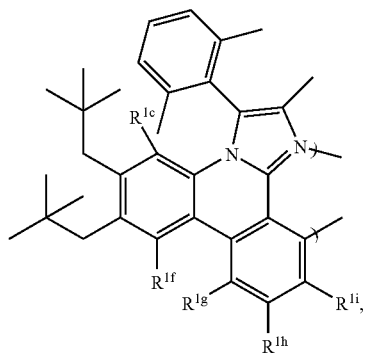
gs1-40
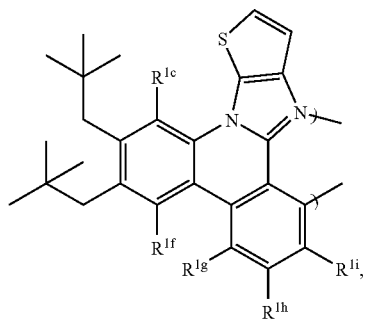
ga1-41
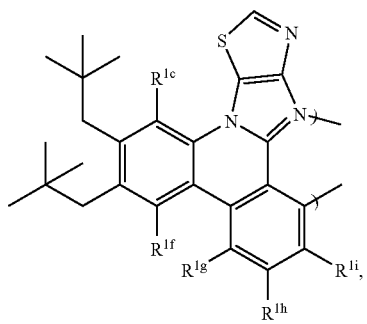
gs1-42
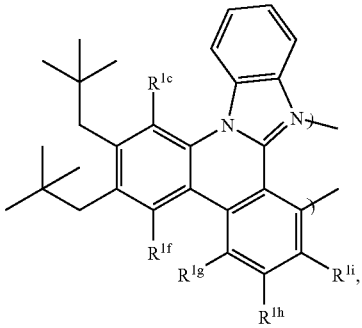
gs1-43
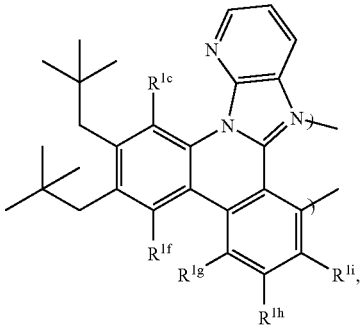
gs1-44
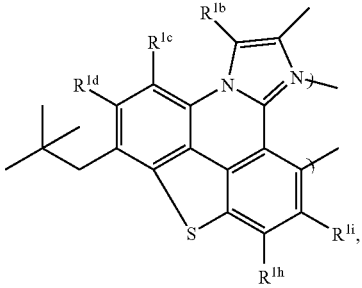
gs1-45
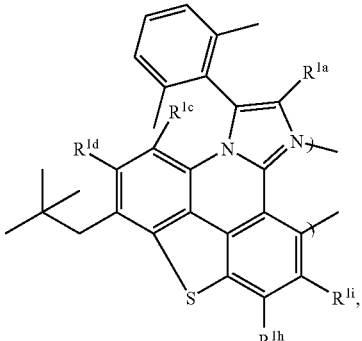
gs1-46
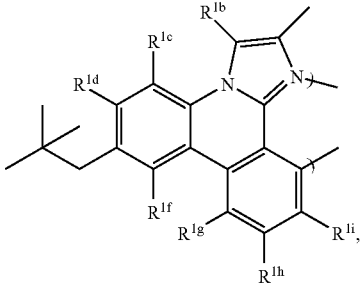

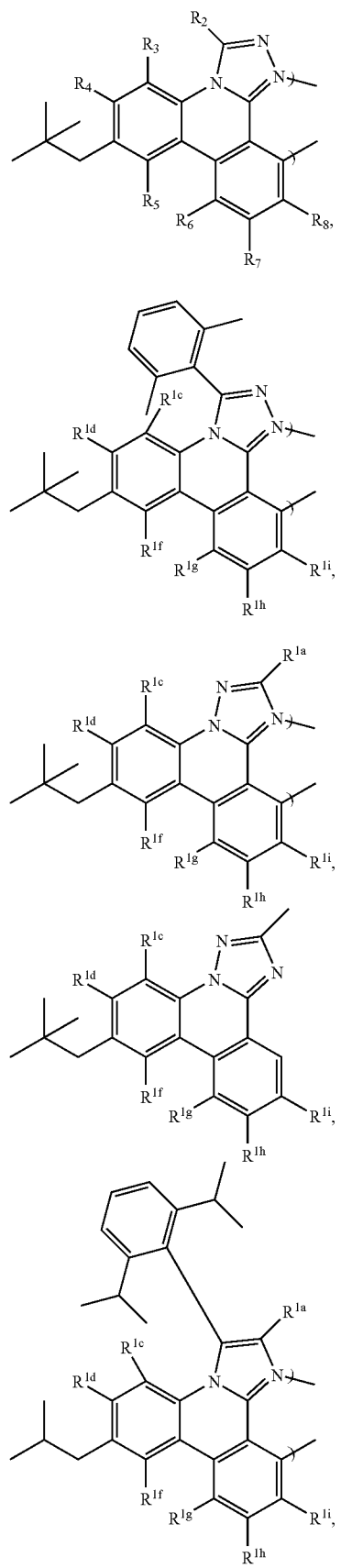
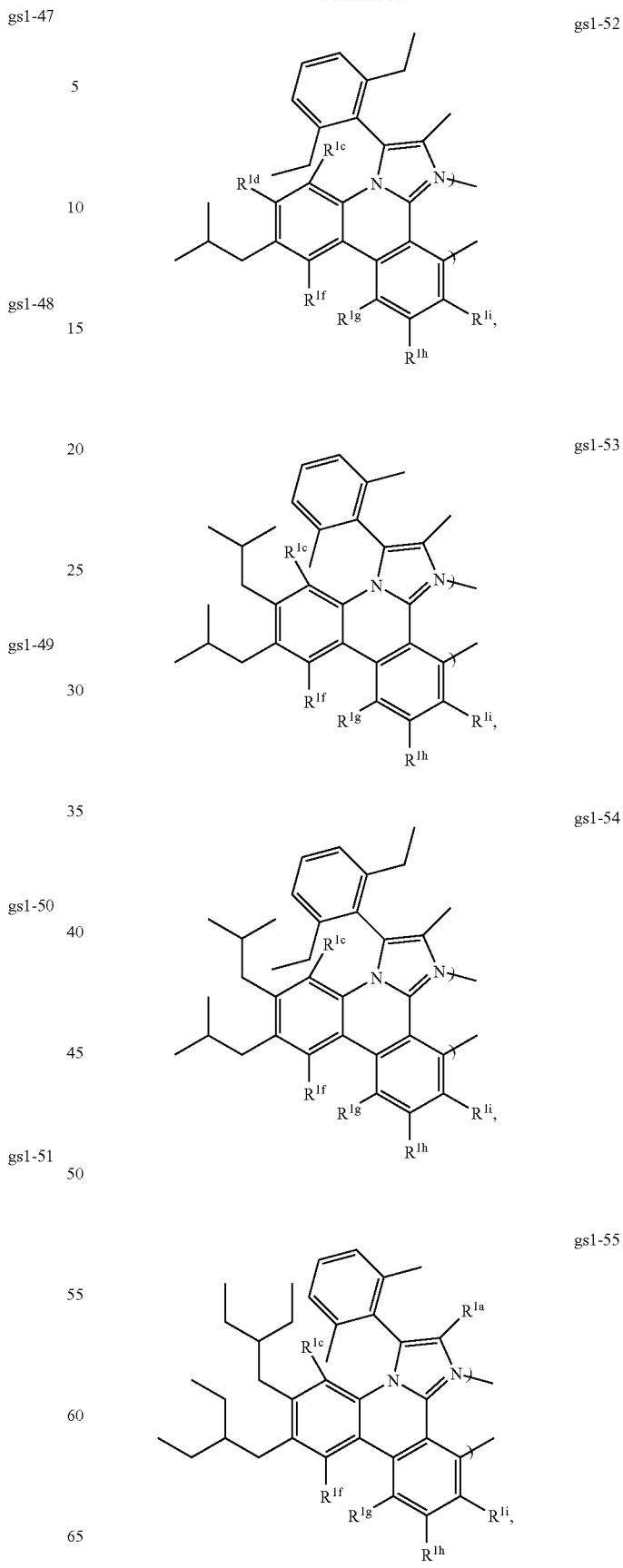

-continued gs1-56

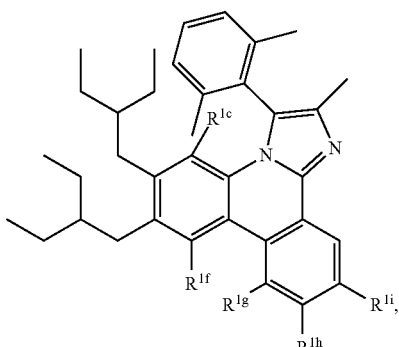

gs1-59

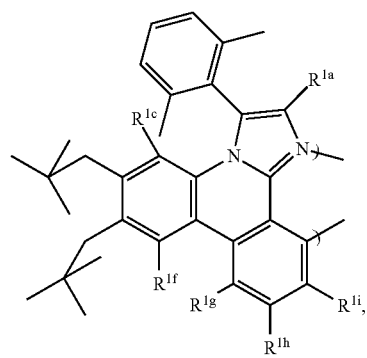

gs1-60

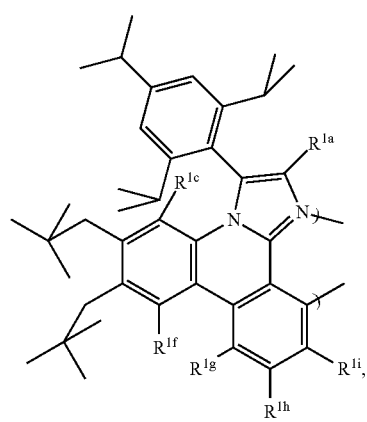

gs1-61

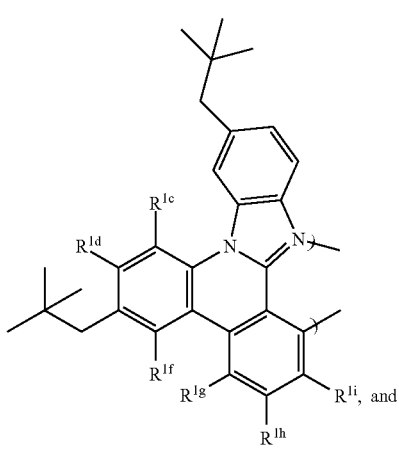

-continued gs1-62

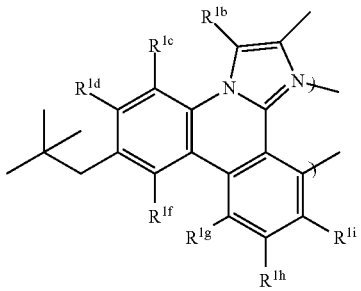

where $R^{1a}$, $R^{1b}$, $R^{1c}$, $R^{1d}$, $R^{1f}$, $R^{1g}$, $R^{1h}$, and $R^{1i}$, and are independently H or substitutions selected from the group of alkyl or aryl.

28. The device of claim 27, wherein the organic emissive layer further comprises a host, wherein the host is an organic material that contains a carbazole group.

29. The device of claim 28, wherein the host is mCBP.

30. The device of claim 21, wherein $R^{1b}$ is an aryl group having the structure:

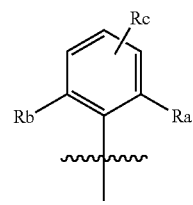

wherein Ra, Rb and Rc are independently H, alkyl or aryl; at least one of Ra and Rb is an alkyl or aryl; and
Ra, Rb and Rc can join to form fused rings.

31. The device of claim 30, wherein the organic emissive layer further comprises a host, wherein the host is an organic material that contains a carbazole group.

32. The device of claim 31, wherein the host is mCBP.

33. The complex of claim 30, wherein the complex is:

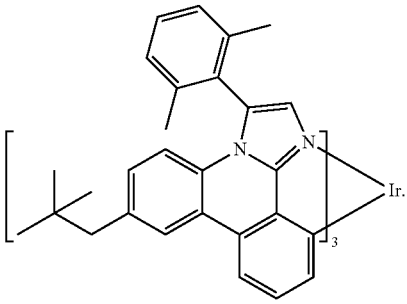

34. The device of claim 33, wherein the organic emissive layer further comprises a host, wherein the host is an organic material that contains a carbazole group.

35. The device of claim 34, wherein the host is mCBP.

36. The device of claim 21 wherein $R^{1a}$ is an electron donating group.

37. The device of claim 36, wherein the organic emissive layer further comprises a host, wherein the host is an organic material that contains a carbazole group.

38. The device of claim 37, wherein the host is mCBP.

39. The complex of claim 36, wherein the complex is:
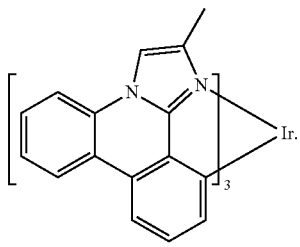
40. The device of claim 39, wherein the organic emissive layer further comprises a host, wherein the host is an organic material that contains a carbazole group.
41. The device of claim 40, wherein the host is mCBP.
42. The complex of claim 36, wherein the complex is selected from the group consisting of:
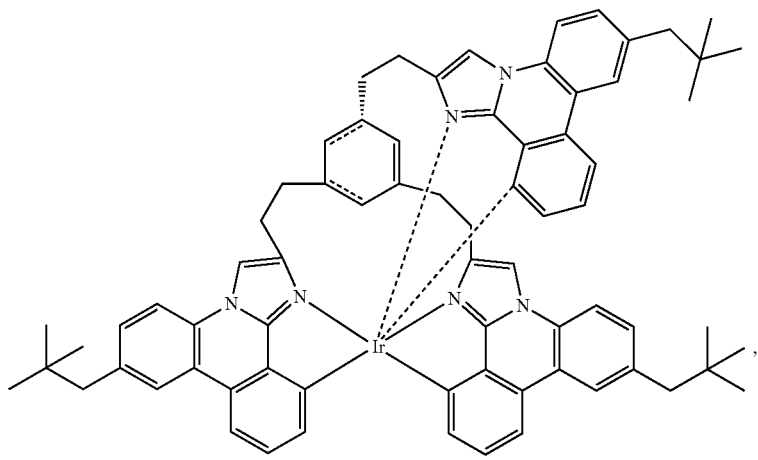
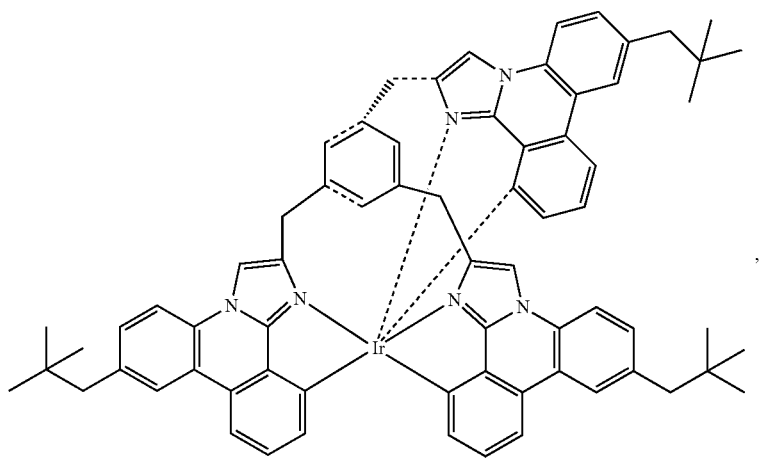
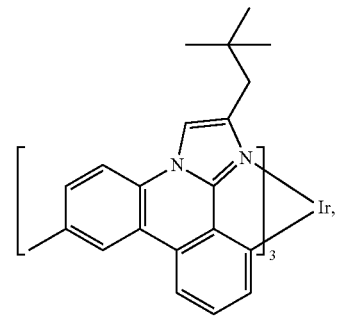
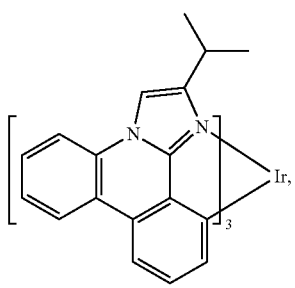
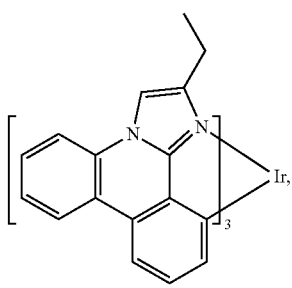
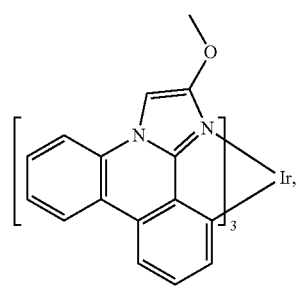

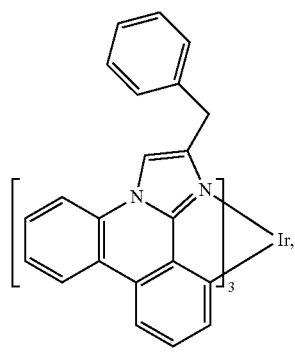 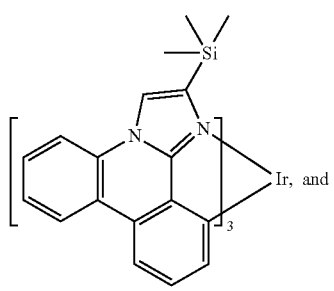 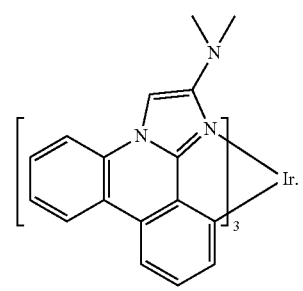
43. The device of claim 42, wherein the organic emissive layer further comprises a host, wherein the host is an organic material that contains a carbazole group.
44. The device of claim 43, wherein the host is mCBP.
* * * * *